(12) United States Patent
Boudreault et al.

(10) Patent No.: US 11,196,010 B2
(45) Date of Patent: *Dec. 7, 2021

(54) ORGANIC ELECTROLUMINESCENT MATERIALS AND DEVICES

(71) Applicant: Universal Display Corporation, Ewing, NJ (US)

(72) Inventors: Pierre-Luc T. Boudreault, Pennington, NJ (US); Mingjuan Su, Ewing, NJ (US); Harvey Wendt, Medford Lakes, NJ (US); Scott Joseph, Ewing, NJ (US)

(73) Assignee: UNIVERSAL DISPLAY CORPORATION, EWING, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/706,186

(22) Filed: Sep. 15, 2017

(65) Prior Publication Data

US 2018/0097179 A1 Apr. 5, 2018

Related U.S. Application Data

(60) Provisional application No. 62/403,424, filed on Oct. 3, 2016.

(51) Int. Cl.
*H01L 51/00* (2006.01)
*C07D 215/06* (2006.01)
(Continued)

(52) U.S. Cl.
CPC .......... *H01L 51/009* (2013.01); *C07D 215/06* (2013.01); *C07D 239/24* (2013.01);
(Continued)

(58) Field of Classification Search
CPC ............... H01L 51/009; H01L 51/0085; H01L 51/5024; H01L 51/5016; H01L 51/50;
(Continued)

(56) References Cited

U.S. PATENT DOCUMENTS

| 4,769,292 A | 9/1988 | Tang et al. |
| 5,061,569 A | 10/1991 | VanSlyke et al. |

(Continued)

FOREIGN PATENT DOCUMENTS

| CN | 104804045 | 7/2015 |
| EP | 0650955 | 5/1995 |

(Continued)

OTHER PUBLICATIONS

Lai, S. L. et al., "Efficient white organic light-emitting devices based on phosphorescent iridium complexes" Organic Electronics, vol. 11, Issue 9, Sep. 2010, pp. 1511-1515.

(Continued)

*Primary Examiner* — Alexander C Kollias
(74) *Attorney, Agent, or Firm* — Duane Morris LLP

(57) ABSTRACT

Novel phosphorescent metal complexes containing ligands having the Formula I:

Formula I (Continued)

bearing either a naphthalene or other fused heterocycle moieties such as benzofuran and benzothiophene useful as emitters in OLEDs and improve the device efficiency and the FWHM of the emission.

21 Claims, 2 Drawing Sheets

(51) Int. Cl.
| | | |
|---|---|---|
| C07D 495/04 | (2006.01) | |
| C07D 491/048 | (2006.01) | |
| C07D 239/24 | (2006.01) | |
| C07F 15/00 | (2006.01) | |
| C09K 11/06 | (2006.01) | |
| H01L 51/50 | (2006.01) | |

(52) U.S. Cl.
CPC ........ *C07D 491/048* (2013.01); *C07D 495/04* (2013.01); *C07F 15/0033* (2013.01); *C09K 11/06* (2013.01); *H01L 51/0085* (2013.01); C09K 2211/1029 (2013.01); C09K 2211/1051 (2013.01); C09K 2211/185 (2013.01); H01L 51/5016 (2013.01); H01L 51/5024 (2013.01)

(58) Field of Classification Search
CPC . H01L 2251/30; H01L 2251/50; C09K 11/06; C09K 2211/1029; C09K 2211/185; C09K 2211/1051; C07D 495/04; C07D 239/24; C07D 491/048; C07D 215/06; C07F 15/0033
See application file for complete search history.

(56) References Cited

U.S. PATENT DOCUMENTS

| | | | |
|---|---|---|---|
| 5,247,190 A | 9/1993 | Friend et al. | |
| 5,703,436 A | 12/1997 | Forrest et al. | |
| 5,707,745 A | 1/1998 | Forrest et al. | |
| 5,834,893 A | 11/1998 | Bulovic et al. | |
| 5,844,363 A | 12/1998 | Gu et al. | |
| 6,013,982 A | 1/2000 | Thompson et al. | |
| 6,087,196 A | 7/2000 | Sturm et al. | |
| 6,091,195 A | 7/2000 | Forrest et al. | |
| 6,097,147 A | 8/2000 | Baldo et al. | |
| 6,278,237 B1 | 8/2001 | Campos | |
| 6,294,398 B1 | 9/2001 | Kim et al. | |
| 6,303,238 B1 | 10/2001 | Thompson et al. | |
| 6,337,102 B1 | 1/2002 | Forrest et al. | |
| 6,468,819 B1 | 10/2002 | Kim et al. | |
| 6,528,187 B1 | 3/2003 | Okada | |
| 6,687,266 B1 | 2/2004 | Ma et al. | |
| 6,835,469 B2 | 12/2004 | Kwong et al. | |
| 6,921,915 B2 | 7/2005 | Takiguchi et al. | |
| 7,087,321 B2 | 8/2006 | Kwong et al. | |
| 7,090,928 B2 | 8/2006 | Thompson et al. | |
| 7,154,114 B2 | 12/2006 | Brooks et al. | |
| 7,250,226 B2 | 7/2007 | Tokito et al. | |
| 7,279,704 B2 | 10/2007 | Walters et al. | |
| 7,332,232 B2 | 2/2008 | Ma et al. | |
| 7,338,722 B2 | 3/2008 | Thompson et al. | |
| 7,393,599 B2 | 7/2008 | Thompson et al. | |
| 7,396,598 B2 | 7/2008 | Takeuchi et al. | |
| 7,431,968 B1 | 10/2008 | Shtein et al. | |
| 7,445,855 B2 | 11/2008 | Mackenzie et al. | |
| 7,534,505 B2 | 5/2009 | Lin et al. | |
| 10,164,199 B2 | 12/2018 | Lin et al. | |
| 10,230,060 B2 | 3/2019 | Kwong et al. | |
| 2002/0034656 A1 | 3/2002 | Thompson et al. | |
| 2002/0134984 A1 | 9/2002 | Igarashi | |
| 2002/0158242 A1 | 10/2002 | Son et al. | |
| 2003/0068526 A1* | 4/2003 | Kamatani | C07F 15/004 428/690 |
| 2003/0068536 A1* | 4/2003 | Tsuboyama | C07F 15/0033 428/704 |
| 2003/0072964 A1* | 4/2003 | Kwong | C07D 215/04 428/690 |
| 2003/0138657 A1 | 7/2003 | Li et al. | |
| 2003/0152802 A1 | 8/2003 | Tsuboyama et al. | |
| 2003/0162053 A1 | 8/2003 | Marks et al. | |
| 2003/0175553 A1 | 9/2003 | Thompson et al. | |
| 2003/0230980 A1 | 12/2003 | Forrest et al. | |
| 2004/0036077 A1 | 2/2004 | Ise | |
| 2004/0137267 A1 | 7/2004 | Igarashi et al. | |
| 2004/0137268 A1 | 7/2004 | Igarashi et al. | |
| 2004/0174116 A1 | 9/2004 | Lu et al. | |
| 2004/0214038 A1* | 10/2004 | Kwong | C09K 11/06 428/690 |
| 2005/0025993 A1 | 2/2005 | Thompson et al. | |
| 2005/0112407 A1 | 5/2005 | Ogasawara et al. | |
| 2005/0191519 A1 | 9/2005 | Mishima | |
| 2005/0238919 A1 | 10/2005 | Ogasawara | |
| 2005/0244673 A1 | 11/2005 | Satoh et al. | |
| 2005/0260441 A1 | 11/2005 | Thompson et al. | |
| 2005/0260449 A1 | 11/2005 | Walters et al. | |
| 2006/0008670 A1 | 1/2006 | Lin et al. | |
| 2006/0134462 A1 | 6/2006 | Yeh et al. | |
| 2006/0202194 A1 | 9/2006 | Jeong et al. | |
| 2006/0240279 A1 | 10/2006 | Adamovich et al. | |
| 2006/0251923 A1 | 11/2006 | Lin et al. | |
| 2006/0263635 A1 | 11/2006 | Ise | |
| 2006/0280965 A1 | 12/2006 | Kwong et al. | |
| 2007/0190359 A1 | 8/2007 | Knowles et al. | |
| 2007/0278938 A1 | 12/2007 | Yabunouchi et al. | |
| 2008/0015355 A1 | 1/2008 | Schafer et al. | |
| 2008/0018221 A1 | 1/2008 | Egen et al. | |
| 2008/0106190 A1 | 5/2008 | Yabunouchi et al. | |
| 2008/0124572 A1 | 5/2008 | Mizuki et al. | |
| 2008/0220265 A1 | 9/2008 | Xia et al. | |
| 2008/0297033 A1 | 12/2008 | Knowles et al. | |
| 2009/0008605 A1 | 1/2009 | Kawamura et al. | |
| 2009/0009065 A1 | 1/2009 | Nishimura et al. | |
| 2009/0017330 A1 | 1/2009 | Iwakuma et al. | |
| 2009/0030202 A1 | 1/2009 | Iwakuma et al. | |
| 2009/0039776 A1 | 2/2009 | Yamada et al. | |
| 2009/0045730 A1 | 2/2009 | Nishimura et al. | |
| 2009/0045731 A1 | 2/2009 | Nishimura et al. | |
| 2009/0101870 A1 | 4/2009 | Prakash et al. | |
| 2009/0108737 A1 | 4/2009 | Kwong et al. | |
| 2009/0115316 A1 | 5/2009 | Zheng et al. | |
| 2009/0165846 A1 | 7/2009 | Johannes et al. | |
| 2009/0167162 A1 | 7/2009 | Lin et al. | |
| 2009/0179554 A1 | 7/2009 | Kuma et al. | |
| 2010/0237334 A1 | 9/2010 | Ma et al. | |
| 2010/0283043 A1* | 11/2010 | Nishimura | C09K 11/06 257/40 |
| 2011/0285275 A1 | 11/2011 | Huang et al. | |
| 2012/0068165 A1 | 3/2012 | Hayashi | |
| 2012/0098417 A1 | 8/2012 | Inoue et al. | |
| 2015/0060830 A1 | 3/2015 | Thompson et al. | |
| 2015/0155502 A1* | 6/2015 | Ishibashi | H01L 51/5012 257/40 |
| 2015/0171348 A1* | 6/2015 | Stoessel | H05B 33/10 252/301.16 |
| 2015/0188059 A1 | 7/2015 | Chao et al. | |
| 2015/0207082 A1 | 7/2015 | Dyatkin et al. | |
| 2016/0233443 A1* | 8/2016 | Stoessel | C07D 491/048 |
| 2017/0025623 A1* | 1/2017 | Namanga | H01L 51/0072 |
| 2018/0097179 A1 | 4/2018 | Boudreault et al. | |
| 2018/0097187 A1* | 4/2018 | Boudreault | H01L 51/0085 |
| 2018/0240988 A1* | 8/2018 | Boudreault | C07F 15/0033 |
| 2019/0237683 A1* | 8/2019 | Boudreault | C07F 15/0033 |
| 2020/0227659 A1 | 7/2020 | Boudreault et al. | |
| 2020/0335706 A1 | 10/2020 | Watanabe et al. | |

FOREIGN PATENT DOCUMENTS

| | | |
|---|---|---|
| EP | 1725079 | 11/2006 |
| EP | 2034538 | 3/2009 |
| JP | 200511610 | 1/2005 |
| JP | 2007123392 | 5/2007 |

(56) References Cited

FOREIGN PATENT DOCUMENTS

| | | |
|---|---|---|
| JP | 2007-254540 | 10/2007 |
| JP | 2007254297 | 10/2007 |
| JP | 2008074939 | 4/2008 |
| JP | 2010135689 | 6/2010 |
| JP | 2011051919 | 3/2011 |
| JP | 2011-166102 | 8/2011 |
| KR | 20130128322 | 11/2013 |
| KR | 20140121991 | 10/2014 |
| KR | 20160041223 | 4/2016 |
| TW | 201430103 | 8/2014 |
| TW | 201502129 | 1/2015 |
| WO | 01/39234 | 5/2001 |
| WO | 02/02714 | 1/2002 |
| WO | 02015654 | 2/2002 |
| WO | 03040257 | 5/2003 |
| WO | 03060956 | 7/2003 |
| WO | 2004093207 | 10/2004 |
| WO | 04107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | 2009050290 | 4/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |
| WO | 2011024977 | 3/2011 |
| WO | 2012/122605 | 9/2012 |

OTHER PUBLICATIONS

Lai, S. L. et al., "Iridium(III) bis[2-(20naphthyl)pyridine] (acetylacetonate)-based yellow and white organic light-emitting devices" Journal of Materials Chemistry, 2011, 21, pp. 4983-4988.
Adachi, Chihaya et al., "Organic Electroluminescent Device Having a Hole Conductor as an Emitting Layer," Appl. Phys. Lett., 55(15): 1489-1491 (1989).
Adachi, Chihaya et al., "Nearly 100% Internal Phosphorescence Efficiency in an Organic Light Emitting Device," J. Appl. Phys., 90(10): 5048-5051 (2001).
Adachi, Chihaya et al., "High-Efficiency Red Electrophosphorescence Devices," Appl. Phys. Lett., 78(11)1622-1624 (2001).
Aonuma, Masaki et al., "Material Design of Hole Transport Materials Capable of Thick-Film Formation in Organic Light Emitting Diodes," Appl. Phys. Lett., 90, Apr. 30, 2007, 183503-1-183503-3.
Baldo et al., Highly Efficient Phosphorescent Emission from Organic Electroluminescent Devices, Nature, vol. 395, 151-154, (1998).
Baldo et al., Very high-efficiency green organic light-emitting devices based on electrophosphorescence, Appl. Phys. Lett., vol. 75, No. 1, 4-6 (1999).
Gao, Zhiqiang et al., "Bright-Blue Electroluminescence From a Silyl-Substituted ter-(phenylene-vinylene) derivative," Appl. Phys. Lett., 74(6): 865-867 (1999).
Guo, Tzung-Fang et al., "Highly Efficient Electrophosphorescent Polymer Light-Emitting Devices," Organic Electronics, 1: 15-20 (2000).
Hamada, Yuji et al., "High Luminance in Organic Electroluminescent Devices with Bis(10-hydroxybenzo[h]quinolinato) beryllium as an Emitter," Chem. Lett., 905-906 (1993).
Holmes, R.J. et al., "Blue Organic Electrophosphorescence Using Exothermic Host-Guest Energy Transfer," Appl. Phys. Lett., 82(15):2422-2424 (2003).
Hu, Nan-Xing et al., "Novel High Tg Hole-Transport Molecules Based on Indolo[3,2-b]carbazoles for Organic Light-Emitting Devices," Synthetic Metals, 111-112:421-424 (2000).
Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Hung, L.S. et al., "Anode Modification in Organic Light-Emitting Diodes by Low-Frequency Plasma Polymerization of CHF3," Appl. Phys. Lett., 78(5):673-675 (2001).
Ikai, Masamichi et al., "Highly Efficient Phosphorescence From Organic Light-Emitting Devices with an Exciton-Block Layer," Appl. Phys. Lett., 79(2):156-158 (2001).
Ikeda, Hisao et al., "P-185 Low-Drive-Voltage OLEDs with a Buffer Layer Having Molybdenum Oxide," SID Symposium Digest, 37:923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1) 162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18 (21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).

(56) References Cited

OTHER PUBLICATIONS

Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota,Yasuhiko, "5,5'-Bis(dimesitylbory1)-2,2'-bithiophene and 5,5"-Bis (dimesitylboryl)-2,40 5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91: 209-215 (1997).
Shirota, Yasuhiko et al., "Starburst Molecules Based on pi-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes Containing N^C^N-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergard et al., "Langmuir-Blodgett Light-Emitting Diodes of Poly(3-Hexylthiophene) Electro-Optical Characteristics Related to Structure," Synthetic Metals, 88:171-177 (1997).
Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 16(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett., 69 (15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).
Extended European Search Report dated Jan. 9, 2018 for corresponding EP Patent Application No. 17193570.3.
Wenjing Xiong et al: "Dinuclear platinum complexes containing aryl-isoquinoline and oxadiazole-thiol with an efficiency of over 8.8%: in-depth investigation of the relationship between their molecular structure and near-infrared electroluminescent properties in PLEDs", Journal of Materials Chemistry C, vol. 4, No. 25, Jan. 1, 2016 (Jan. 1, 2016), pp. 6007-6015, XP055670739, GB ISSN: 2050-7526, DOI: 10.1039/C6TC00825A.
Communication pursuant to Article 94(3) EPC dated Feb. 26, 2020 for corresponding European Application No. 17193570.3.
Richard J. Lewis, Sr., "Hawley's Condensed Chemical Dictionary, 12th Edition", John Wiley & Sons, Inc., New York p. 796 (1993).
K. R. Justin Thomas et al., Efficient Red-Emitting Cyclometalated Iridium(III) Complexes Containing Lepidine-Based Ligands, Inorganic Chemistry, vol. 40, Issue 16, pp. 5677-5685.
Li Xiao-Na et al., Theoretical study on the structure and spectral properties of Ir complexes with quinoline derivatives and acetylacetone as ligands, Chemical Journal of Chinese Universities, vol. 29, full texts.
Office Action dated Oct. 14, 2020 in corresponding PRC (Chinese) Patent Application No. 201710908461.2.
Search Report dated Nov. 11, 2020 for Corresponding ROC (Taiwan) Patent Application No. 106134036.
Notice of Reasons for Rejection dated Mar. 16, 2021 in corresponding Japanese Patent Application No. JP 2017-187961.

* cited by examiner

ORGANIC ELECTROLUMINESCENT MATERIALS AND DEVICES

CROSS-REFERENCE TO RELATE APPLICATIONS

This application claims priority to U.S. Provisional application No. 62/403,424, filed Oct. 3, 2016, the disclosure of which is incorporated herein by reference.

FIELD

The present disclosure relates to compounds for use as phosphorescent emitters for organic electroluminescent devices, such as organic light emitting diodes (OLEDs). More specifically, the present disclosure relates to phosphorescent metal complexes containing ligands bearing either a naphthalene or other fused heterocycle moieties such as benzofuran and benzothiophene.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting diodes/devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" COLORS. In particular, these standards call for saturated red, green, and blue pixels. Alternatively, the OLED can be designed to emit white light. In conventional liquid crystal displays emission from a white backlight is filtered using absorption filters to produce red, green and blue emission. The same technique can also be used with OLEDs. The white OLED can be either a single EML device or a stack structure. Color may be measured using CIE coordinates, which are well known to the art.

One example of a green emissive molecule is tris(2-phenylpyridine) iridium, denoted Ir(ppy)$_3$, which has the following structure:

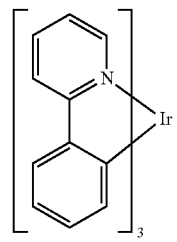

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule" and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY

According to an aspect of the present disclosure, a compound comprising a ligand $L_A$ of the Formula I:

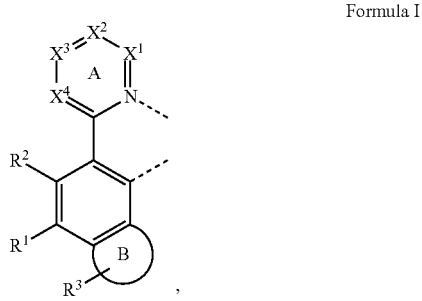

Formula I is disclosed, where Ring B represents a five- or six-membered aromatic ring; $R^3$ represents from none to the maximum possible number of substitutions;
$X^1$, $X^2$, $X^3$, and $X^4$ are each independently a CR or N;
wherein:
  (1) at least two adjacent ones of $X^1$, $X^2$, $X^3$, and $X^4$ are CR and fused into a five or six-membered aromatic ring, or
  (2) at least one of $X^1$, $X^2$, $X^3$, and $X^4$ is nitrogen, or
  (3) both (1) and (2) are true;
  wherein (a) $R^1$ is $CR^{11}R^{12}R^{13}$ or join with $R^2$ to form into a ring; or
  (b) $R^2$ is not hydrogen; or
  (c) both (a) and (b) are true;
  wherein R, $R^1$, $R^2$, $R^3$, $R^{11}$, $R^{12}$, and $R^{13}$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; any two substituents among R, $R^1$, $R^2$, $R^3$, $R^{11}$, $R^{12}$, and $R^{13}$ are optionally joined to form into a ring; $L_A$ is coordinated to a metal M; $L_A$ is optionally linked with other ligands to comprise a tridentate, tetradentate, pentadentate, or hexadentate ligand; and M is optionally coordinated to other ligands.

According to another aspect, a formulation comprising a compound comprising the ligand $L_A$ of Formula I is disclosed.

According to another aspect, an emissive region in an OLED is disclosed where the emissive region comprises a compound comprising the ligand $L_A$ of Formula I.

According to another aspect, a first device comprising a first OLED is disclosed where the first OLED comprises an anode, a cathode, and an organic layer, disposed between the anode and the cathode, where the organic layer comprises a compound comprising the ligand $L_A$ of Formula I.

According to another aspect, a consumer product comprising the first OLED is disclosed. The first OLED comprising an anode, a cathode, and an organic layer, disposed between the anode and the cathode, where the organic layer comprises a compound comprising the ligand $L_A$ of Formula I.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), are incorporated by reference in their entireties. Phosphorescence is described in more detail in U.S. Pat. No. 7,279,704 at cols. 5-6, which are incorporated by reference.

Figure 1:
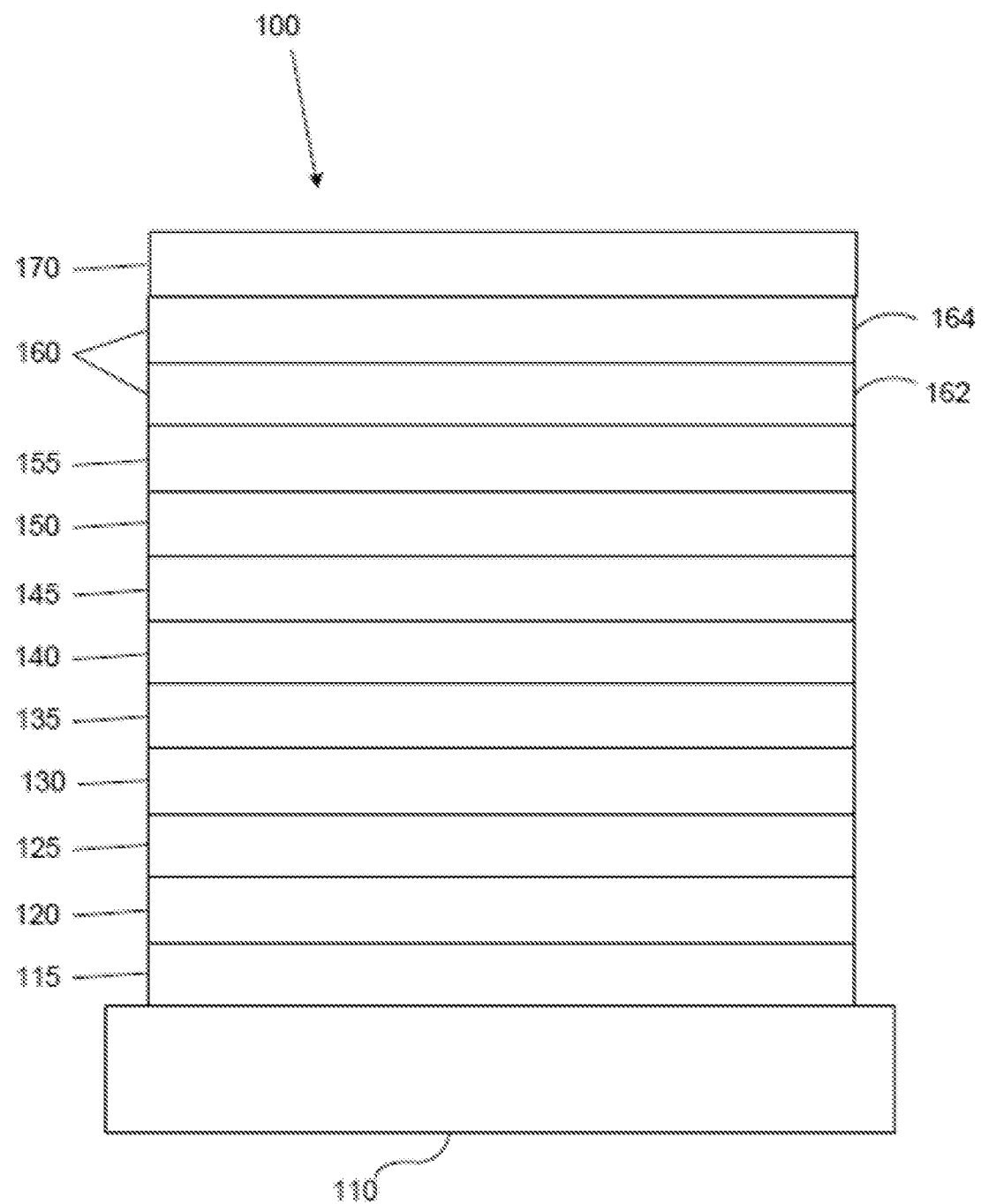
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
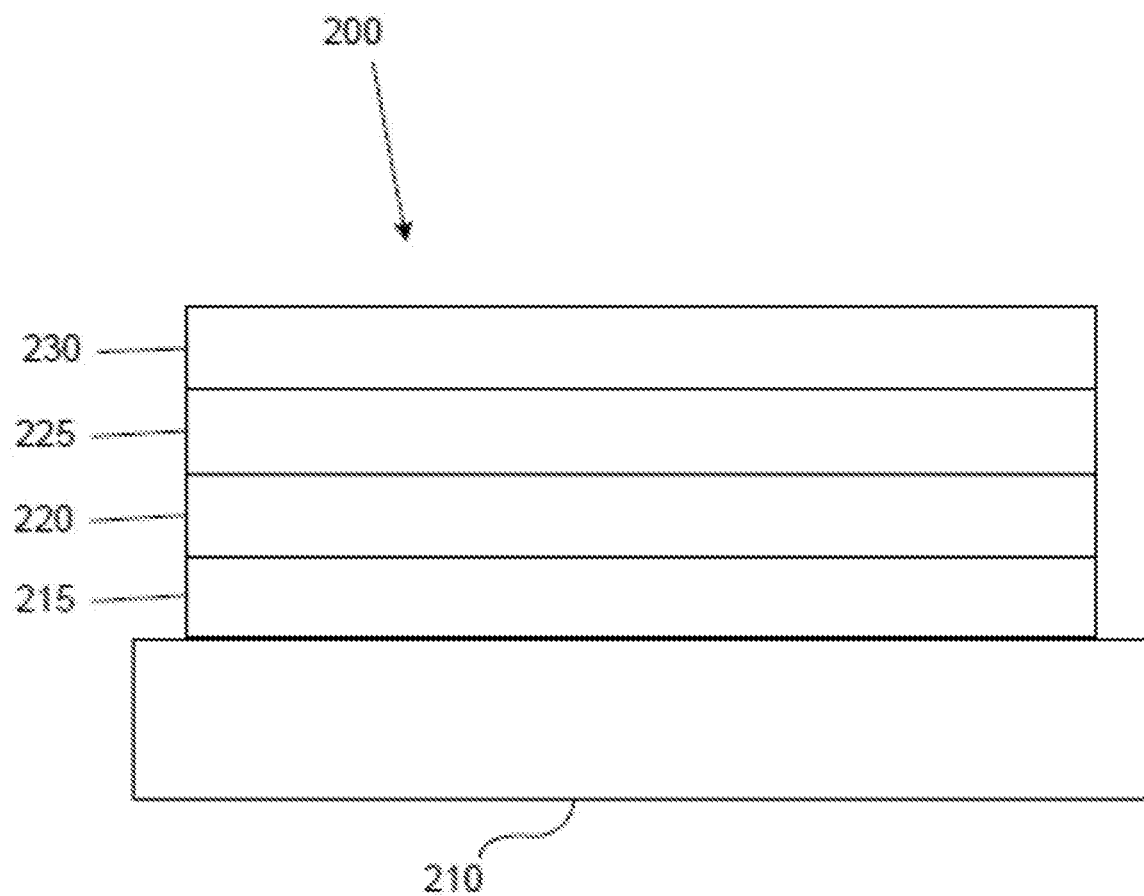
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJP. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the invention can be incorporated into a wide variety of consumer products that have one or more of the electronic component modules (or units) incorporated therein. A consumer product comprising an OLED that includes the compound of the present disclosure in the organic layer in the OLED is disclosed. Such consumer products would include any kind of products that include one or more light source(s) and/or one or more of some type of visual displays. Some examples of such consumer products include flat panel displays, computer monitors, medical monitors, televisions, billboards, lights for interior or exterior illumination and/or signaling, heads-up displays, fully or partially transparent displays, flexible displays, laser printers, telephones, cell phones, tablets, phablets, personal digital assistants (PDAs), wearable devices, laptop computers, digital cameras, camcorders, viewfinders, micro-displays (displays that are less than 2 inches diagonal), 3-D displays, virtual reality or augmented reality displays, vehicles, video walls comprising multiple displays tiled together, theater or stadium screen, and a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "halo," "halogen," or "halide" as used herein includes fluorine, chlorine, bromine, and iodine.

The term "alkyl" as used herein contemplates both straight and branched chain alkyl radicals. Preferred alkyl groups are those containing from one to fifteen carbon atoms and includes methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, and the like. Additionally, the alkyl group may be optionally substituted.

The term "cycloalkyl" as used herein contemplates cyclic alkyl radicals. Preferred cycloalkyl groups are those containing 3 to 10 ring carbon atoms and includes cyclopropyl, cyclopentyl, cyclohexyl, adamantyl, and the like. Additionally, the cycloalkyl group may be optionally substituted.

The term "alkenyl" as used herein contemplates both straight and branched chain alkene radicals. Preferred alkenyl groups are those containing two to fifteen carbon atoms. Additionally, the alkenyl group may be optionally substituted.

The term "alkynyl" as used herein contemplates both straight and branched chain alkyne radicals. Preferred alkynyl groups are those containing two to fifteen carbon atoms. Additionally, the alkynyl group may be optionally substituted.

The terms "aralkyl" or "arylalkyl" as used herein are used interchangeably and contemplate an alkyl group that has as a substituent an aromatic group. Additionally, the aralkyl group may be optionally substituted.

The term "heterocyclic group" as used herein contemplates aromatic and non-aromatic cyclic radicals. Heteroaromatic cyclic radicals also means heteroaryl. Preferred hetero-non-aromatic cyclic groups are those containing 3 to 7 ring atoms which includes at least one hetero atom, and includes cyclic amines such as morpholino, piperidino, pyrrolidino, and the like, and cyclic ethers, such as tetrahydrofuran, tetrahydropyran, and the like. Additionally, the heterocyclic group may be optionally substituted.

The term "aryl" or "aromatic group" as used herein contemplates single-ring groups and polycyclic ring systems. The polycyclic rings may have two or more rings in which two carbons are common to two adjoining rings (the rings are "fused") wherein at least one of the rings is aromatic, e.g., the other rings can be cycloalkyls, cycloalkenyls, aryl, heterocycles, and/or heteroaryls. Preferred aryl groups are those containing six to thirty carbon atoms, preferably six to twenty carbon atoms, more preferably six to twelve carbon atoms. Especially preferred is an aryl group having six carbons, ten carbons or twelve carbons. Suitable aryl groups include phenyl, biphenyl, triphenyl, triphenylene, tetraphenylene, naphthalene, anthracene, phenalene, phenanthrene, fluorene, pyrene, chrysene, perylene, and azulene, preferably phenyl, biphenyl, triphenyl, triphenylene, fluorene, and naphthalene. Additionally, the aryl group may be optionally substituted.

The term "heteroaryl" as used herein contemplates single-ring hetero-aromatic groups that may include from one to five heteroatoms. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group may be optionally substituted.

The alkyl, cycloalkyl, alkenyl, alkynyl, aralkyl, heterocyclic group, aryl, and heteroaryl may be unsubstituted or may be substituted with one or more substituents selected from the group consisting of deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

As used herein, "substituted" indicates that a substituent other than H is bonded to the relevant position, such as carbon. Thus, for example, where $R^1$ is mono-substituted, then one $R^1$ must be other than H. Similarly, where $R^1$ is di-substituted, then two of $R^1$ must be other than H. Similarly, where $R^1$ is unsubstituted, $R^1$ is hydrogen for all available positions.

The "aza" designation in the fragments described herein, i.e. aza-dibenzofuran, aza-dibenzothiophene, etc. means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

The present disclosure relates to novel ligands for metal complexes. These ligands include a naphthalene or other similar fused heterocycles. In addition, this fused unit includes a blocking side chain which is a tert-Butyl or a tert-Butyl derivative. The combination of these elements within the ligand allows to obtain only one isomer of the final cyclometallated complex. It also affords a better efficiency, a red shift in the color of the emission as well as an emission that is narrower.

The present disclosure relates to phosphorescent metal complexes containing ligands bearing either a naphthalene or other fused heterocycle moieties such as benzofuran and benzothiophene. These moieties are substituted with an aliphatic side chain on the phenyl which is linked to the Iridium atom in a way where it will block the configuration and prevent any ligation at an unwanted position. The side chain is a tert-Butyl or a derivative of tert-Butyl. In addition to afford a material with a much better purity, the addition of the tert-Butyl side chain allows better EQE (external quantum efficiency), better FWHM (Full width at half maximum) of the emission. The fused cycles at the bottom of the ligand lead to a red shift of the color of the emission while the side chain on these cycles lead to a blue shift.

According to an aspect of the present disclosure, a compound comprising a ligand $L_A$ of the Formula I:

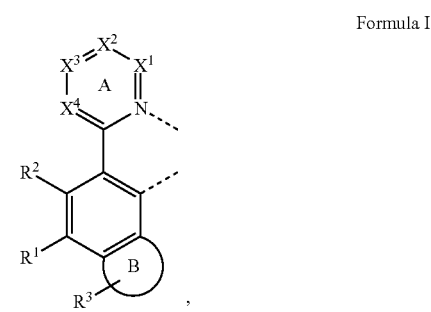

Formula I is disclosed, where Ring B represents a five- or six-membered aromatic ring; $R^3$ represents from none to the maximum possible number of substitutions;

$X^1$, $X^2$, $X^3$, and $X^4$ are each independently a CR or N; wherein:

(1) at least two adjacent ones of $X^1$, $X^2$, $X^3$, and $X^4$ are CR and fused into a five or six-membered aromatic ring, or (2) at least one of $X^1$, $X^2$, $X^3$, and $X^4$ is nitrogen, or (3) both (1) and (2) are true;

wherein (a) $R^1$ is $CR^{11}R^{12}R^{13}$ or join with $R^2$ to form into a ring; or (b) $R^2$ is not hydrogen; or (c) both (a) and (b) are true;

wherein R, $R^1$, $R^2$, $R^3$, $R^{11}$, $R^{12}$, and $R^{13}$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof;

any two substituents among R, $R^1$, $R^2$, $R^3$, $R^{11}$, $R^{12}$, and $R^{13}$ are optionally joined to form into a ring;

$L_A$ is coordinated to a metal M;

$L_A$ is optionally linked with other ligands to comprise a tridentate, tetradentate, pentadentate, or hexadentate ligand; and M is optionally coordinated to other ligands.

In some embodiments of the compound, M is selected from the group consisting of Ir, Rh, Re, Ru, Os, Pt, Au, and Cu. In some embodiments, M is Ir or Pt.

In some embodiments of the compound, at least one of $X^1$, $X^2$, $X^3$, and $X^4$ is nitrogen.

In some embodiments of the compound, $R^1$ is tert-butyl or substituted tert-butyl. In some embodiments of the compound, $R^1$ and $R^2$ form into an aromatic ring, which can be further substituted.

In some embodiments of the compound, Ring B is phenyl.

In some embodiments of the compound, the ligand $L_A$ is selected from the group consisting of:

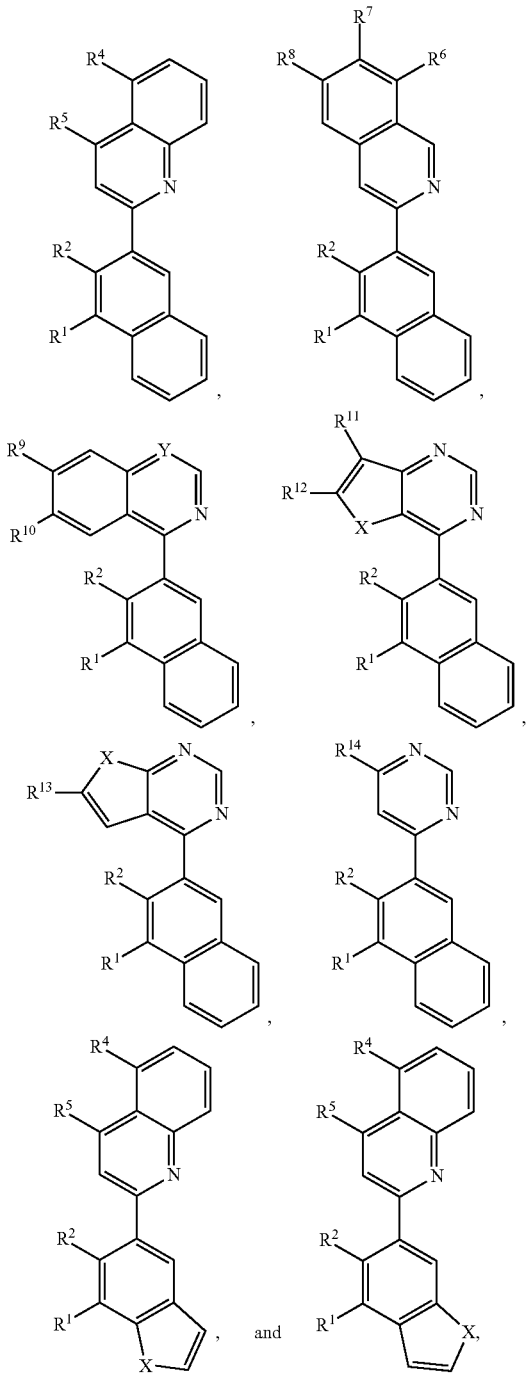

wherein $R^1$, $R^2$, $R^4$, $R^5$, $R^6$, $R^7$, $R^8$, $R^9$, $R^{10}$, $R^{11}$, $R^{12}$, $R^{13}$, and $R^{14}$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; wherein any two substituents are optionally joined to form into a ring.

In some embodiments of the compound, the ligand $L_A$ is selected from the group consisting of $L_{A1}$ through $L_{A260}$ which are based on a structure of Formula II,

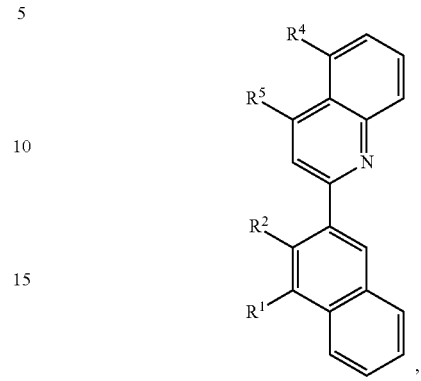

in which $R^1$, $R^2$, $R^4$, and $R^5$ are defined as provided below:

| Ligand | $R^1$ | $R^2$ | $R^4$ | $R^5$ | Ligand | $R^1$ | $R^2$ | $R^4$ | $R^5$ |
|---|---|---|---|---|---|---|---|---|---|
| $L_{A1}$ | $R_{B6}$ | H | H | H | $L_{A131}$ | H | $R_{B6}$ | H | H |
| $L_{A2}$ | $R_{B6}$ | H | $R_{B1}$ | H | $L_{A132}$ | H | $R_{B6}$ | $R_{B1}$ | H |
| $L_{A3}$ | $R_{B6}$ | H | $R_{B3}$ | H | $L_{A133}$ | H | $R_{B6}$ | $R_{B3}$ | H |
| $L_{A4}$ | $R_{B6}$ | H | $R_{B4}$ | H | $L_{A134}$ | H | $R_{B6}$ | $R_{B4}$ | H |
| $L_{A5}$ | $R_{B6}$ | H | $R_{B7}$ | H | $L_{A135}$ | H | $R_{B6}$ | $R_{B7}$ | H |
| $L_{A6}$ | $R_{B6}$ | H | $R_{B10}$ | H | $L_{A136}$ | H | $R_{B6}$ | $R_{B10}$ | H |
| $L_{A7}$ | $R_{B6}$ | H | $R_{43}$ | H | $L_{A137}$ | H | $R_{B6}$ | $R_{43}$ | H |
| $L_{A8}$ | $R_{B6}$ | H | $R_{434}$ | H | $L_{A138}$ | H | $R_{B6}$ | $R_{434}$ | H |
| $L_{A9}$ | $R_{B6}$ | H | H | $R_{B1}$ | $L_{A139}$ | H | $R_{B6}$ | H | $R_{B1}$ |
| $L_{A10}$ | $R_{B6}$ | H | H | $R_{B2}$ | $L_{A140}$ | H | $R_{B6}$ | H | $R_{B2}$ |
| $L_{A11}$ | $R_{B6}$ | H | H | $R_{B3}$ | $L_{A141}$ | H | $R_{B6}$ | H | $R_{B3}$ |
| $L_{A12}$ | $R_{B6}$ | H | H | $R_{B4}$ | $L_{A142}$ | H | $R_{B6}$ | H | $R_{B4}$ |
| $L_{A13}$ | $R_{B6}$ | H | H | $R_{B7}$ | $L_{A143}$ | H | $R_{B6}$ | H | $R_{B7}$ |
| $L_{A14}$ | $R_{B6}$ | H | H | $R_{B10}$ | $L_{A144}$ | H | $R_{B6}$ | H | $R_{B10}$ |
| $L_{A15}$ | $R_{B6}$ | H | H | $R_{43}$ | $L_{A145}$ | H | $R_{B6}$ | H | $R_{43}$ |
| $L_{A16}$ | $R_{B6}$ | H | H | $R_{434}$ | $L_{A146}$ | H | $R_{B6}$ | H | $R_{434}$ |
| $L_{A17}$ | $R_{B6}$ | H | $R_{B1}$ | $R_{B1}$ | $L_{A147}$ | H | $R_{B6}$ | $R_{B1}$ | $R_{B1}$ |
| $L_{A18}$ | $R_{B6}$ | H | $R_{B3}$ | $R_{B3}$ | $L_{A148}$ | H | $R_{B6}$ | $R_{B3}$ | $R_{B3}$ |
| $L_{A19}$ | $R_{B6}$ | H | $R_{B4}$ | $R_{B4}$ | $L_{A149}$ | H | $R_{B6}$ | $R_{B4}$ | $R_{B4}$ |
| $L_{A20}$ | $R_{B6}$ | H | $R_{B7}$ | $R_{B7}$ | $L_{A150}$ | H | $R_{B6}$ | $R_{B7}$ | $R_{B7}$ |
| $L_{A21}$ | $R_{B6}$ | H | $R_{B10}$ | $R_{B10}$ | $L_{A151}$ | H | $R_{B6}$ | $R_{B10}$ | $R_{B10}$ |
| $L_{A22}$ | $R_{B6}$ | H | $R_{43}$ | $R_{43}$ | $L_{A152}$ | H | $R_{B6}$ | $R_{43}$ | $R_{43}$ |
| $L_{A23}$ | $R_{B6}$ | H | $R_{434}$ | $R_{434}$ | $L_{A153}$ | H | $R_{B6}$ | $R_{434}$ | $R_{434}$ |
| $L_{A24}$ | $R_{B6}$ | H | $R_{B1}$ | $R_{B3}$ | $L_{A154}$ | H | $R_{B6}$ | $R_{B1}$ | $R_{B3}$ |
| $L_{A25}$ | $R_{B6}$ | H | $R_{B1}$ | $R_{B4}$ | $L_{A155}$ | H | $R_{B6}$ | $R_{B1}$ | $R_{B4}$ |
| $L_{A26}$ | $R_{B6}$ | H | $R_{B1}$ | $R_{B7}$ | $L_{A156}$ | H | $R_{B6}$ | $R_{B1}$ | $R_{B7}$ |
| $L_{A27}$ | $R_{B6}$ | H | $R_{B1}$ | $R_{B10}$ | $L_{A157}$ | H | $R_{B6}$ | $R_{B1}$ | $R_{B10}$ |
| $L_{A28}$ | $R_{B6}$ | H | $R_{B1}$ | $R_{43}$ | $L_{A158}$ | H | $R_{B6}$ | $R_{B1}$ | $R_{43}$ |
| $L_{A29}$ | $R_{B6}$ | H | $R_{B1}$ | $R_{434}$ | $L_{A159}$ | H | $R_{B6}$ | $R_{B1}$ | $R_{434}$ |
| $L_{A30}$ | $R_{B6}$ | H | $R_{B3}$ | $R_{B1}$ | $L_{A160}$ | H | $R_{B6}$ | $R_{B3}$ | $R_{B1}$ |
| $L_{A31}$ | $R_{B6}$ | H | $R_{B3}$ | $R_{B4}$ | $L_{A161}$ | H | $R_{B6}$ | $R_{B3}$ | $R_{B4}$ |
| $L_{A32}$ | $R_{B6}$ | H | $R_{B3}$ | $R_{B7}$ | $L_{A162}$ | H | $R_{B6}$ | $R_{B3}$ | $R_{B7}$ |
| $L_{A33}$ | $R_{B6}$ | H | $R_{B3}$ | $R_{B10}$ | $L_{A163}$ | H | $R_{B6}$ | $R_{B3}$ | $R_{B10}$ |
| $L_{A34}$ | $R_{B6}$ | H | $R_{B3}$ | $R_{43}$ | $L_{A164}$ | H | $R_{B6}$ | $R_{B3}$ | $R_{43}$ |
| $L_{A35}$ | $R_{B6}$ | H | $R_{B3}$ | $R_{434}$ | $L_{A165}$ | H | $R_{B6}$ | $R_{B3}$ | $R_{434}$ |
| $L_{A36}$ | $R_{B6}$ | H | $R_{B4}$ | $R_{B1}$ | $L_{A166}$ | H | $R_{B6}$ | $R_{B4}$ | $R_{B1}$ |
| $L_{A37}$ | $R_{B6}$ | H | $R_{B4}$ | $R_{B3}$ | $L_{A167}$ | H | $R_{B6}$ | $R_{B4}$ | $R_{B3}$ |
| $L_{A38}$ | $R_{B6}$ | H | $R_{B4}$ | $R_{B7}$ | $L_{A168}$ | H | $R_{B6}$ | $R_{B4}$ | $R_{B7}$ |
| $L_{A39}$ | $R_{B6}$ | H | $R_{B4}$ | $R_{B10}$ | $L_{A169}$ | H | $R_{B6}$ | $R_{B4}$ | $R_{B10}$ |
| $L_{A40}$ | $R_{B6}$ | H | $R_{B4}$ | $R_{43}$ | $L_{A170}$ | H | $R_{B6}$ | $R_{B4}$ | $R_{43}$ |
| $L_{A41}$ | $R_{B6}$ | H | $R_{B4}$ | $R_{434}$ | $L_{A171}$ | H | $R_{B6}$ | $R_{B4}$ | $R_{434}$ |
| $L_{A42}$ | $R_{B6}$ | H | $R_{B7}$ | $R_{B1}$ | $L_{A172}$ | H | $R_{B6}$ | $R_{B7}$ | $R_{B1}$ |
| $L_{A43}$ | $R_{B6}$ | H | $R_{B7}$ | $R_{B3}$ | $L_{A173}$ | H | $R_{B6}$ | $R_{B7}$ | $R_{B3}$ |
| $L_{A44}$ | $R_{B6}$ | H | $R_{B7}$ | $R_{B4}$ | $L_{A174}$ | H | $R_{B6}$ | $R_{B7}$ | $R_{B4}$ |
| $L_{A45}$ | $R_{B6}$ | H | $R_{B7}$ | $R_{B10}$ | $L_{A175}$ | H | $R_{B6}$ | $R_{B7}$ | $R_{B10}$ |
| $L_{A46}$ | $R_{B6}$ | H | $R_{B7}$ | $R_{43}$ | $L_{A176}$ | H | $R_{B6}$ | $R_{B7}$ | $R_{43}$ |
| $L_{A47}$ | $R_{B6}$ | H | $R_{B7}$ | $R_{434}$ | $L_{A177}$ | H | $R_{B6}$ | $R_{B7}$ | $R_{434}$ |
| $L_{A48}$ | $R_{B6}$ | H | $R_{B10}$ | $R_{B1}$ | $L_{A178}$ | H | $R_{B6}$ | $R_{B10}$ | $R_{B1}$ |
| $L_{A49}$ | $R_{B6}$ | H | $R_{B10}$ | $R_{B3}$ | $L_{A179}$ | H | $R_{B6}$ | $R_{B10}$ | $R_{B3}$ |
| $L_{A50}$ | $R_{B6}$ | H | $R_{B10}$ | $R_{B4}$ | $L_{A180}$ | H | $R_{B6}$ | $R_{B10}$ | $R_{B4}$ |
| $L_{A51}$ | $R_{B6}$ | H | $R_{B10}$ | $R_{B7}$ | $L_{A181}$ | H | $R_{B6}$ | $R_{B10}$ | $R_{B7}$ |
| $L_{A52}$ | $R_{B6}$ | H | $R_{B10}$ | $R_{43}$ | $L_{A182}$ | H | $R_{B6}$ | $R_{B10}$ | $R_{43}$ |

| Ligand | R¹ | R² | R⁴ | R⁵ | Ligand | R¹ | R² | R⁴ | R⁵ |
|---|---|---|---|---|---|---|---|---|---|
| $L_{A53}$ | $R_{B6}$ | H | $R_{B10}$ | $R_{434}$ | $L_{A183}$ | H | $R_{B6}$ | $R_{B10}$ | $R_{434}$ |
| $L_{A54}$ | $R_{B6}$ | H | $R_{43}$ | $R_{B1}$ | $L_{A184}$ | H | $R_{B6}$ | $R_{43}$ | $R_{B1}$ |
| $L_{A55}$ | $R_{B6}$ | H | $R_{43}$ | $R_{B3}$ | $L_{A185}$ | H | $R_{B6}$ | $R_{43}$ | $R_{B3}$ |
| $L_{A56}$ | $R_{B6}$ | H | $R_{43}$ | $R_{B4}$ | $L_{A186}$ | H | $R_{B6}$ | $R_{43}$ | $R_{B4}$ |
| $L_{A57}$ | $R_{B6}$ | H | $R_{43}$ | $R_{B7}$ | $L_{A187}$ | H | $R_{B6}$ | $R_{43}$ | $R_{B7}$ |
| $L_{A58}$ | $R_{B6}$ | H | $R_{43}$ | $R_{B10}$ | $L_{A188}$ | H | $R_{B6}$ | $R_{43}$ | $R_{B10}$ |
| $L_{A59}$ | $R_{B6}$ | H | $R_{43}$ | $R_{434}$ | $L_{A189}$ | H | $R_{B6}$ | $R_{43}$ | $R_{434}$ |
| $L_{A60}$ | $R_{B6}$ | H | $R_{434}$ | $R_{B1}$ | $L_{A190}$ | H | $R_{B6}$ | $R_{434}$ | $R_{B1}$ |
| $L_{A61}$ | $R_{B6}$ | H | $R_{434}$ | $R_{B3}$ | $L_{A191}$ | H | $R_{B6}$ | $R_{434}$ | $R_{B3}$ |
| $L_{A62}$ | $R_{B6}$ | H | $R_{434}$ | $R_{B4}$ | $L_{A192}$ | H | $R_{B6}$ | $R_{434}$ | $R_{B4}$ |
| $L_{A63}$ | $R_{B6}$ | H | $R_{434}$ | $R_{B7}$ | $L_{A193}$ | H | $R_{B6}$ | $R_{434}$ | $R_{B7}$ |
| $L_{A64}$ | $R_{B6}$ | H | $R_{434}$ | $R_{B10}$ | $L_{A194}$ | H | $R_{B6}$ | $R_{434}$ | $R_{B10}$ |
| $L_{A65}$ | $R_{B6}$ | H | $R_{434}$ | $R_{43}$ | $L_{A195}$ | H | $R_{B6}$ | $R_{434}$ | $R_{43}$ |
| $L_{A66}$ | $R_{B8}$ | H | H | H | $L_{A196}$ | H | $R_{B8}$ | H | H |
| $L_{A67}$ | $R_{B8}$ | H | $R_{B1}$ | H | $L_{A197}$ | H | $R_{B8}$ | $R_{B1}$ | H |
| $L_{A68}$ | $R_{B8}$ | H | $R_{B3}$ | H | $L_{A198}$ | H | $R_{B8}$ | $R_{B3}$ | H |
| $L_{A69}$ | $R_{B8}$ | H | $R_{B4}$ | H | $L_{A199}$ | H | $R_{B8}$ | $R_{B4}$ | H |
| $L_{A70}$ | $R_{B8}$ | H | $R_{B7}$ | H | $L_{A200}$ | H | $R_{B8}$ | $R_{B7}$ | H |
| $L_{A71}$ | $R_{B8}$ | H | $R_{B10}$ | H | $L_{A201}$ | H | $R_{B8}$ | $R_{B10}$ | H |
| $L_{A72}$ | $R_{B8}$ | H | $R_{43}$ | H | $L_{A202}$ | H | $R_{B8}$ | $R_{43}$ | H |
| $L_{A73}$ | $R_{B8}$ | H | $R_{434}$ | H | $L_{A203}$ | H | $R_{B8}$ | $R_{434}$ | H |
| $L_{A74}$ | $R_{B8}$ | H | H | $R_{B1}$ | $L_{A204}$ | H | $R_{B8}$ | H | $R_{B1}$ |
| $L_{A75}$ | $R_{B8}$ | H | H | $R_{B2}$ | $L_{A205}$ | H | $R_{B8}$ | H | $R_{B2}$ |
| $L_{A76}$ | $R_{B8}$ | H | H | $R_{B3}$ | $L_{A206}$ | H | $R_{B8}$ | H | $R_{B3}$ |
| $L_{A77}$ | $R_{B8}$ | H | H | $R_{B4}$ | $L_{A207}$ | H | $R_{B8}$ | H | $R_{B4}$ |
| $L_{A78}$ | $R_{B8}$ | H | H | $R_{B7}$ | $L_{A208}$ | H | $R_{B8}$ | H | $R_{B7}$ |
| $L_{A79}$ | $R_{B8}$ | H | H | $R_{B10}$ | $L_{A209}$ | H | $R_{B8}$ | H | $R_{B10}$ |
| $L_{A80}$ | $R_{B8}$ | H | H | $R_{43}$ | $L_{A210}$ | H | $R_{B8}$ | H | $R_{43}$ |
| $L_{A81}$ | $R_{B8}$ | H | H | $R_{434}$ | $L_{A211}$ | H | $R_{B8}$ | H | $R_{434}$ |
| $L_{A82}$ | $R_{B8}$ | H | $R_{B1}$ | $R_{B1}$ | $L_{A212}$ | H | $R_{B8}$ | $R_{B1}$ | $R_{B1}$ |
| $L_{A83}$ | $R_{B8}$ | H | $R_{B3}$ | $R_{B3}$ | $L_{A213}$ | H | $R_{B8}$ | $R_{B3}$ | $R_{B3}$ |
| $L_{A84}$ | $R_{B8}$ | H | $R_{B4}$ | $R_{B4}$ | $L_{A214}$ | H | $R_{B8}$ | $R_{B4}$ | $R_{B4}$ |
| $L_{A85}$ | $R_{B8}$ | H | $R_{B7}$ | $R_{B7}$ | $L_{A215}$ | H | $R_{B8}$ | $R_{B7}$ | $R_{B7}$ |
| $L_{A86}$ | $R_{B8}$ | H | $R_{B10}$ | $R_{B10}$ | $L_{A216}$ | H | $R_{B8}$ | $R_{B10}$ | $R_{B10}$ |
| $L_{A87}$ | $R_{B8}$ | H | $R_{43}$ | $R_{43}$ | $L_{A217}$ | H | $R_{B8}$ | $R_{43}$ | $R_{43}$ |
| $L_{A88}$ | $R_{B8}$ | H | $R_{434}$ | $R_{434}$ | $L_{A218}$ | H | $R_{B8}$ | $R_{434}$ | $R_{434}$ |
| $L_{A89}$ | $R_{B8}$ | H | $R_{B1}$ | $R_{B3}$ | $L_{A219}$ | H | $R_{B8}$ | $R_{B1}$ | $R_{B3}$ |
| $L_{A90}$ | $R_{B8}$ | H | $R_{B1}$ | $R_{B4}$ | $L_{A220}$ | H | $R_{B8}$ | $R_{B1}$ | $R_{B4}$ |
| $L_{A91}$ | $R_{B8}$ | H | $R_{B1}$ | $R_{B7}$ | $L_{A221}$ | H | $R_{B8}$ | $R_{B1}$ | $R_{B7}$ |
| $L_{A92}$ | $R_{B8}$ | H | $R_{B1}$ | $R_{B10}$ | $L_{A222}$ | H | $R_{B8}$ | $R_{B1}$ | $R_{B10}$ |
| $L_{A93}$ | $R_{B8}$ | H | $R_{B1}$ | $R_{43}$ | $L_{A223}$ | H | $R_{B8}$ | $R_{B1}$ | $R_{43}$ |
| $L_{A94}$ | $R_{B8}$ | H | $R_{B1}$ | $R_{434}$ | $L_{A224}$ | H | $R_{B8}$ | $R_{B1}$ | $R_{434}$ |
| $L_{A95}$ | $R_{B8}$ | H | $R_{B3}$ | $R_{B1}$ | $L_{A225}$ | H | $R_{B8}$ | $R_{B3}$ | $R_{B1}$ |
| $L_{A96}$ | $R_{B8}$ | H | $R_{B3}$ | $R_{B4}$ | $L_{A226}$ | H | $R_{B8}$ | $R_{B3}$ | $R_{B4}$ |
| $L_{A97}$ | $R_{B8}$ | H | $R_{B3}$ | $R_{B7}$ | $L_{A227}$ | H | $R_{B8}$ | $R_{B3}$ | $R_{B7}$ |
| $L_{A98}$ | $R_{B8}$ | H | $R_{B3}$ | $R_{B10}$ | $L_{A228}$ | H | $R_{B8}$ | $R_{B3}$ | $R_{B10}$ |
| $L_{A99}$ | $R_{B8}$ | H | $R_{B3}$ | $R_{43}$ | $L_{A229}$ | H | $R_{B8}$ | $R_{B3}$ | $R_{43}$ |
| $L_{A100}$ | $R_{B8}$ | H | $R_{B3}$ | $R_{434}$ | $L_{A230}$ | H | $R_{B8}$ | $R_{B3}$ | $R_{434}$ |
| $L_{A101}$ | $R_{B8}$ | H | $R_{B4}$ | $R_{B1}$ | $L_{A231}$ | H | $R_{B8}$ | $R_{B4}$ | $R_{B1}$ |
| $L_{A102}$ | $R_{B8}$ | H | $R_{B4}$ | $R_{B3}$ | $L_{A232}$ | H | $R_{B8}$ | $R_{B4}$ | $R_{B3}$ |
| $L_{A103}$ | $R_{B8}$ | H | $R_{B4}$ | $R_{B7}$ | $L_{A233}$ | H | $R_{B8}$ | $R_{B4}$ | $R_{B7}$ |
| $L_{A104}$ | $R_{B8}$ | H | $R_{B4}$ | $R_{B10}$ | $L_{A234}$ | H | $R_{B8}$ | $R_{B4}$ | $R_{B10}$ |
| $L_{A105}$ | $R_{B8}$ | H | $R_{B4}$ | $R_{43}$ | $L_{A235}$ | H | $R_{B8}$ | $R_{B4}$ | $R_{43}$ |
| $L_{A106}$ | $R_{B8}$ | H | $R_{B4}$ | $R_{434}$ | $L_{A236}$ | H | $R_{B8}$ | $R_{B4}$ | $R_{434}$ |
| $L_{A107}$ | $R_{B8}$ | H | $R_{B7}$ | $R_{B1}$ | $L_{A237}$ | H | $R_{B8}$ | $R_{B7}$ | $R_{B1}$ |
| $L_{A108}$ | $R_{B8}$ | H | $R_{B7}$ | $R_{B3}$ | $L_{A238}$ | H | $R_{B8}$ | $R_{B7}$ | $R_{B3}$ |
| $L_{A109}$ | $R_{B8}$ | H | $R_{B7}$ | $R_{B4}$ | $L_{A239}$ | H | $R_{B8}$ | $R_{B7}$ | $R_{B4}$ |
| $L_{A110}$ | $R_{B8}$ | H | $R_{B7}$ | $R_{B10}$ | $L_{A240}$ | H | $R_{B8}$ | $R_{B7}$ | $R_{B10}$ |
| $L_{A111}$ | $R_{B8}$ | H | $R_{B7}$ | $R_{43}$ | $L_{A241}$ | H | $R_{B8}$ | $R_{B7}$ | $R_{43}$ |
| $L_{A112}$ | $R_{B8}$ | H | $R_{B7}$ | $R_{434}$ | $L_{A242}$ | H | $R_{B8}$ | $R_{B7}$ | $R_{434}$ |
| $L_{A113}$ | $R_{B8}$ | H | $R_{B10}$ | $R_{B1}$ | $L_{A243}$ | H | $R_{B8}$ | $R_{B10}$ | $R_{B1}$ |
| $L_{A114}$ | $R_{B8}$ | H | $R_{B10}$ | $R_{B3}$ | $L_{A244}$ | H | $R_{B8}$ | $R_{B10}$ | $R_{B3}$ |
| $L_{A115}$ | $R_{B8}$ | H | $R_{B10}$ | $R_{B4}$ | $L_{A245}$ | H | $R_{B8}$ | $R_{B10}$ | $R_{B4}$ |
| $L_{A116}$ | $R_{B8}$ | H | $R_{B10}$ | $R_{B7}$ | $L_{A246}$ | H | $R_{B8}$ | $R_{B10}$ | $R_{B7}$ |
| $L_{A117}$ | $R_{B8}$ | H | $R_{B10}$ | $R_{43}$ | $L_{A247}$ | H | $R_{B8}$ | $R_{B10}$ | $R_{43}$ |
| $L_{A118}$ | $R_{B8}$ | H | $R_{B10}$ | $R_{434}$ | $L_{A248}$ | H | $R_{B8}$ | $R_{B10}$ | $R_{434}$ |
| $L_{A119}$ | $R_{B8}$ | H | $R_{43}$ | $R_{B1}$ | $L_{A249}$ | H | $R_{B8}$ | $R_{43}$ | $R_{B1}$ |
| $L_{A120}$ | $R_{B8}$ | H | $R_{43}$ | $R_{B3}$ | $L_{A250}$ | H | $R_{B8}$ | $R_{43}$ | $R_{B3}$ |
| $L_{A121}$ | $R_{B8}$ | H | $R_{43}$ | $R_{B4}$ | $L_{A251}$ | H | $R_{B8}$ | $R_{43}$ | $R_{B4}$ |
| $L_{A122}$ | $R_{B8}$ | H | $R_{43}$ | $R_{B7}$ | $L_{A252}$ | H | $R_{B8}$ | $R_{43}$ | $R_{B7}$ |
| $L_{A123}$ | $R_{B8}$ | H | $R_{43}$ | $R_{B10}$ | $L_{A253}$ | H | $R_{B8}$ | $R_{43}$ | $R_{B10}$ |
| $L_{A124}$ | $R_{B8}$ | H | $R_{43}$ | $R_{434}$ | $L_{A254}$ | H | $R_{B8}$ | $R_{43}$ | $R_{434}$ |
| $L_{A125}$ | $R_{B8}$ | H | $R_{434}$ | $R_{B1}$ | $L_{A255}$ | H | $R_{B8}$ | $R_{434}$ | $R_{B1}$ |
| $L_{A126}$ | $R_{B8}$ | H | $R_{434}$ | $R_{B3}$ | $L_{A256}$ | H | $R_{B8}$ | $R_{434}$ | $R_{B3}$ |
| $L_{A127}$ | $R_{B8}$ | H | $R_{434}$ | $R_{B4}$ | $L_{A257}$ | H | $R_{B8}$ | $R_{434}$ | $R_{B4}$ |
| $L_{A128}$ | $R_{B8}$ | H | $R_{434}$ | $R_{B7}$ | $L_{A258}$ | H | $R_{B8}$ | $R_{434}$ | $R_{B7}$ |
| $L_{A129}$ | $R_{B8}$ | H | $R_{434}$ | $R_{B10}$ | $L_{A259}$ | H | $R_{B8}$ | $R_{434}$ | $R_{B10}$ |
| $L_{A130}$ | $R_{B8}$ | H | $R_{434}$ | $R_{43}$ | $L_{A260}$ | H | $R_{B8}$ | $R_{434}$ | $R_{43}$, | wherein $L_{A261}$ through $L_{A520}$ that are based on a structure of Formula III,

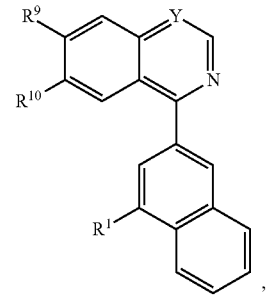

in which $R^1$, $R^9$, $R^{10}$, and Y are defined as provided below:

| Ligand | R¹ | R⁹ | R¹⁰ | Y | Ligand | R¹ | R⁹ | R¹⁰ | Y |
|---|---|---|---|---|---|---|---|---|---|
| $L_{A261}$ | $R_{B6}$ | H | H | C | $L_{A391}$ | $R_{B6}$ | H | H | N |
| $L_{A262}$ | $R_{B6}$ | $R_{B1}$ | H | C | $L_{A392}$ | $R_{B6}$ | $R_{B1}$ | H | N |
| $L_{A263}$ | $R_{B6}$ | $R_{B3}$ | H | C | $L_{A393}$ | $R_{B6}$ | $R_{B3}$ | H | N |
| $L_{A264}$ | $R_{B6}$ | $R_{B4}$ | H | C | $L_{A394}$ | $R_{B6}$ | $R_{B4}$ | H | N |
| $L_{A265}$ | $R_{B6}$ | $R_{B7}$ | H | C | $L_{A395}$ | $R_{B6}$ | $R_{B7}$ | H | N |
| $L_{A266}$ | $R_{B6}$ | $R_{B10}$ | H | C | $L_{A396}$ | $R_{B6}$ | $R_{B10}$ | H | N |
| $L_{A267}$ | $R_{B6}$ | $R_{43}$ | H | C | $L_{A397}$ | $R_{B6}$ | $R_{43}$ | H | N |
| $L_{A268}$ | $R_{B6}$ | $R_{434}$ | H | C | $L_{A398}$ | $R_{B6}$ | $R_{434}$ | H | N |
| $L_{A269}$ | $R_{B6}$ | H | $R_{B1}$ | C | $L_{A399}$ | $R_{B6}$ | H | $R_{B1}$ | N |
| $L_{A270}$ | $R_{B6}$ | H | $R_{B2}$ | C | $L_{A400}$ | $R_{B6}$ | H | $R_{B2}$ | N |
| $L_{A271}$ | $R_{B6}$ | H | $R_{B3}$ | C | $L_{A401}$ | $R_{B6}$ | H | $R_{B3}$ | N |
| $L_{A272}$ | $R_{B6}$ | H | $R_{B4}$ | C | $L_{A402}$ | $R_{B6}$ | H | $R_{B4}$ | N |
| $L_{A273}$ | $R_{B6}$ | H | $R_{B7}$ | C | $L_{A403}$ | $R_{B6}$ | H | $R_{B7}$ | N |
| $L_{A274}$ | $R_{B6}$ | H | $R_{B10}$ | C | $L_{A404}$ | $R_{B6}$ | H | $R_{B10}$ | N |
| $L_{A275}$ | $R_{B6}$ | H | $R_{43}$ | C | $L_{A405}$ | $R_{B6}$ | H | $R_{43}$ | N |
| $L_{A276}$ | $R_{B6}$ | H | $R_{434}$ | C | $L_{A406}$ | $R_{B6}$ | H | $R_{434}$ | N |
| $L_{A277}$ | $R_{B6}$ | $R_{B1}$ | $R_{B1}$ | C | $L_{A407}$ | $R_{B6}$ | $R_{B1}$ | $R_{B1}$ | N |
| $L_{A278}$ | $R_{B6}$ | $R_{B3}$ | $R_{B3}$ | C | $L_{A408}$ | $R_{B6}$ | $R_{B3}$ | $R_{B3}$ | N |
| $L_{A279}$ | $R_{B6}$ | $R_{B4}$ | $R_{B4}$ | C | $L_{A409}$ | $R_{B6}$ | $R_{B4}$ | $R_{B4}$ | N |
| $L_{A280}$ | $R_{B6}$ | $R_{B7}$ | $R_{B7}$ | C | $L_{A410}$ | $R_{B6}$ | $R_{B7}$ | $R_{B7}$ | N |
| $L_{A281}$ | $R_{B6}$ | $R_{B10}$ | $R_{B10}$ | C | $L_{A411}$ | $R_{B6}$ | $R_{B10}$ | $R_{B10}$ | N |
| $L_{A282}$ | $R_{B6}$ | $R_{43}$ | $R_{43}$ | C | $L_{A412}$ | $R_{B6}$ | $R_{43}$ | $R_{43}$ | N |
| $L_{A283}$ | $R_{B6}$ | $R_{434}$ | $R_{434}$ | C | $L_{A413}$ | $R_{B6}$ | $R_{434}$ | $R_{434}$ | N |
| $L_{A284}$ | $R_{B6}$ | $R_{B1}$ | $R_{B3}$ | C | $L_{A414}$ | $R_{B6}$ | $R_{B1}$ | $R_{B3}$ | N |
| $L_{A285}$ | $R_{B6}$ | $R_{B1}$ | $R_{B4}$ | C | $L_{A415}$ | $R_{B6}$ | $R_{B1}$ | $R_{B4}$ | N |
| $L_{A286}$ | $R_{B6}$ | $R_{B1}$ | $R_{B7}$ | C | $L_{A416}$ | $R_{B6}$ | $R_{B1}$ | $R_{B7}$ | N |
| $L_{A287}$ | $R_{B6}$ | $R_{B1}$ | $R_{B10}$ | C | $L_{A417}$ | $R_{B6}$ | $R_{B1}$ | $R_{B10}$ | N |
| $L_{A288}$ | $R_{B6}$ | $R_{B1}$ | $R_{43}$ | C | $L_{A418}$ | $R_{B6}$ | $R_{B1}$ | $R_{43}$ | N |
| $L_{A289}$ | $R_{B6}$ | $R_{B1}$ | $R_{434}$ | C | $L_{A419}$ | $R_{B6}$ | $R_{B1}$ | $R_{434}$ | N |
| $L_{A290}$ | $R_{B6}$ | $R_{B3}$ | $R_{B1}$ | C | $L_{A420}$ | $R_{B6}$ | $R_{B3}$ | $R_{B1}$ | N |
| $L_{A291}$ | $R_{B6}$ | $R_{B3}$ | $R_{B4}$ | C | $L_{A421}$ | $R_{B6}$ | $R_{B3}$ | $R_{B4}$ | N |
| $L_{A292}$ | $R_{B6}$ | $R_{B3}$ | $R_{B7}$ | C | $L_{A422}$ | $R_{B6}$ | $R_{B3}$ | $R_{B7}$ | N |
| $L_{A293}$ | $R_{B6}$ | $R_{B3}$ | $R_{B10}$ | C | $L_{A423}$ | $R_{B6}$ | $R_{B3}$ | $R_{B10}$ | N |
| $L_{A294}$ | $R_{B6}$ | $R_{B3}$ | $R_{43}$ | C | $L_{A424}$ | $R_{B6}$ | $R_{B3}$ | $R_{43}$ | N |
| $L_{A295}$ | $R_{B6}$ | $R_{B3}$ | $R_{434}$ | C | $L_{A425}$ | $R_{B6}$ | $R_{B3}$ | $R_{434}$ | N |
| $L_{A296}$ | $R_{B6}$ | $R_{B4}$ | $R_{B1}$ | C | $L_{A426}$ | $R_{B6}$ | $R_{B4}$ | $R_{B1}$ | N |
| $L_{A297}$ | $R_{B6}$ | $R_{B4}$ | $R_{B3}$ | C | $L_{A427}$ | $R_{B6}$ | $R_{B4}$ | $R_{B3}$ | N |
| $L_{A298}$ | $R_{B6}$ | $R_{B4}$ | $R_{B7}$ | C | $L_{A428}$ | $R_{B6}$ | $R_{B4}$ | $R_{B7}$ | N |
| $L_{A299}$ | $R_{B6}$ | $R_{B4}$ | $R_{B10}$ | C | $L_{A429}$ | $R_{B6}$ | $R_{B4}$ | $R_{B10}$ | N |
| $L_{A300}$ | $R_{B6}$ | $R_{B4}$ | $R_{43}$ | C | $L_{A430}$ | $R_{B6}$ | $R_{B4}$ | $R_{43}$ | N |
| $L_{A301}$ | $R_{B6}$ | $R_{B4}$ | $R_{434}$ | C | $L_{A431}$ | $R_{B6}$ | $R_{B4}$ | $R_{434}$ | N |
| $L_{A302}$ | $R_{B6}$ | $R_{B7}$ | $R_{B1}$ | C | $L_{A432}$ | $R_{B6}$ | $R_{B7}$ | $R_{B1}$ | N |
| $L_{A303}$ | $R_{B6}$ | $R_{B7}$ | $R_{B3}$ | C | $L_{A433}$ | $R_{B6}$ | $R_{B7}$ | $R_{B3}$ | N |
| $L_{A304}$ | $R_{B6}$ | $R_{B7}$ | $R_{B4}$ | C | $L_{A434}$ | $R_{B6}$ | $R_{B7}$ | $R_{B4}$ | N |
| $L_{A305}$ | $R_{B6}$ | $R_{B7}$ | $R_{B10}$ | C | $L_{A435}$ | $R_{B6}$ | $R_{B7}$ | $R_{B10}$ | N |
| $L_{A306}$ | $R_{B6}$ | $R_{B7}$ | $R_{43}$ | C | $L_{A436}$ | $R_{B6}$ | $R_{B7}$ | $R_{43}$ | N |
| $L_{A307}$ | $R_{B6}$ | $R_{B7}$ | $R_{434}$ | C | $L_{A437}$ | $R_{B6}$ | $R_{B7}$ | $R_{434}$ | N |

-continued

| Ligand | R¹ | R⁹ | R¹⁰ | Y | Ligand | R¹ | R⁹ | R¹⁰ | Y |
|---|---|---|---|---|---|---|---|---|---|
| $L_{A308}$ | $R_{B6}$ | $R_{B10}$ | $R_{B1}$ | C | $L_{A438}$ | $R_{B6}$ | $R_{B10}$ | $R_{B1}$ | N |
| $L_{A309}$ | $R_{B6}$ | $R_{B10}$ | $R_{B3}$ | C | $L_{A439}$ | $R_{B6}$ | $R_{B10}$ | $R_{B3}$ | N |
| $L_{A310}$ | $R_{B6}$ | $R_{B10}$ | $R_{B4}$ | C | $L_{A440}$ | $R_{B6}$ | $R_{B10}$ | $R_{B4}$ | N |
| $L_{A311}$ | $R_{B6}$ | $R_{B10}$ | $R_{B7}$ | C | $L_{A441}$ | $R_{B6}$ | $R_{B10}$ | $R_{B7}$ | N |
| $L_{A312}$ | $R_{B6}$ | $R_{B10}$ | $R_{A3}$ | C | $L_{A442}$ | $R_{B6}$ | $R_{B10}$ | $R_{A3}$ | N |
| $L_{A313}$ | $R_{B6}$ | $R_{B10}$ | $R_{A34}$ | C | $L_{A443}$ | $R_{B6}$ | $R_{B10}$ | $R_{A34}$ | N |
| $L_{A314}$ | $R_{B6}$ | $R_{A3}$ | $R_{B1}$ | C | $L_{A444}$ | $R_{B6}$ | $R_{A3}$ | $R_{B1}$ | N |
| $L_{A315}$ | $R_{B6}$ | $R_{A3}$ | $R_{B3}$ | C | $L_{A445}$ | $R_{B6}$ | $R_{A3}$ | $R_{B3}$ | N |
| $L_{A316}$ | $R_{B6}$ | $R_{A3}$ | $R_{B4}$ | C | $L_{A446}$ | $R_{B6}$ | $R_{A3}$ | $R_{B4}$ | N |
| $L_{A317}$ | $R_{B6}$ | $R_{A3}$ | $R_{B7}$ | C | $L_{A447}$ | $R_{B6}$ | $R_{A3}$ | $R_{B7}$ | N |
| $L_{A318}$ | $R_{B6}$ | $R_{A3}$ | $R_{B10}$ | C | $L_{A448}$ | $R_{B6}$ | $R_{A3}$ | $R_{B10}$ | N |
| $L_{A319}$ | $R_{B6}$ | $R_{A3}$ | $R_{A34}$ | C | $L_{A449}$ | $R_{B6}$ | $R_{A3}$ | $R_{A34}$ | N |
| $L_{A320}$ | $R_{B6}$ | $R_{A34}$ | $R_{B1}$ | C | $L_{A450}$ | $R_{B6}$ | $R_{A34}$ | $R_{B1}$ | N |
| $L_{A321}$ | $R_{B6}$ | $R_{A34}$ | $R_{B3}$ | C | $L_{A451}$ | $R_{B6}$ | $R_{A34}$ | $R_{B3}$ | N |
| $L_{A322}$ | $R_{B6}$ | $R_{A34}$ | $R_{B4}$ | C | $L_{A452}$ | $R_{B6}$ | $R_{A34}$ | $R_{B4}$ | N |
| $L_{A323}$ | $R_{B6}$ | $R_{A34}$ | $R_{B7}$ | C | $L_{A453}$ | $R_{B6}$ | $R_{A34}$ | $R_{B7}$ | N |
| $L_{A324}$ | $R_{B6}$ | $R_{A34}$ | $R_{B10}$ | C | $L_{A454}$ | $R_{B6}$ | $R_{A34}$ | $R_{B10}$ | N |
| $L_{A325}$ | $R_{B6}$ | $R_{A34}$ | $R_{A3}$ | C | $L_{A455}$ | $R_{B6}$ | $R_{A34}$ | $R_{A3}$ | N |
| $L_{A326}$ | $R_{B8}$ | H | H | C | $L_{A456}$ | $R_{B8}$ | H | H | N |
| $L_{A327}$ | $R_{B8}$ | $R_{B1}$ | H | C | $L_{A457}$ | $R_{B8}$ | $R_{B1}$ | H | N |
| $L_{A328}$ | $R_{B8}$ | $R_{B3}$ | H | C | $L_{A458}$ | $R_{B8}$ | $R_{B3}$ | H | N |
| $L_{A329}$ | $R_{B8}$ | $R_{B4}$ | H | C | $L_{A459}$ | $R_{B8}$ | $R_{B4}$ | H | N |
| $L_{A330}$ | $R_{B8}$ | $R_{B7}$ | H | C | $L_{A460}$ | $R_{B8}$ | $R_{B7}$ | H | N |
| $L_{A331}$ | $R_{B8}$ | $R_{B10}$ | H | C | $L_{A461}$ | $R_{B8}$ | $R_{B10}$ | H | N |
| $L_{A332}$ | $R_{B8}$ | $R_{A3}$ | H | C | $L_{A462}$ | $R_{B8}$ | $R_{A3}$ | H | N |
| $L_{A333}$ | $R_{B8}$ | $R_{A34}$ | H | C | $L_{A463}$ | $R_{B8}$ | $R_{A34}$ | H | N |
| $L_{A334}$ | $R_{B8}$ | H | $R_{B1}$ | C | $L_{A464}$ | $R_{B8}$ | H | $R_{B1}$ | N |
| $L_{A335}$ | $R_{B8}$ | H | $R_{B2}$ | C | $L_{A465}$ | $R_{B8}$ | H | $R_{B2}$ | N |
| $L_{A336}$ | $R_{B8}$ | H | $R_{B3}$ | C | $L_{A466}$ | $R_{B8}$ | H | $R_{B3}$ | N |
| $L_{A337}$ | $R_{B8}$ | H | $R_{B4}$ | C | $L_{A467}$ | $R_{B8}$ | H | $R_{B4}$ | N |
| $L_{A338}$ | $R_{B8}$ | H | $R_{B7}$ | C | $L_{A468}$ | $R_{B8}$ | H | $R_{B7}$ | N |
| $L_{A339}$ | $R_{B8}$ | H | $R_{B10}$ | C | $L_{A469}$ | $R_{B8}$ | H | $R_{B10}$ | N |
| $L_{A340}$ | $R_{B8}$ | H | $R_{A3}$ | C | $L_{A470}$ | $R_{B8}$ | H | $R_{A3}$ | N |
| $L_{A341}$ | $R_{B8}$ | H | $R_{A34}$ | C | $L_{A471}$ | $R_{B8}$ | H | $R_{A34}$ | N |
| $L_{A342}$ | $R_{B8}$ | $R_{B1}$ | $R_{B1}$ | C | $L_{A472}$ | $R_{B8}$ | $R_{B1}$ | $R_{B1}$ | N |
| $L_{A343}$ | $R_{B8}$ | $R_{B3}$ | $R_{B3}$ | C | $L_{A473}$ | $R_{B8}$ | $R_{B3}$ | $R_{B3}$ | N |
| $L_{A344}$ | $R_{B8}$ | $R_{B4}$ | $R_{B4}$ | C | $L_{A474}$ | $R_{B8}$ | $R_{B4}$ | $R_{B4}$ | N |
| $L_{A345}$ | $R_{B8}$ | $R_{B7}$ | $R_{B7}$ | C | $L_{A475}$ | $R_{B8}$ | $R_{B7}$ | $R_{B7}$ | N |
| $L_{A346}$ | $R_{B8}$ | $R_{B10}$ | $R_{B10}$ | C | $L_{A476}$ | $R_{B8}$ | $R_{B10}$ | $R_{B10}$ | N |
| $L_{A347}$ | $R_{B8}$ | $R_{A3}$ | $R_{A3}$ | C | $L_{A477}$ | $R_{B8}$ | $R_{A3}$ | $R_{A3}$ | N |
| $L_{A348}$ | $R_{B8}$ | $R_{A34}$ | $R_{A34}$ | C | $L_{A478}$ | $R_{B8}$ | $R_{A34}$ | $R_{A34}$ | N |
| $L_{A349}$ | $R_{B8}$ | $R_{B1}$ | $R_{B3}$ | C | $L_{A479}$ | $R_{B8}$ | $R_{B1}$ | $R_{B3}$ | N |
| $L_{A350}$ | $R_{B8}$ | $R_{B1}$ | $R_{B4}$ | C | $L_{A480}$ | $R_{B8}$ | $R_{B1}$ | $R_{B4}$ | N |
| $L_{A351}$ | $R_{B8}$ | $R_{B1}$ | $R_{B7}$ | C | $L_{A481}$ | $R_{B8}$ | $R_{B1}$ | $R_{B7}$ | N |
| $L_{A352}$ | $R_{B8}$ | $R_{B1}$ | $R_{B10}$ | C | $L_{A482}$ | $R_{B8}$ | $R_{B1}$ | $R_{B10}$ | N |
| $L_{A353}$ | $R_{B8}$ | $R_{B1}$ | $R_{A3}$ | C | $L_{A483}$ | $R_{B8}$ | $R_{B1}$ | $R_{A3}$ | N |
| $L_{A354}$ | $R_{B8}$ | $R_{B1}$ | $R_{A34}$ | C | $L_{A484}$ | $R_{B8}$ | $R_{B1}$ | $R_{A34}$ | N |
| $L_{A355}$ | $R_{B8}$ | $R_{B3}$ | $R_{B1}$ | C | $L_{A485}$ | $R_{B8}$ | $R_{B3}$ | $R_{B1}$ | N |
| $L_{A356}$ | $R_{B8}$ | $R_{B3}$ | $R_{B4}$ | C | $L_{A486}$ | $R_{B8}$ | $R_{B3}$ | $R_{B4}$ | N |
| $L_{A357}$ | $R_{B8}$ | $R_{B3}$ | $R_{B7}$ | C | $L_{A487}$ | $R_{B8}$ | $R_{B3}$ | $R_{B7}$ | N |
| $L_{A358}$ | $R_{B8}$ | $R_{B3}$ | $R_{B10}$ | C | $L_{A488}$ | $R_{B8}$ | $R_{B3}$ | $R_{B10}$ | N |
| $L_{A359}$ | $R_{B8}$ | $R_{B3}$ | $R_{A3}$ | C | $L_{A489}$ | $R_{B8}$ | $R_{B3}$ | $R_{A3}$ | N |
| $L_{A360}$ | $R_{B8}$ | $R_{B3}$ | $R_{A34}$ | C | $L_{A490}$ | $R_{B8}$ | $R_{B3}$ | $R_{A34}$ | N |
| $L_{A361}$ | $R_{B8}$ | $R_{B4}$ | $R_{B1}$ | C | $L_{A491}$ | $R_{B8}$ | $R_{B4}$ | $R_{B1}$ | N |
| $L_{A362}$ | $R_{B8}$ | $R_{B4}$ | $R_{B3}$ | C | $L_{A492}$ | $R_{B8}$ | $R_{B4}$ | $R_{B3}$ | N |
| $L_{A363}$ | $R_{B8}$ | $R_{B4}$ | $R_{B7}$ | C | $L_{A493}$ | $R_{B8}$ | $R_{B4}$ | $R_{B7}$ | N |
| $L_{A364}$ | $R_{B8}$ | $R_{B4}$ | $R_{B10}$ | C | $L_{A494}$ | $R_{B8}$ | $R_{B4}$ | $R_{B10}$ | N |
| $L_{A365}$ | $R_{B8}$ | $R_{B4}$ | $R_{A3}$ | C | $L_{A495}$ | $R_{B8}$ | $R_{B4}$ | $R_{A3}$ | N |
| $L_{A366}$ | $R_{B8}$ | $R_{B4}$ | $R_{A34}$ | C | $L_{A496}$ | $R_{B8}$ | $R_{B4}$ | $R_{A34}$ | N |
| $L_{A367}$ | $R_{B8}$ | $R_{B7}$ | $R_{B1}$ | C | $L_{A497}$ | $R_{B8}$ | $R_{B7}$ | $R_{B1}$ | N |
| $L_{A368}$ | $R_{B8}$ | $R_{B7}$ | $R_{B3}$ | C | $L_{A498}$ | $R_{B8}$ | $R_{B7}$ | $R_{B3}$ | N |
| $L_{A369}$ | $R_{B8}$ | $R_{B7}$ | $R_{B4}$ | C | $L_{A499}$ | $R_{B8}$ | $R_{B7}$ | $R_{B4}$ | N |
| $L_{A370}$ | $R_{B8}$ | $R_{B7}$ | $R_{B10}$ | C | $L_{A500}$ | $R_{B8}$ | $R_{B7}$ | $R_{B10}$ | N |
| $L_{A371}$ | $R_{B8}$ | $R_{B7}$ | $R_{A3}$ | C | $L_{A501}$ | $R_{B8}$ | $R_{B7}$ | $R_{A3}$ | N |
| $L_{A372}$ | $R_{B8}$ | $R_{B7}$ | $R_{A34}$ | C | $L_{A502}$ | $R_{B8}$ | $R_{B7}$ | $R_{A34}$ | N |
| $L_{A373}$ | $R_{B8}$ | $R_{B10}$ | $R_{B1}$ | C | $L_{A503}$ | $R_{B8}$ | $R_{B10}$ | $R_{B1}$ | N |
| $L_{A374}$ | $R_{B8}$ | $R_{B10}$ | $R_{B3}$ | C | $L_{A504}$ | $R_{B8}$ | $R_{B10}$ | $R_{B3}$ | N |
| $L_{A375}$ | $R_{B8}$ | $R_{B10}$ | $R_{B4}$ | C | $L_{A505}$ | $R_{B8}$ | $R_{B10}$ | $R_{B4}$ | N |
| $L_{A376}$ | $R_{B8}$ | $R_{B10}$ | $R_{B7}$ | C | $L_{A506}$ | $R_{B8}$ | $R_{B10}$ | $R_{B7}$ | N |
| $L_{A377}$ | $R_{B8}$ | $R_{B10}$ | $R_{A3}$ | C | $L_{A507}$ | $R_{B8}$ | $R_{B10}$ | $R_{A3}$ | N |
| $L_{A378}$ | $R_{B8}$ | $R_{B10}$ | $R_{A34}$ | C | $L_{A508}$ | $R_{B8}$ | $R_{B10}$ | $R_{A34}$ | N |
| $L_{A379}$ | $R_{B8}$ | $R_{A3}$ | $R_{B1}$ | C | $L_{A509}$ | $R_{B8}$ | $R_{A3}$ | $R_{B1}$ | N |
| $L_{A380}$ | $R_{B8}$ | $R_{A3}$ | $R_{B3}$ | C | $L_{A510}$ | $R_{B8}$ | $R_{A3}$ | $R_{B3}$ | N |
| $L_{A381}$ | $R_{B8}$ | $R_{A3}$ | $R_{B4}$ | C | $L_{A511}$ | $R_{B8}$ | $R_{A3}$ | $R_{B4}$ | N |
| $L_{A382}$ | $R_{B8}$ | $R_{A3}$ | $R_{B7}$ | C | $L_{A512}$ | $R_{B8}$ | $R_{A3}$ | $R_{B7}$ | N |
| $L_{A383}$ | $R_{B8}$ | $R_{A3}$ | $R_{B10}$ | C | $L_{A513}$ | $R_{B8}$ | $R_{A3}$ | $R_{B10}$ | N |
| $L_{A384}$ | $R_{B8}$ | $R_{A3}$ | $R_{A34}$ | C | $L_{A514}$ | $R_{B8}$ | $R_{A3}$ | $R_{A34}$ | N |
| $L_{A385}$ | $R_{B8}$ | $R_{A34}$ | $R_{B1}$ | C | $L_{A515}$ | $R_{B8}$ | $R_{A34}$ | $R_{B1}$ | N |
| $L_{A386}$ | $R_{B8}$ | $R_{A34}$ | $R_{B3}$ | C | $L_{A516}$ | $R_{B8}$ | $R_{A34}$ | $R_{B3}$ | N |
| $L_{A387}$ | $R_{B8}$ | $R_{A34}$ | $R_{B4}$ | C | $L_{A517}$ | $R_{B8}$ | $R_{A34}$ | $R_{B4}$ | N |
| $L_{A388}$ | $R_{B8}$ | $R_{A34}$ | $R_{B7}$ | C | $L_{A518}$ | $R_{B8}$ | $R_{A34}$ | $R_{B7}$ | N |
| $L_{A389}$ | $R_{B8}$ | $R_{A34}$ | $R_{B10}$ | C | $L_{A519}$ | $R_{B8}$ | $R_{A34}$ | $R_{B10}$ | N |
| $L_{A390}$ | $R_{B8}$ | $R_{A34}$ | $R_{A3}$ | C | $L_{A520}$ | $R_{B8}$ | $R_{A34}$ | $R_{A3}$ | N, |

$L_{A521}$ through $L_{A780}$ that are based on a structure of Formula IV,

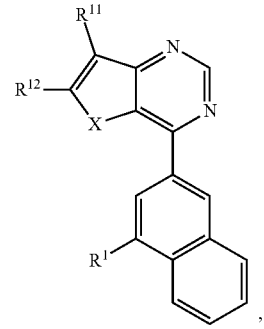

in which $R^1$, $R^{11}$, $R^{12}$, and X are defined as provided below:

| Ligand | R¹ | R¹¹ | R¹² | X | Ligand | R¹ | R¹¹ | R¹² | X |
|---|---|---|---|---|---|---|---|---|---|
| $L_{A521}$ | $R_{B6}$ | H | H | S | $L_{A651}$ | $R_{B6}$ | H | H | O |
| $L_{A522}$ | $R_{B6}$ | $R_{B1}$ | H | S | $L_{A652}$ | $R_{B6}$ | $R_{B1}$ | H | O |
| $L_{A523}$ | $R_{B6}$ | $R_{B3}$ | H | S | $L_{A653}$ | $R_{B6}$ | $R_{B3}$ | H | O |
| $L_{A524}$ | $R_{B6}$ | $R_{B4}$ | H | S | $L_{A654}$ | $R_{B6}$ | $R_{B4}$ | H | O |
| $L_{A525}$ | $R_{B6}$ | $R_{B7}$ | H | S | $L_{A655}$ | $R_{B6}$ | $R_{B7}$ | H | O |
| $L_{A526}$ | $R_{B6}$ | $R_{B10}$ | H | S | $L_{A656}$ | $R_{B6}$ | $R_{B10}$ | H | O |
| $L_{A527}$ | $R_{B6}$ | $R_{A3}$ | H | S | $L_{A657}$ | $R_{B6}$ | $R_{A3}$ | H | O |
| $L_{A528}$ | $R_{B6}$ | $R_{A34}$ | H | S | $L_{A658}$ | $R_{B6}$ | $R_{A34}$ | H | O |
| $L_{A529}$ | $R_{B6}$ | H | $R_{B1}$ | S | $L_{A659}$ | $R_{B6}$ | H | $R_{B1}$ | O |
| $L_{A530}$ | $R_{B6}$ | H | $R_{B2}$ | S | $L_{A660}$ | $R_{B6}$ | H | $R_{B2}$ | O |
| $L_{A531}$ | $R_{B6}$ | H | $R_{B3}$ | S | $L_{A661}$ | $R_{B6}$ | H | $R_{B3}$ | O |
| $L_{A532}$ | $R_{B6}$ | H | $R_{B4}$ | S | $L_{A662}$ | $R_{B6}$ | H | $R_{B4}$ | O |
| $L_{A533}$ | $R_{B6}$ | H | $R_{B7}$ | S | $L_{A663}$ | $R_{B6}$ | H | $R_{B7}$ | O |
| $L_{A534}$ | $R_{B6}$ | H | $R_{B10}$ | S | $L_{A664}$ | $R_{B6}$ | H | $R_{B10}$ | O |
| $L_{A535}$ | $R_{B6}$ | H | $R_{A3}$ | S | $L_{A665}$ | $R_{B6}$ | H | $R_{A3}$ | O |
| $L_{A536}$ | $R_{B6}$ | H | $R_{A34}$ | S | $L_{A666}$ | $R_{B6}$ | H | $R_{A34}$ | O |
| $L_{A537}$ | $R_{B6}$ | $R_{B1}$ | $R_{B1}$ | S | $L_{A667}$ | $R_{B6}$ | $R_{B1}$ | $R_{B1}$ | O |
| $L_{A538}$ | $R_{B6}$ | $R_{B3}$ | $R_{B3}$ | S | $L_{A668}$ | $R_{B6}$ | $R_{B3}$ | $R_{B3}$ | O |
| $L_{A539}$ | $R_{B6}$ | $R_{B4}$ | $R_{B4}$ | S | $L_{A669}$ | $R_{B6}$ | $R_{B4}$ | $R_{B4}$ | O |
| $L_{A540}$ | $R_{B6}$ | $R_{B7}$ | $R_{B7}$ | S | $L_{A670}$ | $R_{B6}$ | $R_{B7}$ | $R_{B7}$ | O |
| $L_{A541}$ | $R_{B6}$ | $R_{B10}$ | $R_{B10}$ | S | $L_{A671}$ | $R_{B6}$ | $R_{B10}$ | $R_{B10}$ | O |
| $L_{A542}$ | $R_{B6}$ | $R_{A3}$ | $R_{A3}$ | S | $L_{A672}$ | $R_{B6}$ | $R_{A3}$ | $R_{A3}$ | O |
| $L_{A543}$ | $R_{B6}$ | $R_{A34}$ | $R_{A34}$ | S | $L_{A673}$ | $R_{B6}$ | $R_{A34}$ | $R_{A34}$ | O |
| $L_{A544}$ | $R_{B6}$ | $R_{B1}$ | $R_{B3}$ | S | $L_{A674}$ | $R_{B6}$ | $R_{B1}$ | $R_{B3}$ | O |
| $L_{A545}$ | $R_{B6}$ | $R_{B1}$ | $R_{B4}$ | S | $L_{A675}$ | $R_{B6}$ | $R_{B1}$ | $R_{B4}$ | O |
| $L_{A546}$ | $R_{B6}$ | $R_{B1}$ | $R_{B7}$ | S | $L_{A676}$ | $R_{B6}$ | $R_{B1}$ | $R_{B7}$ | O |
| $L_{A547}$ | $R_{B6}$ | $R_{B1}$ | $R_{B10}$ | S | $L_{A677}$ | $R_{B6}$ | $R_{B1}$ | $R_{B10}$ | O |
| $L_{A548}$ | $R_{B6}$ | $R_{B1}$ | $R_{A3}$ | S | $L_{A678}$ | $R_{B6}$ | $R_{B1}$ | $R_{A3}$ | O |
| $L_{A549}$ | $R_{B6}$ | $R_{B1}$ | $R_{A34}$ | S | $L_{A679}$ | $R_{B6}$ | $R_{B1}$ | $R_{A34}$ | O |
| $L_{A550}$ | $R_{B6}$ | $R_{B3}$ | $R_{B1}$ | S | $L_{A680}$ | $R_{B6}$ | $R_{B3}$ | $R_{B1}$ | O |
| $L_{A551}$ | $R_{B6}$ | $R_{B3}$ | $R_{B4}$ | S | $L_{A681}$ | $R_{B6}$ | $R_{B3}$ | $R_{B4}$ | O |
| $L_{A552}$ | $R_{B6}$ | $R_{B3}$ | $R_{B7}$ | S | $L_{A682}$ | $R_{B6}$ | $R_{B3}$ | $R_{B7}$ | O |
| $L_{A553}$ | $R_{B6}$ | $R_{B3}$ | $R_{B10}$ | S | $L_{A683}$ | $R_{B6}$ | $R_{B3}$ | $R_{B10}$ | O |
| $L_{A554}$ | $R_{B6}$ | $R_{B3}$ | $R_{A3}$ | S | $L_{A684}$ | $R_{B6}$ | $R_{B3}$ | $R_{A3}$ | O |
| $L_{A555}$ | $R_{B6}$ | $R_{B3}$ | $R_{A34}$ | S | $L_{A685}$ | $R_{B6}$ | $R_{B3}$ | $R_{A34}$ | O |
| $L_{A556}$ | $R_{B6}$ | $R_{B4}$ | $R_{B1}$ | S | $L_{A686}$ | $R_{B6}$ | $R_{B4}$ | $R_{B1}$ | O |
| $L_{A557}$ | $R_{B6}$ | $R_{B4}$ | $R_{B3}$ | S | $L_{A687}$ | $R_{B6}$ | $R_{B4}$ | $R_{B3}$ | O |
| $L_{A558}$ | $R_{B6}$ | $R_{B4}$ | $R_{B7}$ | S | $L_{A688}$ | $R_{B6}$ | $R_{B4}$ | $R_{B7}$ | O |
| $L_{A559}$ | $R_{B6}$ | $R_{B4}$ | $R_{B10}$ | S | $L_{A689}$ | $R_{B6}$ | $R_{B4}$ | $R_{B10}$ | O |
| $L_{A560}$ | $R_{B6}$ | $R_{B4}$ | $R_{A3}$ | S | $L_{A690}$ | $R_{B6}$ | $R_{B4}$ | $R_{A3}$ | O |
| $L_{A561}$ | $R_{B6}$ | $R_{B4}$ | $R_{A34}$ | S | $L_{A691}$ | $R_{B6}$ | $R_{B4}$ | $R_{A34}$ | O |
| $L_{A562}$ | $R_{B6}$ | $R_{B7}$ | $R_{B1}$ | S | $L_{A692}$ | $R_{B6}$ | $R_{B7}$ | $R_{B1}$ | O |

| Ligand | R$^1$ | R$^{11}$ | R$^{12}$ | X | Ligand | R$^1$ | R$^{11}$ | R$^{12}$ | X |
|---|---|---|---|---|---|---|---|---|---|
| L$_{A563}$ | R$_{B6}$ | R$_{B7}$ | R$_{B3}$ | S | L$_{A693}$ | R$_{B6}$ | R$_{B7}$ | R$_{B3}$ | O |
| L$_{A564}$ | R$_{B6}$ | R$_{B7}$ | R$_{B4}$ | S | L$_{A694}$ | R$_{B6}$ | R$_{B7}$ | R$_{B4}$ | O |
| L$_{A565}$ | R$_{B6}$ | R$_{B7}$ | R$_{B10}$ | S | L$_{A695}$ | R$_{B6}$ | R$_{B7}$ | R$_{B10}$ | O |
| L$_{A566}$ | R$_{B6}$ | R$_{B7}$ | R$_{43}$ | S | L$_{A696}$ | R$_{B6}$ | R$_{B7}$ | R$_{43}$ | O |
| L$_{A567}$ | R$_{B6}$ | R$_{B7}$ | R$_{A34}$ | S | L$_{A697}$ | R$_{B6}$ | R$_{B7}$ | R$_{A34}$ | O |
| L$_{A568}$ | R$_{B6}$ | R$_{B10}$ | R$_{B1}$ | S | L$_{A698}$ | R$_{B6}$ | R$_{B10}$ | R$_{B1}$ | O |
| L$_{A569}$ | R$_{B6}$ | R$_{B10}$ | R$_{B3}$ | S | L$_{A699}$ | R$_{B6}$ | R$_{B10}$ | R$_{B3}$ | O |
| L$_{A570}$ | R$_{B6}$ | R$_{B10}$ | R$_{B4}$ | S | L$_{A700}$ | R$_{B6}$ | R$_{B10}$ | R$_{B4}$ | O |
| L$_{A571}$ | R$_{B6}$ | R$_{B10}$ | R$_{B7}$ | S | L$_{A701}$ | R$_{B6}$ | R$_{B10}$ | R$_{B7}$ | O |
| L$_{A572}$ | R$_{B6}$ | R$_{B10}$ | R$_{43}$ | S | L$_{A702}$ | R$_{B6}$ | R$_{B10}$ | R$_{43}$ | O |
| L$_{A573}$ | R$_{B6}$ | R$_{B10}$ | R$_{A34}$ | S | L$_{A703}$ | R$_{B6}$ | R$_{B10}$ | R$_{A34}$ | O |
| L$_{A574}$ | R$_{B6}$ | R$_{43}$ | R$_{B1}$ | S | L$_{A704}$ | R$_{B6}$ | R$_{43}$ | R$_{B1}$ | O |
| L$_{A575}$ | R$_{B6}$ | R$_{43}$ | R$_{B3}$ | S | L$_{A705}$ | R$_{B6}$ | R$_{43}$ | R$_{B3}$ | O |
| L$_{A576}$ | R$_{B6}$ | R$_{43}$ | R$_{B4}$ | S | L$_{A706}$ | R$_{B6}$ | R$_{43}$ | R$_{B4}$ | O |
| L$_{A577}$ | R$_{B6}$ | R$_{43}$ | R$_{B7}$ | S | L$_{A707}$ | R$_{B6}$ | R$_{43}$ | R$_{B7}$ | O |
| L$_{A578}$ | R$_{B6}$ | R$_{43}$ | R$_{B10}$ | S | L$_{A708}$ | R$_{B6}$ | R$_{43}$ | R$_{B10}$ | O |
| L$_{A579}$ | R$_{B6}$ | R$_{43}$ | R$_{A34}$ | S | L$_{A709}$ | R$_{B6}$ | R$_{43}$ | R$_{A34}$ | O |
| L$_{A580}$ | R$_{B6}$ | R$_{A34}$ | R$_{B1}$ | S | L$_{A710}$ | R$_{B6}$ | R$_{A34}$ | R$_{B1}$ | O |
| L$_{A581}$ | R$_{B6}$ | R$_{A34}$ | R$_{B3}$ | S | L$_{A711}$ | R$_{B6}$ | R$_{A34}$ | R$_{B3}$ | O |
| L$_{A582}$ | R$_{B6}$ | R$_{A34}$ | R$_{B4}$ | S | L$_{A712}$ | R$_{B6}$ | R$_{A34}$ | R$_{B4}$ | O |
| L$_{A583}$ | R$_{B6}$ | R$_{A34}$ | R$_{B7}$ | S | L$_{A713}$ | R$_{B6}$ | R$_{A34}$ | R$_{B7}$ | O |
| L$_{A584}$ | R$_{B6}$ | R$_{A34}$ | R$_{B10}$ | S | L$_{A714}$ | R$_{B6}$ | R$_{A34}$ | R$_{B10}$ | O |
| L$_{A585}$ | R$_{B6}$ | R$_{A34}$ | R$_{43}$ | S | L$_{A715}$ | R$_{B6}$ | R$_{A34}$ | R$_{43}$ | O |
| L$_{A586}$ | R$_{B8}$ | H | H | S | L$_{A716}$ | R$_{B8}$ | H | H | O |
| L$_{A587}$ | R$_{B8}$ | R$_{B1}$ | H | S | L$_{A717}$ | R$_{B8}$ | R$_{B1}$ | H | O |
| L$_{A588}$ | R$_{B8}$ | R$_{B3}$ | H | S | L$_{A718}$ | R$_{B8}$ | R$_{B3}$ | H | O |
| L$_{A589}$ | R$_{B8}$ | R$_{B4}$ | H | S | L$_{A719}$ | R$_{B8}$ | R$_{B4}$ | H | O |
| L$_{A590}$ | R$_{B8}$ | R$_{B7}$ | H | S | L$_{A720}$ | R$_{B8}$ | R$_{B7}$ | H | O |
| L$_{A591}$ | R$_{B8}$ | R$_{B10}$ | H | S | L$_{A721}$ | R$_{B8}$ | R$_{B10}$ | H | O |
| L$_{A592}$ | R$_{B8}$ | R$_{43}$ | H | S | L$_{A722}$ | R$_{B8}$ | R$_{43}$ | H | O |
| L$_{A593}$ | R$_{B8}$ | R$_{A34}$ | H | S | L$_{A723}$ | R$_{B8}$ | R$_{A34}$ | H | O |
| L$_{A594}$ | R$_{B8}$ | H | R$_{B1}$ | S | L$_{A724}$ | R$_{B8}$ | H | R$_{B1}$ | O |
| L$_{A595}$ | R$_{B8}$ | H | R$_{B2}$ | S | L$_{A725}$ | R$_{B8}$ | H | R$_{B2}$ | O |
| L$_{A596}$ | R$_{B8}$ | H | R$_{B3}$ | S | L$_{A726}$ | R$_{B8}$ | H | R$_{B3}$ | O |
| L$_{A597}$ | R$_{B8}$ | H | R$_{B4}$ | S | L$_{A727}$ | R$_{B8}$ | H | R$_{B4}$ | O |
| L$_{A598}$ | R$_{B8}$ | H | R$_{B7}$ | S | L$_{A728}$ | R$_{B8}$ | H | R$_{B7}$ | O |
| L$_{A599}$ | R$_{B8}$ | H | R$_{B10}$ | S | L$_{A729}$ | R$_{B8}$ | H | R$_{B10}$ | O |
| L$_{A600}$ | R$_{B8}$ | H | R$_{43}$ | S | L$_{A730}$ | R$_{B8}$ | H | R$_{43}$ | O |
| L$_{A601}$ | R$_{B8}$ | H | R$_{A34}$ | S | L$_{A731}$ | R$_{B8}$ | H | R$_{A34}$ | O |
| L$_{A602}$ | R$_{B8}$ | R$_{B1}$ | R$_{B1}$ | S | L$_{A732}$ | R$_{B8}$ | R$_{B1}$ | R$_{B1}$ | O |
| L$_{A603}$ | R$_{B8}$ | R$_{B3}$ | R$_{B3}$ | S | L$_{A733}$ | R$_{B8}$ | R$_{B3}$ | R$_{B3}$ | O |
| L$_{A604}$ | R$_{B8}$ | R$_{B4}$ | R$_{B4}$ | S | L$_{A734}$ | R$_{B8}$ | R$_{B4}$ | R$_{B4}$ | O |
| L$_{A605}$ | R$_{B8}$ | R$_{B7}$ | R$_{B7}$ | S | L$_{A735}$ | R$_{B8}$ | R$_{B7}$ | R$_{B7}$ | O |
| L$_{A606}$ | R$_{B8}$ | R$_{B10}$ | R$_{B10}$ | S | L$_{A736}$ | R$_{B8}$ | R$_{B10}$ | R$_{B10}$ | O |
| L$_{A607}$ | R$_{B8}$ | R$_{43}$ | R$_{43}$ | S | L$_{A737}$ | R$_{B8}$ | R$_{43}$ | R$_{43}$ | O |
| L$_{A608}$ | R$_{B8}$ | R$_{A34}$ | R$_{A34}$ | S | L$_{A738}$ | R$_{B8}$ | R$_{A34}$ | R$_{A34}$ | O |
| L$_{A609}$ | R$_{B8}$ | R$_{B1}$ | R$_{B3}$ | S | L$_{A739}$ | R$_{B8}$ | R$_{B1}$ | R$_{B3}$ | O |
| L$_{A610}$ | R$_{B8}$ | R$_{B1}$ | R$_{B4}$ | S | L$_{A740}$ | R$_{B8}$ | R$_{B1}$ | R$_{B4}$ | O |
| L$_{A611}$ | R$_{B8}$ | R$_{B1}$ | R$_{B7}$ | S | L$_{A741}$ | R$_{B8}$ | R$_{B1}$ | R$_{B7}$ | O |
| L$_{A612}$ | R$_{B8}$ | R$_{B1}$ | R$_{B10}$ | S | L$_{A742}$ | R$_{B8}$ | R$_{B1}$ | R$_{B10}$ | O |
| L$_{A613}$ | R$_{B8}$ | R$_{B1}$ | R$_{43}$ | S | L$_{A743}$ | R$_{B8}$ | R$_{B1}$ | R$_{43}$ | O |
| L$_{A614}$ | R$_{B8}$ | R$_{B1}$ | R$_{A34}$ | S | L$_{A744}$ | R$_{B8}$ | R$_{B1}$ | R$_{A34}$ | O |
| L$_{A615}$ | R$_{B8}$ | R$_{B3}$ | R$_{B1}$ | S | L$_{A745}$ | R$_{B8}$ | R$_{B3}$ | R$_{B1}$ | O |
| L$_{A616}$ | R$_{B8}$ | R$_{B3}$ | R$_{B4}$ | S | L$_{A746}$ | R$_{B8}$ | R$_{B3}$ | R$_{B4}$ | O |
| L$_{A617}$ | R$_{B8}$ | R$_{B3}$ | R$_{B7}$ | S | L$_{A747}$ | R$_{B8}$ | R$_{B3}$ | R$_{B7}$ | O |
| L$_{A618}$ | R$_{B8}$ | R$_{B3}$ | R$_{B10}$ | S | L$_{A748}$ | R$_{B8}$ | R$_{B3}$ | R$_{B10}$ | O |
| L$_{A619}$ | R$_{B8}$ | R$_{B3}$ | R$_{43}$ | S | L$_{A749}$ | R$_{B8}$ | R$_{B3}$ | R$_{43}$ | O |
| L$_{A620}$ | R$_{B8}$ | R$_{B3}$ | R$_{A34}$ | S | L$_{A750}$ | R$_{B8}$ | R$_{B3}$ | R$_{A34}$ | O |
| L$_{A621}$ | R$_{B8}$ | R$_{B4}$ | R$_{B1}$ | S | L$_{A751}$ | R$_{B8}$ | R$_{B4}$ | R$_{B1}$ | O |
| L$_{A622}$ | R$_{B8}$ | R$_{B4}$ | R$_{B3}$ | S | L$_{A752}$ | R$_{B8}$ | R$_{B4}$ | R$_{B3}$ | O |
| L$_{A623}$ | R$_{B8}$ | R$_{B4}$ | R$_{B7}$ | S | L$_{A753}$ | R$_{B8}$ | R$_{B4}$ | R$_{B7}$ | O |
| L$_{A624}$ | R$_{B8}$ | R$_{B4}$ | R$_{B10}$ | S | L$_{A754}$ | R$_{B8}$ | R$_{B4}$ | R$_{B10}$ | O |
| L$_{A625}$ | R$_{B8}$ | R$_{B4}$ | R$_{43}$ | S | L$_{A755}$ | R$_{B8}$ | R$_{B4}$ | R$_{43}$ | O |
| L$_{A626}$ | R$_{B8}$ | R$_{B4}$ | R$_{A34}$ | S | L$_{A756}$ | R$_{B8}$ | R$_{B4}$ | R$_{A34}$ | O |
| L$_{A627}$ | R$_{B8}$ | R$_{B7}$ | R$_{B1}$ | S | L$_{A757}$ | R$_{B8}$ | R$_{B7}$ | R$_{B1}$ | O |
| L$_{A628}$ | R$_{B8}$ | R$_{B7}$ | R$_{B3}$ | S | L$_{A758}$ | R$_{B8}$ | R$_{B7}$ | R$_{B3}$ | O |
| L$_{A629}$ | R$_{B8}$ | R$_{B7}$ | R$_{B4}$ | S | L$_{A759}$ | R$_{B8}$ | R$_{B7}$ | R$_{B4}$ | O |
| L$_{A630}$ | R$_{B8}$ | R$_{B7}$ | R$_{B10}$ | S | L$_{A760}$ | R$_{B8}$ | R$_{B7}$ | R$_{B10}$ | O |
| L$_{A631}$ | R$_{B8}$ | R$_{B7}$ | R$_{43}$ | S | L$_{A761}$ | R$_{B8}$ | R$_{B7}$ | R$_{43}$ | O |
| L$_{A632}$ | R$_{B8}$ | R$_{B7}$ | R$_{A34}$ | S | L$_{A762}$ | R$_{B8}$ | R$_{B7}$ | R$_{A34}$ | O |
| L$_{A633}$ | R$_{B8}$ | R$_{B10}$ | R$_{B1}$ | S | L$_{A763}$ | R$_{B8}$ | R$_{B10}$ | R$_{B1}$ | O |
| L$_{A634}$ | R$_{B8}$ | R$_{B10}$ | R$_{B3}$ | S | L$_{A764}$ | R$_{B8}$ | R$_{B10}$ | R$_{B3}$ | O |
| L$_{A635}$ | R$_{B8}$ | R$_{B10}$ | R$_{B4}$ | S | L$_{A765}$ | R$_{B8}$ | R$_{B10}$ | R$_{B4}$ | O |
| L$_{A636}$ | R$_{B8}$ | R$_{B10}$ | R$_{B7}$ | S | L$_{A766}$ | R$_{B8}$ | R$_{B10}$ | R$_{B7}$ | O |
| L$_{A637}$ | R$_{B8}$ | R$_{B10}$ | R$_{43}$ | S | L$_{A767}$ | R$_{B8}$ | R$_{B10}$ | R$_{43}$ | O |
| L$_{A638}$ | R$_{B8}$ | R$_{B10}$ | R$_{A34}$ | S | L$_{A768}$ | R$_{B8}$ | R$_{B10}$ | R$_{A34}$ | O |
| L$_{A639}$ | R$_{B8}$ | R$_{43}$ | R$_{B1}$ | S | L$_{A769}$ | R$_{B8}$ | R$_{43}$ | R$_{B1}$ | O |
| L$_{A640}$ | R$_{B8}$ | R$_{43}$ | R$_{B3}$ | S | L$_{A770}$ | R$_{B8}$ | R$_{43}$ | R$_{B3}$ | O |
| L$_{A641}$ | R$_{B8}$ | R$_{43}$ | R$_{B4}$ | S | L$_{A771}$ | R$_{B8}$ | R$_{43}$ | R$_{B4}$ | O |
| L$_{A642}$ | R$_{B8}$ | R$_{43}$ | R$_{B7}$ | S | L$_{A772}$ | R$_{B8}$ | R$_{43}$ | R$_{B7}$ | O |
| L$_{A643}$ | R$_{B8}$ | R$_{43}$ | R$_{B10}$ | S | L$_{A773}$ | R$_{B8}$ | R$_{43}$ | R$_{B10}$ | O |
| L$_{A644}$ | R$_{B8}$ | R$_{43}$ | R$_{A34}$ | S | L$_{A774}$ | R$_{B8}$ | R$_{43}$ | R$_{A34}$ | O |
| L$_{A645}$ | R$_{B8}$ | R$_{A34}$ | R$_{B1}$ | S | L$_{A775}$ | R$_{B8}$ | R$_{A34}$ | R$_{B1}$ | O |
| L$_{A646}$ | R$_{B8}$ | R$_{A34}$ | R$_{B3}$ | S | L$_{A776}$ | R$_{B8}$ | R$_{A34}$ | R$_{B3}$ | O |
| L$_{A647}$ | R$_{B8}$ | R$_{A34}$ | R$_{B4}$ | S | L$_{A777}$ | R$_{B8}$ | R$_{A34}$ | R$_{B4}$ | O |
| L$_{A648}$ | R$_{B8}$ | R$_{A34}$ | R$_{B7}$ | S | L$_{A778}$ | R$_{B8}$ | R$_{A34}$ | R$_{B7}$ | O |
| L$_{A649}$ | R$_{B8}$ | R$_{A34}$ | R$_{B10}$ | S | L$_{A779}$ | R$_{B8}$ | R$_{A34}$ | R$_{B10}$ | O |
| L$_{A650}$ | R$_{B8}$ | R$_{A34}$ | R$_{43}$ | S | L$_{A780}$ | R$_{B8}$ | R$_{A34}$ | R$_{43}$ | O, |

L$_{A781}$ through L$_{A1170}$ that are based on a structure of Formula IV,

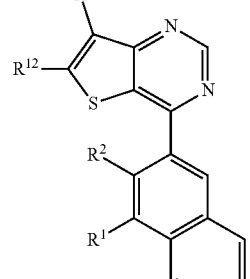

in which R$^1$, R$^2$, R$^{11}$, and R$^{12}$ are defined as provided below:

| Ligand | R$^1$ | R$^2$ | R$^{11}$ | R$^{12}$ | Ligand | R$^1$ | R$^2$ | R$^{11}$ | R$^{12}$ |
|---|---|---|---|---|---|---|---|---|---|
| L$_{A781}$ | H | F | H | H | L$_{A976}$ | R$_{B6}$ | F | H | H |
| L$_{A782}$ | H | F | R$_{B1}$ | H | L$_{A977}$ | R$_{B6}$ | F | R$_{B1}$ | H |
| L$_{A783}$ | H | F | R$_{B3}$ | H | L$_{A978}$ | R$_{B6}$ | F | R$_{B3}$ | H |
| L$_{A784}$ | H | F | R$_{B4}$ | H | L$_{A979}$ | R$_{B6}$ | F | R$_{B4}$ | H |
| L$_{A785}$ | H | F | R$_{B7}$ | H | L$_{A980}$ | R$_{B6}$ | F | R$_{B7}$ | H |
| L$_{A786}$ | H | F | R$_{B10}$ | H | L$_{A981}$ | R$_{B6}$ | F | R$_{B10}$ | H |
| L$_{A787}$ | H | F | R$_{43}$ | H | L$_{A982}$ | R$_{B6}$ | F | R$_{43}$ | H |
| L$_{A788}$ | H | F | R$_{A34}$ | H | L$_{A983}$ | R$_{B6}$ | F | R$_{A34}$ | H |
| L$_{A789}$ | H | F | H | R$_{B1}$ | L$_{A984}$ | R$_{B6}$ | F | H | R$_{B1}$ |
| L$_{A790}$ | H | F | H | R$_{B2}$ | L$_{A985}$ | R$_{B6}$ | F | H | R$_{B2}$ |
| L$_{A791}$ | H | F | H | R$_{B3}$ | L$_{A986}$ | R$_{B6}$ | F | H | R$_{B3}$ |
| L$_{A792}$ | H | F | H | R$_{B4}$ | L$_{A987}$ | R$_{B6}$ | F | H | R$_{B4}$ |
| L$_{A793}$ | H | F | H | R$_{B7}$ | L$_{A988}$ | R$_{B6}$ | F | H | R$_{B7}$ |
| L$_{A794}$ | H | F | H | R$_{B10}$ | L$_{A989}$ | R$_{B6}$ | F | H | R$_{B10}$ |
| L$_{A795}$ | H | F | H | R$_{43}$ | L$_{A990}$ | R$_{B6}$ | F | H | R$_{43}$ |
| L$_{A796}$ | H | F | H | R$_{A34}$ | L$_{A991}$ | R$_{B6}$ | F | H | R$_{A34}$ |
| L$_{A797}$ | H | F | R$_{B1}$ | R$_{B1}$ | L$_{A992}$ | R$_{B6}$ | F | R$_{B1}$ | R$_{B1}$ |
| L$_{A798}$ | H | F | R$_{B3}$ | R$_{B3}$ | L$_{A993}$ | R$_{B6}$ | F | R$_{B3}$ | R$_{B3}$ |
| L$_{A799}$ | H | F | R$_{B4}$ | R$_{B4}$ | L$_{A994}$ | R$_{B6}$ | F | R$_{B4}$ | R$_{B4}$ |
| L$_{A800}$ | H | F | R$_{B7}$ | R$_{B7}$ | L$_{A995}$ | R$_{B6}$ | F | R$_{B7}$ | R$_{B7}$ |
| L$_{A801}$ | H | F | R$_{B10}$ | R$_{B10}$ | L$_{A996}$ | R$_{B6}$ | F | R$_{B10}$ | R$_{B10}$ |
| L$_{A802}$ | H | F | R$_{43}$ | R$_{43}$ | L$_{A997}$ | R$_{B6}$ | F | R$_{43}$ | R$_{43}$ |
| L$_{A803}$ | H | F | R$_{A34}$ | R$_{A34}$ | L$_{A998}$ | R$_{B6}$ | F | R$_{A34}$ | R$_{A34}$ |
| L$_{A804}$ | H | F | R$_{B1}$ | R$_{B3}$ | L$_{A999}$ | R$_{B6}$ | F | R$_{B1}$ | R$_{B3}$ |
| L$_{A805}$ | H | F | R$_{B1}$ | R$_{B4}$ | L$_{A1000}$ | R$_{B6}$ | F | R$_{B1}$ | R$_{B4}$ |
| L$_{A806}$ | H | F | R$_{B1}$ | R$_{B7}$ | L$_{A1001}$ | R$_{B6}$ | F | R$_{B1}$ | R$_{B7}$ |
| L$_{A807}$ | H | F | R$_{B1}$ | R$_{B10}$ | L$_{A1002}$ | R$_{B6}$ | F | R$_{B1}$ | R$_{B10}$ |
| L$_{A808}$ | H | F | R$_{B1}$ | R$_{43}$ | L$_{A1003}$ | R$_{B6}$ | F | R$_{B1}$ | R$_{43}$ |
| L$_{A809}$ | H | F | R$_{B1}$ | R$_{A34}$ | L$_{A1004}$ | R$_{B6}$ | F | R$_{B1}$ | R$_{A34}$ |
| L$_{A810}$ | H | F | R$_{B3}$ | R$_{B1}$ | L$_{A1005}$ | R$_{B6}$ | F | R$_{B3}$ | R$_{B1}$ |
| L$_{A811}$ | H | F | R$_{B3}$ | R$_{B4}$ | L$_{A1006}$ | R$_{B6}$ | F | R$_{B3}$ | R$_{B4}$ |
| L$_{A812}$ | H | F | R$_{B3}$ | R$_{B7}$ | L$_{A1007}$ | R$_{B6}$ | F | R$_{B3}$ | R$_{B7}$ |
| L$_{A813}$ | H | F | R$_{B3}$ | R$_{B10}$ | L$_{A1008}$ | R$_{B6}$ | F | R$_{B3}$ | R$_{B10}$ |
| L$_{A814}$ | H | F | R$_{B3}$ | R$_{43}$ | L$_{A1009}$ | R$_{B6}$ | F | R$_{B3}$ | R$_{43}$ |
| L$_{A815}$ | H | F | R$_{B3}$ | R$_{A34}$ | L$_{A1010}$ | R$_{B6}$ | F | R$_{B3}$ | R$_{A34}$ |
| L$_{A816}$ | H | F | R$_{B4}$ | R$_{B1}$ | L$_{A1011}$ | R$_{B6}$ | F | R$_{B4}$ | R$_{B1}$ |
| L$_{A817}$ | H | F | R$_{B4}$ | R$_{B3}$ | L$_{A1012}$ | R$_{B6}$ | F | R$_{B4}$ | R$_{B3}$ |

| Ligand | R¹ | R² | R¹¹ | R¹² | Ligand | R¹ | R² | R¹¹ | R¹² | Ligand | R¹ | R² | R¹¹ | R¹² | Ligand | R¹ | R² | R¹¹ | R¹² |
|---|---|---|---|---|---|---|---|---|---|---|---|---|---|---|---|---|---|---|---|
| $L_{4818}$ | H | F | $R_{B4}$ | $R_{B7}$ | $L_{41013}$ | $R_{B6}$ | F | $R_{B4}$ | $R_{B7}$ | $L_{4895}$ | H | $R_{B1}$ | $R_{B10}$ | $R_{B4}$ | $L_{41090}$ | $R_{B1}$ | $R_{B1}$ | $R_{B10}$ | $R_{B4}$ |
| $L_{4819}$ | H | F | $R_{B4}$ | $R_{B10}$ | $L_{41014}$ | $R_{B6}$ | F | $R_{B4}$ | $R_{B10}$ | $L_{4896}$ | H | $R_{B1}$ | $R_{B10}$ | $R_{B7}$ | $L_{41091}$ | $R_{B1}$ | $R_{B1}$ | $R_{B10}$ | $R_{B7}$ |
| $L_{4820}$ | H | F | $R_{B4}$ | $R_{43}$ | $L_{41015}$ | $R_{B6}$ | F | $R_{B4}$ | $R_{43}$ | $L_{4897}$ | H | $R_{B1}$ | $R_{B10}$ | $R_{43}$ | $L_{41092}$ | $R_{B1}$ | $R_{B1}$ | $R_{B10}$ | $R_{43}$ |
| $L_{4821}$ | H | F | $R_{B4}$ | $R_{434}$ | $L_{41016}$ | $R_{B6}$ | F | $R_{B4}$ | $R_{434}$ | $L_{4898}$ | H | $R_{B1}$ | $R_{B10}$ | $R_{434}$ | $L_{41093}$ | $R_{B1}$ | $R_{B1}$ | $R_{B10}$ | $R_{434}$ |
| $L_{4822}$ | H | F | $R_{B7}$ | $R_{B1}$ | $L_{41017}$ | $R_{B6}$ | F | $R_{B7}$ | $R_{B1}$ | $L_{4899}$ | H | $R_{B1}$ | $R_{43}$ | $R_{B1}$ | $L_{41094}$ | $R_{B1}$ | $R_{B1}$ | $R_{43}$ | $R_{B1}$ |
| $L_{4823}$ | H | F | $R_{B7}$ | $R_{B3}$ | $L_{41018}$ | $R_{B6}$ | F | $R_{B7}$ | $R_{B3}$ | $L_{4900}$ | H | $R_{B1}$ | $R_{43}$ | $R_{B3}$ | $L_{41095}$ | $R_{B1}$ | $R_{B1}$ | $R_{43}$ | $R_{B3}$ |
| $L_{4824}$ | H | F | $R_{B7}$ | $R_{B4}$ | $L_{41019}$ | $R_{B6}$ | F | $R_{B7}$ | $R_{B4}$ | $L_{4901}$ | H | $R_{B1}$ | $R_{43}$ | $R_{B4}$ | $L_{41096}$ | $R_{B1}$ | $R_{B1}$ | $R_{43}$ | $R_{B4}$ |
| $L_{4825}$ | H | F | $R_{B7}$ | $R_{B10}$ | $L_{41020}$ | $R_{B6}$ | F | $R_{B7}$ | $R_{B10}$ | $L_{4902}$ | H | $R_{B1}$ | $R_{43}$ | $R_{B7}$ | $L_{41097}$ | $R_{B1}$ | $R_{B1}$ | $R_{43}$ | $R_{B7}$ |
| $L_{4826}$ | H | F | $R_{B7}$ | $R_{43}$ | $L_{41021}$ | $R_{B6}$ | F | $R_{B7}$ | $R_{43}$ | $L_{4903}$ | H | $R_{B1}$ | $R_{43}$ | $R_{B10}$ | $L_{41098}$ | $R_{B1}$ | $R_{B1}$ | $R_{43}$ | $R_{B10}$ |
| $L_{4827}$ | H | F | $R_{B7}$ | $R_{434}$ | $L_{41022}$ | $R_{B6}$ | F | $R_{B7}$ | $R_{434}$ | $L_{4904}$ | H | $R_{B1}$ | $R_{43}$ | $R_{434}$ | $L_{41099}$ | $R_{B1}$ | $R_{B1}$ | $R_{43}$ | $R_{434}$ |
| $L_{4828}$ | H | F | $R_{B10}$ | $R_{B1}$ | $L_{41023}$ | $R_{B6}$ | F | $R_{B10}$ | $R_{B1}$ | $L_{4905}$ | H | $R_{B1}$ | $R_{434}$ | $R_{B1}$ | $L_{41100}$ | $R_{B1}$ | $R_{B1}$ | $R_{434}$ | $R_{B1}$ |
| $L_{4829}$ | H | F | $R_{B10}$ | $R_{B3}$ | $L_{41024}$ | $R_{B6}$ | F | $R_{B10}$ | $R_{B3}$ | $L_{4906}$ | H | $R_{B1}$ | $R_{434}$ | $R_{B3}$ | $L_{41101}$ | $R_{B1}$ | $R_{B1}$ | $R_{434}$ | $R_{B3}$ |
| $L_{4830}$ | H | F | $R_{B10}$ | $R_{B4}$ | $L_{41025}$ | $R_{B6}$ | F | $R_{B10}$ | $R_{B4}$ | $L_{4907}$ | H | $R_{B1}$ | $R_{434}$ | $R_{B4}$ | $L_{41102}$ | $R_{B1}$ | $R_{B1}$ | $R_{434}$ | $R_{B4}$ |
| $L_{4831}$ | H | F | $R_{B10}$ | $R_{B7}$ | $L_{41026}$ | $R_{B6}$ | F | $R_{B10}$ | $R_{B7}$ | $L_{4908}$ | H | $R_{B1}$ | $R_{434}$ | $R_{B7}$ | $L_{41103}$ | $R_{B1}$ | $R_{B1}$ | $R_{434}$ | $R_{B7}$ |
| $L_{4832}$ | H | F | $R_{B10}$ | $R_{43}$ | $L_{41027}$ | $R_{B6}$ | F | $R_{B10}$ | $R_{43}$ | $L_{4909}$ | H | $R_{B1}$ | $R_{434}$ | $R_{B10}$ | $L_{41104}$ | $R_{B1}$ | $R_{B1}$ | $R_{434}$ | $R_{B10}$ |
| $L_{4833}$ | H | F | $R_{B10}$ | $R_{434}$ | $L_{41028}$ | $R_{B6}$ | F | $R_{B10}$ | $R_{434}$ | $L_{4910}$ | H | $R_{B1}$ | $R_{434}$ | $R_{43}$ | $L_{41105}$ | $R_{B1}$ | $R_{B1}$ | $R_{434}$ | $R_{43}$ |
| $L_{4834}$ | H | F | $R_{43}$ | $R_{B1}$ | $L_{41029}$ | $R_{B6}$ | F | $R_{43}$ | $R_{B1}$ | $L_{4911}$ | $R_{B1}$ | F | H | H | $L_{41106}$ | $R_{B6}$ | $R_{B1}$ | H | H |
| $L_{4835}$ | H | F | $R_{43}$ | $R_{B3}$ | $L_{41030}$ | $R_{B6}$ | F | $R_{43}$ | $R_{B3}$ | $L_{4912}$ | $R_{B1}$ | F | $R_{B1}$ | H | $L_{41107}$ | $R_{B6}$ | $R_{B1}$ | $R_{B1}$ | H |
| $L_{4836}$ | H | F | $R_{43}$ | $R_{B4}$ | $L_{41031}$ | $R_{B6}$ | F | $R_{43}$ | $R_{B4}$ | $L_{4913}$ | $R_{B1}$ | F | $R_{B3}$ | H | $L_{41108}$ | $R_{B6}$ | $R_{B1}$ | $R_{B3}$ | H |
| $L_{4837}$ | H | F | $R_{43}$ | $R_{B7}$ | $L_{41032}$ | $R_{B6}$ | F | $R_{43}$ | $R_{B7}$ | $L_{4914}$ | $R_{B1}$ | F | $R_{B4}$ | H | $L_{41109}$ | $R_{B6}$ | $R_{B1}$ | $R_{B4}$ | H |
| $L_{4838}$ | H | F | $R_{43}$ | $R_{B10}$ | $L_{41033}$ | $R_{B6}$ | F | $R_{43}$ | $R_{B10}$ | $L_{4915}$ | $R_{B1}$ | F | $R_{B7}$ | H | $L_{41110}$ | $R_{B6}$ | $R_{B1}$ | $R_{B7}$ | H |
| $L_{4839}$ | H | F | $R_{43}$ | $R_{434}$ | $L_{41034}$ | $R_{B6}$ | F | $R_{43}$ | $R_{434}$ | $L_{4916}$ | $R_{B1}$ | F | $R_{B10}$ | H | $L_{41111}$ | $R_{B6}$ | $R_{B1}$ | $R_{B10}$ | H |
| $L_{4840}$ | H | F | $R_{434}$ | $R_{B1}$ | $L_{41035}$ | $R_{B6}$ | F | $R_{434}$ | $R_{B1}$ | $L_{4917}$ | $R_{B1}$ | F | $R_{43}$ | H | $L_{41112}$ | $R_{B6}$ | $R_{B1}$ | $R_{43}$ | H |
| $L_{4841}$ | H | F | $R_{434}$ | $R_{B3}$ | $L_{41036}$ | $R_{B6}$ | F | $R_{434}$ | $R_{B3}$ | $L_{4918}$ | $R_{B1}$ | F | $R_{434}$ | H | $L_{41113}$ | $R_{B6}$ | $R_{B1}$ | $R_{434}$ | H |
| $L_{4842}$ | H | F | $R_{434}$ | $R_{B4}$ | $L_{41037}$ | $R_{B6}$ | F | $R_{434}$ | $R_{B4}$ | $L_{4919}$ | $R_{B1}$ | F | H | $R_{B1}$ | $L_{41114}$ | $R_{B6}$ | $R_{B1}$ | H | $R_{B1}$ |
| $L_{4843}$ | H | F | $R_{434}$ | $R_{B7}$ | $L_{41038}$ | $R_{B6}$ | F | $R_{434}$ | $R_{B7}$ | $L_{4920}$ | $R_{B1}$ | F | H | $R_{B2}$ | $L_{41115}$ | $R_{B6}$ | $R_{B1}$ | H | $R_{B2}$ |
| $L_{4844}$ | H | F | $R_{434}$ | $R_{B10}$ | $L_{41039}$ | $R_{B6}$ | F | $R_{434}$ | $R_{B10}$ | $L_{4921}$ | $R_{B1}$ | F | H | $R_{B3}$ | $L_{41116}$ | $R_{B6}$ | $R_{B1}$ | H | $R_{B3}$ |
| $L_{4845}$ | H | F | $R_{434}$ | $R_{43}$ | $L_{41040}$ | $R_{B6}$ | F | $R_{434}$ | $R_{43}$ | $L_{4922}$ | $R_{B1}$ | F | H | $R_{B4}$ | $L_{41117}$ | $R_{B6}$ | $R_{B1}$ | H | $R_{B4}$ |
| $L_{4846}$ | H | $R_{B1}$ | H | H | $L_{41041}$ | $R_{B1}$ | $R_{B1}$ | H | H | $L_{4923}$ | $R_{B1}$ | F | H | $R_{B7}$ | $L_{41118}$ | $R_{B6}$ | $R_{B1}$ | H | $R_{B7}$ |
| $L_{4847}$ | H | $R_{B1}$ | $R_{B1}$ | H | $L_{41042}$ | $R_{B1}$ | $R_{B1}$ | $R_{B1}$ | H | $L_{4924}$ | $R_{B1}$ | F | H | $R_{B10}$ | $L_{41119}$ | $R_{B6}$ | $R_{B1}$ | H | $R_{B10}$ |
| $L_{4848}$ | H | $R_{B1}$ | $R_{B3}$ | H | $L_{41043}$ | $R_{B1}$ | $R_{B1}$ | $R_{B3}$ | H | $L_{4925}$ | $R_{B1}$ | F | H | $R_{43}$ | $L_{41120}$ | $R_{B6}$ | $R_{B1}$ | H | $R_{43}$ |
| $L_{4849}$ | H | $R_{B1}$ | $R_{B4}$ | H | $L_{41044}$ | $R_{B1}$ | $R_{B1}$ | $R_{B4}$ | H | $L_{4926}$ | $R_{B1}$ | F | H | $R_{434}$ | $L_{41121}$ | $R_{B6}$ | $R_{B1}$ | H | $R_{434}$ |
| $L_{4850}$ | H | $R_{B1}$ | $R_{B7}$ | H | $L_{41045}$ | $R_{B1}$ | $R_{B1}$ | $R_{B7}$ | H | $L_{4927}$ | $R_{B1}$ | F | $R_{B1}$ | $R_{B1}$ | $L_{41122}$ | $R_{B6}$ | $R_{B1}$ | $R_{B1}$ | $R_{B1}$ |
| $L_{4851}$ | H | $R_{B1}$ | $R_{B10}$ | H | $L_{41046}$ | $R_{B1}$ | $R_{B1}$ | $R_{B10}$ | H | $L_{4928}$ | $R_{B1}$ | F | $R_{B3}$ | $R_{B3}$ | $L_{41123}$ | $R_{B6}$ | $R_{B1}$ | $R_{B3}$ | $R_{B3}$ |
| $L_{4852}$ | H | $R_{B1}$ | $R_{43}$ | H | $L_{41047}$ | $R_{B1}$ | $R_{B1}$ | $R_{43}$ | H | $L_{4929}$ | $R_{B1}$ | F | $R_{B4}$ | $R_{B4}$ | $L_{41124}$ | $R_{B6}$ | $R_{B1}$ | $R_{B4}$ | $R_{B4}$ |
| $L_{4853}$ | H | $R_{B1}$ | $R_{434}$ | H | $L_{41048}$ | $R_{B1}$ | $R_{B1}$ | $R_{434}$ | H | $L_{4930}$ | $R_{B1}$ | F | $R_{B7}$ | $R_{B7}$ | $L_{41125}$ | $R_{B6}$ | $R_{B1}$ | $R_{B7}$ | $R_{B7}$ |
| $L_{4854}$ | H | $R_{B1}$ | H | $R_{B1}$ | $L_{41049}$ | $R_{B1}$ | $R_{B1}$ | H | $R_{B1}$ | $L_{4931}$ | $R_{B1}$ | F | $R_{B10}$ | $R_{B10}$ | $L_{41126}$ | $R_{B6}$ | $R_{B1}$ | $R_{B10}$ | $R_{B10}$ |
| $L_{4855}$ | H | $R_{B1}$ | H | $R_{B2}$ | $L_{41050}$ | $R_{B1}$ | $R_{B1}$ | H | $R_{B2}$ | $L_{4932}$ | $R_{B1}$ | F | $R_{43}$ | $R_{43}$ | $L_{41127}$ | $R_{B6}$ | $R_{B1}$ | $R_{43}$ | $R_{43}$ |
| $L_{4856}$ | H | $R_{B1}$ | H | $R_{B3}$ | $L_{41051}$ | $R_{B1}$ | $R_{B1}$ | H | $R_{B3}$ | $L_{4933}$ | $R_{B1}$ | F | $R_{434}$ | $R_{434}$ | $L_{41128}$ | $R_{B6}$ | $R_{B1}$ | $R_{434}$ | $R_{434}$ |
| $L_{4857}$ | H | $R_{B1}$ | H | $R_{B4}$ | $L_{41052}$ | $R_{B1}$ | $R_{B1}$ | H | $R_{B4}$ | $L_{4934}$ | $R_{B1}$ | F | $R_{B1}$ | $R_{B3}$ | $L_{41129}$ | $R_{B6}$ | $R_{B1}$ | $R_{B1}$ | $R_{B3}$ |
| $L_{4858}$ | H | $R_{B1}$ | H | $R_{B7}$ | $L_{41053}$ | $R_{B1}$ | $R_{B1}$ | H | $R_{B7}$ | $L_{4935}$ | $R_{B1}$ | F | $R_{B1}$ | $R_{B4}$ | $L_{41130}$ | $R_{B6}$ | $R_{B1}$ | $R_{B1}$ | $R_{B4}$ |
| $L_{4859}$ | H | $R_{B1}$ | H | $R_{B10}$ | $L_{41054}$ | $R_{B1}$ | $R_{B1}$ | H | $R_{B10}$ | $L_{4936}$ | $R_{B1}$ | F | $R_{B1}$ | $R_{B7}$ | $L_{41131}$ | $R_{B6}$ | $R_{B1}$ | $R_{B1}$ | $R_{B7}$ |
| $L_{4860}$ | H | $R_{B1}$ | H | $R_{43}$ | $L_{41055}$ | $R_{B1}$ | $R_{B1}$ | H | $R_{43}$ | $L_{4937}$ | $R_{B1}$ | F | $R_{B1}$ | $R_{B10}$ | $L_{41132}$ | $R_{B6}$ | $R_{B1}$ | $R_{B1}$ | $R_{B10}$ |
| $L_{4861}$ | H | $R_{B1}$ | H | $R_{434}$ | $L_{41056}$ | $R_{B1}$ | $R_{B1}$ | H | $R_{434}$ | $L_{4938}$ | $R_{B1}$ | F | $R_{B1}$ | $R_{43}$ | $L_{41133}$ | $R_{B6}$ | $R_{B1}$ | $R_{B1}$ | $R_{43}$ |
| $L_{4862}$ | H | $R_{B1}$ | $R_{B1}$ | $R_{B1}$ | $L_{41057}$ | $R_{B1}$ | $R_{B1}$ | $R_{B1}$ | $R_{B1}$ | $L_{4939}$ | $R_{B1}$ | F | $R_{B1}$ | $R_{434}$ | $L_{41134}$ | $R_{B6}$ | $R_{B1}$ | $R_{B1}$ | $R_{434}$ |
| $L_{4863}$ | H | $R_{B1}$ | $R_{B3}$ | $R_{B3}$ | $L_{41058}$ | $R_{B1}$ | $R_{B1}$ | $R_{B3}$ | $R_{B3}$ | $L_{4940}$ | $R_{B1}$ | F | $R_{B3}$ | $R_{B1}$ | $L_{41135}$ | $R_{B6}$ | $R_{B1}$ | $R_{B3}$ | $R_{B1}$ |
| $L_{4864}$ | H | $R_{B1}$ | $R_{B4}$ | $R_{B4}$ | $L_{41059}$ | $R_{B1}$ | $R_{B1}$ | $R_{B4}$ | $R_{B4}$ | $L_{4941}$ | $R_{B1}$ | F | $R_{B3}$ | $R_{B4}$ | $L_{41136}$ | $R_{B6}$ | $R_{B1}$ | $R_{B3}$ | $R_{B4}$ |
| $L_{4865}$ | H | $R_{B1}$ | $R_{B7}$ | $R_{B7}$ | $L_{41060}$ | $R_{B1}$ | $R_{B1}$ | $R_{B7}$ | $R_{B7}$ | $L_{4942}$ | $R_{B1}$ | F | $R_{B3}$ | $R_{B7}$ | $L_{41137}$ | $R_{B6}$ | $R_{B1}$ | $R_{B3}$ | $R_{B7}$ |
| $L_{4866}$ | H | $R_{B1}$ | $R_{B10}$ | $R_{B10}$ | $L_{41061}$ | $R_{B1}$ | $R_{B1}$ | $R_{B10}$ | $R_{B10}$ | $L_{4943}$ | $R_{B1}$ | F | $R_{B3}$ | $R_{B10}$ | $L_{41138}$ | $R_{B6}$ | $R_{B1}$ | $R_{B3}$ | $R_{B10}$ |
| $L_{4867}$ | H | $R_{B1}$ | $R_{43}$ | $R_{43}$ | $L_{41062}$ | $R_{B1}$ | $R_{B1}$ | $R_{43}$ | $R_{43}$ | $L_{4944}$ | $R_{B1}$ | F | $R_{B3}$ | $R_{43}$ | $L_{41139}$ | $R_{B6}$ | $R_{B1}$ | $R_{B3}$ | $R_{43}$ |
| $L_{4868}$ | H | $R_{B1}$ | $R_{434}$ | $R_{434}$ | $L_{41063}$ | $R_{B1}$ | $R_{B1}$ | $R_{434}$ | $R_{434}$ | $L_{4945}$ | $R_{B1}$ | F | $R_{B3}$ | $R_{434}$ | $L_{41140}$ | $R_{B6}$ | $R_{B1}$ | $R_{B3}$ | $R_{434}$ |
| $L_{4869}$ | H | $R_{B1}$ | $R_{B1}$ | $R_{B3}$ | $L_{41064}$ | $R_{B1}$ | $R_{B1}$ | $R_{B1}$ | $R_{B3}$ | $L_{4946}$ | $R_{B1}$ | F | $R_{B4}$ | $R_{B1}$ | $L_{41141}$ | $R_{B6}$ | $R_{B1}$ | $R_{B4}$ | $R_{B1}$ |
| $L_{4870}$ | H | $R_{B1}$ | $R_{B1}$ | $R_{B4}$ | $L_{41065}$ | $R_{B1}$ | $R_{B1}$ | $R_{B1}$ | $R_{B4}$ | $L_{4947}$ | $R_{B1}$ | F | $R_{B4}$ | $R_{B3}$ | $L_{41142}$ | $R_{B6}$ | $R_{B1}$ | $R_{B4}$ | $R_{B3}$ |
| $L_{4871}$ | H | $R_{B1}$ | $R_{B1}$ | $R_{B7}$ | $L_{41066}$ | $R_{B1}$ | $R_{B1}$ | $R_{B1}$ | $R_{B7}$ | $L_{4948}$ | $R_{B1}$ | F | $R_{B4}$ | $R_{B7}$ | $L_{41143}$ | $R_{B6}$ | $R_{B1}$ | $R_{B4}$ | $R_{B7}$ |
| $L_{4872}$ | H | $R_{B1}$ | $R_{B1}$ | $R_{B10}$ | $L_{41067}$ | $R_{B1}$ | $R_{B1}$ | $R_{B1}$ | $R_{B10}$ | $L_{4949}$ | $R_{B1}$ | F | $R_{B4}$ | $R_{B10}$ | $L_{41144}$ | $R_{B6}$ | $R_{B1}$ | $R_{B4}$ | $R_{B10}$ |
| $L_{4873}$ | H | $R_{B1}$ | $R_{B1}$ | $R_{43}$ | $L_{41068}$ | $R_{B1}$ | $R_{B1}$ | $R_{B1}$ | $R_{43}$ | $L_{4950}$ | $R_{B1}$ | F | $R_{B4}$ | $R_{43}$ | $L_{41145}$ | $R_{B6}$ | $R_{B1}$ | $R_{B4}$ | $R_{43}$ |
| $L_{4874}$ | H | $R_{B1}$ | $R_{B1}$ | $R_{434}$ | $L_{41069}$ | $R_{B1}$ | $R_{B1}$ | $R_{B1}$ | $R_{434}$ | $L_{4951}$ | $R_{B1}$ | F | $R_{B4}$ | $R_{434}$ | $L_{41146}$ | $R_{B6}$ | $R_{B1}$ | $R_{B4}$ | $R_{434}$ |
| $L_{4875}$ | H | $R_{B1}$ | $R_{B3}$ | $R_{B1}$ | $L_{41070}$ | $R_{B1}$ | $R_{B1}$ | $R_{B3}$ | $R_{B1}$ | $L_{4952}$ | $R_{B1}$ | F | $R_{B7}$ | $R_{B1}$ | $L_{41147}$ | $R_{B6}$ | $R_{B1}$ | $R_{B7}$ | $R_{B1}$ |
| $L_{4876}$ | H | $R_{B1}$ | $R_{B3}$ | $R_{B4}$ | $L_{41071}$ | $R_{B1}$ | $R_{B1}$ | $R_{B3}$ | $R_{B4}$ | $L_{4953}$ | $R_{B1}$ | F | $R_{B7}$ | $R_{B3}$ | $L_{41148}$ | $R_{B6}$ | $R_{B1}$ | $R_{B7}$ | $R_{B3}$ |
| $L_{4877}$ | H | $R_{B1}$ | $R_{B3}$ | $R_{B7}$ | $L_{41072}$ | $R_{B1}$ | $R_{B1}$ | $R_{B3}$ | $R_{B7}$ | $L_{4954}$ | $R_{B1}$ | F | $R_{B7}$ | $R_{B4}$ | $L_{41149}$ | $R_{B6}$ | $R_{B1}$ | $R_{B7}$ | $R_{B4}$ |
| $L_{4878}$ | H | $R_{B1}$ | $R_{B3}$ | $R_{B10}$ | $L_{41073}$ | $R_{B1}$ | $R_{B1}$ | $R_{B3}$ | $R_{B10}$ | $L_{4955}$ | $R_{B1}$ | F | $R_{B7}$ | $R_{B10}$ | $L_{41150}$ | $R_{B6}$ | $R_{B1}$ | $R_{B7}$ | $R_{B10}$ |
| $L_{4879}$ | H | $R_{B1}$ | $R_{B3}$ | $R_{43}$ | $L_{41074}$ | $R_{B1}$ | $R_{B1}$ | $R_{B3}$ | $R_{43}$ | $L_{4956}$ | $R_{B1}$ | F | $R_{B7}$ | $R_{43}$ | $L_{41151}$ | $R_{B6}$ | $R_{B1}$ | $R_{B7}$ | $R_{43}$ |
| $L_{4880}$ | H | $R_{B1}$ | $R_{B3}$ | $R_{434}$ | $L_{41075}$ | $R_{B1}$ | $R_{B1}$ | $R_{B3}$ | $R_{434}$ | $L_{4957}$ | $R_{B1}$ | F | $R_{B7}$ | $R_{434}$ | $L_{41152}$ | $R_{B6}$ | $R_{B1}$ | $R_{B7}$ | $R_{434}$ |
| $L_{4881}$ | H | $R_{B1}$ | $R_{B4}$ | $R_{B1}$ | $L_{41076}$ | $R_{B1}$ | $R_{B1}$ | $R_{B4}$ | $R_{B1}$ | $L_{4958}$ | $R_{B1}$ | F | $R_{B10}$ | $R_{B1}$ | $L_{41153}$ | $R_{B6}$ | $R_{B1}$ | $R_{B10}$ | $R_{B1}$ |
| $L_{4882}$ | H | $R_{B1}$ | $R_{B4}$ | $R_{B3}$ | $L_{41077}$ | $R_{B1}$ | $R_{B1}$ | $R_{B4}$ | $R_{B3}$ | $L_{4959}$ | $R_{B1}$ | F | $R_{B10}$ | $R_{B3}$ | $L_{41154}$ | $R_{B6}$ | $R_{B1}$ | $R_{B10}$ | $R_{B3}$ |
| $L_{4883}$ | H | $R_{B1}$ | $R_{B4}$ | $R_{B7}$ | $L_{41078}$ | $R_{B1}$ | $R_{B1}$ | $R_{B4}$ | $R_{B7}$ | $L_{4960}$ | $R_{B1}$ | F | $R_{B10}$ | $R_{B4}$ | $L_{41155}$ | $R_{B6}$ | $R_{B1}$ | $R_{B10}$ | $R_{B4}$ |
| $L_{4884}$ | H | $R_{B1}$ | $R_{B4}$ | $R_{B10}$ | $L_{41079}$ | $R_{B1}$ | $R_{B1}$ | $R_{B4}$ | $R_{B10}$ | $L_{4961}$ | $R_{B1}$ | F | $R_{B10}$ | $R_{B7}$ | $L_{41156}$ | $R_{B6}$ | $R_{B1}$ | $R_{B10}$ | $R_{B7}$ |
| $L_{4885}$ | H | $R_{B1}$ | $R_{B4}$ | $R_{43}$ | $L_{41080}$ | $R_{B1}$ | $R_{B1}$ | $R_{B4}$ | $R_{43}$ | $L_{4962}$ | $R_{B1}$ | F | $R_{B10}$ | $R_{43}$ | $L_{41157}$ | $R_{B6}$ | $R_{B1}$ | $R_{B10}$ | $R_{43}$ |
| $L_{4886}$ | H | $R_{B1}$ | $R_{B4}$ | $R_{434}$ | $L_{41081}$ | $R_{B1}$ | $R_{B1}$ | $R_{B4}$ | $R_{434}$ | $L_{4963}$ | $R_{B1}$ | F | $R_{B10}$ | $R_{434}$ | $L_{41158}$ | $R_{B6}$ | $R_{B1}$ | $R_{B10}$ | $R_{434}$ |
| $L_{4887}$ | H | $R_{B1}$ | $R_{B7}$ | $R_{B1}$ | $L_{41082}$ | $R_{B1}$ | $R_{B1}$ | $R_{B7}$ | $R_{B1}$ | $L_{4964}$ | $R_{B1}$ | F | $R_{43}$ | $R_{B1}$ | $L_{41159}$ | $R_{B6}$ | $R_{B1}$ | $R_{43}$ | $R_{B1}$ |
| $L_{4888}$ | H | $R_{B1}$ | $R_{B7}$ | $R_{B3}$ | $L_{41083}$ | $R_{B1}$ | $R_{B1}$ | $R_{B7}$ | $R_{B3}$ | $L_{4965}$ | $R_{B1}$ | F | $R_{43}$ | $R_{B3}$ | $L_{41160}$ | $R_{B6}$ | $R_{B1}$ | $R_{43}$ | $R_{B3}$ |
| $L_{4889}$ | H | $R_{B1}$ | $R_{B7}$ | $R_{B4}$ | $L_{41084}$ | $R_{B1}$ | $R_{B1}$ | $R_{B7}$ | $R_{B4}$ | $L_{4966}$ | $R_{B1}$ | F | $R_{43}$ | $R_{B4}$ | $L_{41161}$ | $R_{B6}$ | $R_{B1}$ | $R_{43}$ | $R_{B4}$ |
| $L_{4890}$ | H | $R_{B1}$ | $R_{B7}$ | $R_{B10}$ | $L_{41085}$ | $R_{B1}$ | $R_{B1}$ | $R_{B7}$ | $R_{B10}$ | $L_{4967}$ | $R_{B1}$ | F | $R_{43}$ | $R_{B7}$ | $L_{41162}$ | $R_{B6}$ | $R_{B1}$ | $R_{43}$ | $R_{B7}$ |
| $L_{4891}$ | H | $R_{B1}$ | $R_{B7}$ | $R_{43}$ | $L_{41086}$ | $R_{B1}$ | $R_{B1}$ | $R_{B7}$ | $R_{43}$ | $L_{4968}$ | $R_{B1}$ | F | $R_{43}$ | $R_{B10}$ | $L_{41163}$ | $R_{B6}$ | $R_{B1}$ | $R_{43}$ | $R_{B10}$ |
| $L_{4892}$ | H | $R_{B1}$ | $R_{B7}$ | $R_{434}$ | $L_{41087}$ | $R_{B1}$ | $R_{B1}$ | $R_{B7}$ | $R_{434}$ | $L_{4969}$ | $R_{B1}$ | F | $R_{43}$ | $R_{434}$ | $L_{41164}$ | $R_{B6}$ | $R_{B1}$ | $R_{43}$ | $R_{434}$ |
| $L_{4893}$ | H | $R_{B1}$ | $R_{B10}$ | $R_{B1}$ | $L_{41088}$ | $R_{B1}$ | $R_{B1}$ | $R_{B10}$ | $R_{B1}$ | $L_{4970}$ | $R_{B1}$ | F | $R_{434}$ | $R_{B1}$ | $L_{41165}$ | $R_{B6}$ | $R_{B1}$ | $R_{434}$ | $R_{B1}$ |
| $L_{4894}$ | H | $R_{B1}$ | $R_{B10}$ | $R_{B3}$ | $L_{41089}$ | $R_{B1}$ | $R_{B1}$ | $R_{B10}$ | $R_{B3}$ | $L_{4971}$ | $R_{B1}$ | F | $R_{434}$ | $R_{B3}$ | $L_{41166}$ | $R_{B6}$ | $R_{B1}$ | $R_{434}$ | $R_{B3}$ |

-continued

| Ligand | $R^1$ | $R^2$ | $R^{11}$ | $R^{12}$ | Ligand | $R^1$ | $R^2$ | $R^{11}$ | $R^{12}$ |
|---|---|---|---|---|---|---|---|---|---|
| $L_{A972}$ | $R_{B1}$ | F | $R_{A34}$ | $R_{B4}$ | $L_{A1167}$ | $R_{B6}$ | $R_{B1}$ | $R_{A34}$ | $R_{B4}$ |
| $L_{A973}$ | $R_{B1}$ | F | $R_{A34}$ | $R_{B7}$ | $L_{A1168}$ | $R_{B6}$ | $R_{B1}$ | $R_{A34}$ | $R_{B7}$ |
| $L_{A974}$ | $R_{B1}$ | F | $R_{A34}$ | $R_{B10}$ | $L_{A1169}$ | $R_{B6}$ | $R_{B1}$ | $R_{A34}$ | $R_{B10}$ |
| $L_{A975}$ | $R_{B1}$ | F | $R_{A34}$ | $R_{A3}$ | $L_{A1170}$ | $R_{B6}$ | $R_{B1}$ | $R_{A34}$ | $R_{A3}$, |

$L_{A1171}$ through $L_{A1266}$ that are based on a structure of Formula V,

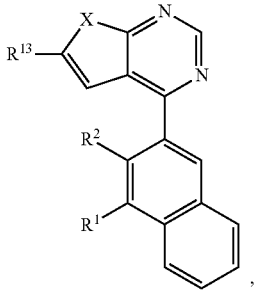

in which $R^1$, $R^2$, $R^{13}$, and X are defined as provided below:

| Ligand | $R^1$ | $R^2$ | $R^{13}$ | X | Ligand | $R^1$ | $R^2$ | $R^{13}$ | X |
|---|---|---|---|---|---|---|---|---|---|
| $L_{A1171}$ | $R_{B6}$ | H | H | S | $L_{A1219}$ | $R_{B6}$ | H | H | O |
| $L_{A1172}$ | $R_{B6}$ | H | $R_{B1}$ | S | $L_{A1220}$ | $R_{B6}$ | H | $R_{B1}$ | O |
| $L_{A1173}$ | $R_{B6}$ | H | $R_{B3}$ | S | $L_{A1221}$ | $R_{B6}$ | H | $R_{B3}$ | O |
| $L_{A1174}$ | $R_{B6}$ | H | $R_{B4}$ | S | $L_{A1222}$ | $R_{B6}$ | H | $R_{B4}$ | O |
| $L_{A1175}$ | $R_{B6}$ | H | $R_{B7}$ | S | $L_{A1223}$ | $R_{B6}$ | H | $R_{B7}$ | O |
| $L_{A1176}$ | $R_{B6}$ | H | $R_{B10}$ | S | $L_{A1224}$ | $R_{B6}$ | H | $R_{B10}$ | O |
| $L_{A1177}$ | $R_{B6}$ | H | $R_{A3}$ | S | $L_{A1225}$ | $R_{B6}$ | H | $R_{A3}$ | O |
| $L_{A1178}$ | $R_{B6}$ | H | $R_{A34}$ | S | $L_{A1226}$ | $R_{B6}$ | H | $R_{A34}$ | O |
| $L_{A1179}$ | $R_{B8}$ | H | $R_{B1}$ | S | $L_{A1227}$ | $R_{B8}$ | H | $R_{B1}$ | O |
| $L_{A1180}$ | $R_{B8}$ | H | $R_{B2}$ | S | $L_{A1228}$ | $R_{B8}$ | H | $R_{B2}$ | O |
| $L_{A1181}$ | $R_{B8}$ | H | $R_{B3}$ | S | $L_{A1229}$ | $R_{B8}$ | H | $R_{B3}$ | O |
| $L_{A1182}$ | $R_{B8}$ | H | $R_{B4}$ | S | $L_{A1230}$ | $R_{B8}$ | H | $R_{B4}$ | O |
| $L_{A1183}$ | $R_{B8}$ | H | $R_{B7}$ | S | $L_{A1231}$ | $R_{B8}$ | H | $R_{B7}$ | O |
| $L_{A1184}$ | $R_{B8}$ | H | $R_{B10}$ | S | $L_{A1232}$ | $R_{B8}$ | H | $R_{B10}$ | O |
| $L_{A1185}$ | $R_{B8}$ | H | $R_{A3}$ | S | $L_{A1233}$ | $R_{B8}$ | H | $R_{A3}$ | O |
| $L_{A1186}$ | $R_{B8}$ | H | $R_{A34}$ | S | $L_{A1234}$ | $R_{B8}$ | H | $R_{A34}$ | O |
| $L_{A1187}$ | $R_{B6}$ | F | H | S | $L_{A1235}$ | $R_{B6}$ | F | H | O |
| $L_{A1188}$ | $R_{B6}$ | F | $R_{B1}$ | S | $L_{A1236}$ | $R_{B6}$ | F | $R_{B1}$ | O |
| $L_{A1189}$ | $R_{B6}$ | F | $R_{B3}$ | S | $L_{A1237}$ | $R_{B6}$ | F | $R_{B3}$ | O |
| $L_{A1190}$ | $R_{B6}$ | F | $R_{B4}$ | S | $L_{A1238}$ | $R_{B6}$ | F | $R_{B4}$ | O |
| $L_{A1191}$ | $R_{B6}$ | F | $R_{B7}$ | S | $L_{A1239}$ | $R_{B6}$ | F | $R_{B7}$ | O |
| $L_{A1192}$ | $R_{B6}$ | F | $R_{B10}$ | S | $L_{A1240}$ | $R_{B6}$ | F | $R_{B10}$ | O |
| $L_{A1193}$ | $R_{B6}$ | F | $R_{A3}$ | S | $L_{A1241}$ | $R_{B6}$ | F | $R_{A3}$ | O |
| $L_{A1194}$ | $R_{B6}$ | F | $R_{A34}$ | S | $L_{A1242}$ | $R_{B6}$ | F | $R_{A34}$ | O |
| $L_{A1195}$ | $R_{B8}$ | F | $R_{B1}$ | S | $L_{A1243}$ | $R_{B8}$ | F | $R_{B1}$ | O |
| $L_{A1196}$ | $R_{B8}$ | F | $R_{B2}$ | S | $L_{A1244}$ | $R_{B8}$ | F | $R_{B2}$ | O |
| $L_{A1197}$ | $R_{B8}$ | F | $R_{B3}$ | S | $L_{A1245}$ | $R_{B8}$ | F | $R_{B3}$ | O |
| $L_{A1198}$ | $R_{B8}$ | F | $R_{B4}$ | S | $L_{A1246}$ | $R_{B8}$ | F | $R_{B4}$ | O |
| $L_{A1199}$ | $R_{B8}$ | F | $R_{B7}$ | S | $L_{A1247}$ | $R_{B8}$ | F | $R_{B7}$ | O |
| $L_{A1200}$ | $R_{B8}$ | F | $R_{B10}$ | S | $L_{A1248}$ | $R_{B8}$ | F | $R_{B10}$ | O |
| $L_{A1201}$ | $R_{B8}$ | F | $R_{A3}$ | S | $L_{A1249}$ | $R_{B8}$ | F | $R_{A3}$ | O |
| $L_{A1202}$ | $R_{B8}$ | F | $R_{A34}$ | S | $L_{A1250}$ | $R_{B8}$ | F | $R_{A34}$ | O |
| $L_{A1203}$ | $R_{B6}$ | $R_{B1}$ | H | S | $L_{A1251}$ | $R_{B6}$ | $R_{B1}$ | H | O |
| $L_{A1204}$ | $R_{B6}$ | $R_{B1}$ | $R_{B1}$ | S | $L_{A1252}$ | $R_{B6}$ | $R_{B1}$ | $R_{B1}$ | O |
| $L_{A1205}$ | $R_{B6}$ | $R_{B1}$ | $R_{B3}$ | S | $L_{A1253}$ | $R_{B6}$ | $R_{B1}$ | $R_{B3}$ | O |
| $L_{A1206}$ | $R_{B6}$ | $R_{B1}$ | $R_{B4}$ | S | $L_{A1254}$ | $R_{B6}$ | $R_{B1}$ | $R_{B4}$ | O |
| $L_{A1207}$ | $R_{B6}$ | $R_{B1}$ | $R_{B7}$ | S | $L_{A1255}$ | $R_{B6}$ | $R_{B1}$ | $R_{B7}$ | O |
| $L_{A1208}$ | $R_{B6}$ | $R_{B1}$ | $R_{B10}$ | S | $L_{A1256}$ | $R_{B6}$ | $R_{B1}$ | $R_{B10}$ | O |
| $L_{A1209}$ | $R_{B6}$ | $R_{B1}$ | $R_{A3}$ | S | $L_{A1257}$ | $R_{B6}$ | $R_{B1}$ | $R_{A3}$ | O |
| $L_{A1210}$ | $R_{B6}$ | $R_{B1}$ | $R_{A34}$ | S | $L_{A1258}$ | $R_{B6}$ | $R_{B1}$ | $R_{A34}$ | O |
| $L_{A1211}$ | $R_{B8}$ | $R_{B1}$ | $R_{B1}$ | S | $L_{A1259}$ | $R_{B8}$ | $R_{B1}$ | $R_{B1}$ | O |
| $L_{A1212}$ | $R_{B8}$ | $R_{B1}$ | $R_{B2}$ | S | $L_{A1260}$ | $R_{B8}$ | $R_{B1}$ | $R_{B2}$ | O |
| $L_{A1213}$ | $R_{B8}$ | $R_{B1}$ | $R_{B3}$ | S | $L_{A1261}$ | $R_{B8}$ | $R_{B1}$ | $R_{B3}$ | O |
| $L_{A1214}$ | $R_{B8}$ | $R_{B1}$ | $R_{B4}$ | S | $L_{A1262}$ | $R_{B8}$ | $R_{B1}$ | $R_{B4}$ | O |
| $L_{A1215}$ | $R_{B8}$ | $R_{B1}$ | $R_{B7}$ | S | $L_{A1263}$ | $R_{B8}$ | $R_{B1}$ | $R_{B7}$ | O |
| $L_{A1216}$ | $R_{B8}$ | $R_{B1}$ | $R_{B10}$ | S | $L_{A1264}$ | $R_{B8}$ | $R_{B1}$ | $R_{B10}$ | O |
| $L_{A1217}$ | $R_{B8}$ | $R_{B1}$ | $R_{A3}$ | S | $L_{A1265}$ | $R_{B8}$ | $R_{B1}$ | $R_{A3}$ | O |
| $L_{A1218}$ | $R_{B8}$ | $R_{B1}$ | $R_{A34}$ | S | $L_{A1266}$ | $R_{B8}$ | $R_{B1}$ | $R_{A34}$ | O, |

$L_{A1267}$ through $L_{A1298}$ that are based on a structure of Formula VI,

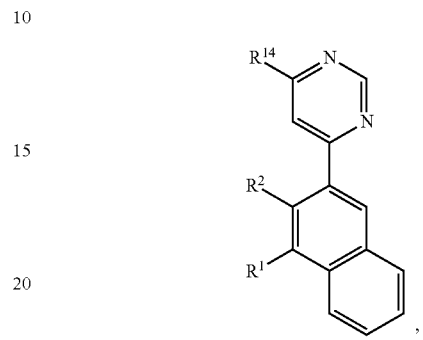

in which $R^1$, $R^2$, and $R^{14}$ are defined as provided below:

| Ligand | $R^1$ | $R^2$ | $R^{14}$ | Ligand | $R^1$ | $R^2$ | $R^{14}$ |
|---|---|---|---|---|---|---|---|
| $L_{A1267}$ | $R_{B6}$ | H | H | $L_{A1283}$ | H | $R_{B6}$ | H |
| $L_{A1268}$ | $R_{B6}$ | H | $R_{B1}$ | $L_{A1284}$ | H | $R_{B6}$ | $R_{B1}$ |
| $L_{A1269}$ | $R_{B6}$ | H | $R_{B3}$ | $L_{A1285}$ | H | $R_{B6}$ | $R_{B3}$ |
| $L_{A1270}$ | $R_{B6}$ | H | $R_{B4}$ | $L_{A1286}$ | H | $R_{B6}$ | $R_{B4}$ |
| $L_{A1271}$ | $R_{B6}$ | H | $R_{B7}$ | $L_{A1287}$ | H | $R_{B6}$ | $R_{B7}$ |
| $L_{A1272}$ | $R_{B6}$ | H | $R_{B10}$ | $L_{A1288}$ | H | $R_{B6}$ | $R_{B10}$ |
| $L_{A1273}$ | $R_{B6}$ | H | $R_{A3}$ | $L_{A1289}$ | H | $R_{B6}$ | $R_{A3}$ |
| $L_{A1274}$ | $R_{B6}$ | H | $R_{A34}$ | $L_{A1290}$ | H | $R_{B6}$ | $R_{A34}$ |
| $L_{A1275}$ | $R_{B8}$ | H | H | $L_{A1291}$ | H | $R_{B8}$ | H |
| $L_{A1276}$ | $R_{B8}$ | H | $R_{B1}$ | $L_{A1292}$ | H | $R_{B8}$ | $R_{B1}$ |
| $L_{A1277}$ | $R_{B8}$ | H | $R_{B3}$ | $L_{A1293}$ | H | $R_{B8}$ | $R_{B3}$ |
| $L_{A1278}$ | $R_{B8}$ | H | $R_{B4}$ | $L_{A1294}$ | H | $R_{B8}$ | $R_{B4}$ |
| $L_{A1279}$ | $R_{B8}$ | H | $R_{B7}$ | $L_{A1295}$ | H | $R_{B8}$ | $R_{B7}$ |
| $L_{A1280}$ | $R_{B8}$ | H | $R_{B10}$ | $L_{A1296}$ | H | $R_{B8}$ | $R_{B10}$ |
| $L_{A1281}$ | $R_{B8}$ | H | $R_{A3}$ | $L_{A1297}$ | H | $R_{B8}$ | $R_{A3}$ |
| $L_{A1282}$ | $R_{B8}$ | H | $R_{A34}$ | $L_{A1298}$ | H | $R_{B8}$ | $R_{A34}$; | wherein $R_{B1}$ to $R_{B23}$ have the following structures:

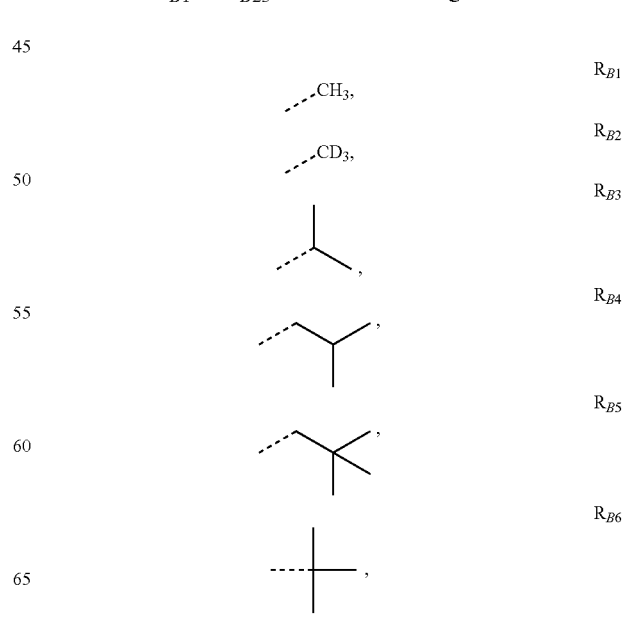

and
wherein $R_{A1}$ to $R_{A51}$ have the following structures:

| Structure | Label |
|---|---|
| ⋯⋯CH₂CH₂CF₃ | R_{A11} |
| ⋯⋯CH₂CH₂CH₂F | R_{A12} |
| ⋯⋯CH₂CH₂CHF₂ | R_{A13} |
| ⋯⋯CH₂CF₂CH₃ | R_{A14} |
| ⋯⋯CH₂CHFCH₃ | R_{A15} |
| ⋯⋯CH₂CF₂CH₃ (gem-diF on middle) | R_{A16} |
| ⋯⋯CH₂CF₂CF₃ | R_{A17} |
| ⋯⋯CH(CH₃)CF₃ | R_{A18} |
| ⋯⋯CH(CH₃)CH₂F | R_{A19} |
| ⋯⋯CH(CH₃)CHF₂ | R_{A20} |
| ⋯⋯CH(CF₃)CF₃ | R_{A21} |
| ⋯⋯CD₂CH(CF₃)CF₃ | R_{A22} |
| ⋯⋯C(CH₃)₂F | R_{A23} |
| ⋯⋯CH(CH₂F)CH₂F | R_{A24} |
| ⋯⋯CH(CHF₂)CHF₂ | R_{A25} |
| ⋯⋯CH₂CH₂CH(CF₃) | R_{A26} |
| ⋯⋯CH₂CH(CF₃)CF₃ | R_{A27} |
| ⋯⋯CD₂CH₂CH(CF₃)CF₃ | R_{A28} |
| ⋯⋯CH₂CH(CH₂F)CH₂F | R_{A29} |
| ⋯⋯CH₂CH(CHF₂)CHF₂ | R_{A30} |
| ⋯⋯CH₂C(CH₃)₂F | R_{A31} |
| ⋯⋯CH(iPr)CF₂ | R_{A32} |
| ⋯⋯C(CF₃)₂CF₃ | R_{A33} |
| ⋯⋯C(CH₃)₂CF₃ | R_{A34} |
| ⋯⋯CD₂C(CH₃)₂CF₃ | R_{A35} |
| ⋯⋯C(CH₃)(CF₃)CF₃ | R_{A36} |
| trans-1,2-bis(CF₃)cyclopentyl | R_{A37} |
| 1,2-bis(CF₃)cyclopentyl-D | R_{A38} |
| 1,2-bis(CF₃)cyclopentyl | R_{A39} |

-continued
R_{A40} 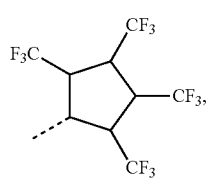
R_{A41} 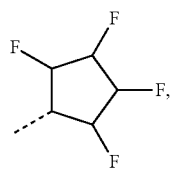
R_{A42} 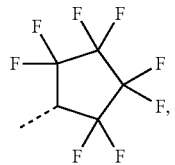
R_{A43} 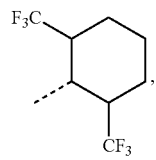
R_{A44} 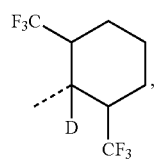
R_{A45} 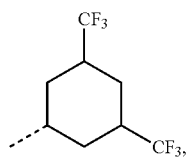
R_{A46} 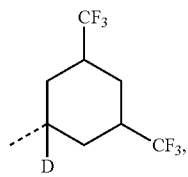
R_{A47} 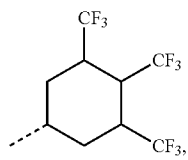
R_{A48} 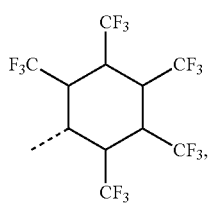
-continued
R_{A49} 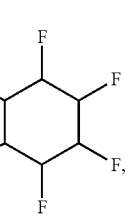
R_{A50} 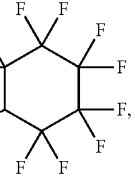
R_{A51} 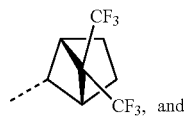, and
R_{A52} 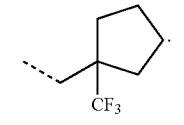.
In some embodiments of the compound, the compound has formula $(L_A)_n Ir(L_B)_{3-n}$;
wherein $L_B$ is a bidentate ligand; and n is 1, 2, or 3.
In some embodiments of the compound, $L_B$ is selected from the group consisting of:
L_{B1} 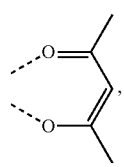
L_{B2} 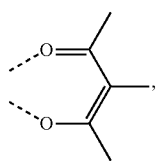
L_{B3} 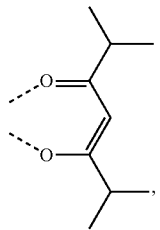, -continued
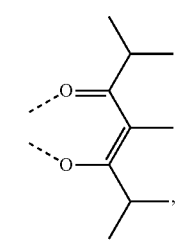 $L_{B4}$
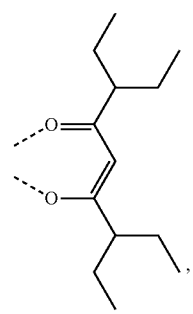 $L_{B5}$
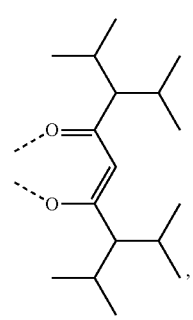 $L_{B6}$
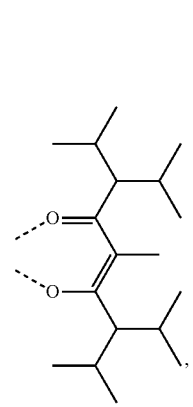 $L_{B7}$
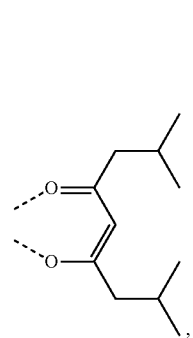 $L_{B8}$
-continued
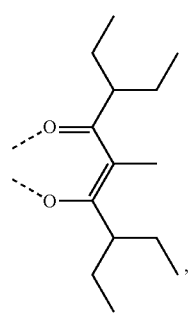 $L_{B9}$
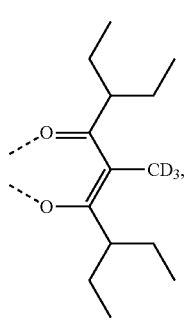 $L_{B10}$
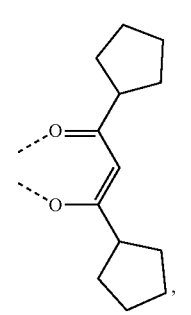 $L_{B11}$
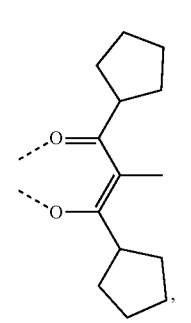 $L_{B12}$
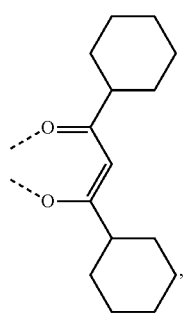 $L_{B13}$ -continued

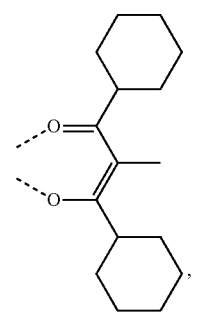 $L_{B14}$

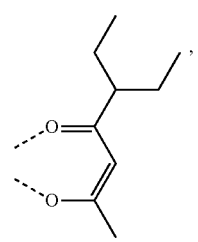 $L_{B15}$

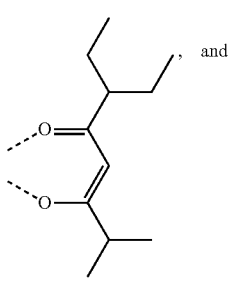 $L_{B16}$, and

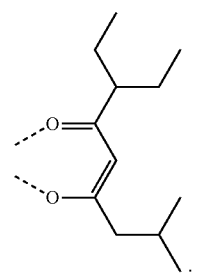 $L_{B17}$

In some embodiments of the compound having the formula Ir($L_A$)($L_B$) where $L_A$ is selected from $L_{A1}$ to $L_{A1298}$, the compound is selected from the group consisting of Compound 1 through Compound 22,066; where each Compound x has the formula Ir($L_{Ak}$)$_2$($L_{Bj}$);

wherein x=1298j+k−1298, k is an integer from 1 to 1298, and j is an integer from 1 to 17; and wherein $L_{B1}$ through $L_{B17}$ are defined as follows:

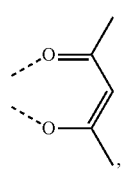 $L_{B1}$

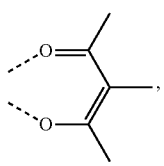 $L_{B2}$

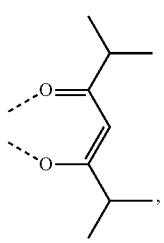 $L_{B3}$

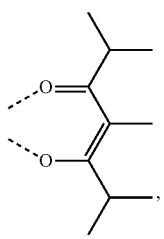 $L_{B4}$

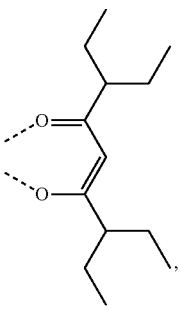 $L_{B5}$

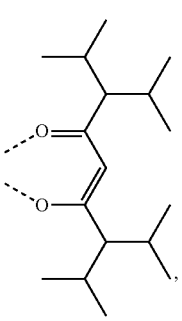 $L_{B6}$

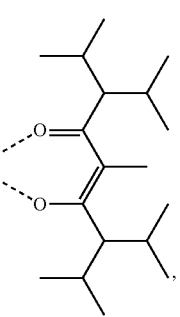 $L_{B7}$

L<sub>B8</sub>
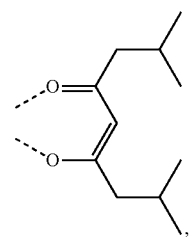

L<sub>B9</sub>
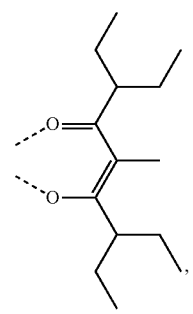

L<sub>B10</sub>
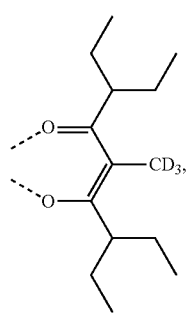

L<sub>B11</sub>
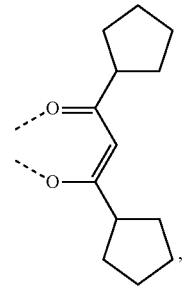

L<sub>B12</sub>
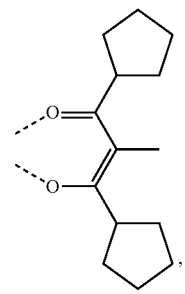

L<sub>B13</sub>
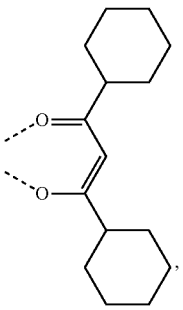

L<sub>B14</sub>
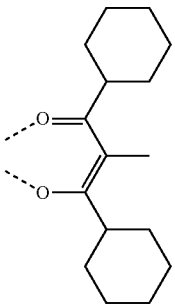

L<sub>B15</sub>
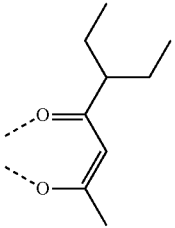

L<sub>B16</sub>
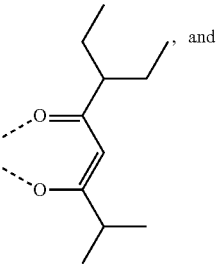, and

L<sub>B17</sub>
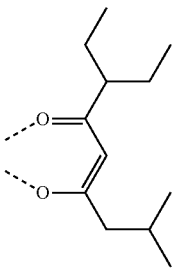.

According to another aspect, a formulation comprising the compound comprising a ligand $L_A$ of Formula I is disclosed.

According to another aspect, a first device comprising a first OLED is disclosed. The first OLED comprising: an anode; a cathode; and an organic layer, disposed between the anode and the cathode, comprising a compound comprising a ligand $L_A$ of Formula I:

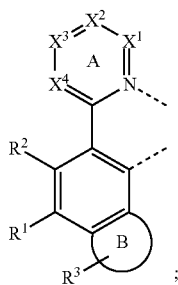

Formula I where Ring B represents a five- or six-membered aromatic ring; $R^3$ represents from none to the maximum number of substitutions; $X^1$, $X^2$, $X^3$, and $X^4$ are each independently a CR or N; wherein:

(1) at least two adjacent ones of $X^1$, $X^2$, $X^3$, and $X^4$ are CR and fused into a five or six-membered aromatic ring, or (2) at least one of $X^1$, $X^2$, $X^3$, and $X^4$ is nitrogen, or (3) both (1) and (2) are true;

wherein (a) $R^1$ is $CR^{11}R^{12}R^{13}$ or join with $R^2$ to form into a ring; or (b) $R^2$ is not hydrogen; or (c) both (a) and (b) are true;

wherein R, $R^1$, $R^2$, $R^3$, $R^{11}$, $R^{12}$, and $R^{13}$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof;

any two substituents among R, $R^1$, $R^2$, $R^3$, $R^{11}$, $R^{12}$, and $R^{13}$ are optionally joined to form into a ring;

$L_A$ is coordinated to a metal M;

$L_A$ is optionally linked with other ligands to comprise a tridentate, tetradentate, pentadentate, or hexadentate ligand; and M is optionally coordinated to other ligands.

In some embodiments of the first device, the organic layer further comprises a host, wherein host comprises at least one chemical group selected from the group consisting of carbazole, dibenzothiophene, dibenzofuran, dibenzoselenophene, azacarbazole, aza-dibenzothiophene, aza-dibenzofuran, and aza-dibenzoselenophene.

In some embodiments of the first device, the organic layer further comprises a host, wherein the host is selected from the Host Group A defined above.

In some embodiments of the first device, wherein the organic layer further comprises a host, wherein the host comprises a metal complex.

In some embodiments, the OLED has one or more characteristics selected from the group consisting of being flexible, being rollable, being foldable, being stretchable, and being curved. In some embodiments, the OLED is transparent or semi-transparent. In some embodiments, the OLED further comprises a layer comprising carbon nanotubes.

In some embodiments, the OLED further comprises a layer comprising a delayed fluorescent emitter. In some embodiments, the OLED comprises a RGB pixel arrangement or white plus color filter pixel arrangement. In some embodiments, the OLED is a mobile device, a hand held device, or a wearable device. In some embodiments, the OLED is a display panel having less than 10 inch diagonal or 50 square inch area. In some embodiments, the OLED is a display panel having at least 10 inch diagonal or 50 square inch area. In some embodiments, the OLED is a lighting panel.

According to another aspect, an emissive region in an OLED is disclosed where the emissive region comprising a compound a compound comprising a ligand $L_A$ of Formula I:

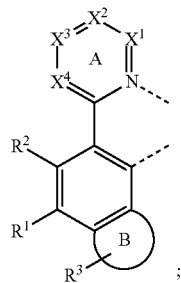

Formula I where Ring B represents a five- or six-membered aromatic ring; $R^3$ represents from none to the maximum possible number of substitutions; $X^1$, $X^2$, $X^3$, and $X^4$ are each independently a CR or N; wherein:

(1) at least two adjacent ones of $X^1$, $X^2$, $X^3$, and $X^4$ are CR and fused into a five or six-membered aromatic ring, or (2) at least one of $X^1$, $X^2$, $X^3$, and $X^4$ is nitrogen, or (3) both (1) and (2) are true;

wherein (a) $R^1$ is $CR^{11}R^{12}R^{13}$ or join with $R^2$ to form into a ring; or (b) $R^2$ is not hydrogen; or (c) both (a) and (b) are true;

wherein R, $R^1$, $R^2$, $R^3$, $R^{11}$, $R^{12}$, and $R^{13}$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof;

any two substituents among R, $R^1$, $R^2$, $R^3$, $R^{11}$, $R^{12}$, and $R^{13}$, are optionally joined to form into a ring;

$L_A$ is coordinated to a metal M;

$L_A$ is optionally linked with other ligands to comprise a tridentate, tetradentate, pentadentate, or hexadentate ligand; and M is optionally coordinated to other ligands.

In some embodiments of the emissive region, the compound is an emissive dopant or a non-emissive dopant.

In some embodiments of the emissive region, the emissive region further comprises a host, wherein the host comprises at least one selected from the group consisting of metal complex, triphenylene, carbazole, dibenzothiophene, dibenzofuran, dibenzoselenophene, aza-triphenylene, azacarbazole, aza-dibenzothiophene, aza-dibenzofuran, and aza-dibenzoselenophene.

In some embodiments of the emissive region, wherein the emissive region further comprises a host, wherein the host is selected from the following Host Group A consisting of:

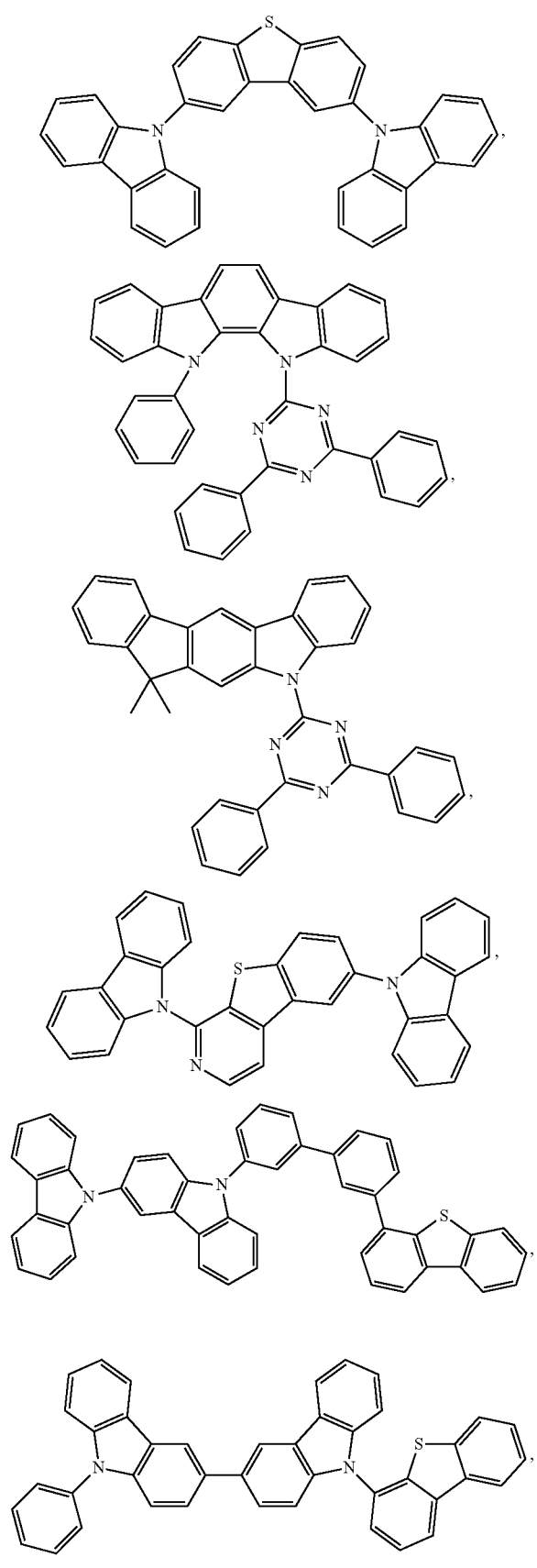
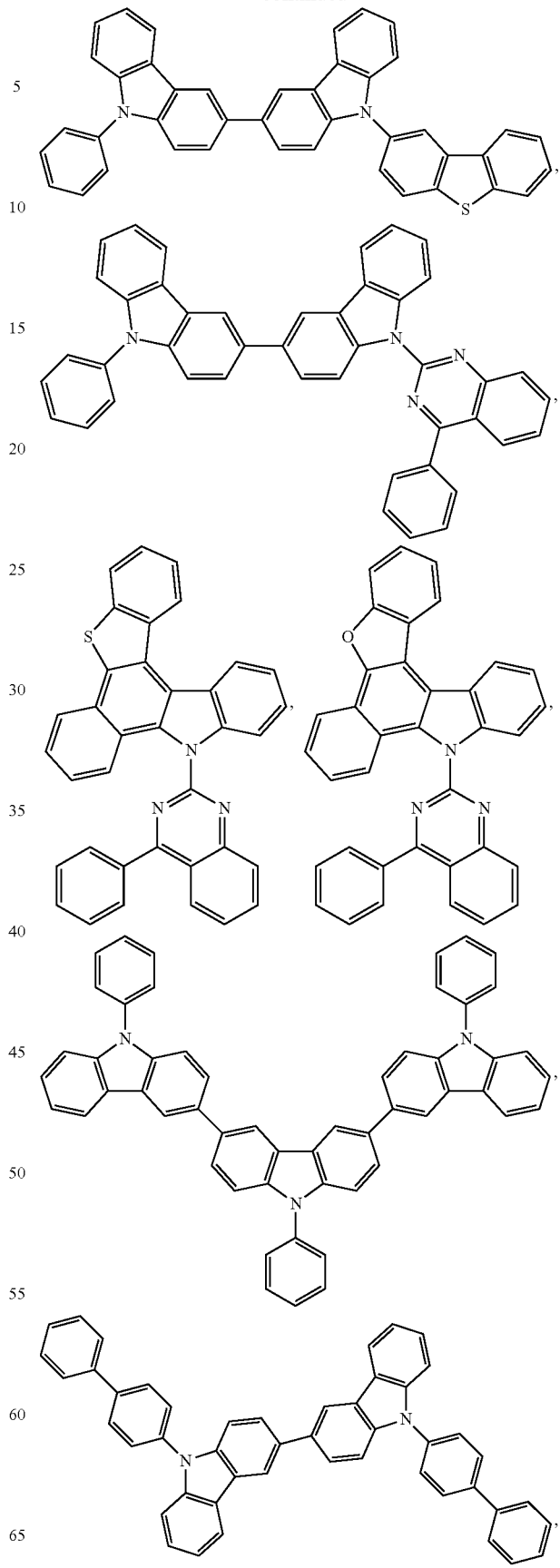

-continued

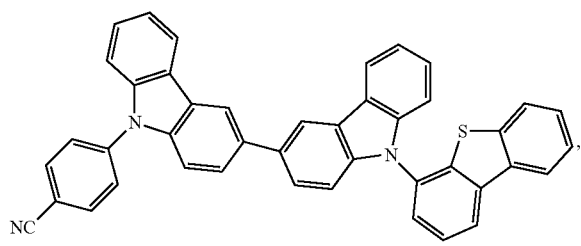

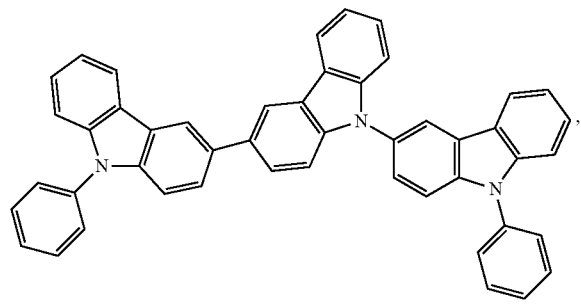

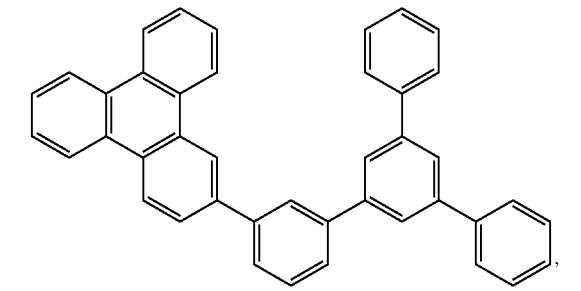

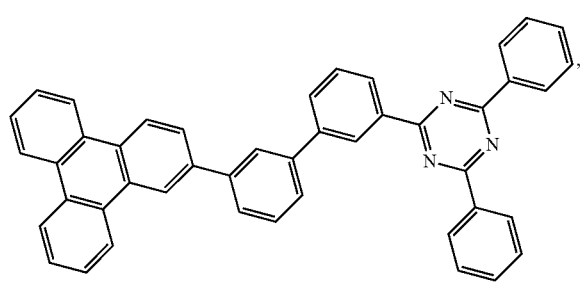

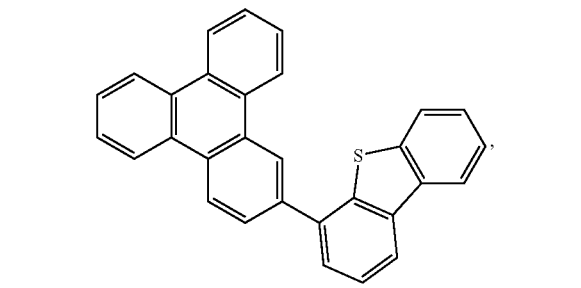

-continued

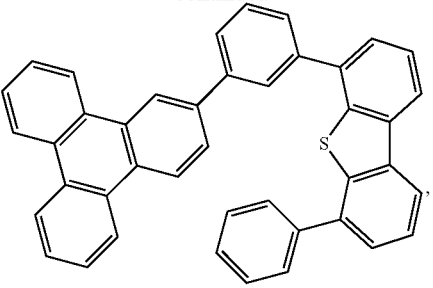

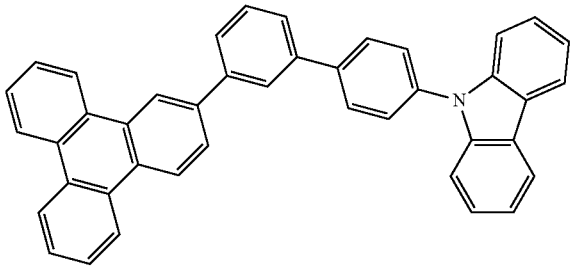

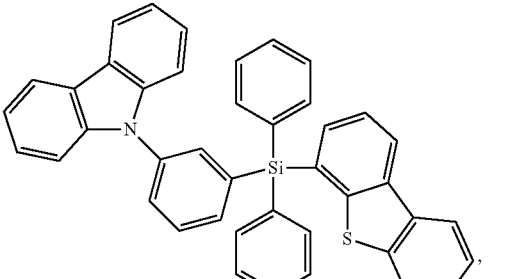

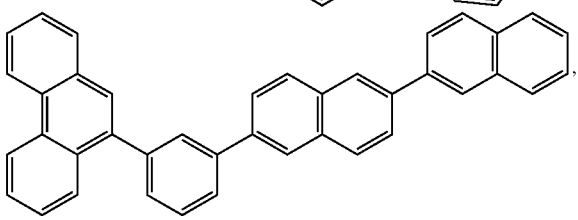

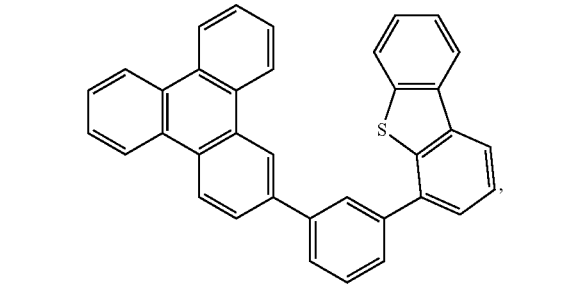

and combinations thereof.

According to another aspect, a consumer product comprising the OLED that includes the compound of the present disclosure in the organic layer of the OLED is disclosed.

In some embodiments, the compound can be an emissive dopant. In some embodiments, the compound can produce emissions via phosphorescence, fluorescence, thermally activated delayed fluorescence, i.e., TADF (also referred to as E-type delayed fluorescence), triplet-triplet annihilation, or combinations of these processes.

According to another aspect, a formulation comprising the compound described herein is also disclosed.

The OLED disclosed herein can be incorporated into one or more of a consumer product, an electronic component module, and a lighting panel. The organic layer can be an emissive layer and the compound can be an emissive dopant in some embodiments, while the compound can be a non-emissive dopant in other embodiments.

The organic layer can also include a host. In some embodiments, two or more hosts are preferred. In some embodiments, the hosts used may be a) bipolar, b) electron transporting, c) hole transporting or d) wide band gap materials that play little role in charge transport. In some embodiments, the host can include a metal complex. The host can be a triphenylene containing benzo-fused thiophene or benzo-fused furan. Any substituent in the host can be an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv C-C_nH_{2n+1}$, $Ar_1$, $Ar_1-Ar_2$, and $C_nH_{2n}-Ar_1$, or the host has no substitutions. In the preceding substituents n can range from 1 to 10; and $Ar_1$ and $Ar_2$ can be independently selected from the group consisting of benzene, biphenyl, naphthalene, triphenylene, carbazole, and heteroaromatic analogs thereof. The host can be an inorganic compound. For example, a Zn containing inorganic material e.g. ZnS.

The host can be a compound comprising at least one chemical group selected from the group consisting of triphenylene, carbazole, dibenzothiophene, dibenzofuran, dibenzoselenophene, azatriphenylene, azacarbazole, aza-dibenzothiophene, aza-dibenzofuran, and aza-dibenzoselenophene. The host can include a metal complex. The host can be, but is not limited to, a specific compound selected from the group consisting of:

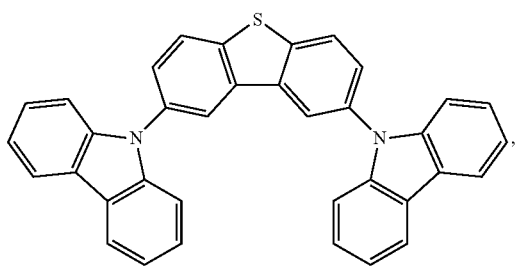

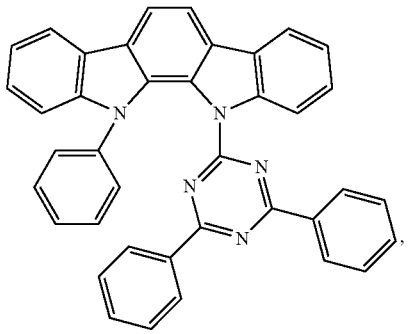

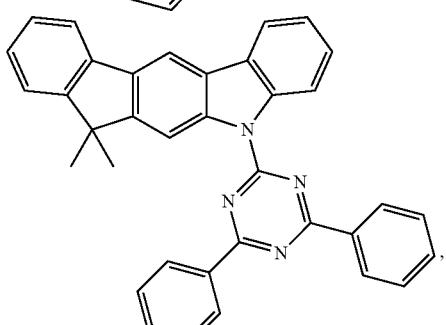

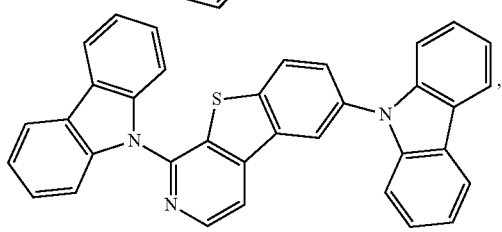

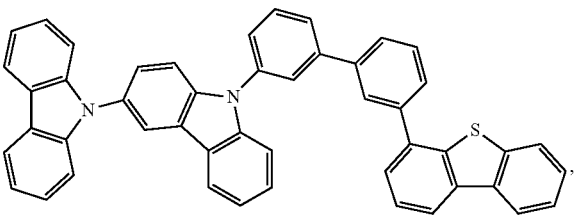

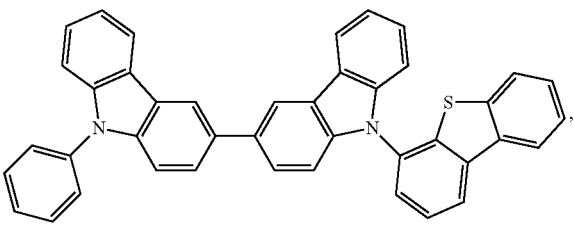

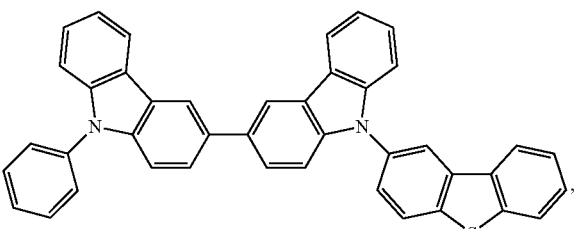

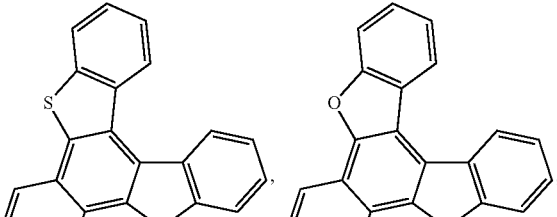

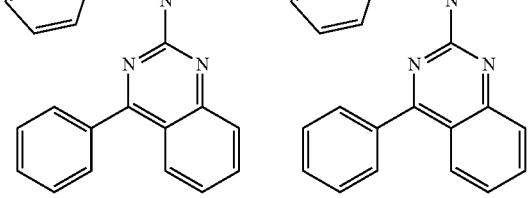

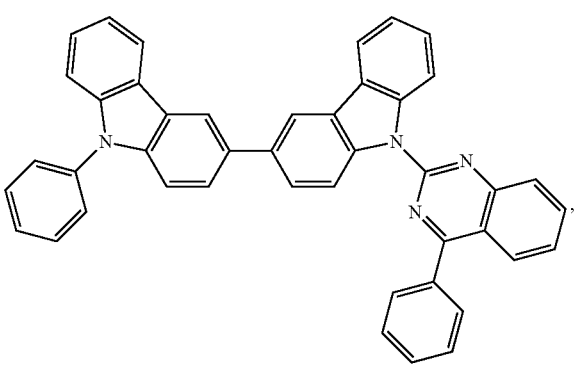

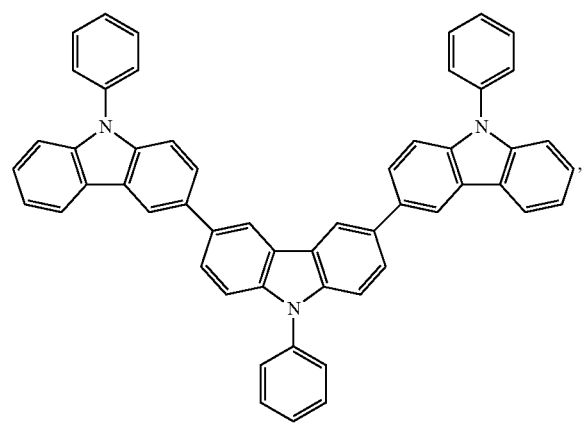
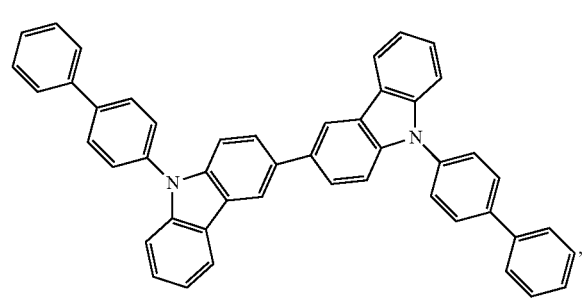
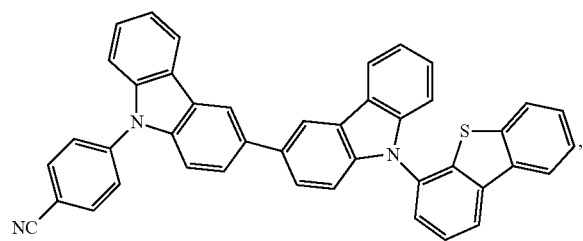
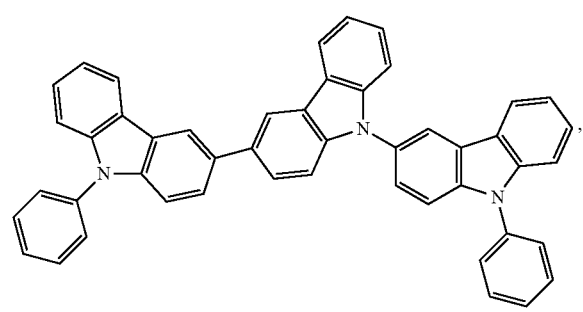
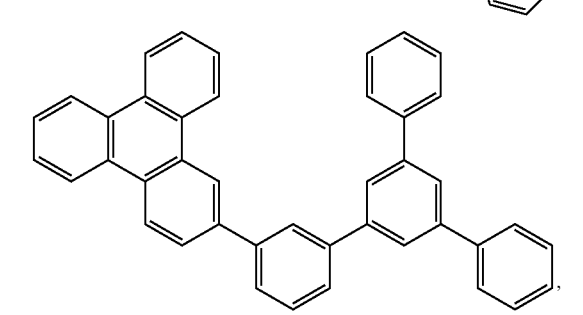
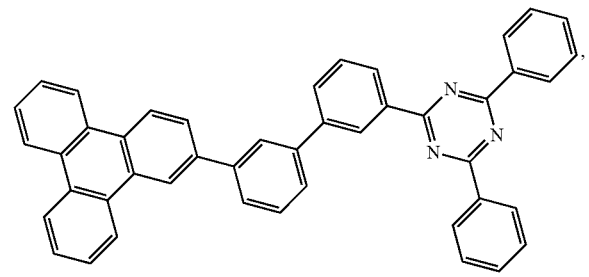
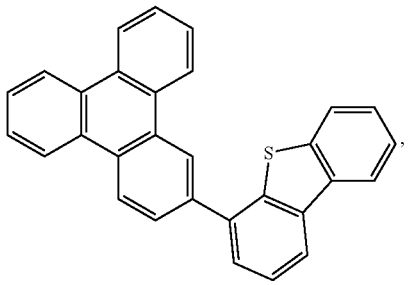
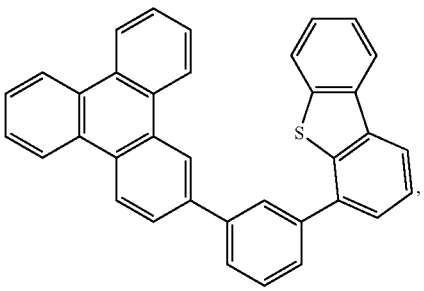
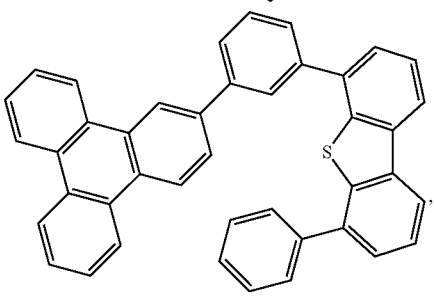
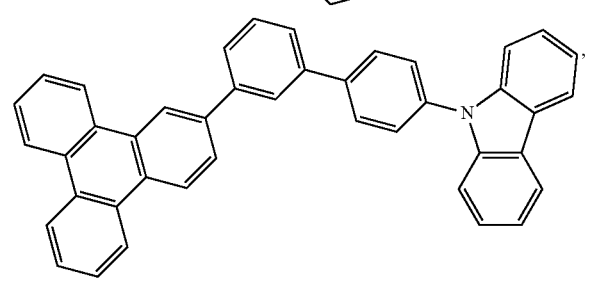
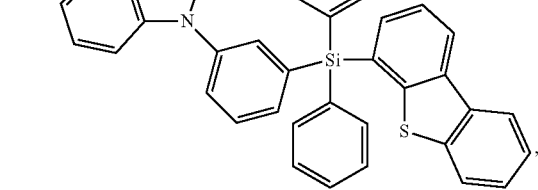

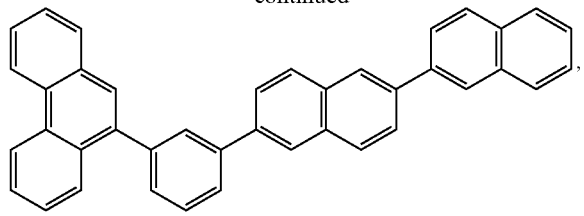

and combinations thereof. Additional information on possible hosts is provided below.

In yet another aspect of the present disclosure, a formulation that comprises the novel compound disclosed herein is described. The formulation can include one or more components selected from the group consisting of a solvent, a host, a hole injection material, hole transport material, and an electron transport layer material, disclosed herein.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

Conductivity Dopants:

A charge transport layer can be doped with conductivity dopants to substantially alter its density of charge carriers, which will in turn alter its conductivity. The conductivity is increased by generating charge carriers in the matrix material, and depending on the type of dopant, a change in the Fermi level of the semiconductor may also be achieved. Hole-transporting layer can be doped by p-type conductivity dopants and n-type conductivity dopants are used in the electron-transporting layer.

Non-limiting examples of the conductivity dopants that may be used in an OLED in combination with materials disclosed herein are exemplified below together with references that disclose those materials: EP01617493, EP01968131, EP2020694, EP2684932, US20050139810, US20070160905, US20090167167, US2010288362, WO06081780, WO2009003455, WO2009008277, WO2009011327, WO2014009310, US2007252140, US2015060804 and US2012146012.

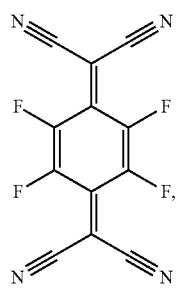

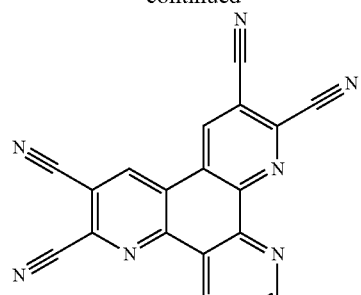

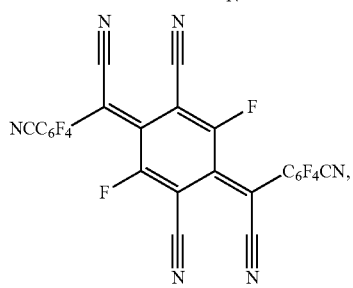

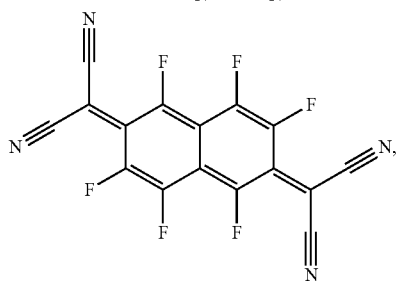

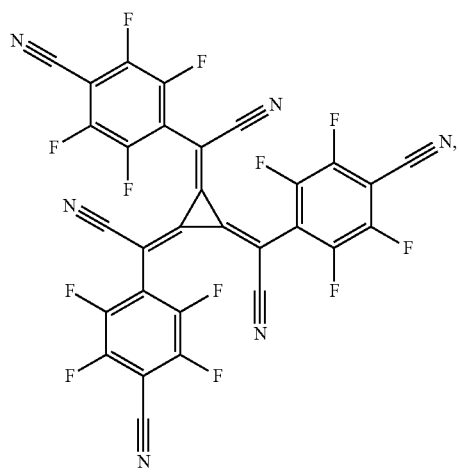

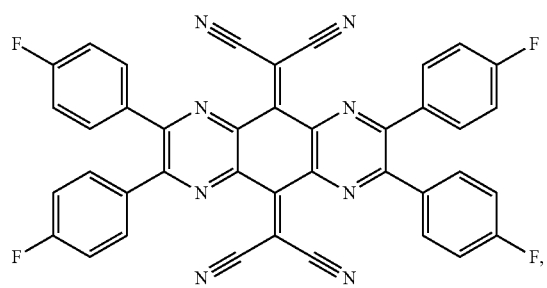

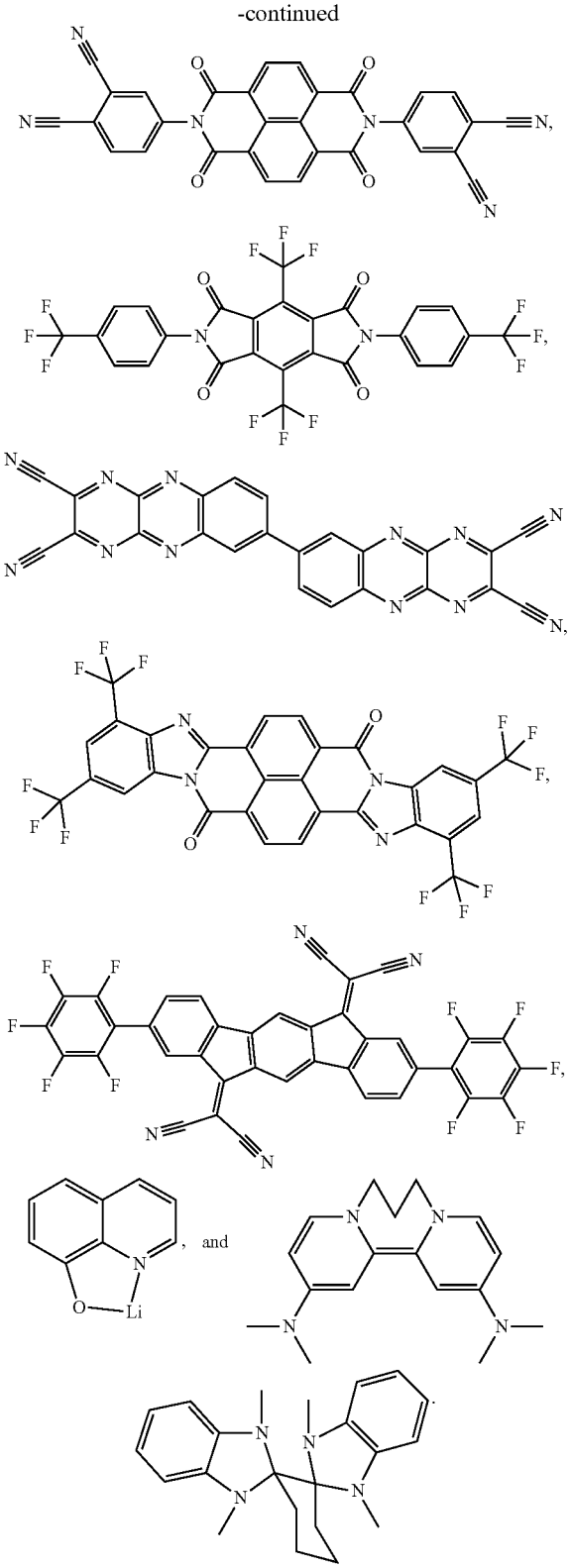

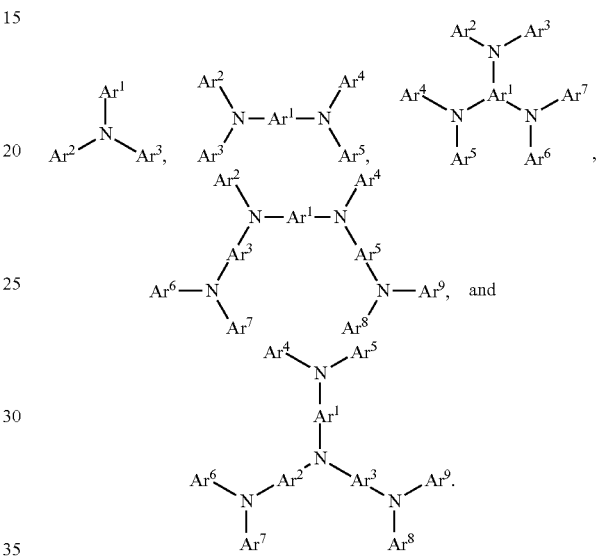

or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

Each of $Ar^1$ to $A^9$ is selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each Ar may be unsubstituted or may be substituted by a substituent selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl,

HIL/HTL:

A hole injecting/transporting material to be used in the present invention is not particularly limited, and any compound may be used as long as the compound is typically used as a hole injecting/transporting material. Examples of the material include, but are not limited to: a phthalocyanine carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

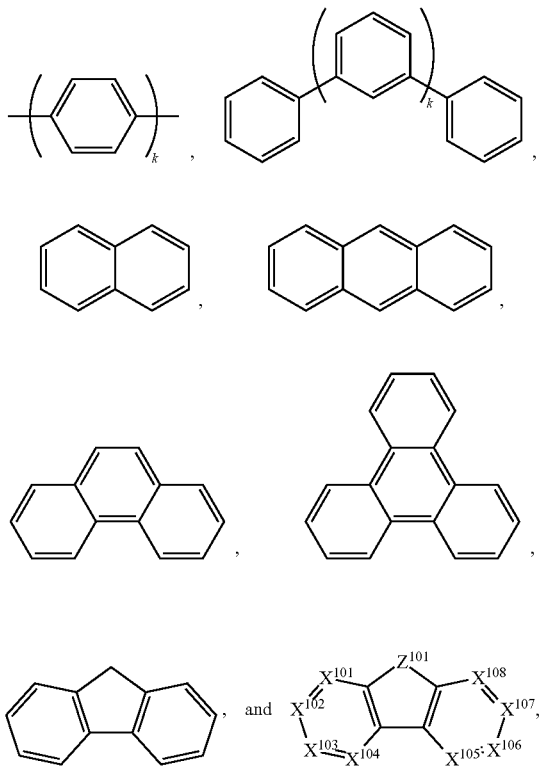

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

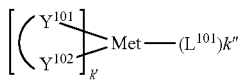

wherein Met is a metal, which can have an atomic weight greater than 40; $(Y_{101}\text{-}Y^{102})$ is a bidentate ligand, $Y^{101}$ and $V^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, $(Y^{101}\text{-}Y^{102})$ is a 2-phenylpyridine derivative. In another aspect, $(Y^{101}\text{-}Y^{102})$ is a carbene ligand. In another aspect, Met is selected from Ir, Pt, Os, and Zn. In a further aspect, the metal complex has a smallest oxidation potential in solution vs. $Fc^+/Fc$ couple less than about 0.6 V.

Non-limiting examples of the HIL and HTL materials that may be used in an OLED in combination with materials disclosed herein are exemplified below together with references that disclose those materials: CN102702075, DE102012005215, EP01624500, EP01698613, EP01806334, EP01930964, EP01972613, EP01997799, EP02011790, EP02055700, EP02055701, EP1725079, EP2085382, EP2660300, EP650955, JP07-073529, JP2005112765, JP2007091719, JP2008021687, JP2014-009196, KR20110088898, KR20130077473, TW201139402, U.S. Ser. No. 06/517,957, US20020158242, US20030162053, US20050123751, US20060182993, US20060240279, US20070145888, US20070181874, US20070278938, US20080014464, US20080091025, US20080106190, US20080124572, US20080145707, US20080220265, US20080233434, US20080303417, US2008107919, US20090115320, US20090167161, US2009066235, US2011007385, US20110163302, US2011240968, US2011278551, US2012205642, US2013241401, US20140117329, US2014183517, U.S. Pat. Nos. 5,061,569, 5,639,914, WO05075451, WO07125714, WO08023550, WO08023759, WO2009145016, WO2010061824, WO2011075644, WO2012177006, WO2013018530, WO2013039073, WO2013087142, WO2013118812, WO2013120577, WO2013157367, WO2013175747, WO2014002873, WO2014015935, WO2014015937, WO2014030872, WO2014030921, WO2014034791, WO2014104514, WO2014157018.

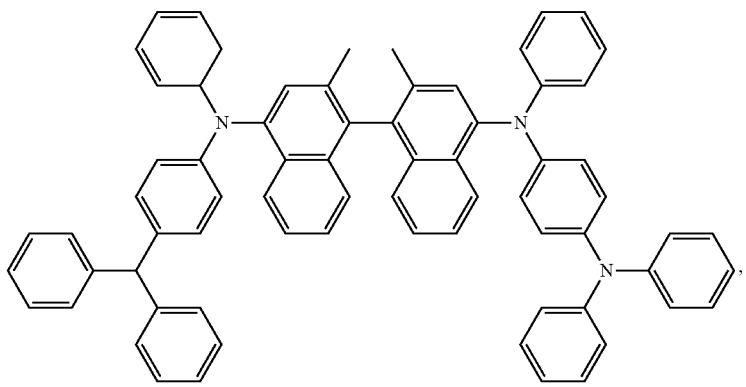

-continued
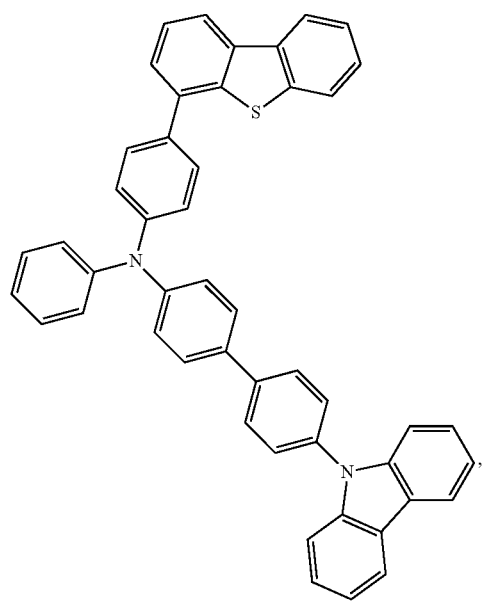
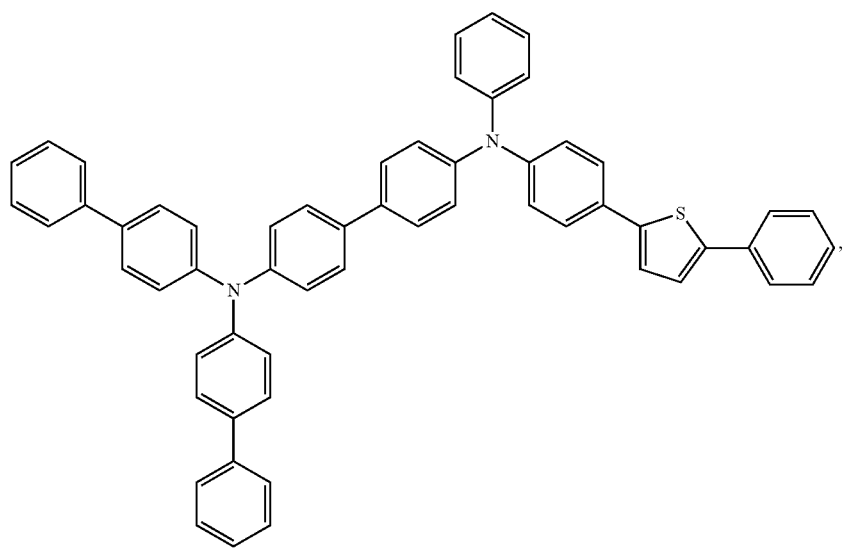
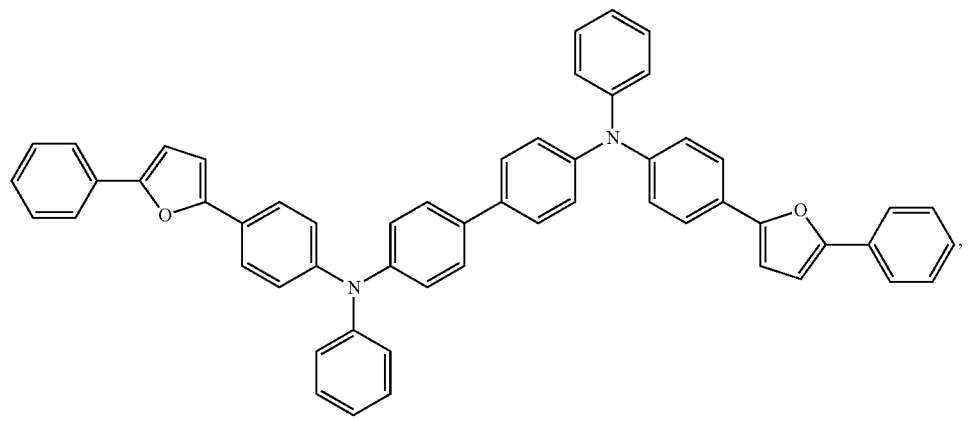

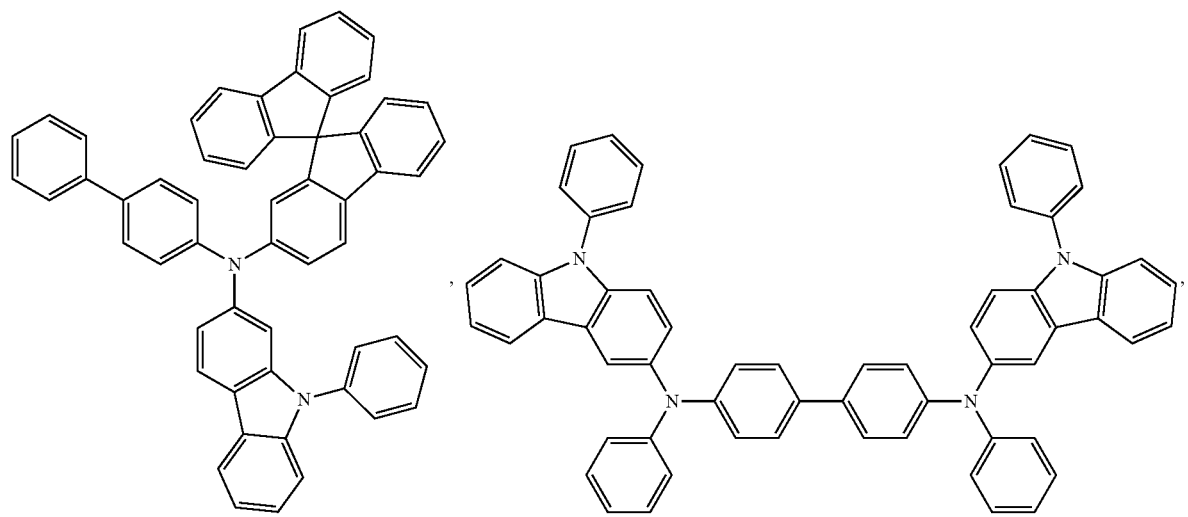
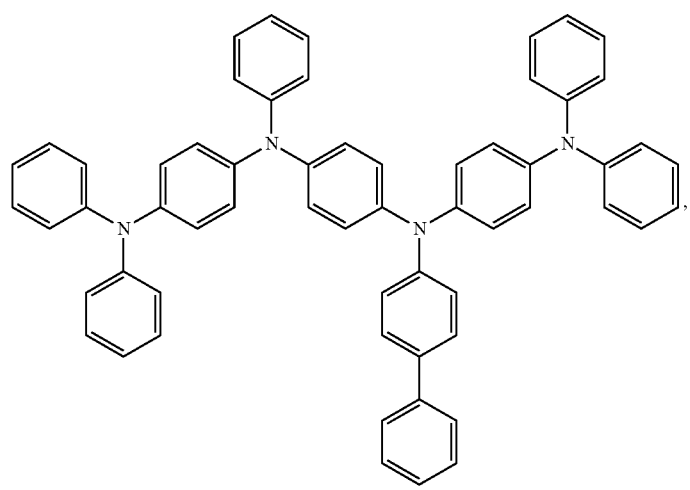
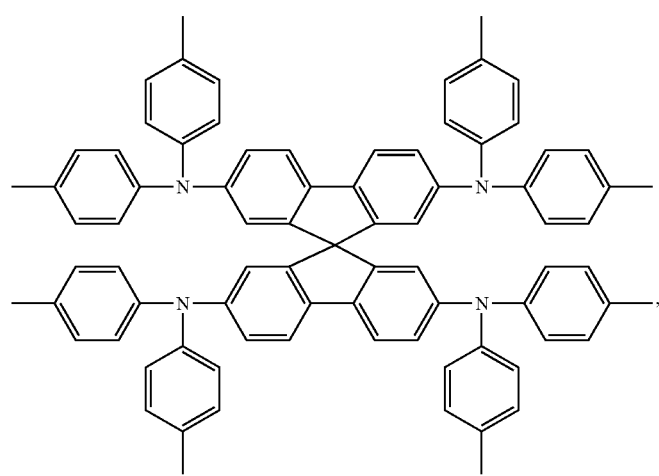

-continued
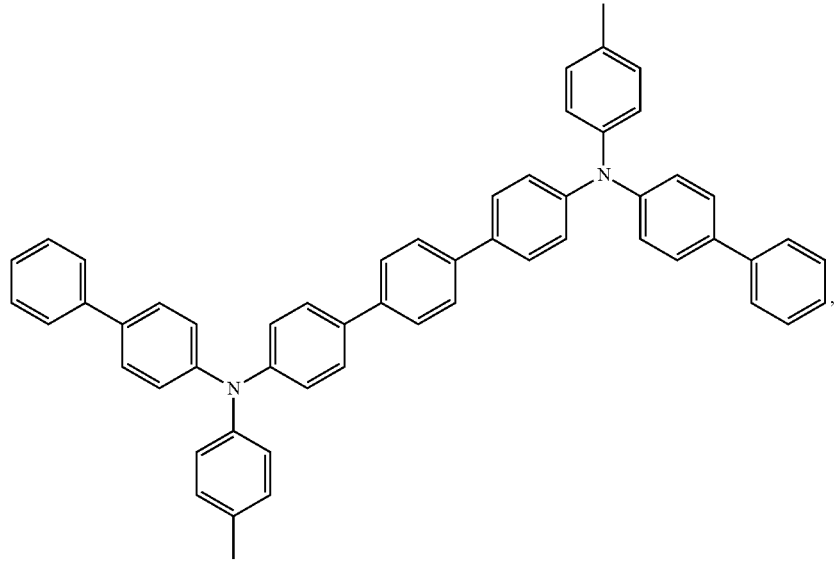
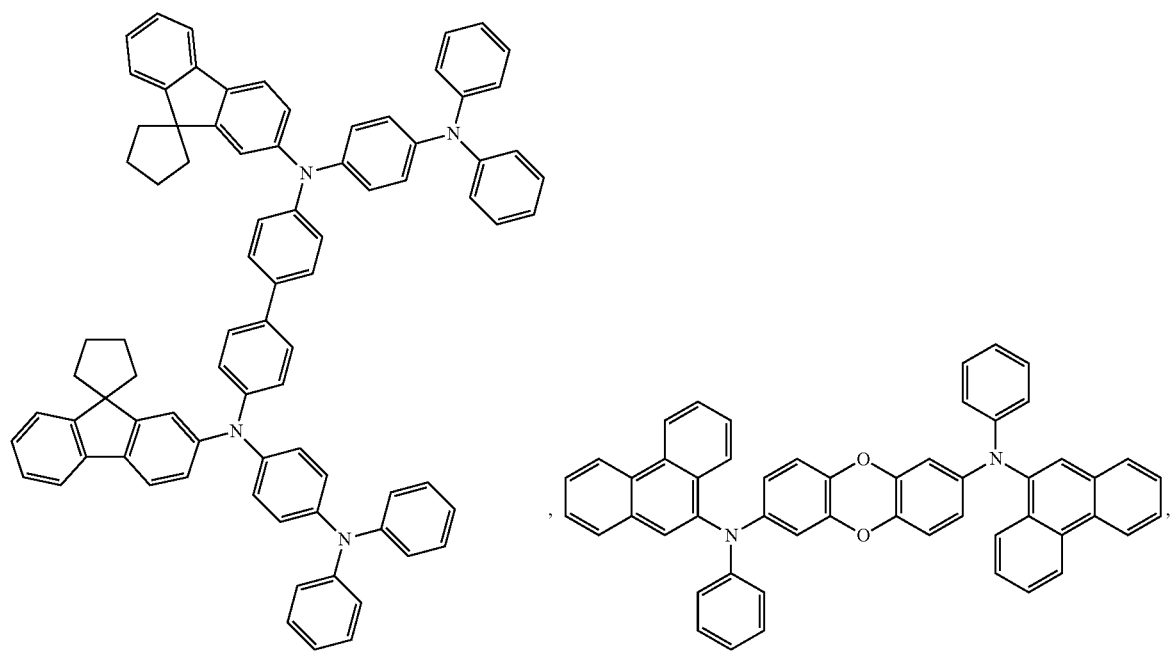
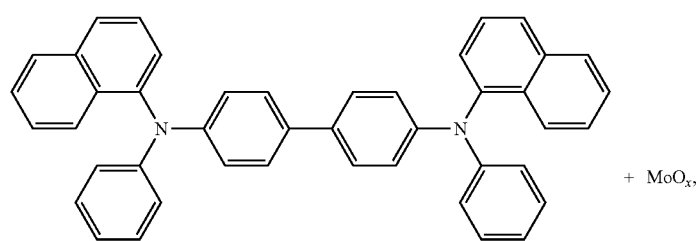 + MoO$_x$,

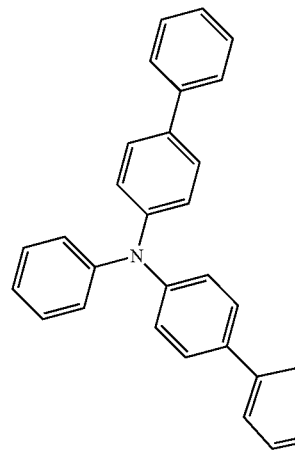
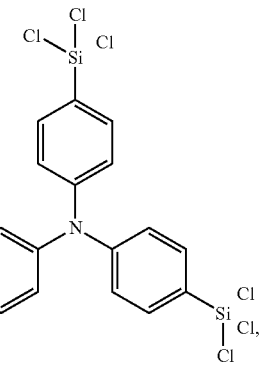
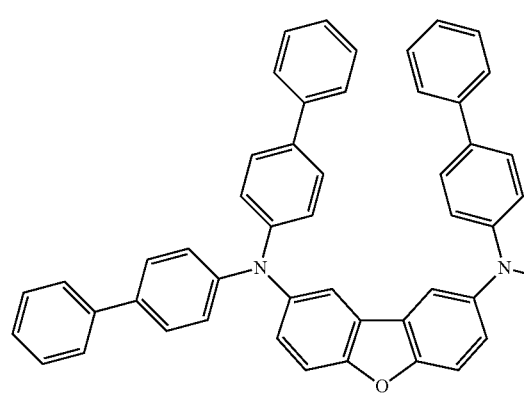
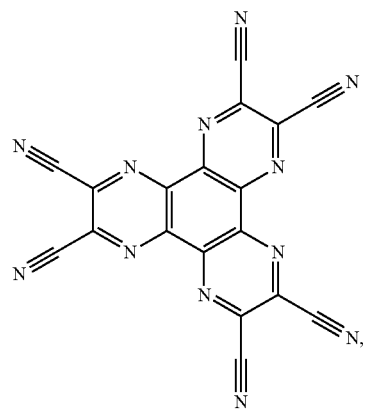
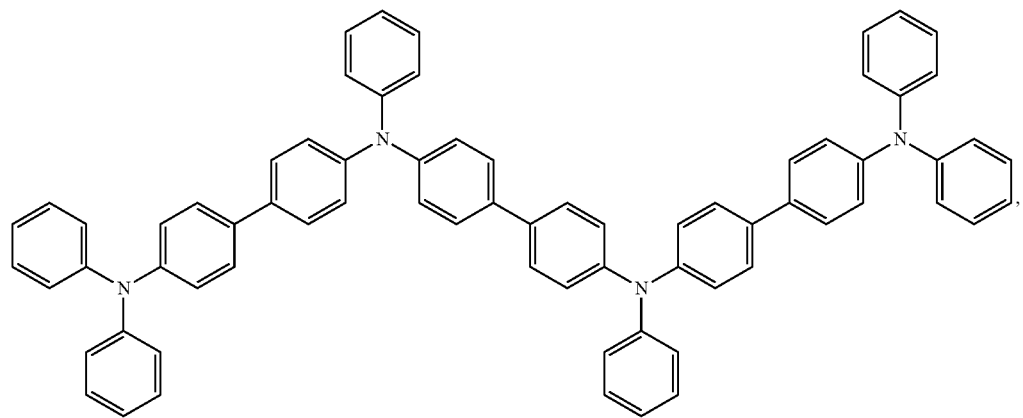

-continued
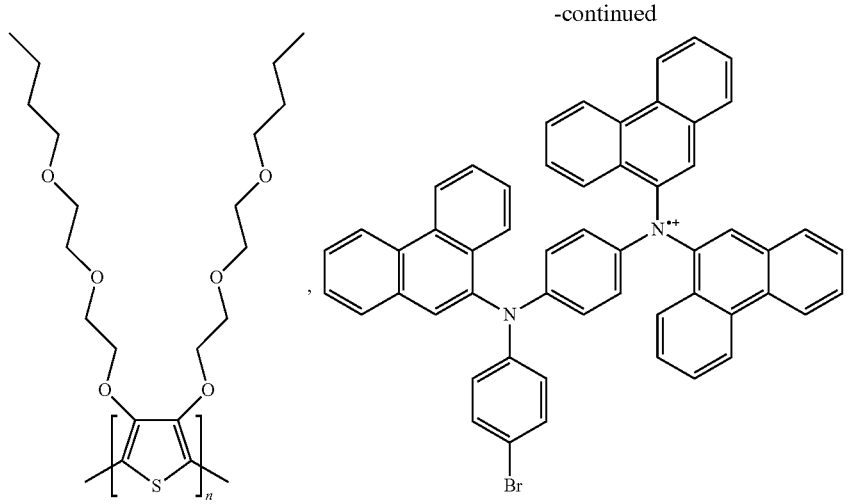
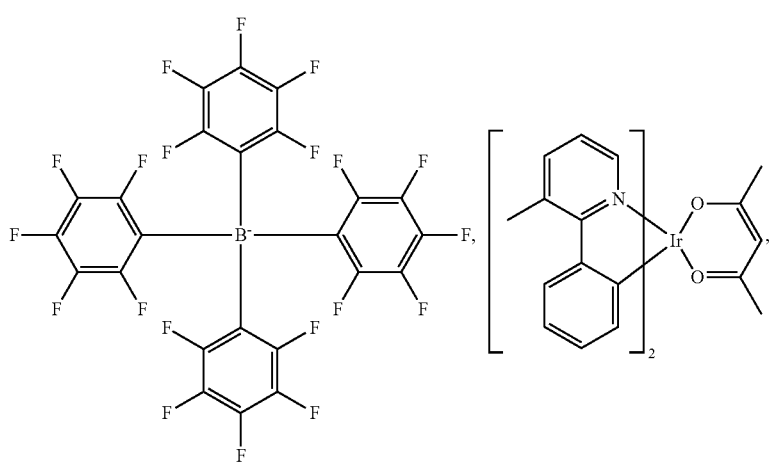
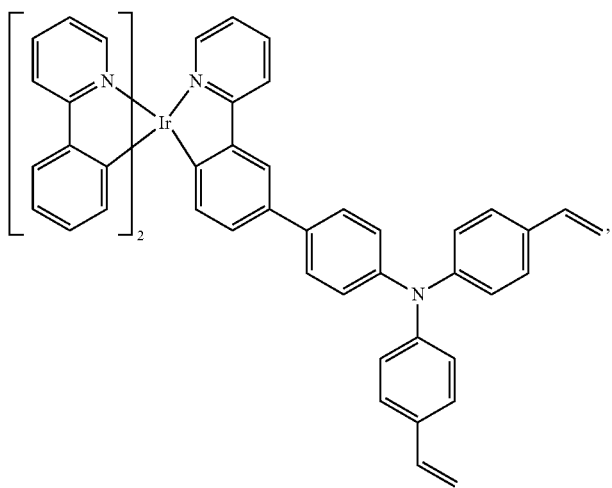

-continued
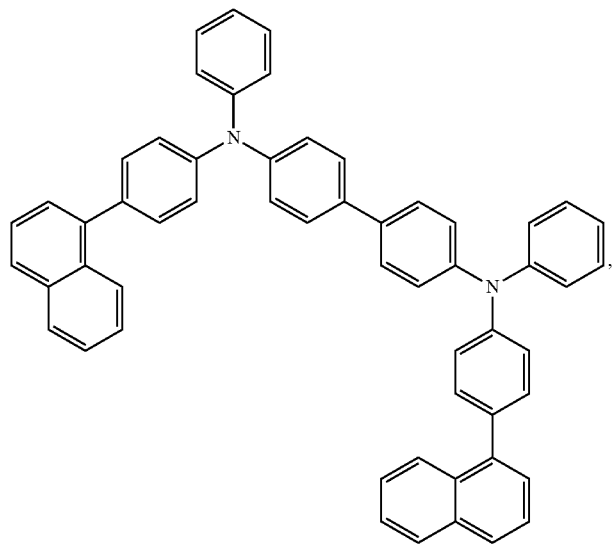
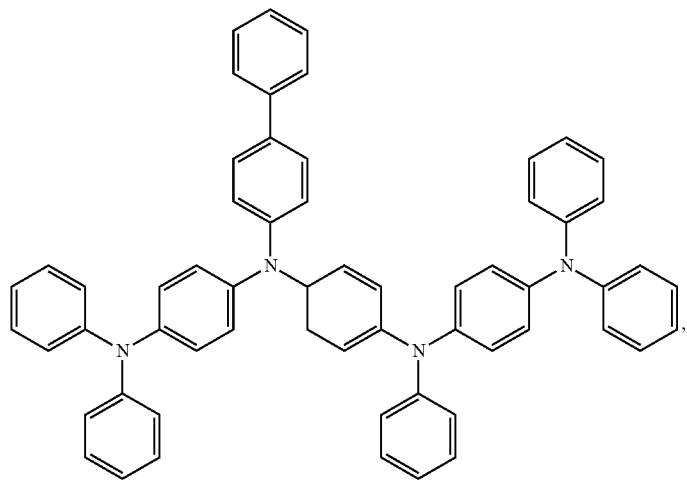
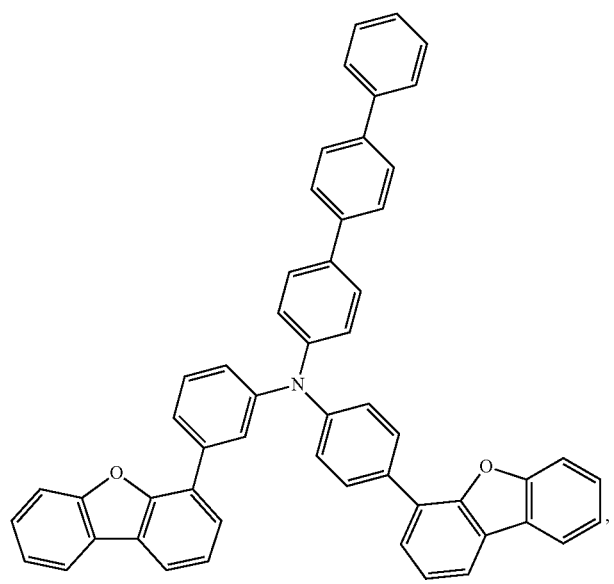

-continued
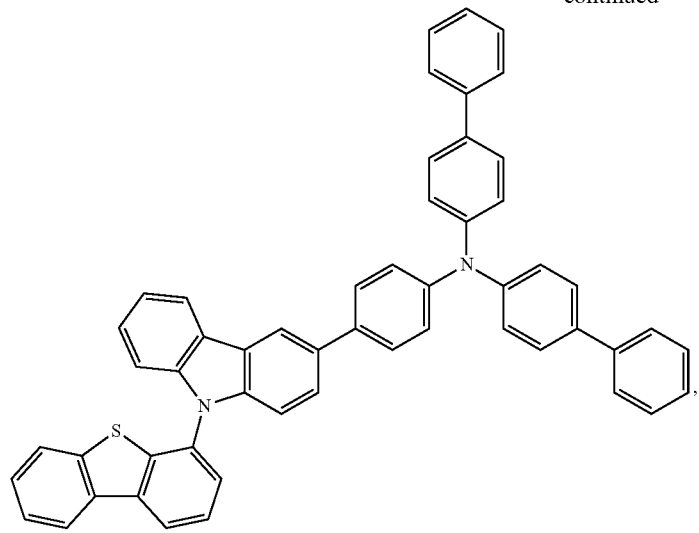
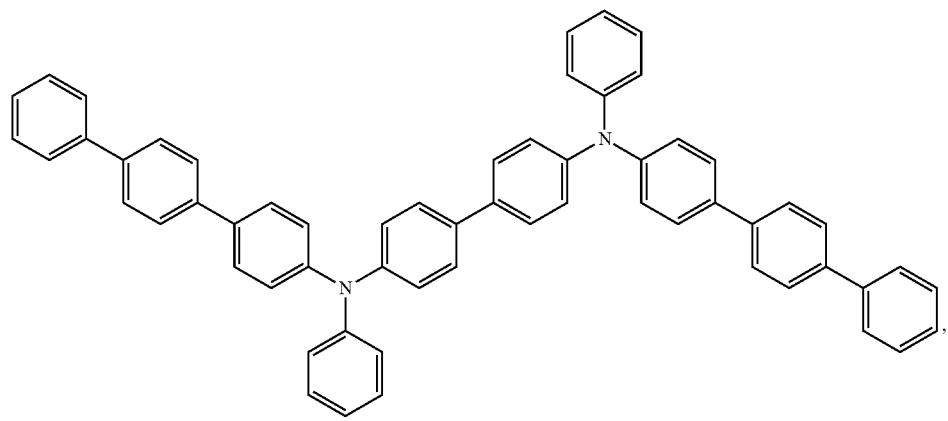
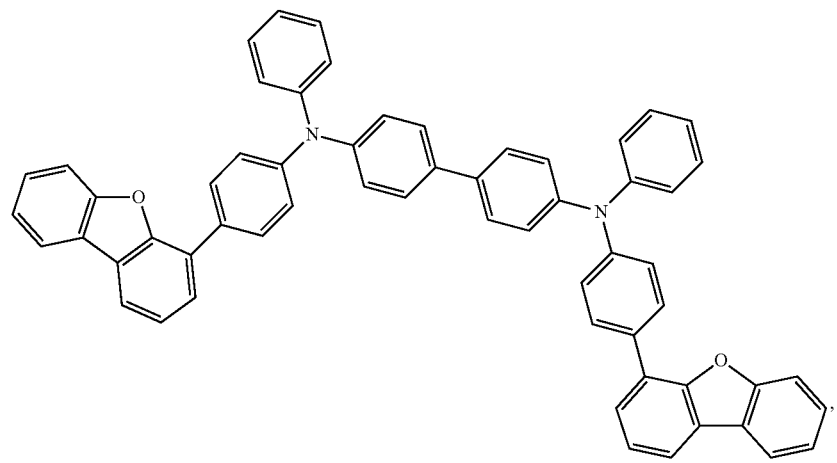

-continued
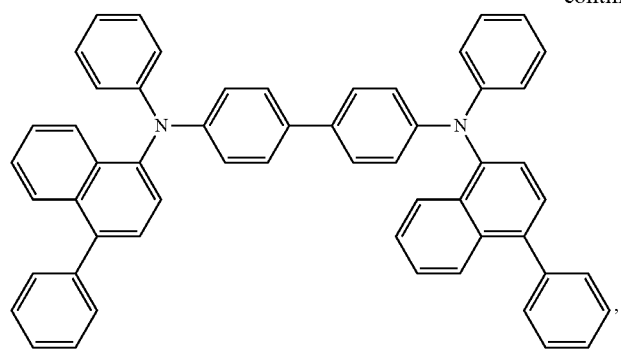
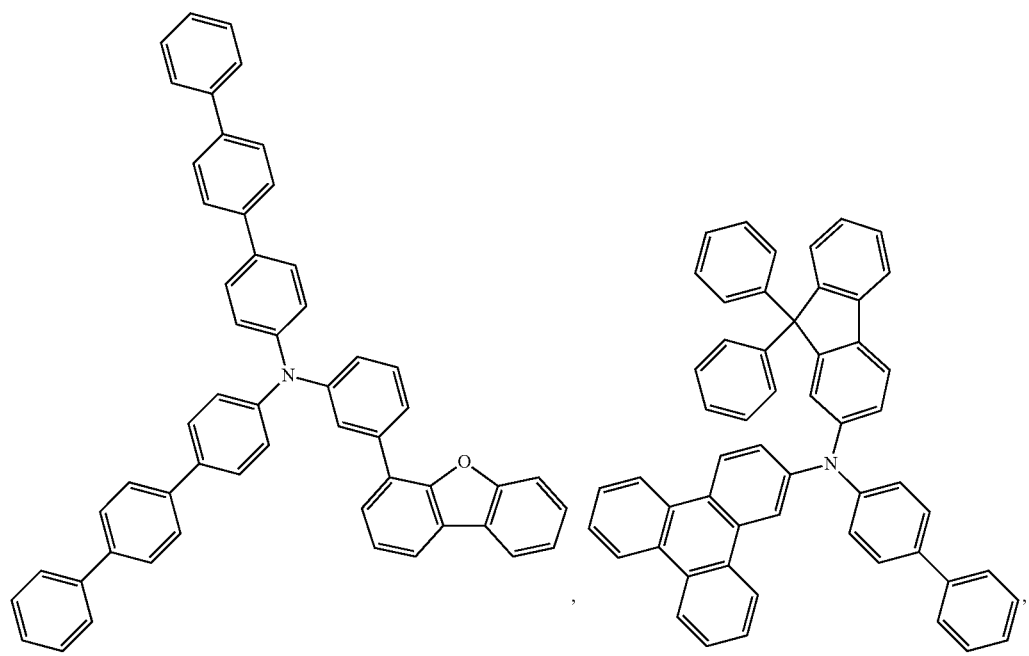
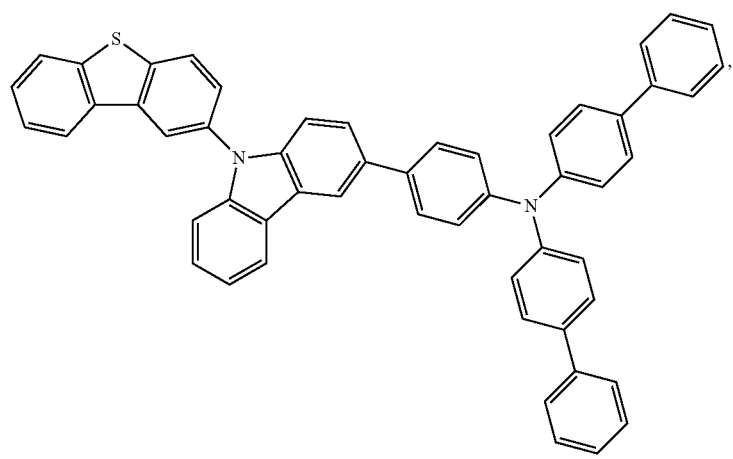

67
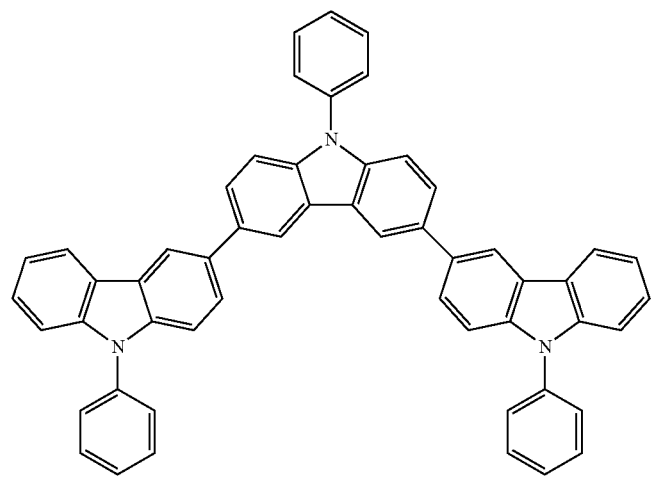
68
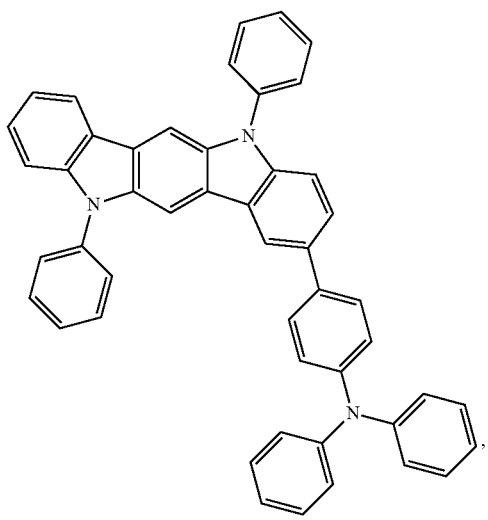
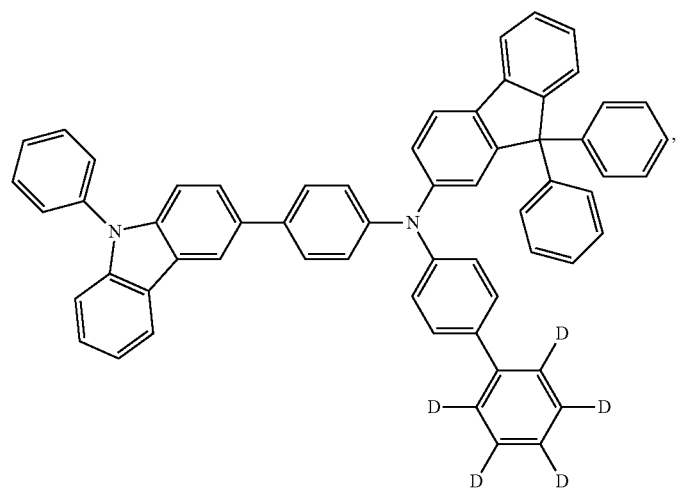
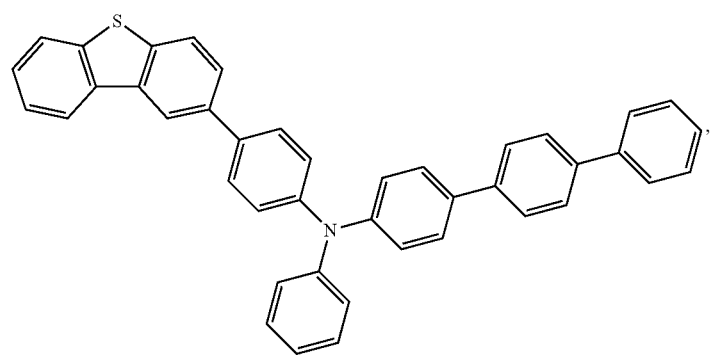

-continued
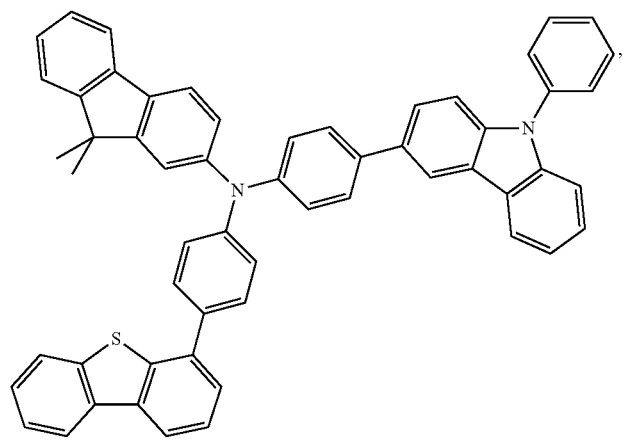
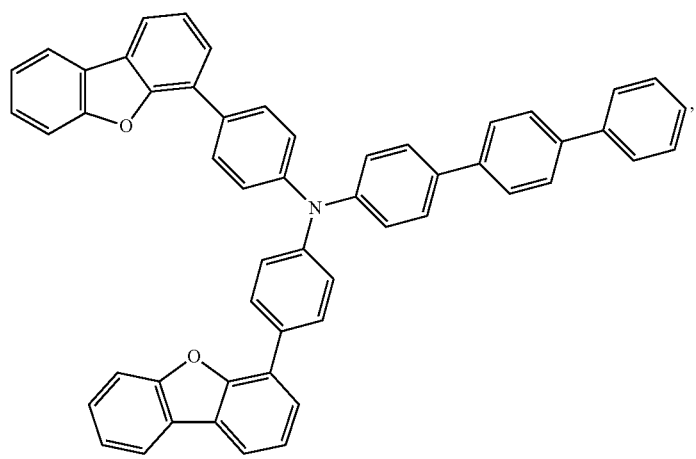
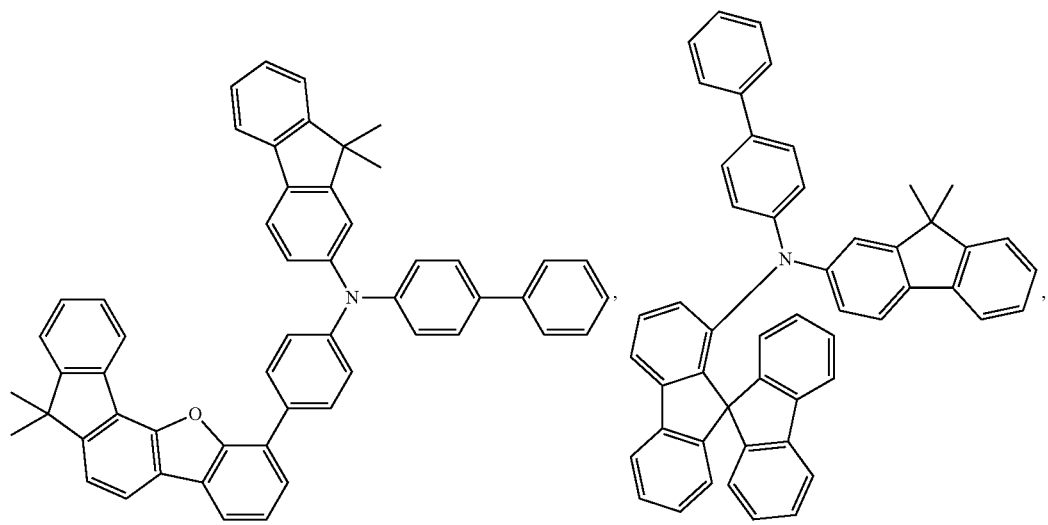

-continued
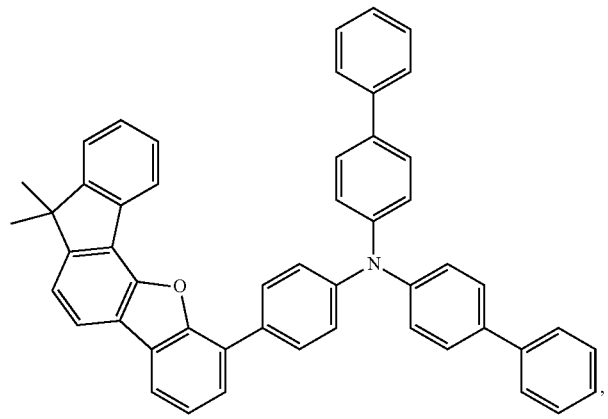
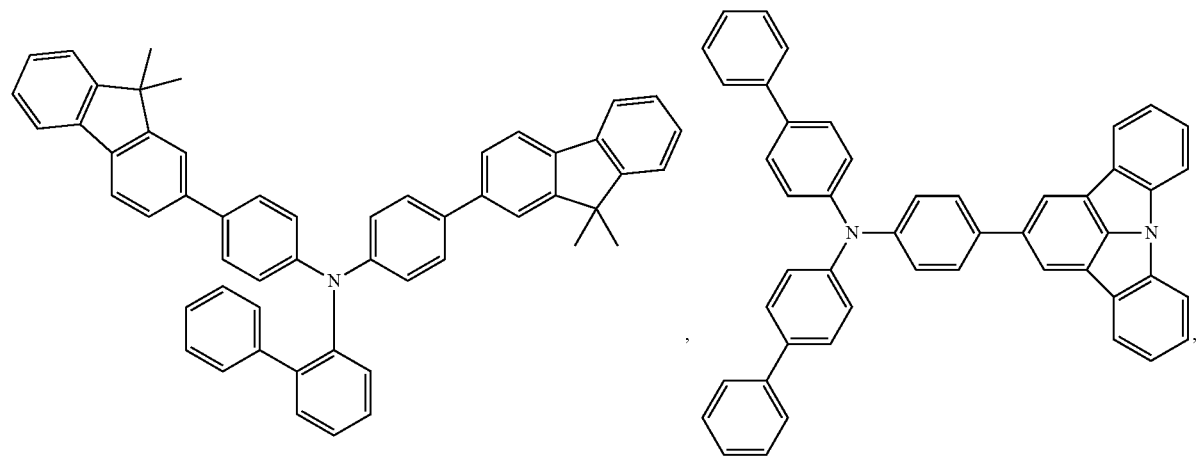
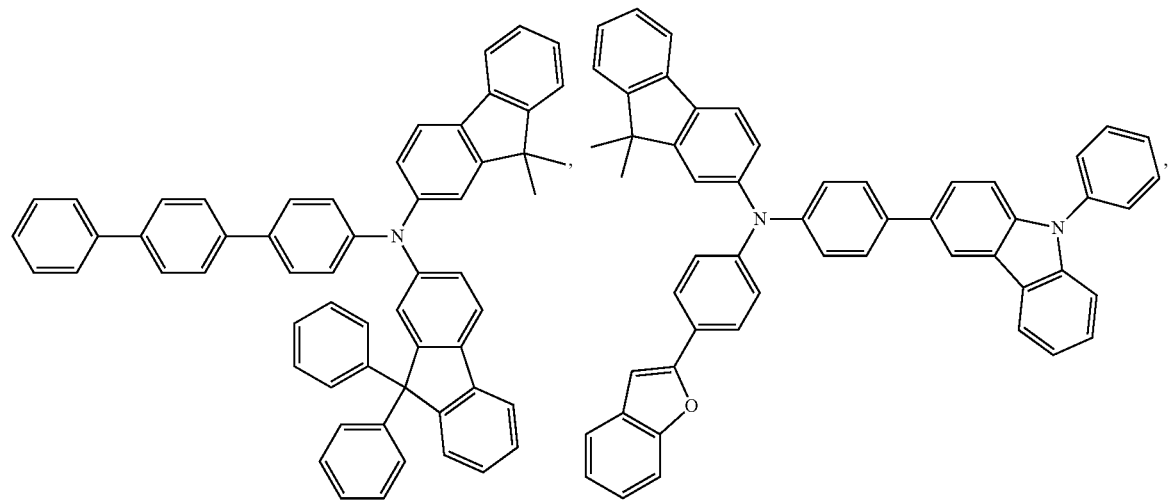

-continued
73
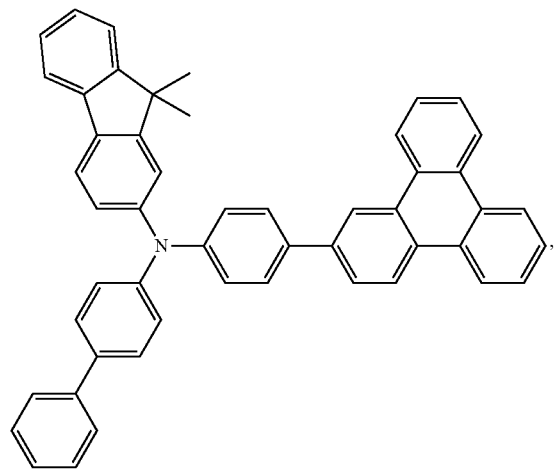
74
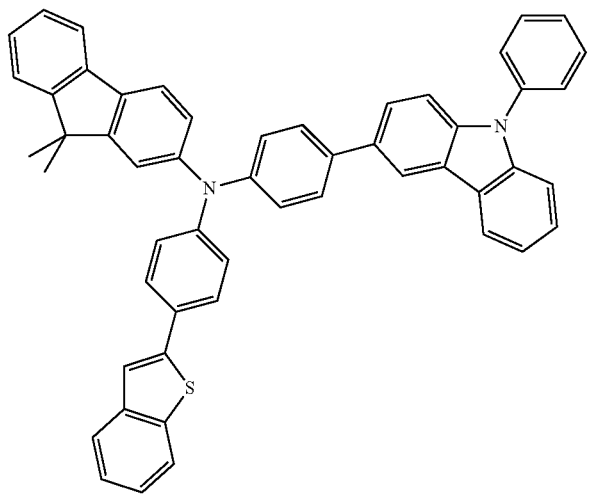
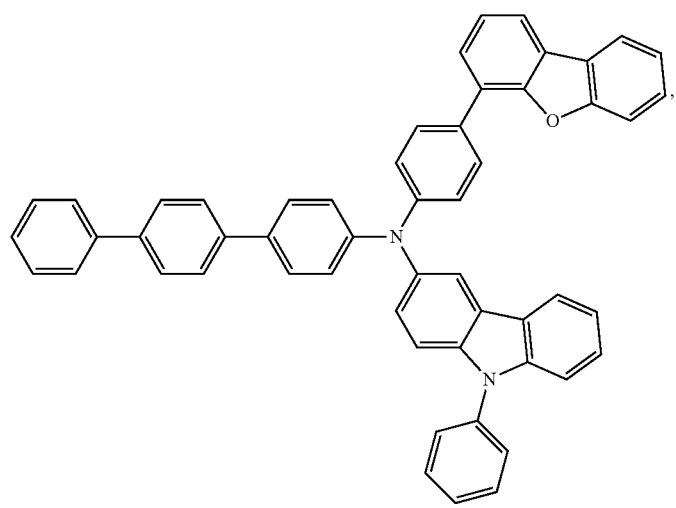
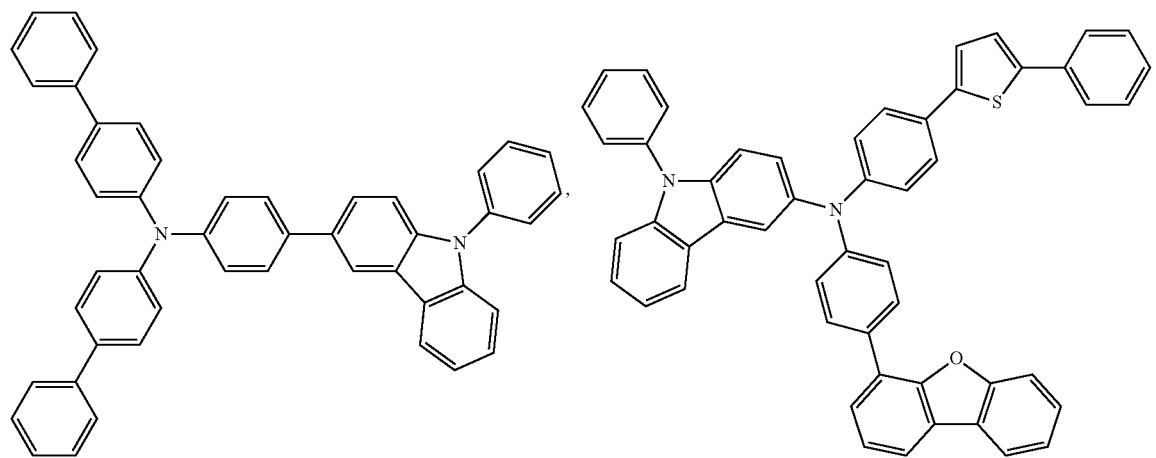

-continued
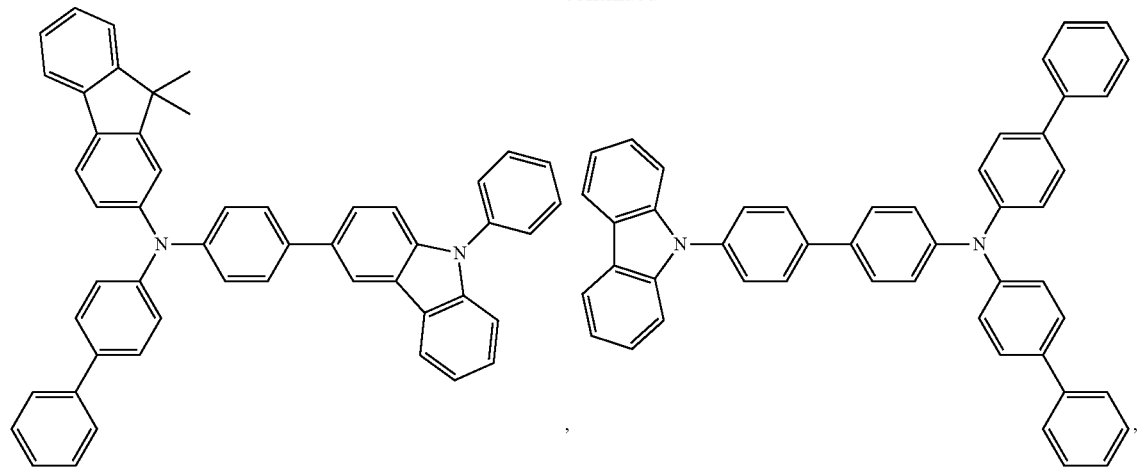
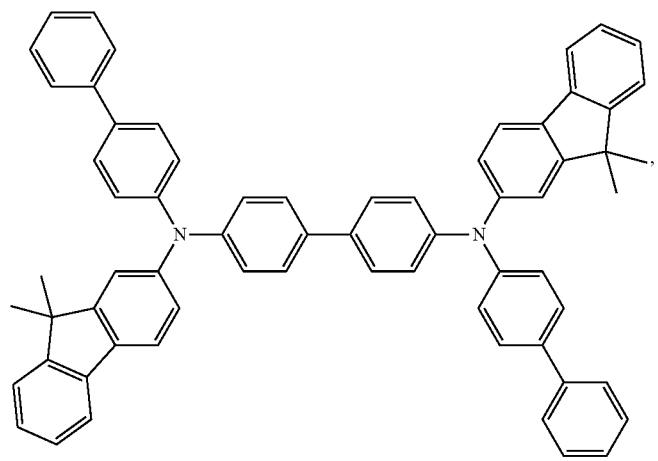
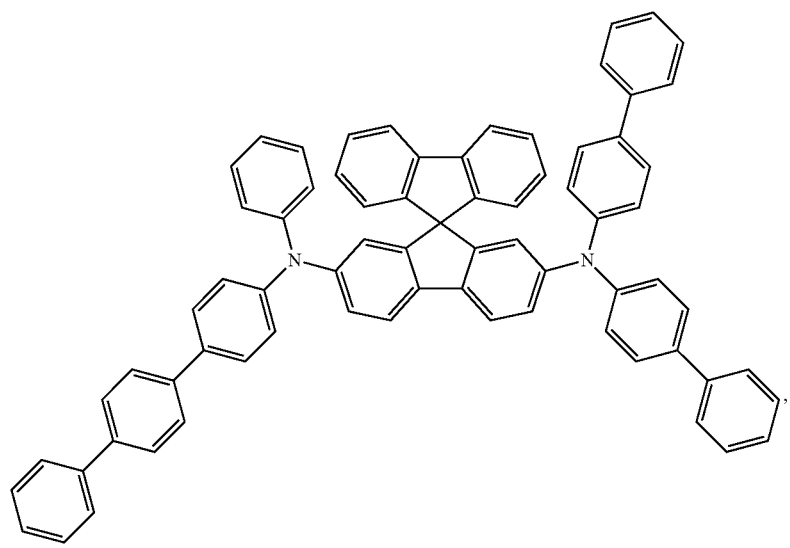

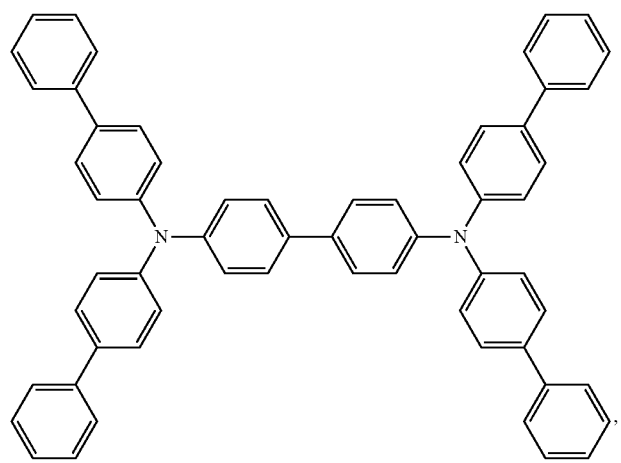
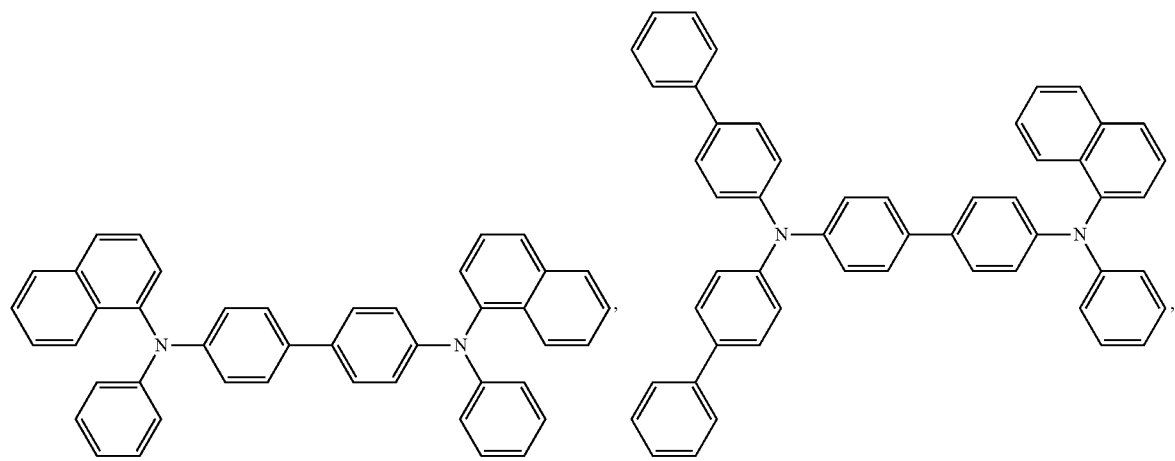
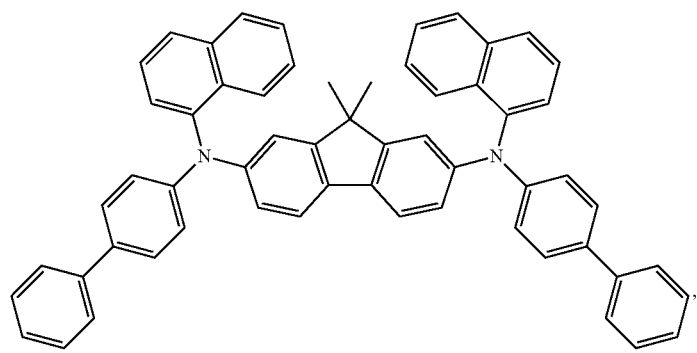

-continued
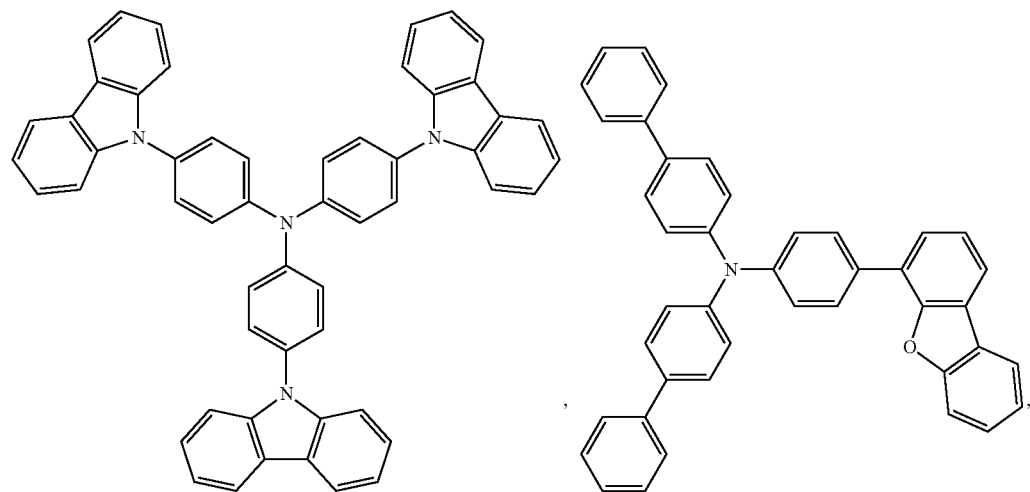
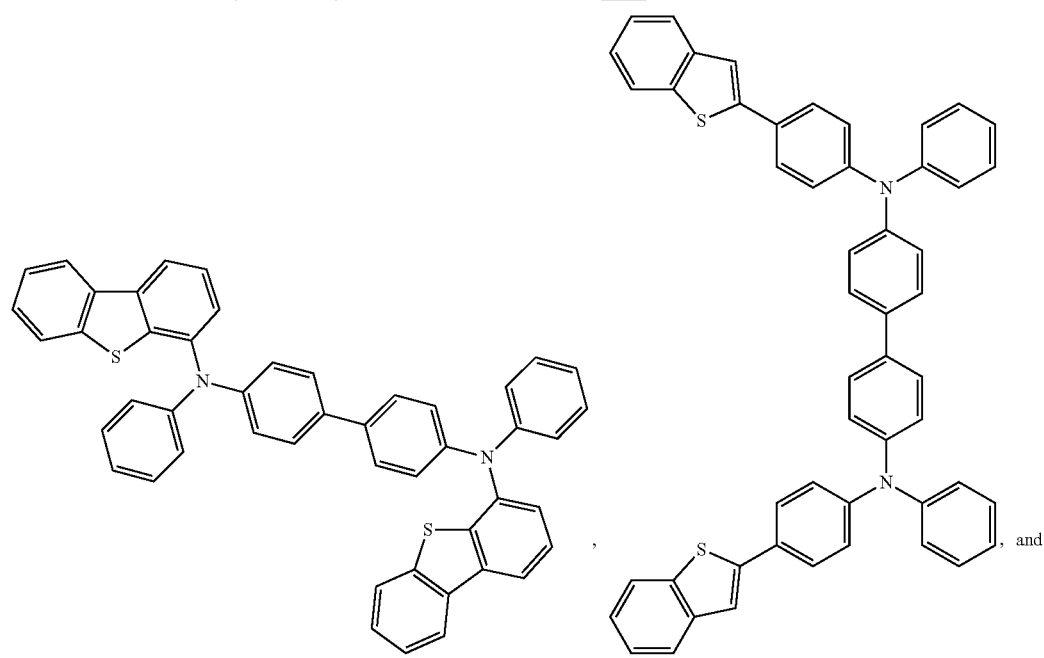
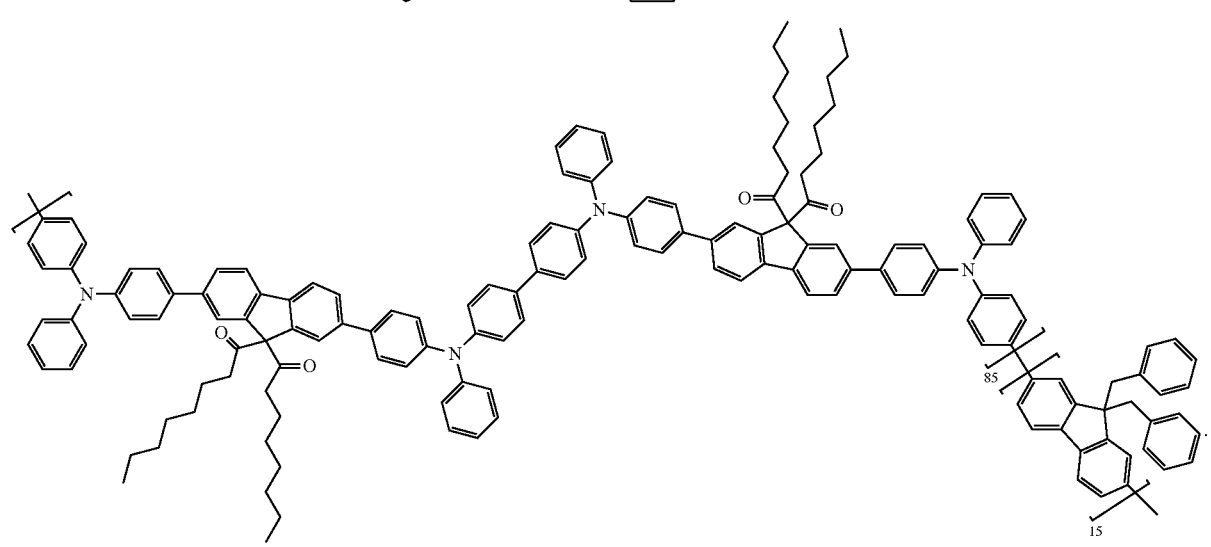

EBL:

An electron blocking layer (EBL) may be used to reduce the number of electrons and/or excitons that leave the emissive layer. The presence of such a blocking layer in a device may result in substantially higher efficiencies, and/or longer lifetime, as compared to a similar device lacking a blocking layer. Also, a blocking layer may be used to confine emission to a desired region of an OLED. In some embodiments, the EBL material has a higher LUMO (closer to the vacuum level) and/or higher triplet energy than the emitter closest to the EBL interface. In some embodiments, the EBL material has a higher LUMO (closer to the vacuum level) and or higher triplet energy than one or more of the hosts closest to the EBL interface. In one aspect, the compound used in EBL contains the same molecule or the same functional groups used as one of the hosts described below.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. Any host material may be used with any dopant so long as the triplet criteria is satisfied.

Examples of metal complexes used as host are preferred to have the following general formula:

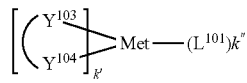

wherein Met is a metal; ($Y^{103}$-$Y^{104}$) is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

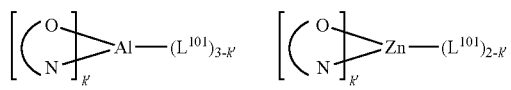

wherein (O—N) is a bidentate ligand, having metal coordinated to atoms O and N.

In another aspect, Met is selected from Ir and Pt. In a further aspect, ($Y^{103}$-$Y^{104}$) is a carbene ligand.

Examples of other organic compounds used as host are selected from the group consisting of aromatic hydrocarbon cyclic compounds such as benzene, biphenyl, triphenyl, triphenylene, tetraphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each option within each group may be unsubstituted or may be substituted by a substituent selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, the host compound contains at least one of the following groups in the molecule:

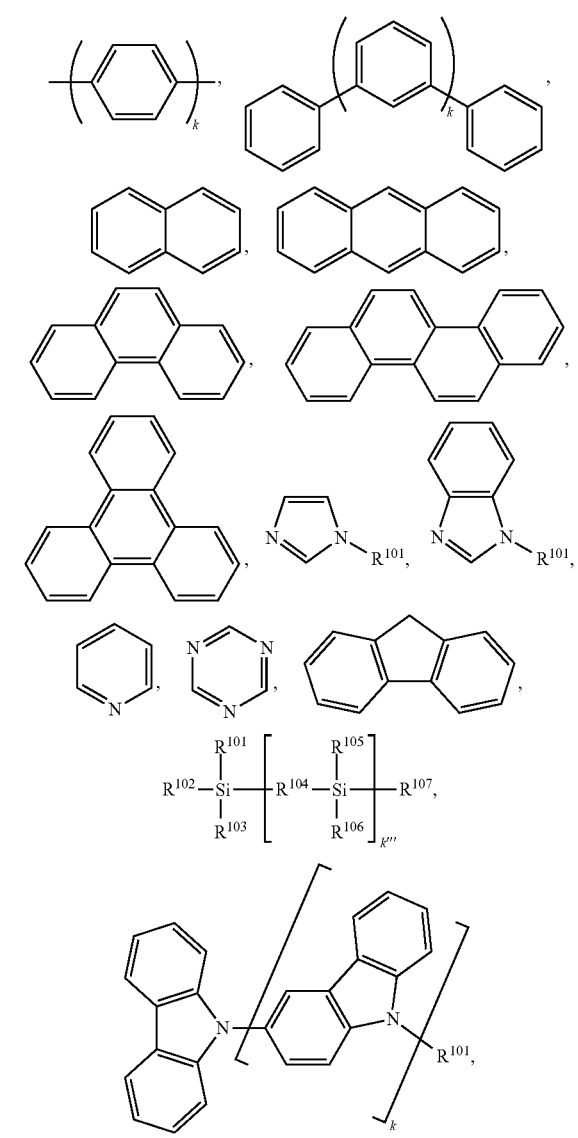

-continued

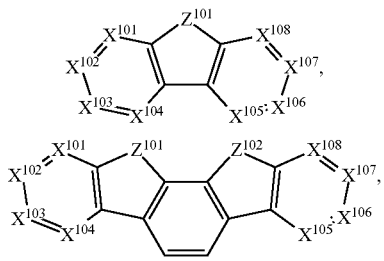

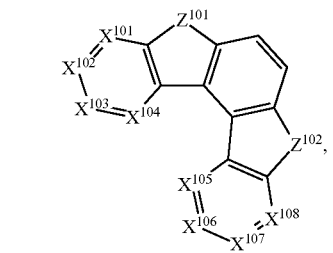

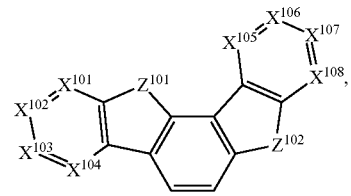

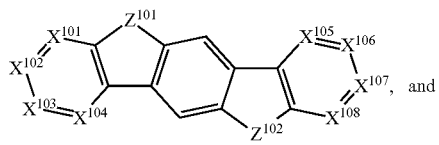

-continued

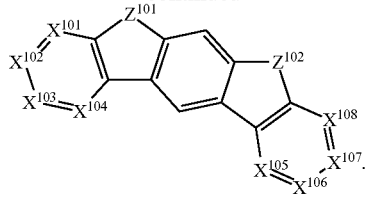

wherein each of $R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and when it is aryl or heteroaryl, it has the similar definition as Ar's mentioned above. k is an integer from 0 to 20 or 1 to 20; k" is an integer from 0 to 20. $X^{101}$ to $X^{108}$ is selected from C (including CH) or N.

$Z^{101}$ and $Z^{102}$ is selected from $NR^{101}$, O, or S.

Non-limiting examples of the host materials that may be used in an OLED in combination with materials disclosed herein are exemplified below together with references that disclose those materials: EP2034538, EP2034538A, EP2757608, JP2007254297, KR20100079458, KR20120088644, KR20120129733, KR20130115564, TW201329200, US20030175553, US20050238919, US20060280965, US20090017330, US20090030202, US20090167162, US20090302743, US20090309488, US20100012931, US20100084966, US20100187984, US2010187984, US2012075273, US2012126221, US2013009543, US2013105787, US2013175519, US2014001446, US20140183503, US20140225088, US2014034914, U.S. Pat. No. 7,154,114, WO2001039234, WO2004093207, WO2005014551, WO2005089025, WO2006072002, WO2006114966, WO2007063754, WO2008056746, WO2009003898, WO2009021126, WO2009063833, WO2009066778, WO2009066779, WO2009086028, WO2010056066, WO2010107244, WO2011081423, WO2011081431, WO2011086863, WO2012128298, WO2012133644, WO2012133649, WO2013024872, WO2013035275, WO2013081315, WO2013191404, WO2014142472,

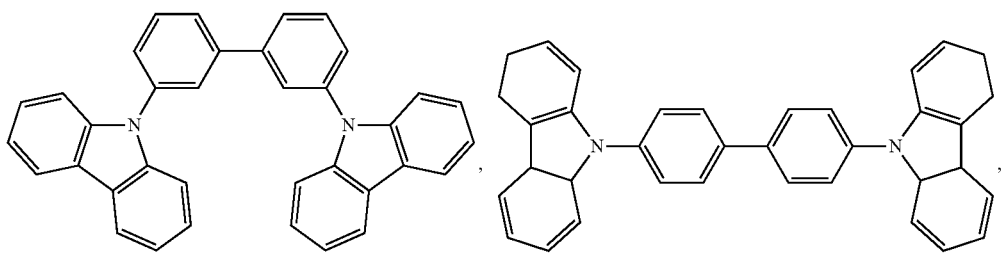

-continued
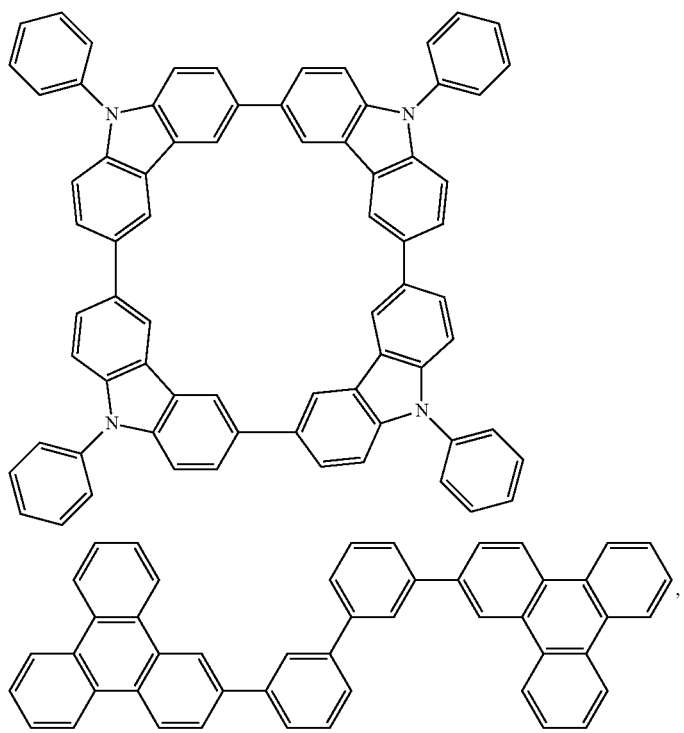
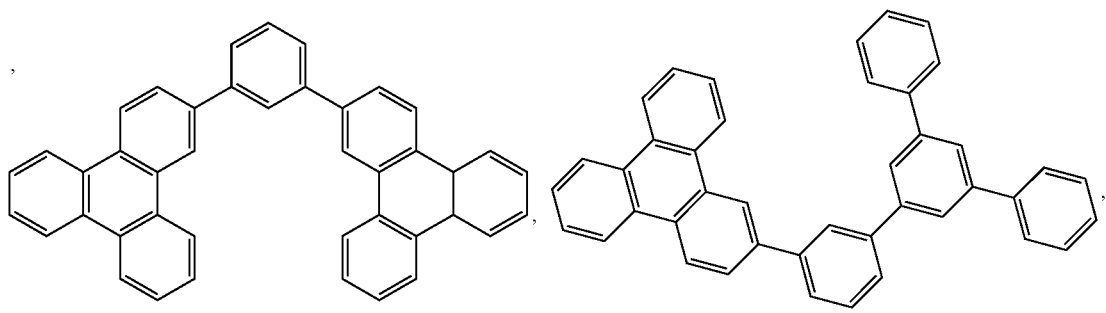
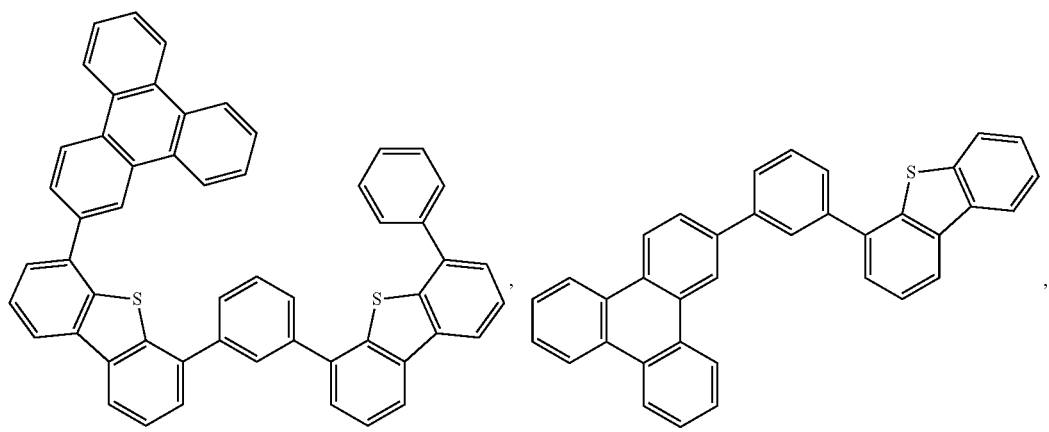

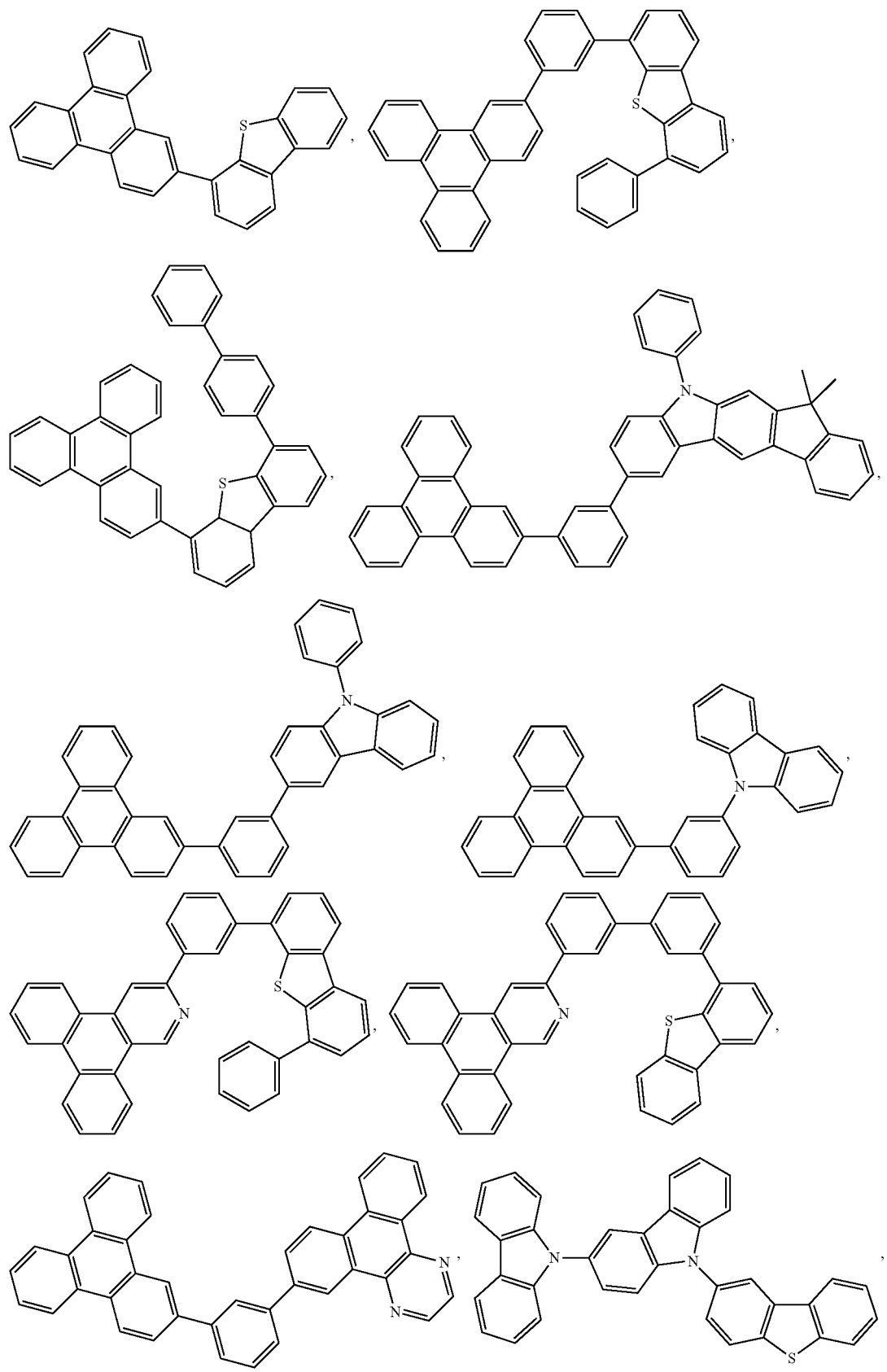

-continued
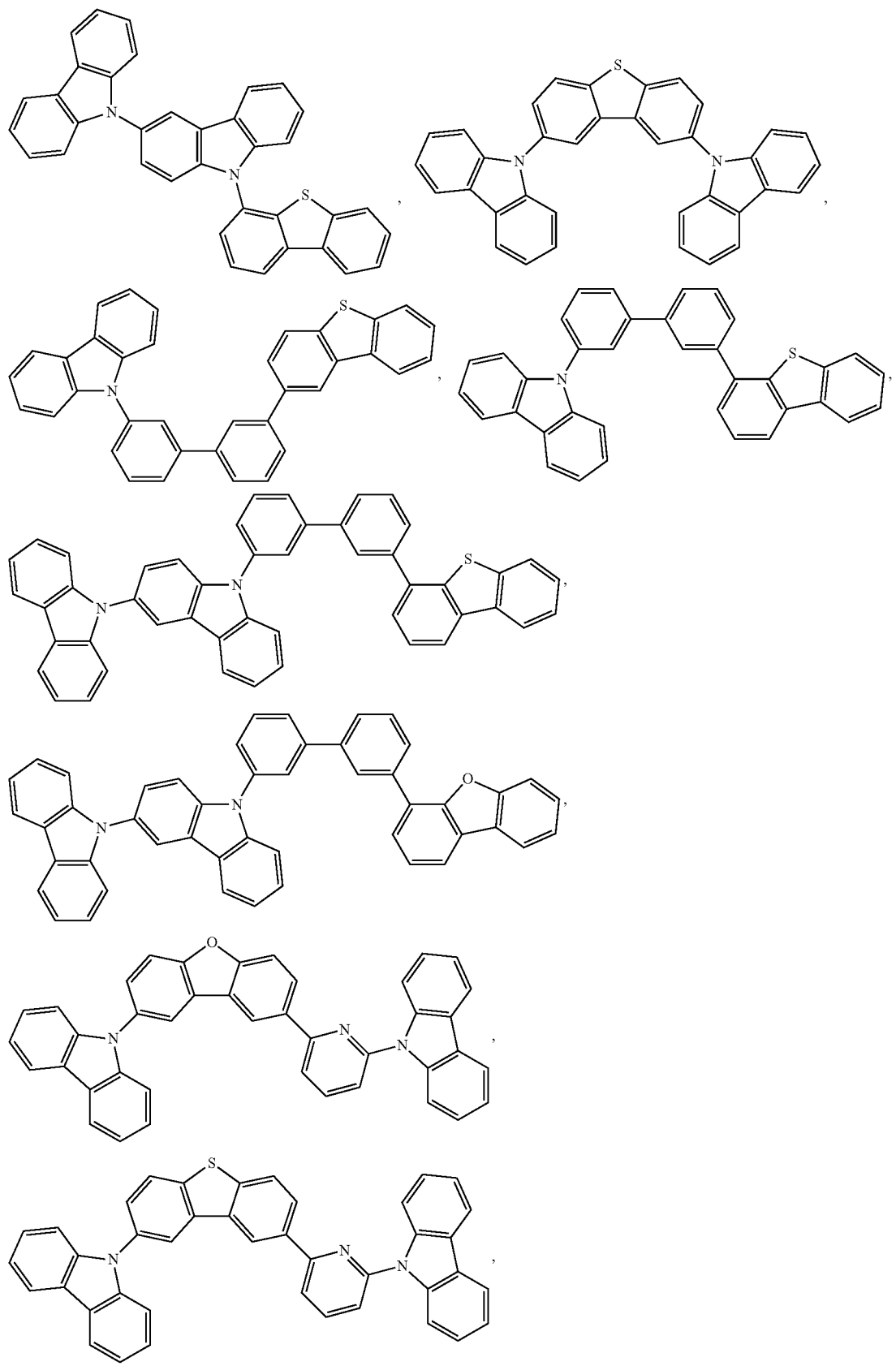

-continued
91
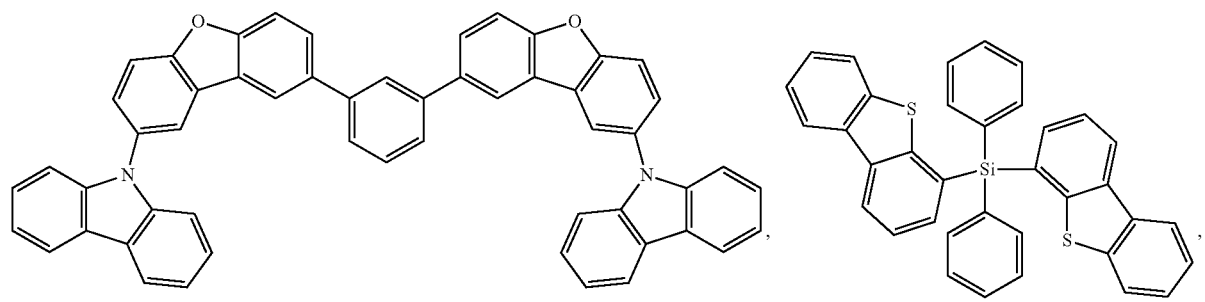
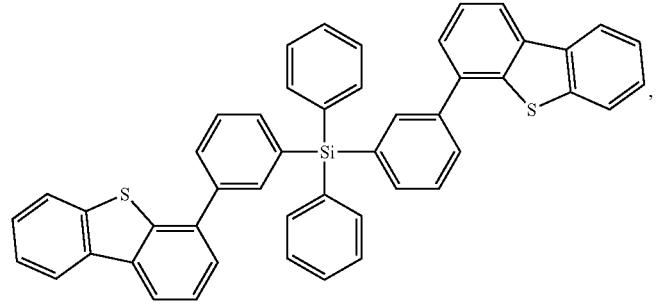
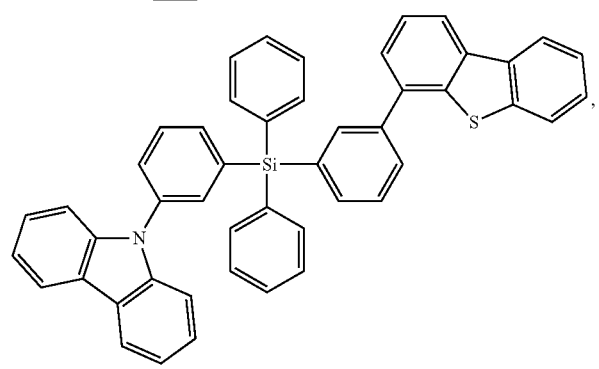
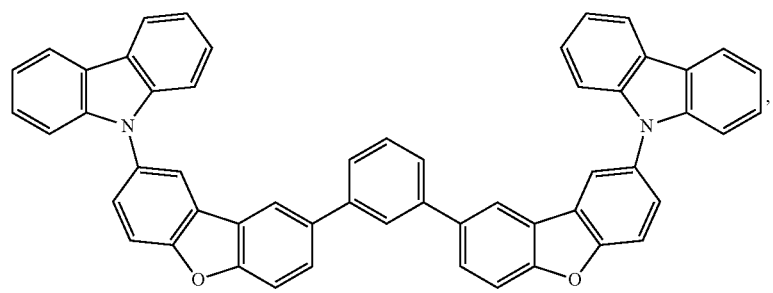
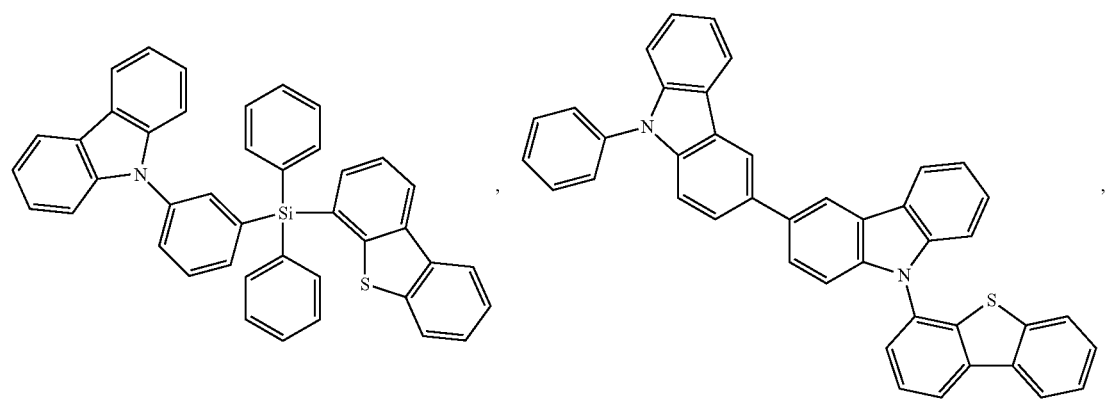
92

-continued
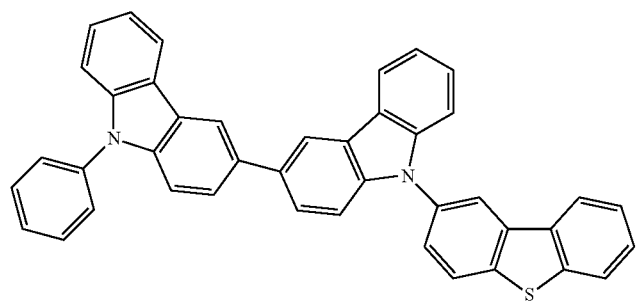
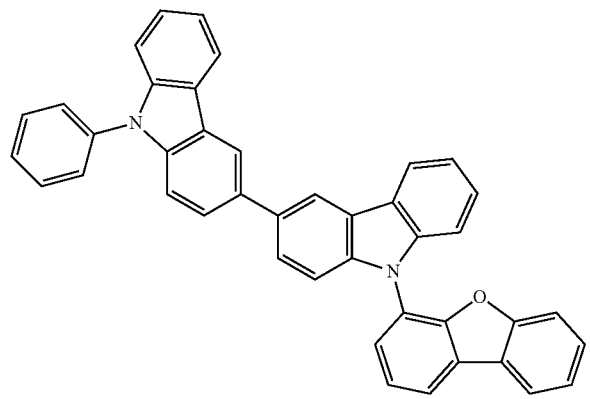
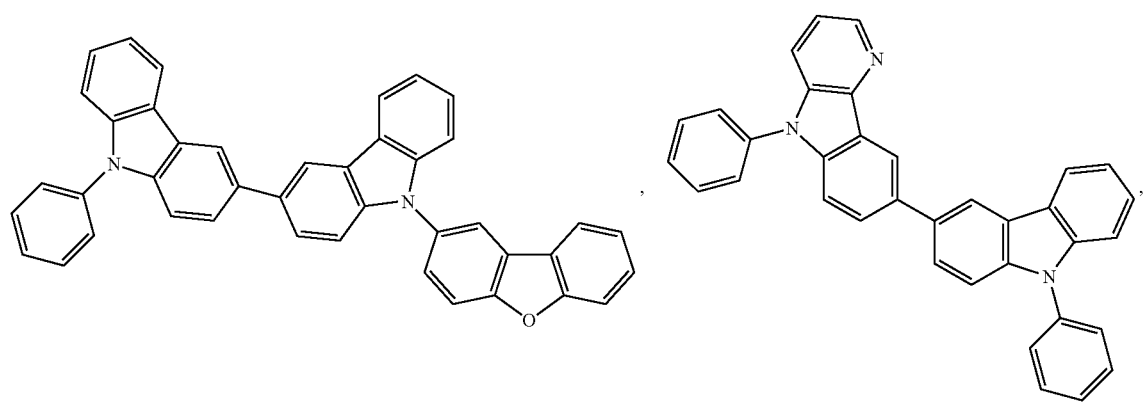
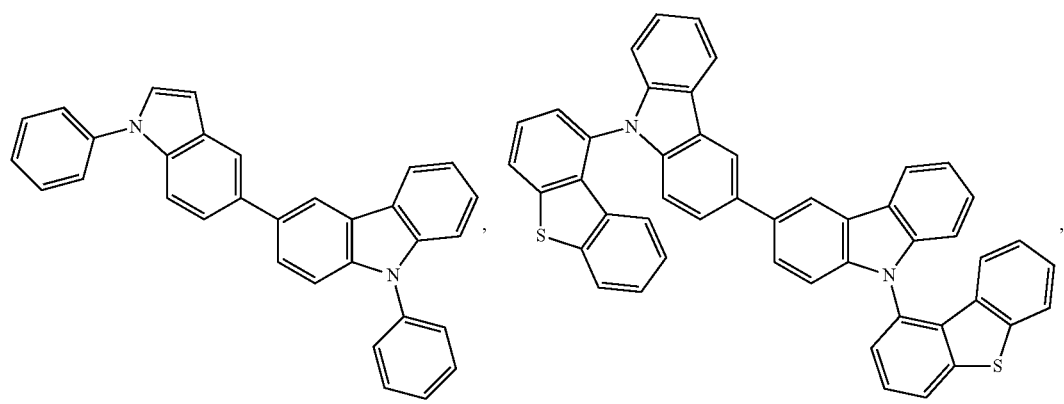

-continued
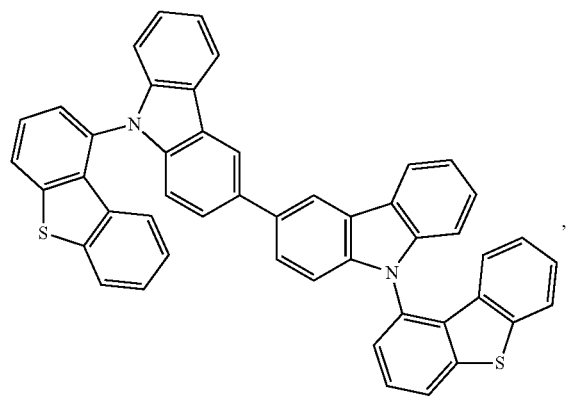
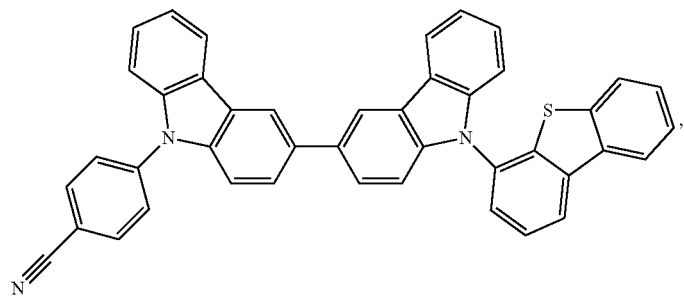
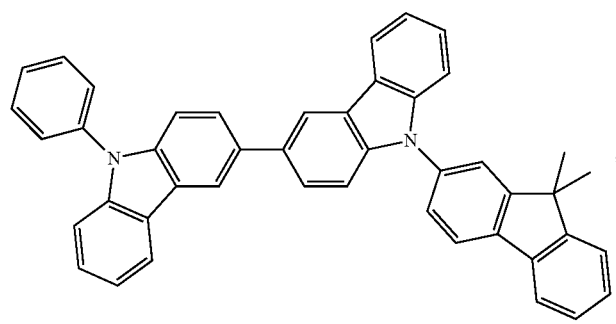
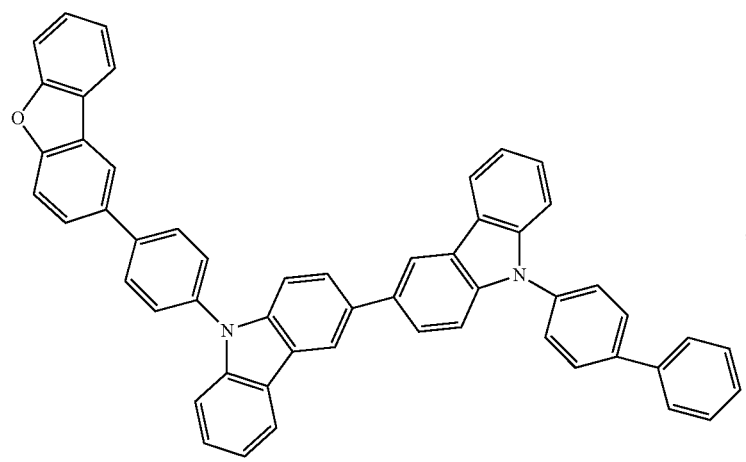

-continued
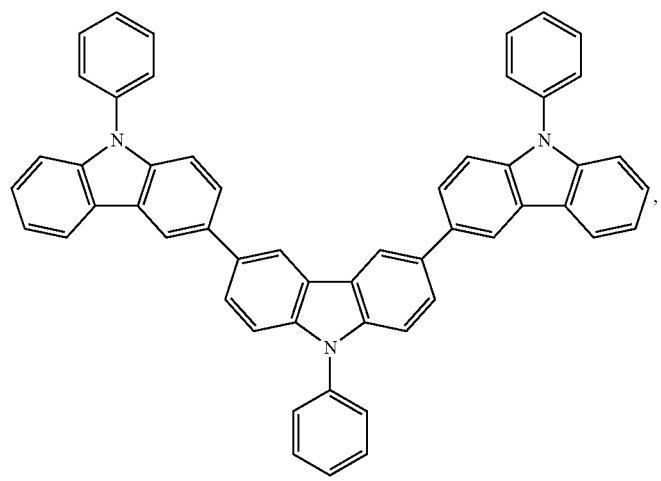
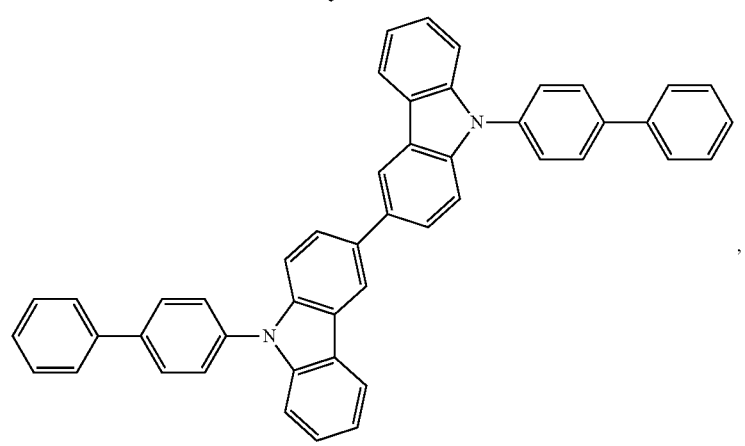
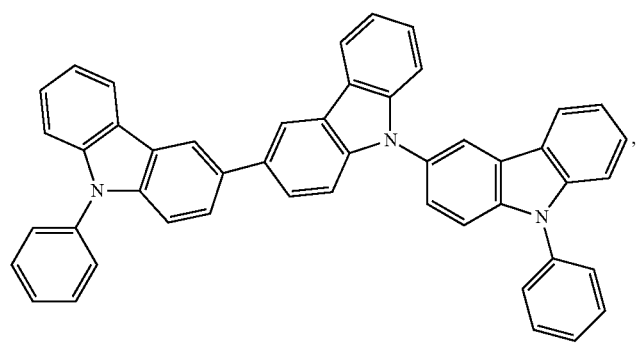
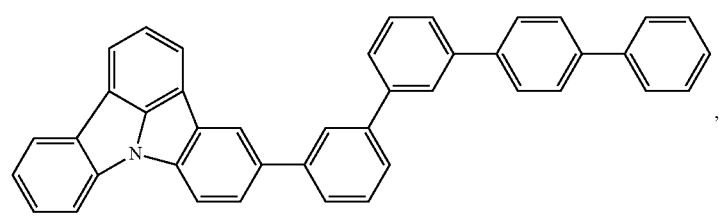

-continued
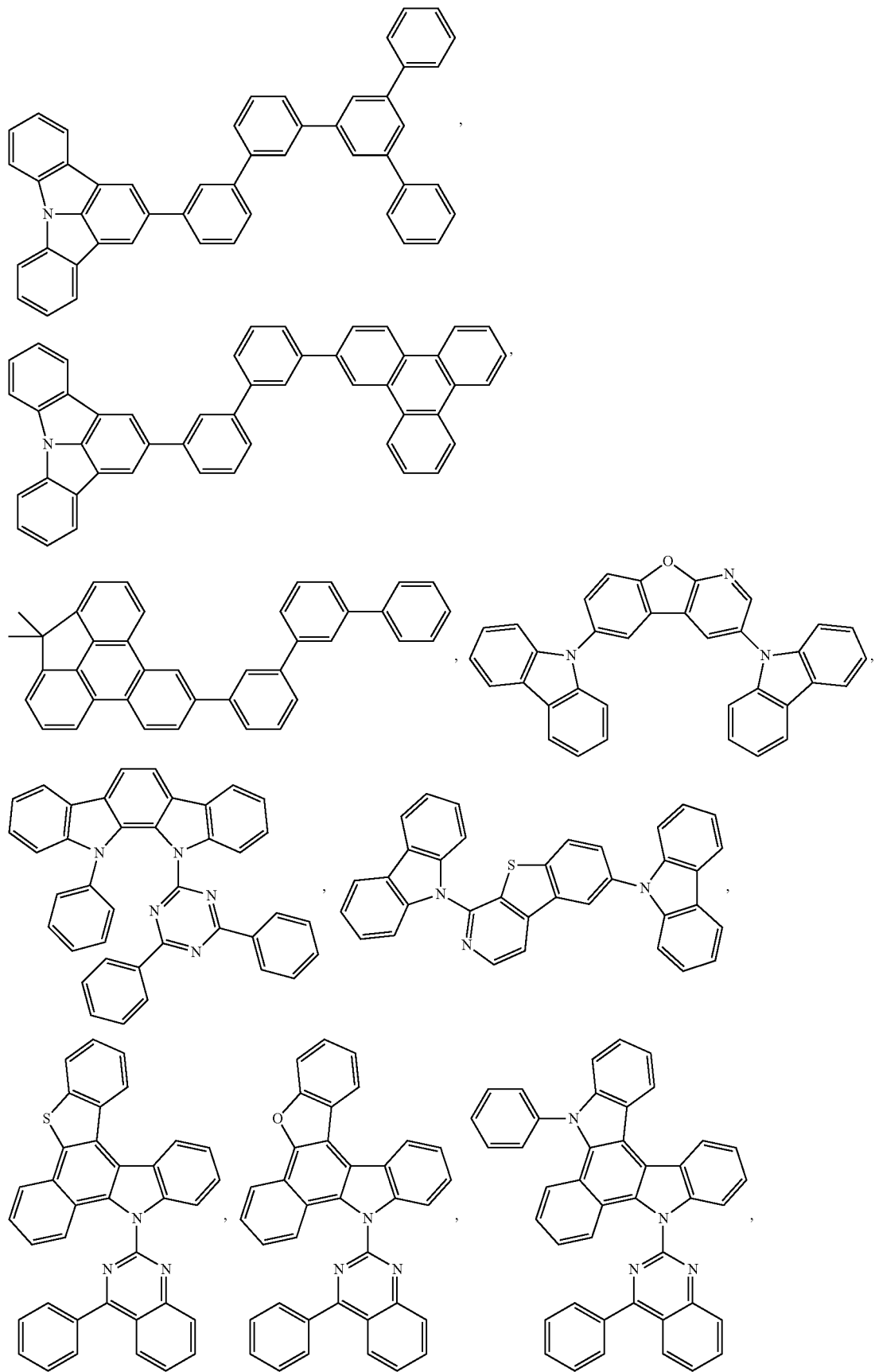

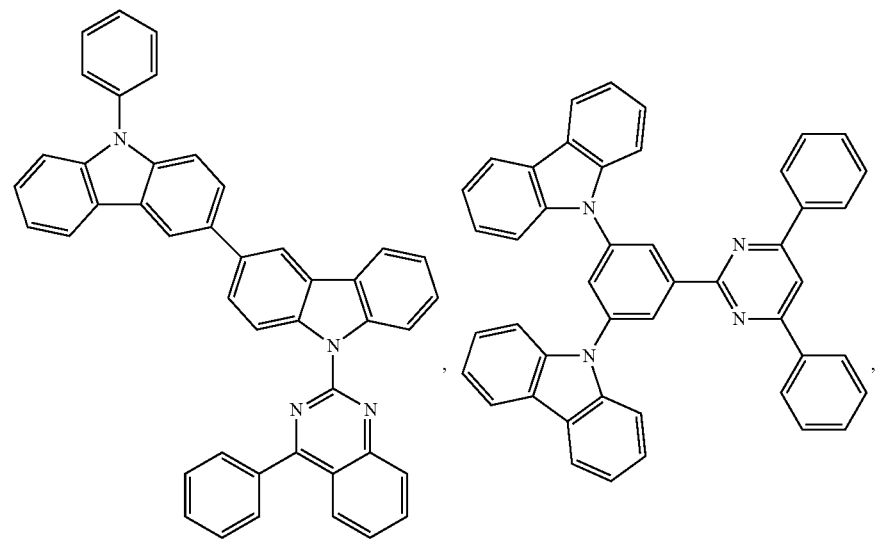
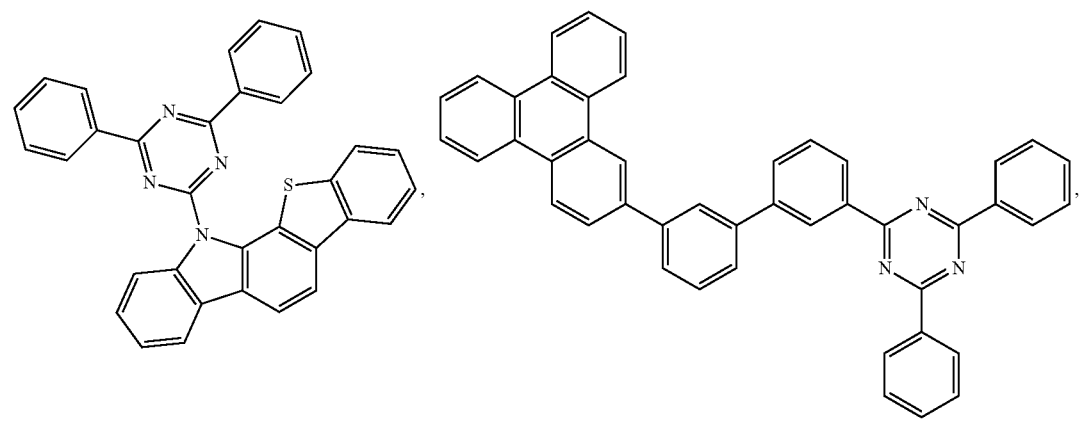
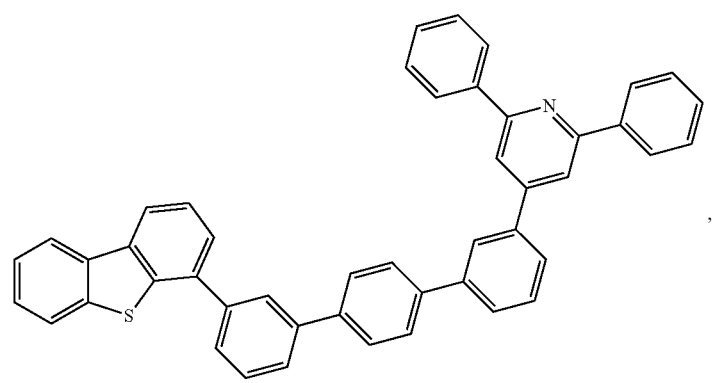
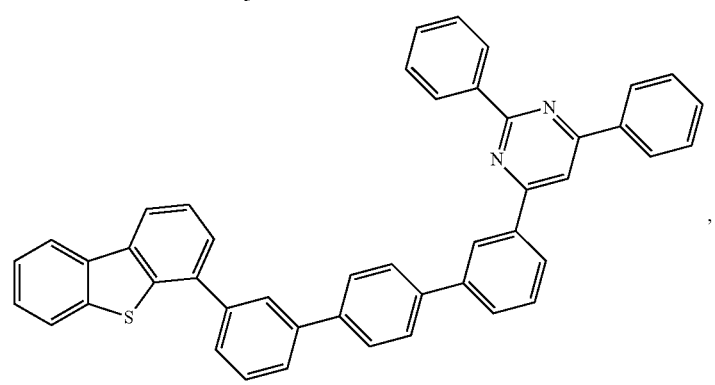

-continued
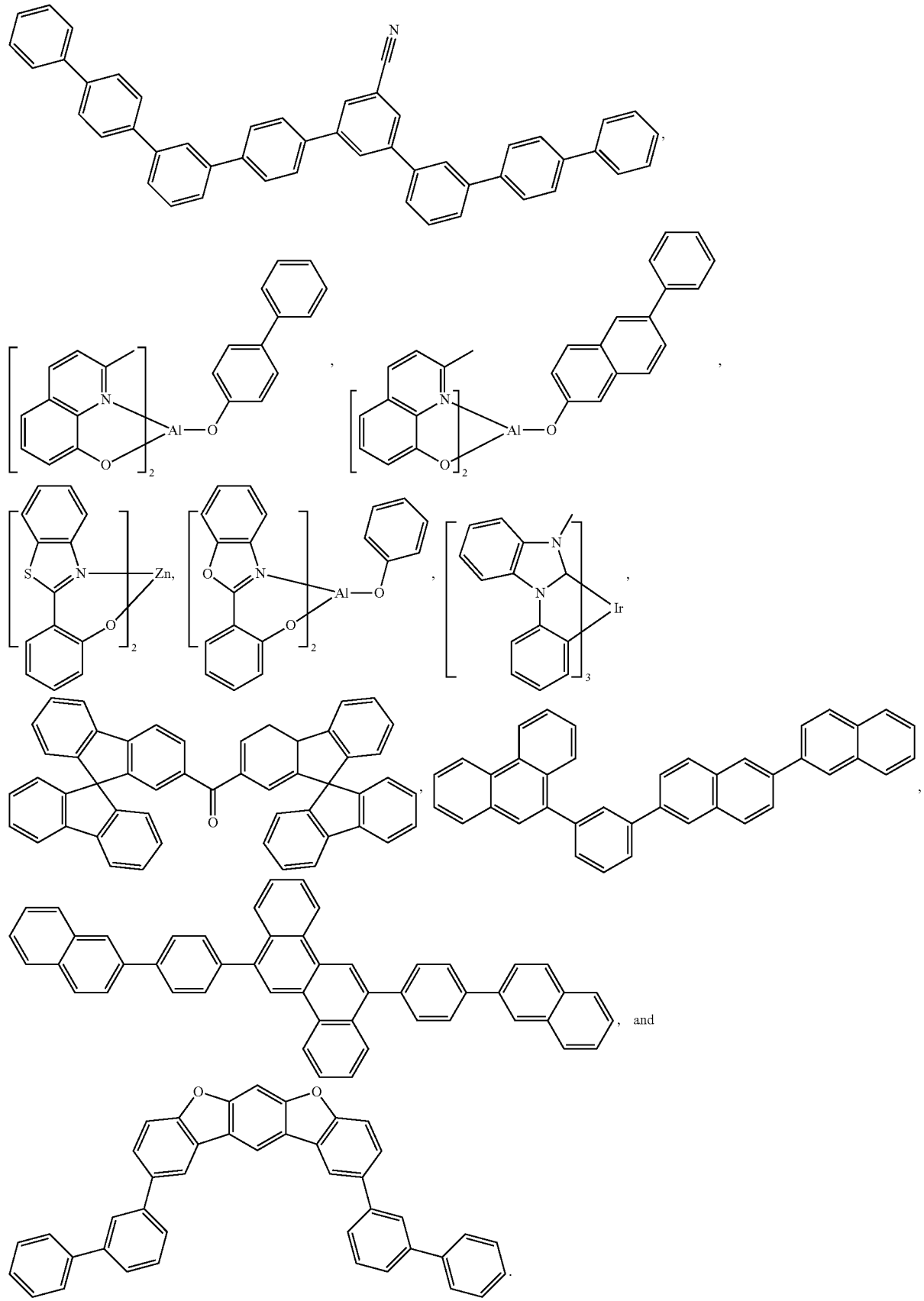

Additional Emitters:

One or more additional emitter dopants may be used in conjunction with the compound of the present disclosure. Examples of the additional emitter dopants are not particularly limited, and any compounds may be used as long as the compounds are typically used as emitter materials. Examples of suitable emitter materials include, but are not limited to, compounds which can produce emissions via phosphorescence, fluorescence, thermally activated delayed fluorescence, i.e., TADF (also referred to as E-type delayed fluorescence), triplet-triplet annihilation, or combinations of these processes.

Non-limiting examples of the emitter materials that may be used in an OLED in combination with materials disclosed herein are exemplified below together with references that disclose those materials: CN103694277, CN1696137, EB01238981, EP01239526, EP01961743, EP1239526, EP1244155, EP1642951, EP1647554, EP1841834, EP1841834B, EP2062907, EP2730583, JP2012074444, JP2013110263, JP4478555, KR1020090133652, KR20120032054, KR20130043460, TW201332980, U.S. Ser. No. 06/699,599, U.S. Ser. No. 06/916,554, US20010019782, US20020034656, US20030068526, US20030072964, US20030138657, US20050123788, US20050244673, US2005123791, US2005260449, US20060008670, US20060065890, US20060127696, US20060134459, US20060134462, US20060202194, US20060251923, US20070034863, US20070087321, US20070103060, US20070111026, US20070190359, US20070231600, US2007034863, US2007104979, US2007104980, US2007138437, US2007224450, US2007278936, US20080020237, US20080233410, US20080261076, US20080297033, US200805851, US2008161567, US2008210930, US20090039776, US20090108737, US20090115322, US20090179555, US2009085476, US2009104472, US20100090591, US20100148663, US20100244004, US20100295032, US2010102716, US2010105902, US2010244004, US2010270916, US20110057559, US20110108822, US20110204333, US2011215710, US2011227049, US2011285275, US2012292601, US20130146848, US2013033172, US2013165653, US2013181190, US2013334521, US20140246656, US2014103305, U.S. Pat. Nos. 6,303,238, 6,413,656, 6,653,654, 6,670,645, 6,687,266, 6,835,469, 6,921,915, 7,279,704, 7,332,232, 7,378,162, 7,534,505, 7,675,228, 7,728,137, 7,740,957, 7,759,489, 7,951,947, 8,067,099, 8,592,586, 8,871,361, WO06081973, WO06121811, WO07018067, WO07108362, WO07115970, WO07115981, WO08035571, WO2002015645, WO2003040257, WO2005019373, WO2006056418, WO2008054584, WO2008078800, WO2008096609, WO2008101842, WO2009000673, WO2009050281, WO2009100991, WO2010028151, WO2010054731, WO2010086089, WO2010118029, WO2011044988, WO2011051404, WO2011107491, WO2012020327, WO2012163471, WO2013094620, WO2013107487, WO2013174471, WO2014007565, WO2014008982, WO2014023377, WO2014024131, WO2014031977, WO2014038456, WO2014112450.

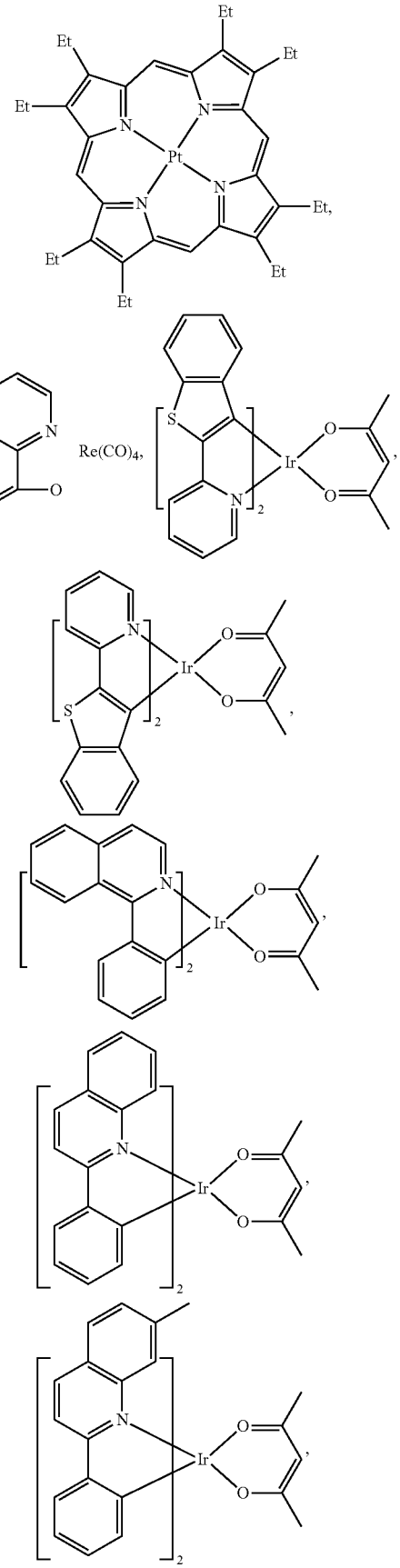

-continued
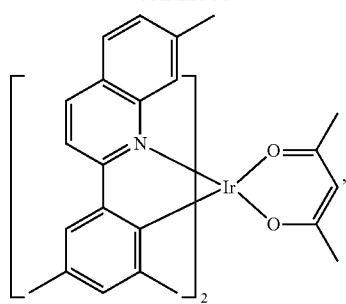
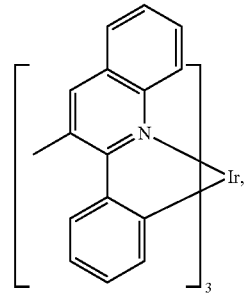
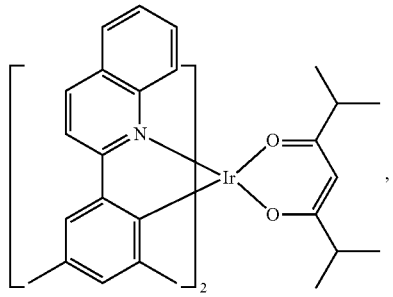
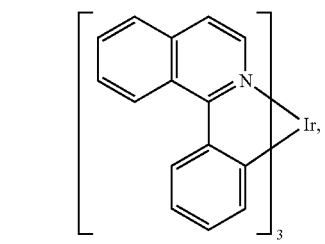
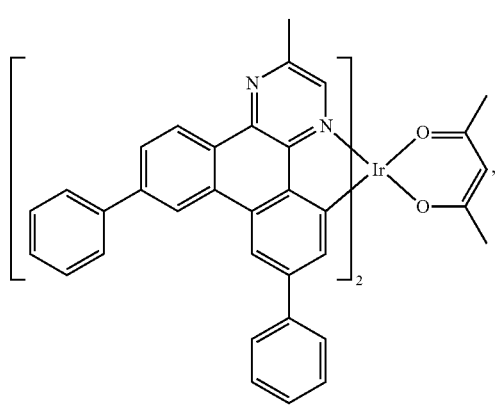
-continued
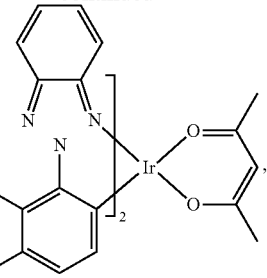
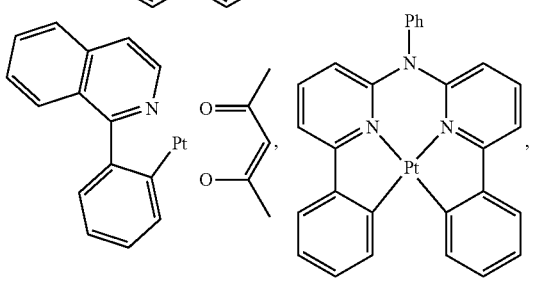
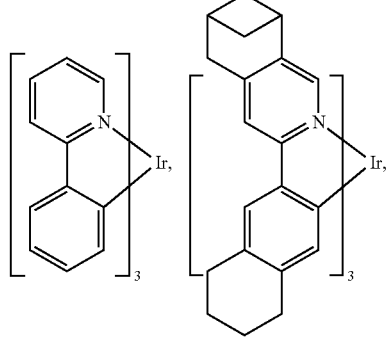
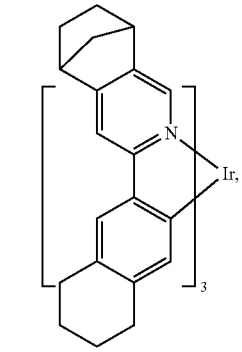
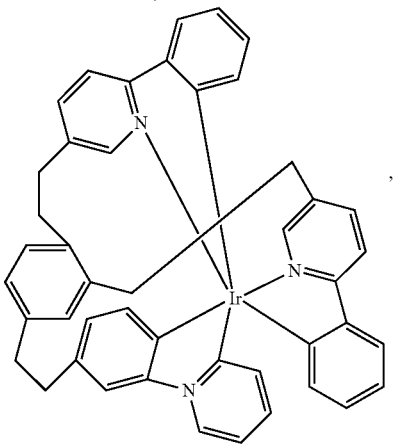

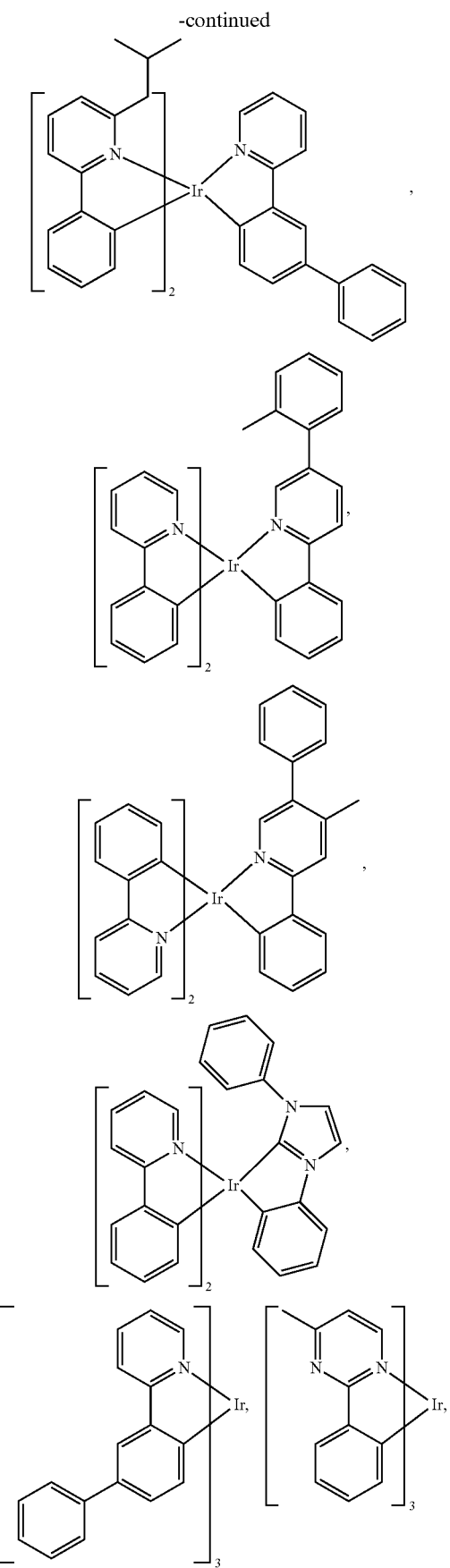
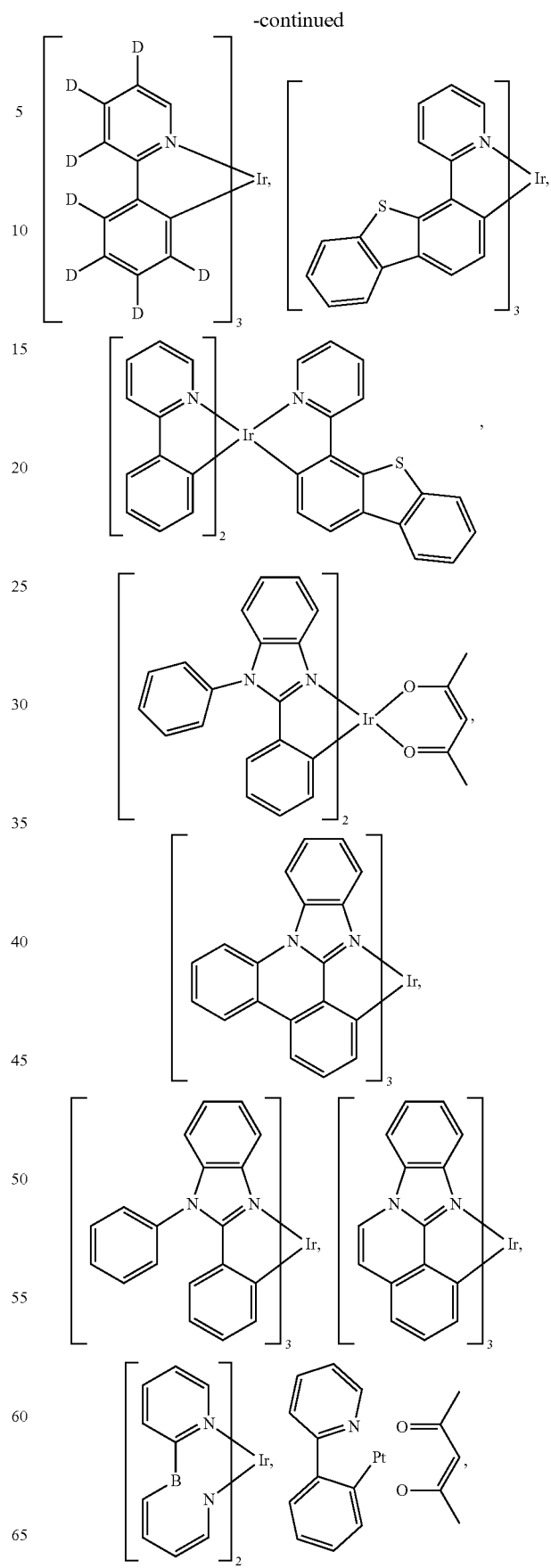

111
-continued
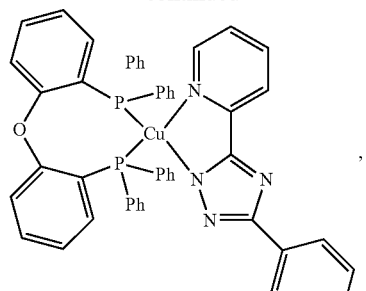
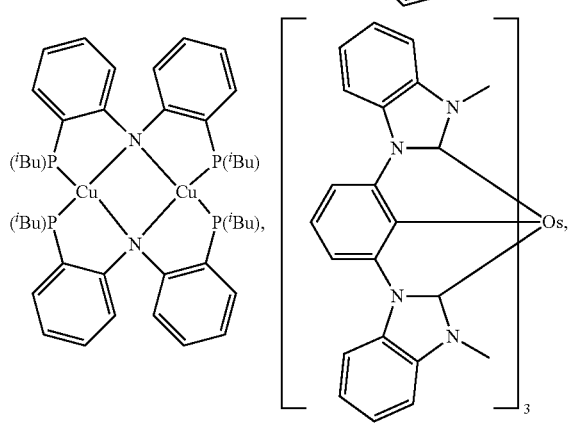
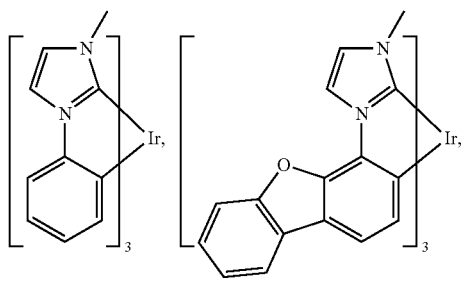
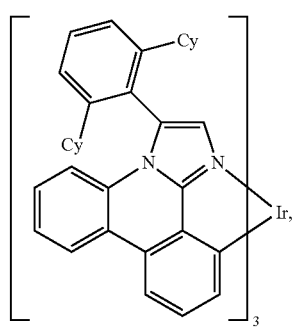
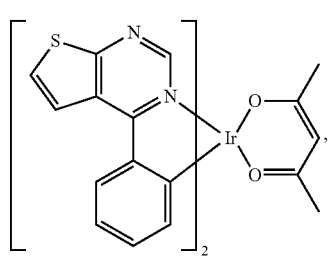
112
-continued
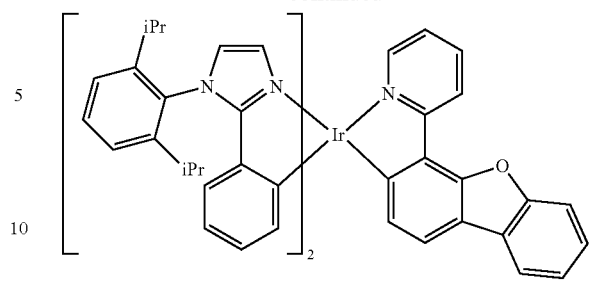
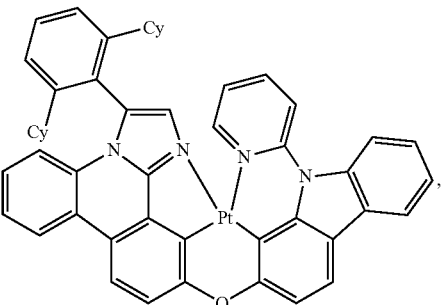
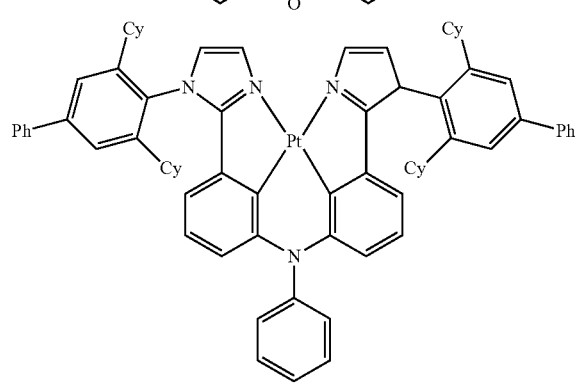
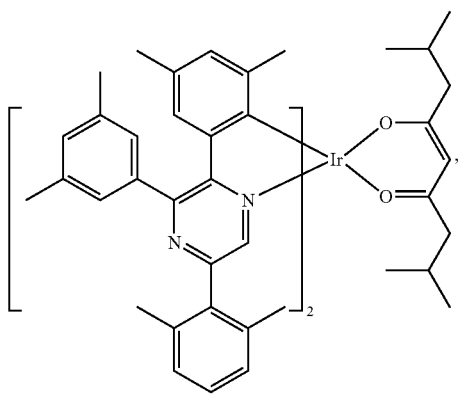
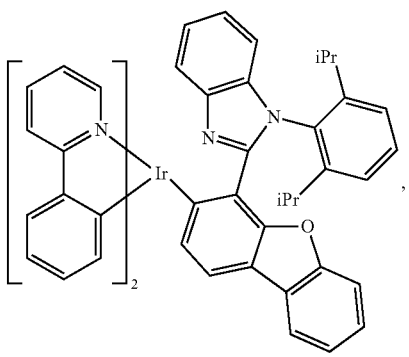

113
-continued
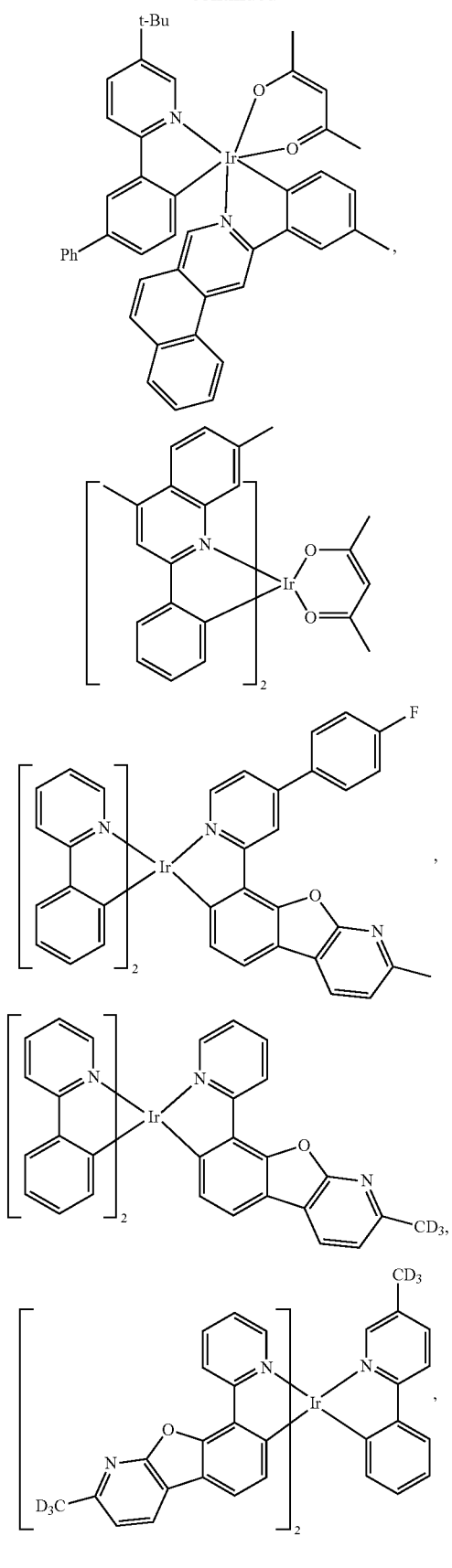
114
-continued
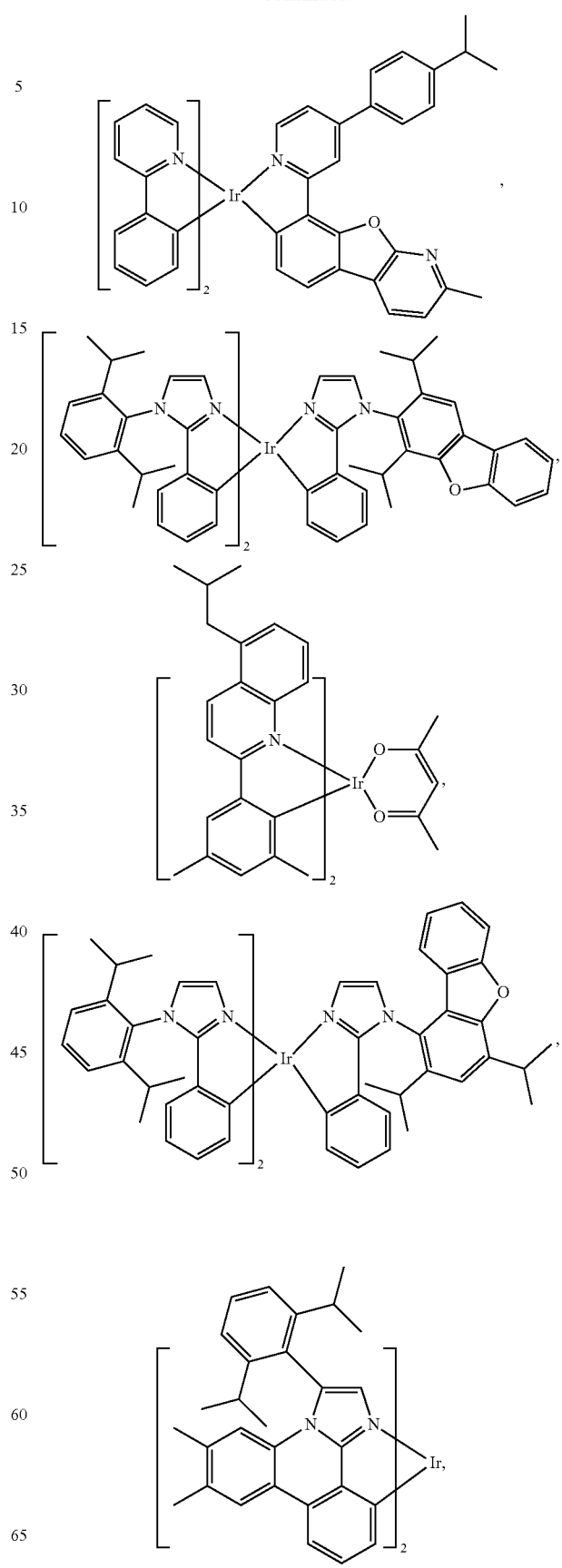

115
-continued
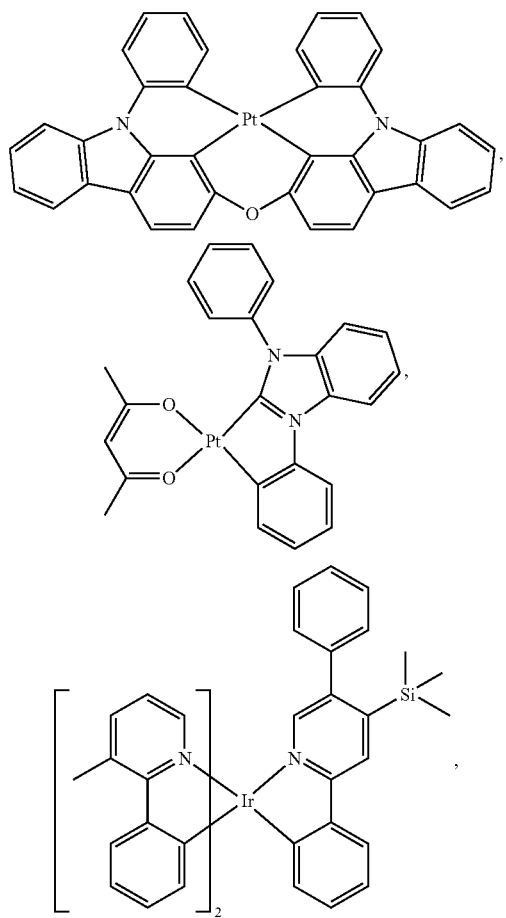
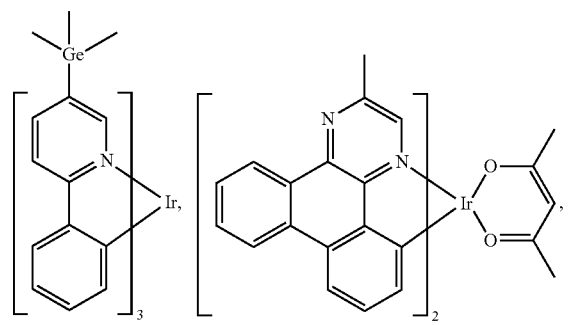
116
-continued
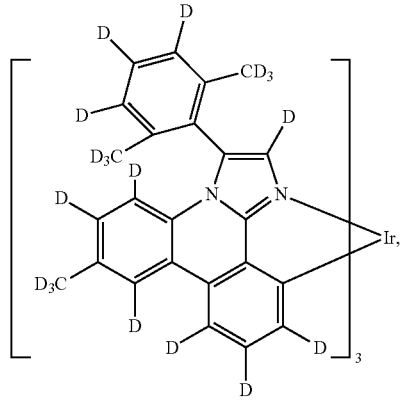
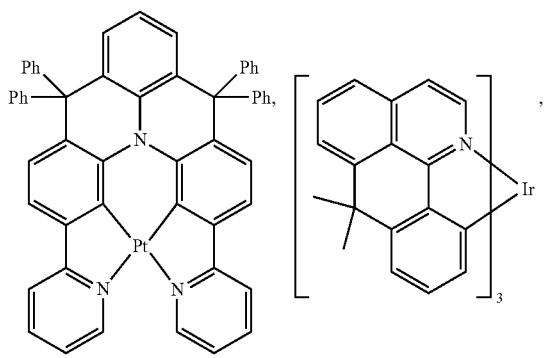
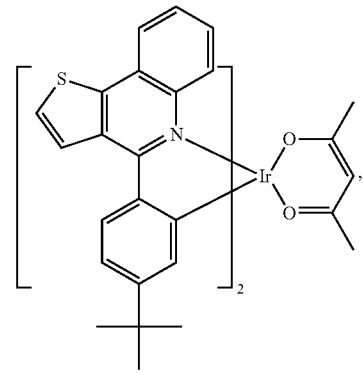
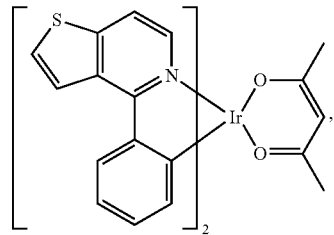

117
-continued
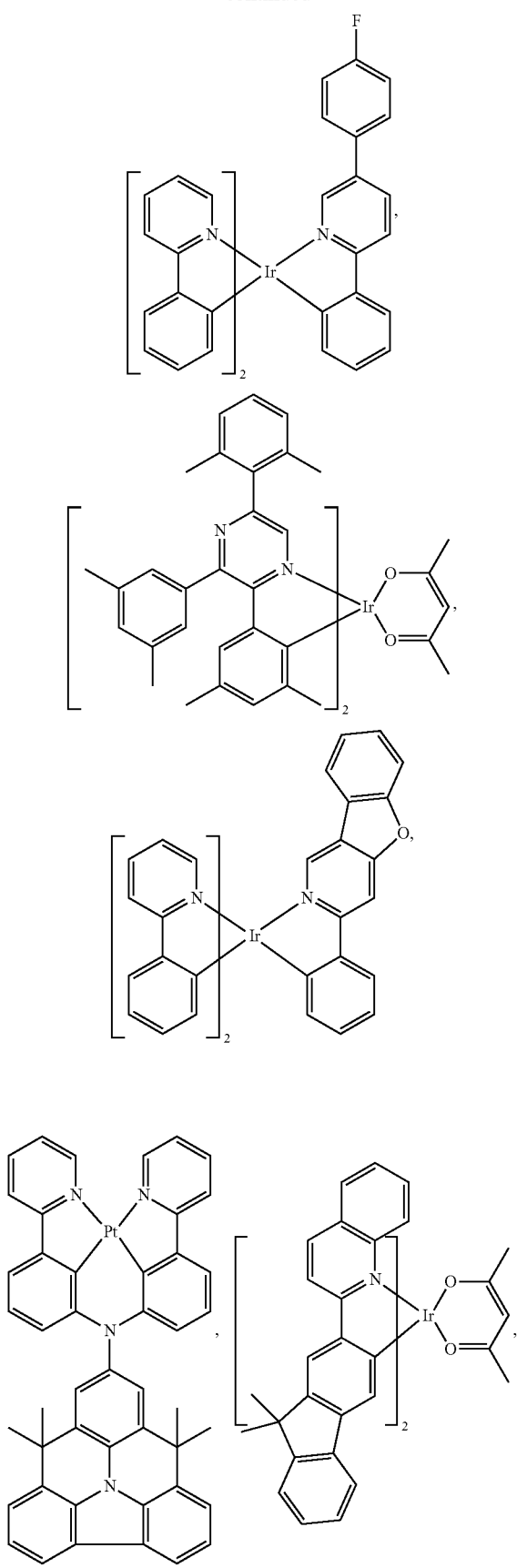
118
-continued
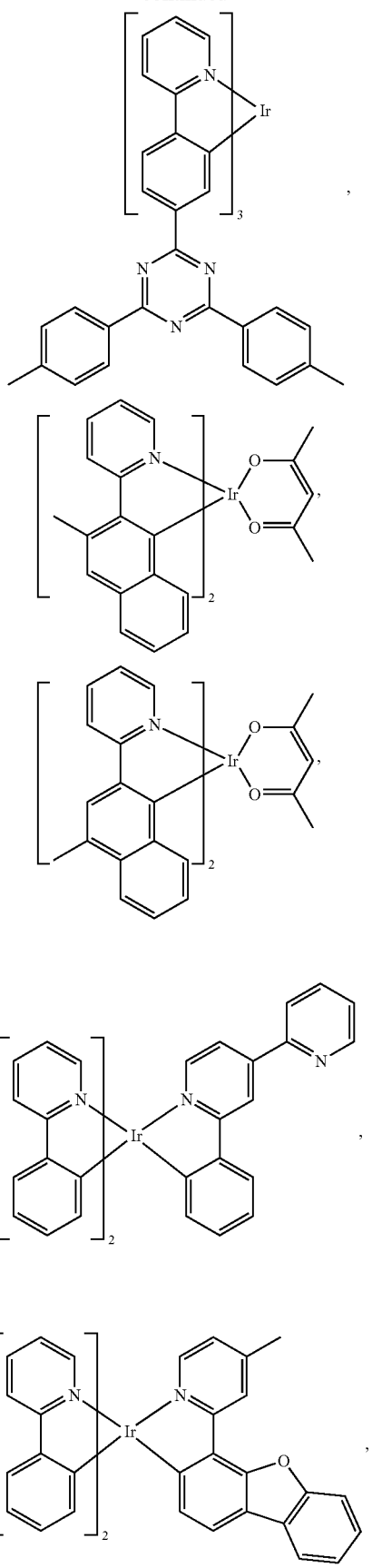

-continued
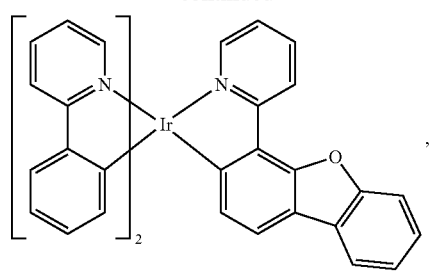
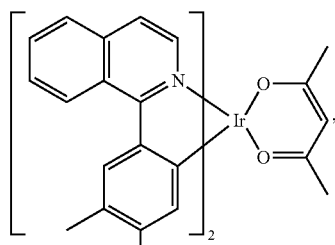
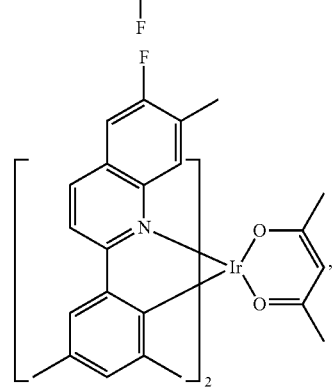
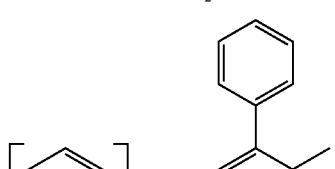
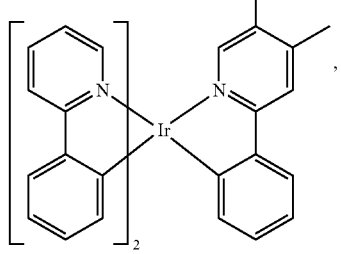
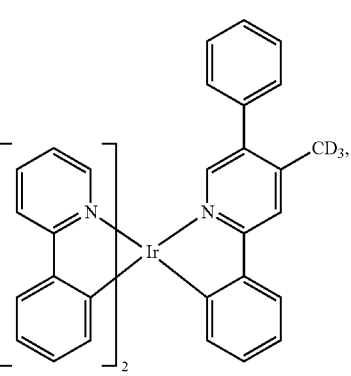
-continued
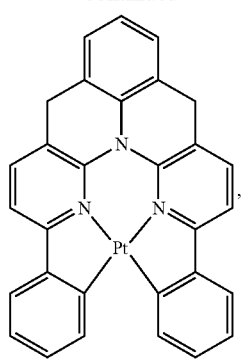
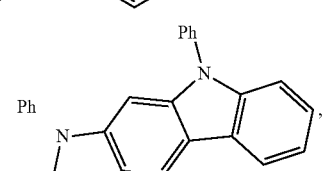
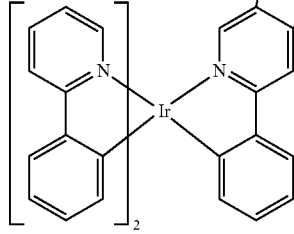
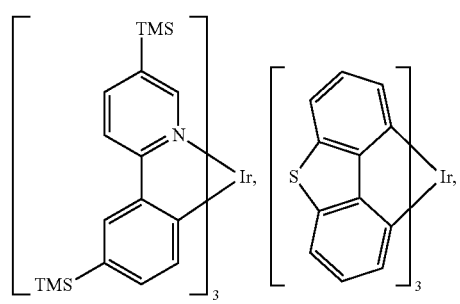
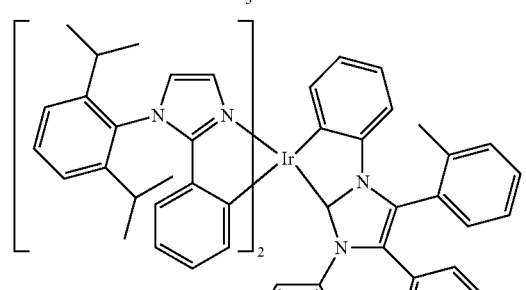
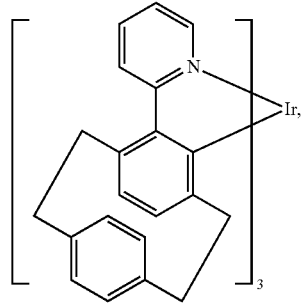

121
-continued
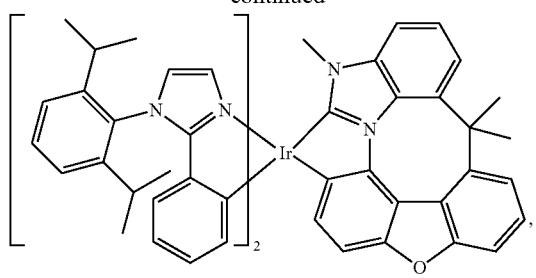
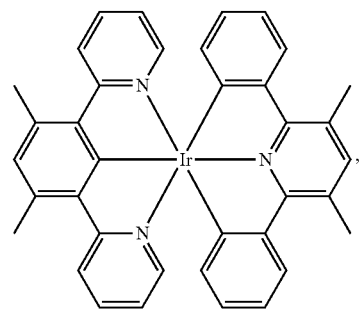
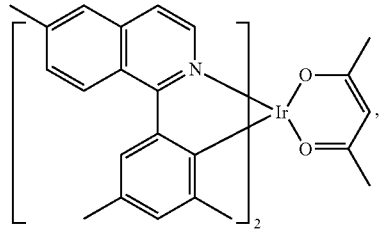
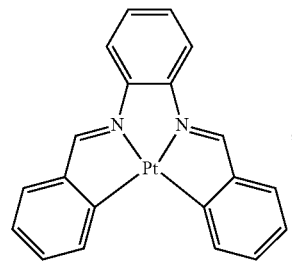
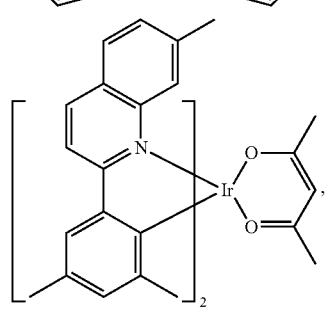
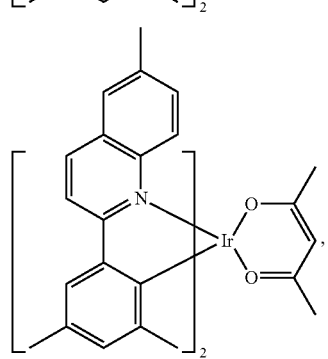
122
-continued
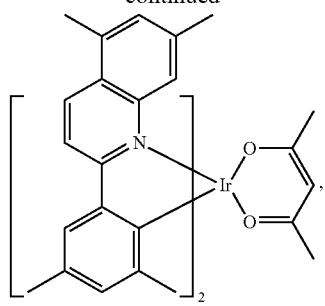
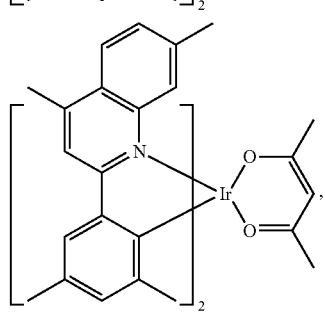
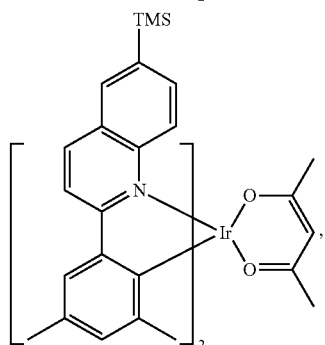
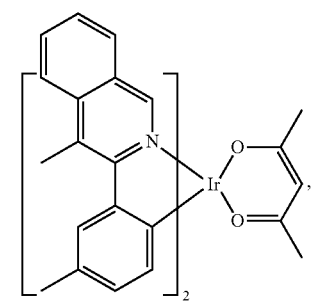
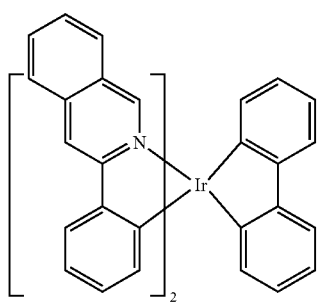

123
-continued
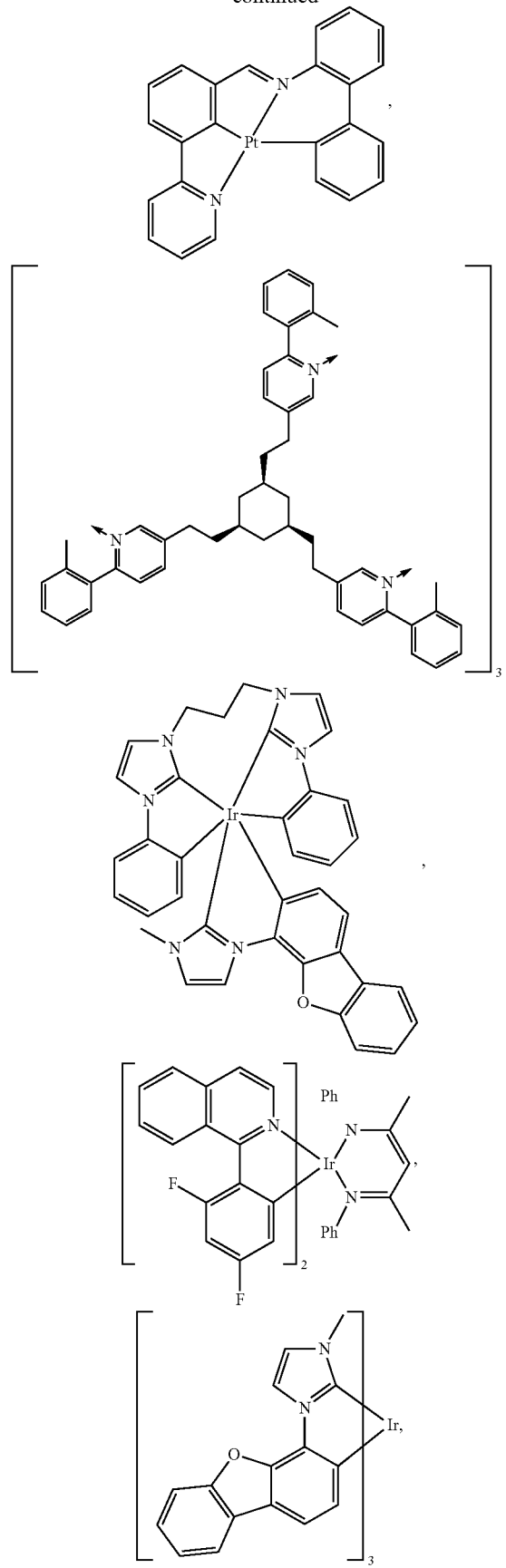
124
-continued
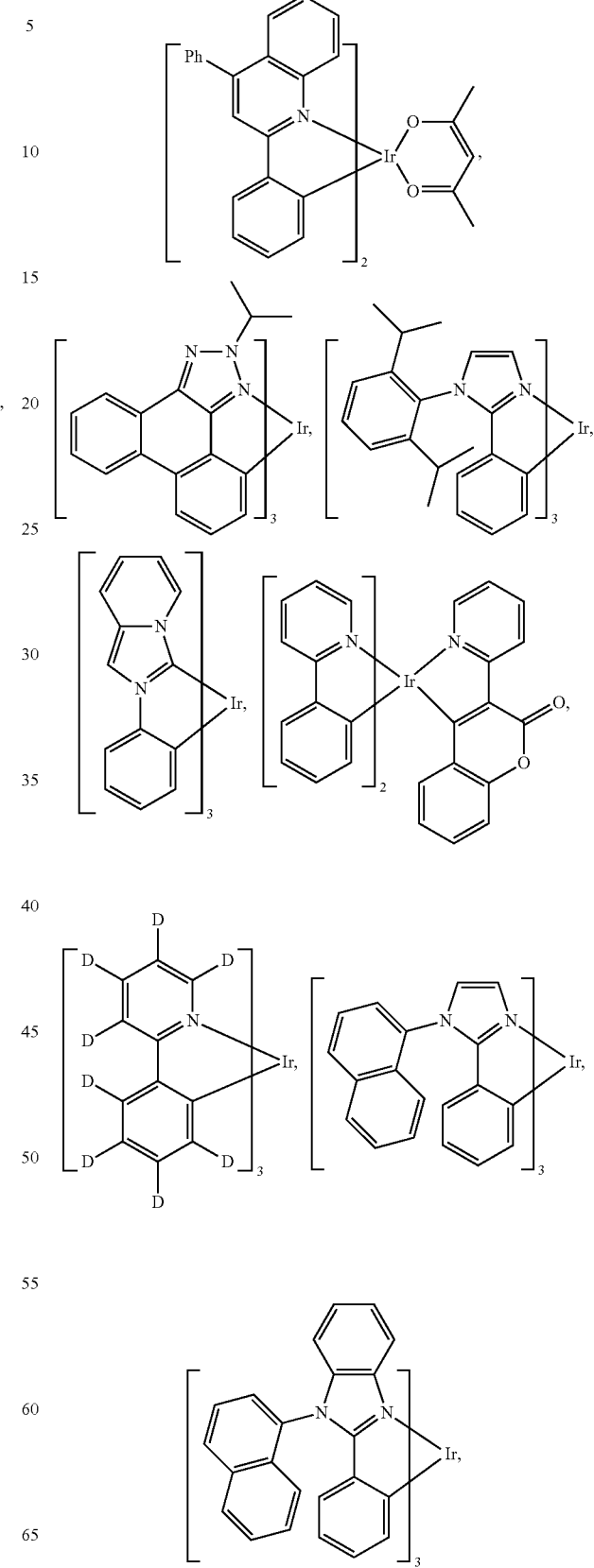

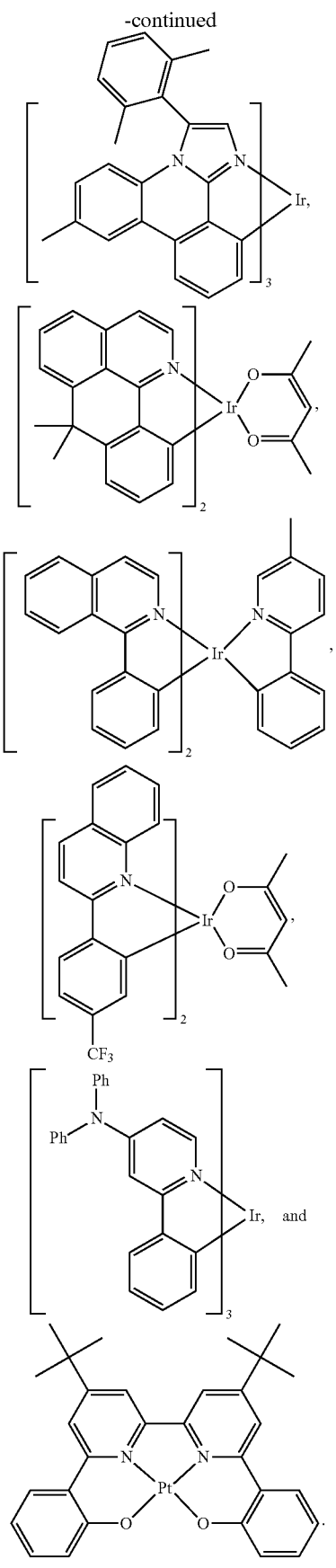

HBL:

A hole blocking layer (HBL) may be used to reduce the number of holes and/or excitons that leave the emissive layer. The presence of such a blocking layer in a device may result in substantially higher efficiencies and/or longer lifetime as compared to a similar device lacking a blocking layer. Also, a blocking layer may be used to confine emission to a desired region of an OLED. In some embodiments, the HBL material has a lower HOMO (further from the vacuum level) and/or higher triplet energy than the emitter closest to the HBL interface. In some embodiments, the HBL material has a lower HOMO (further from the vacuum level) and/or higher triplet energy than one or more of the hosts closest to the HBL interface.

In one aspect, compound used in HBL contains the same molecule or the same functional groups used as host described above.

In another aspect, compound used in HBL contains at least one of the following groups in the molecule:

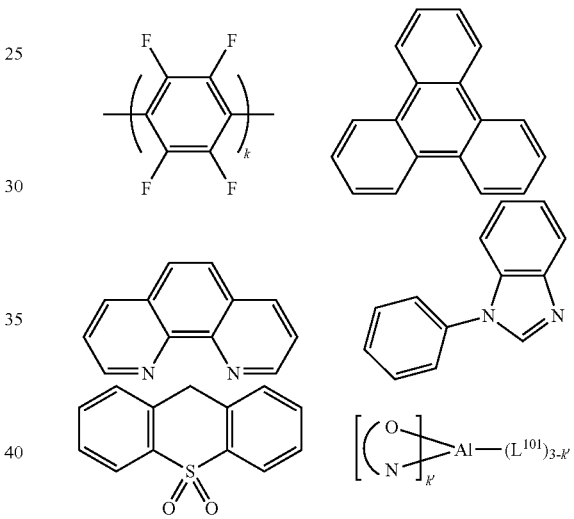

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

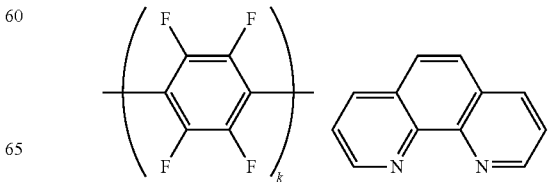

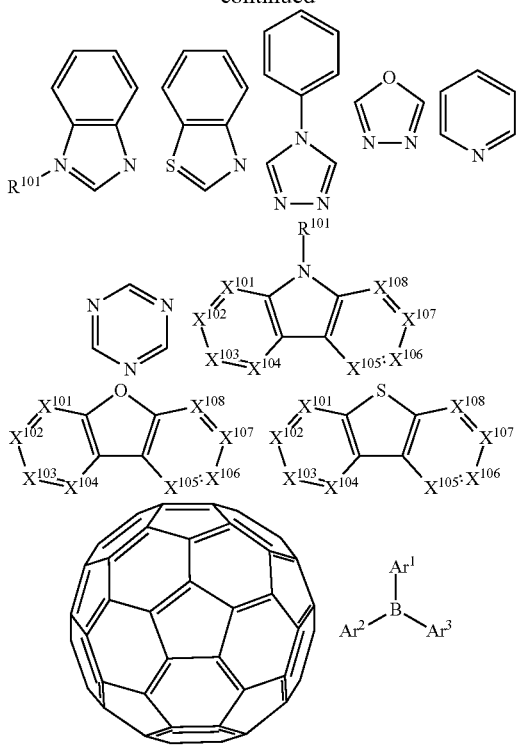

wherein $R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL contains, but not limit to the following general formula:

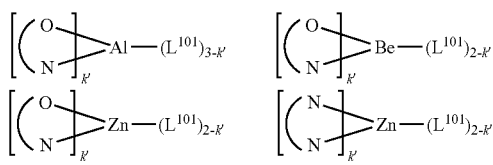

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

Non-limiting examples of the ETL materials that may be used in an OLED in combination with materials disclosed herein are exemplified below together with references that disclose those materials: CN103508940, EP01602648, EP01734038, EP01956007, JP2004-022334, JP2005149918, JP2005-268199, KR0117693, KR20130108183, US20040036077, US20070104977, US2007018155, US20090101870, US20090115316, US20090140637, US20090179554, US2009218940, US2010108990, US2011156017, US2011210320, US2012193612, US2012214993, US2014014925, US2014014927, US20140284580, U.S. Pat. Nos. 6,656,612, 8,415,031, WO2003060956, WO2007111263, WO2009148269, WO2010067894, WO2010072300, WO2011074770, WO2011105373, WO2013079217, WO2013145667, WO2013180376, WO2014104499, WO2014104535,

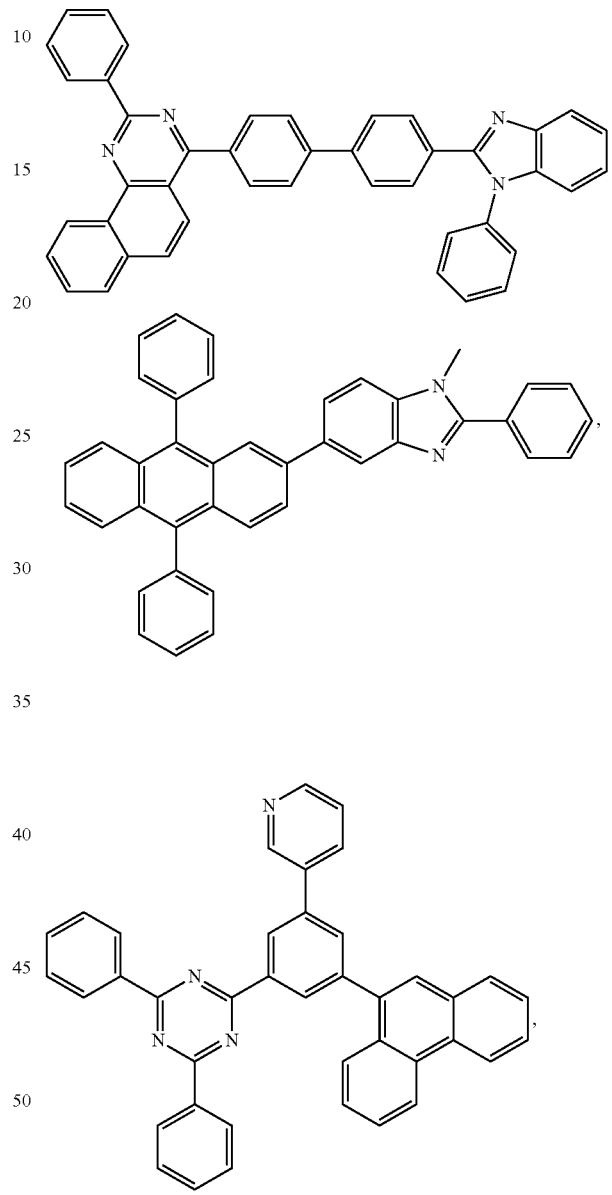

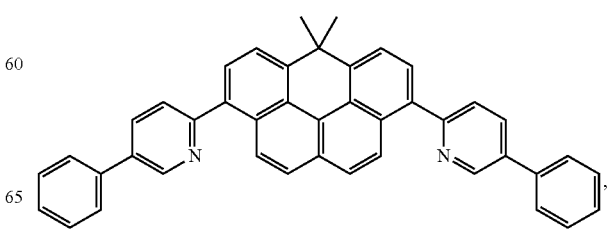

129
-continued
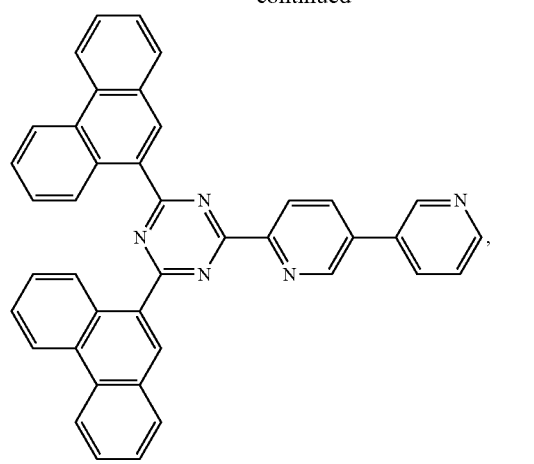
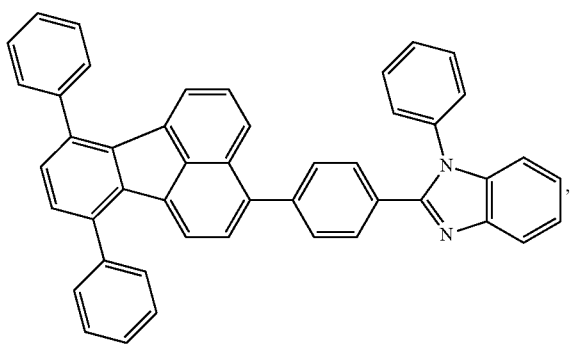
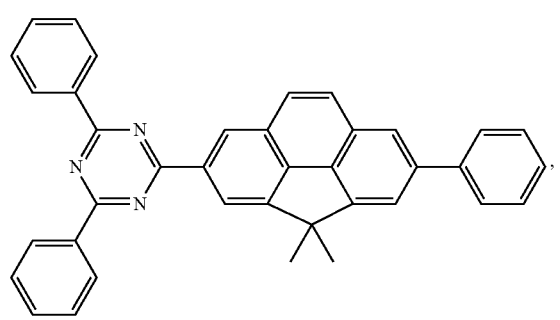
130
-continued
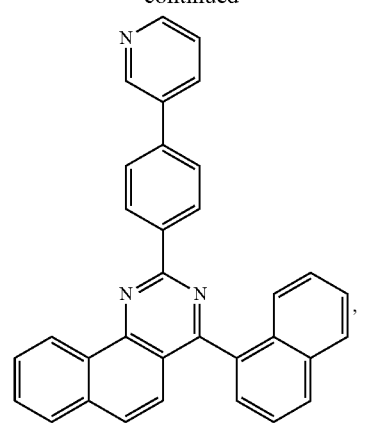
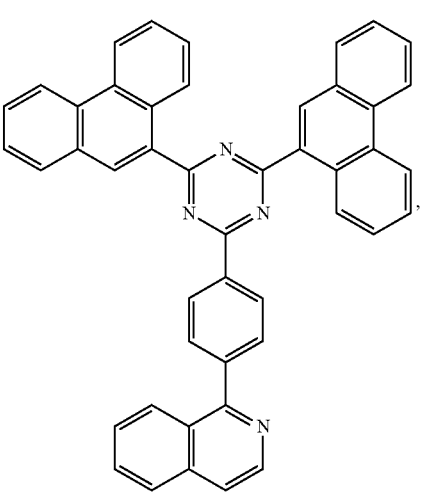
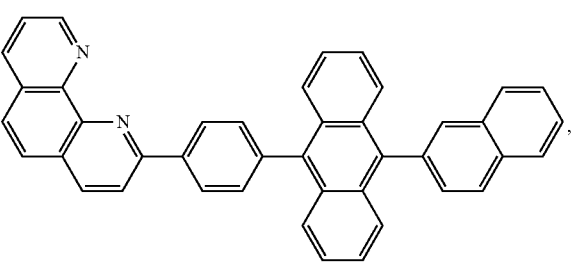
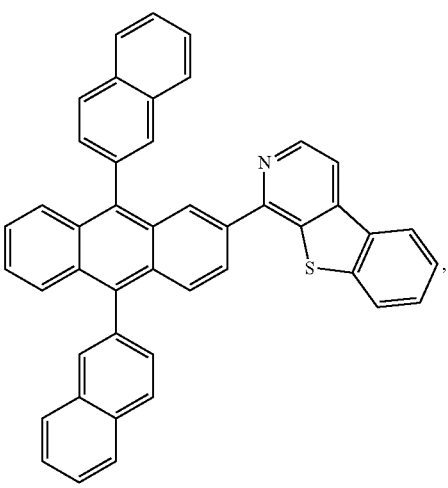

131
-continued
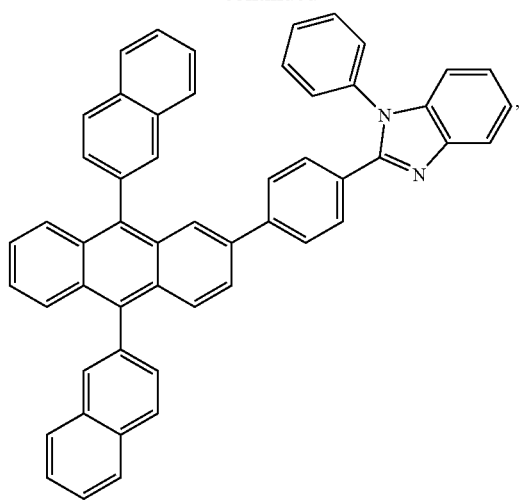
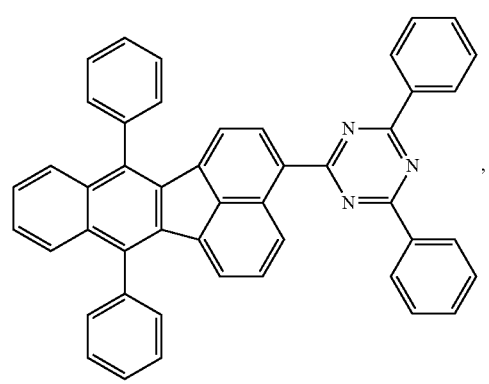
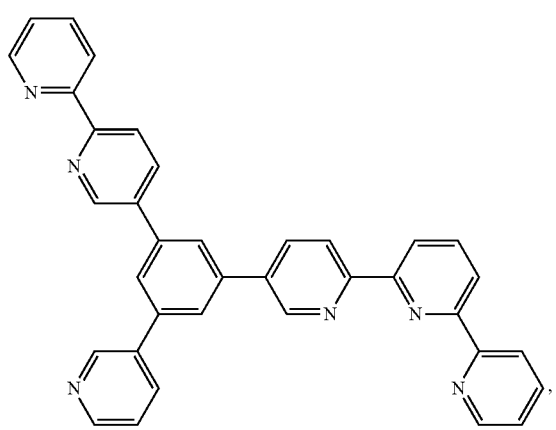
132
-continued
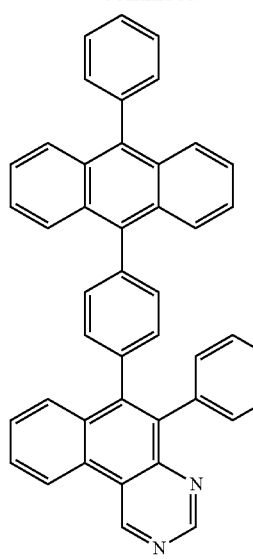
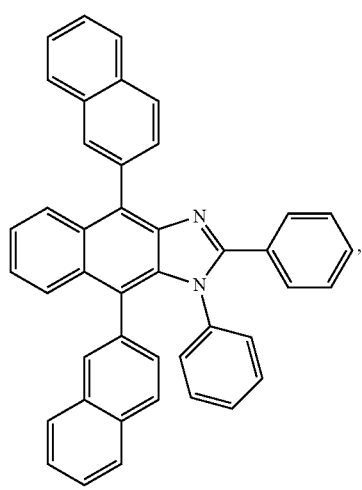
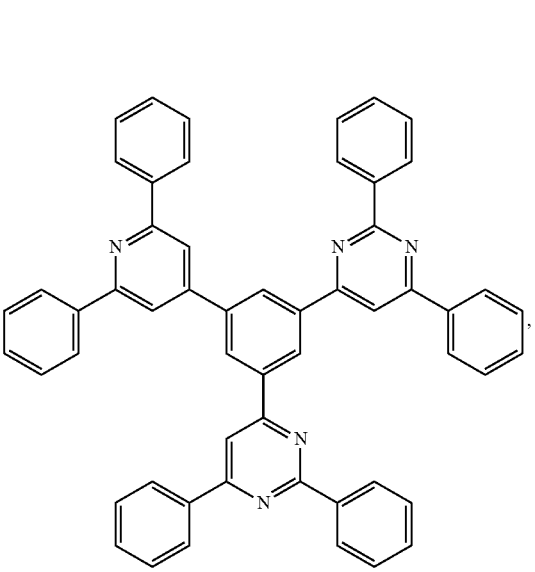

133
-continued
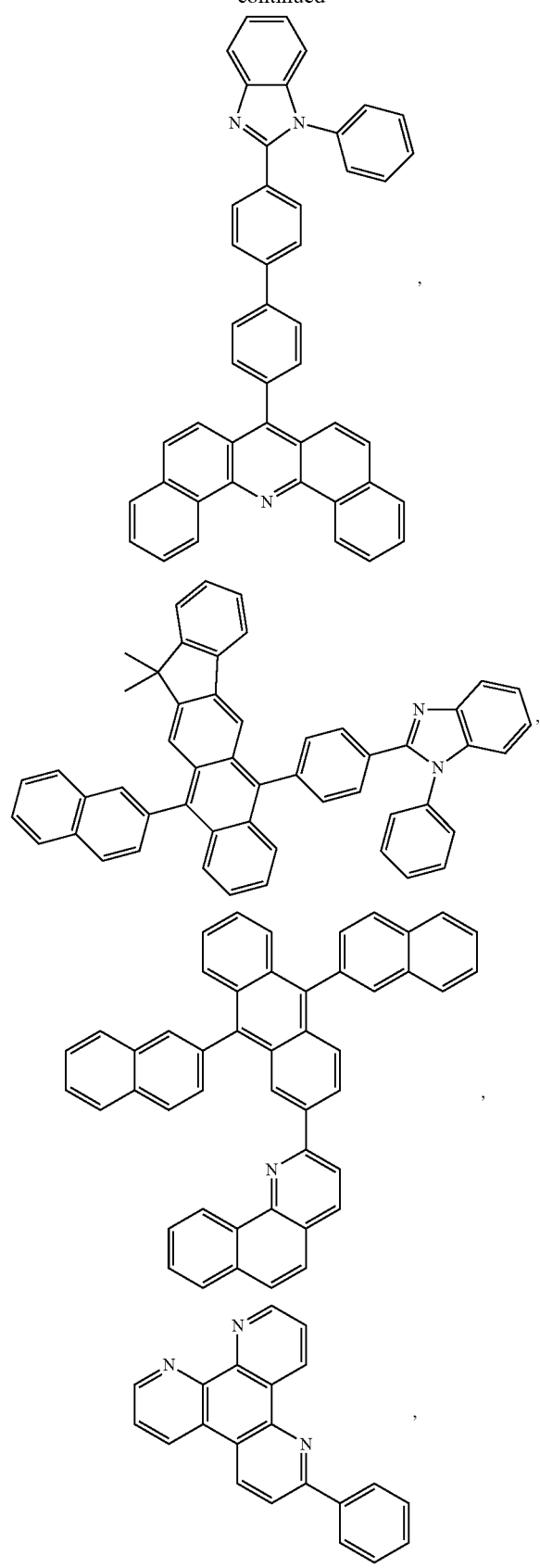
134
-continued
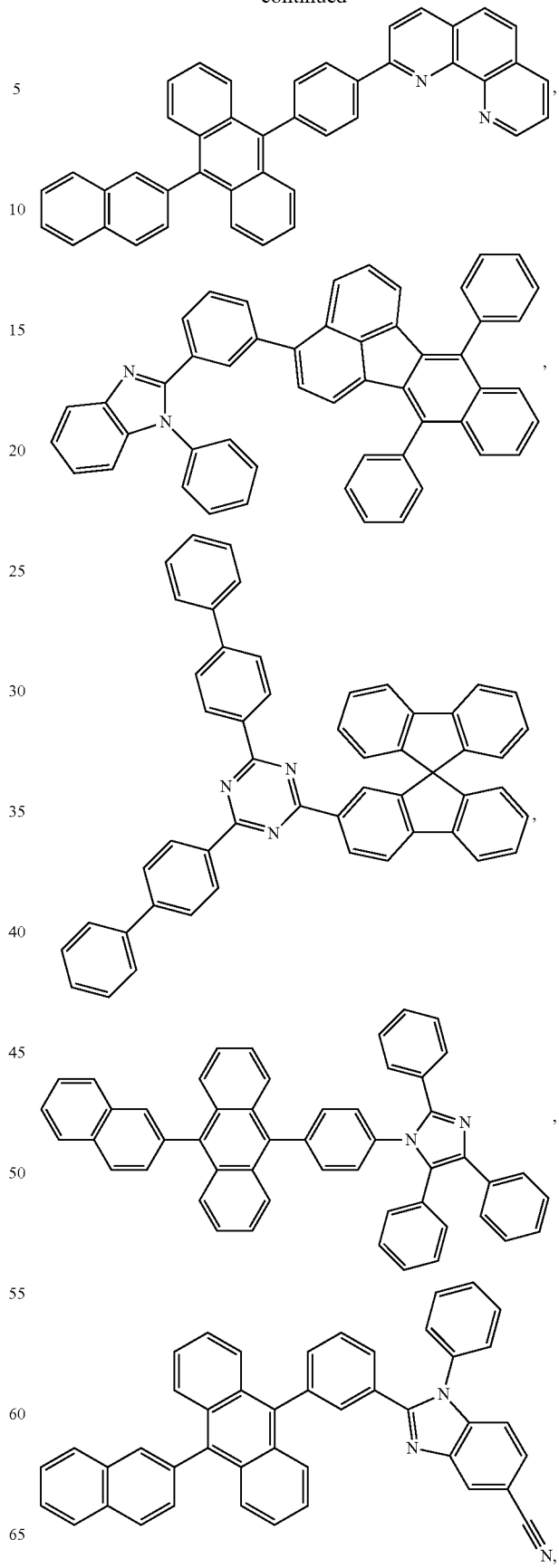

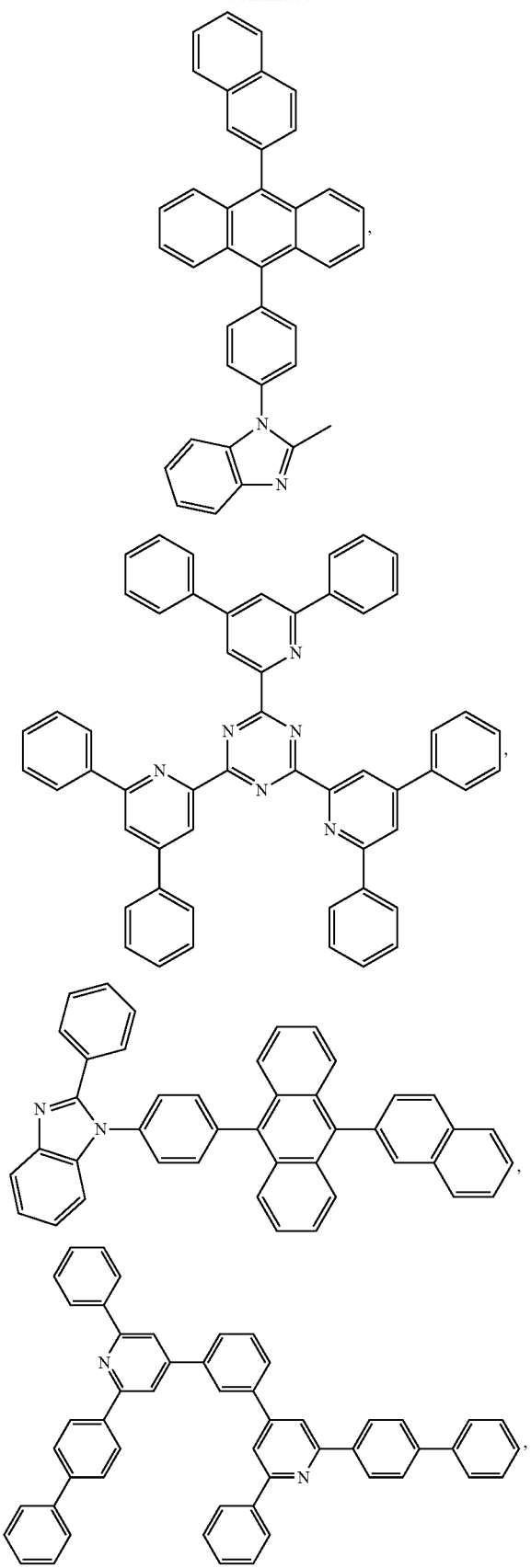
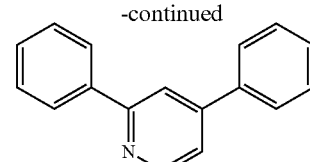
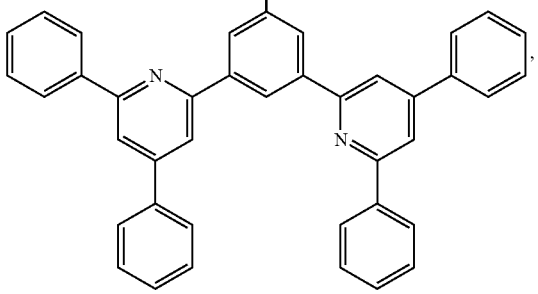
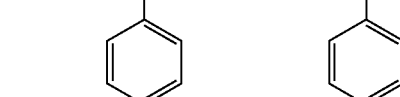
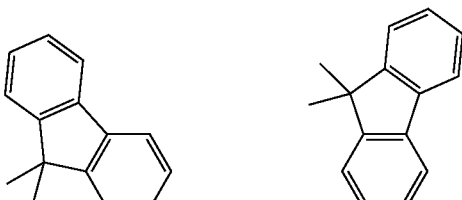
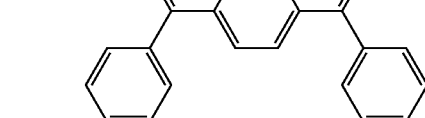
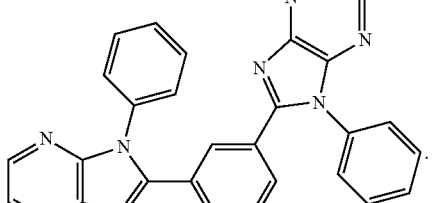
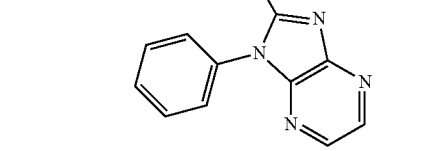

Charge Generation Layer (CGL)

In tandem or stacked OLEDs, the CGL plays an essential role in the performance, which is composed of an n-doped layer and a p-doped layer for injection of electrons and holes, respectively. Electrons and holes are supplied from the CGL and electrodes. The consumed electrons and holes in the CGL are refilled by the electrons and holes injected from the cathode and anode, respectively; then, the bipolar currents reach a steady state gradually. Typical CGL materials include n and p conductivity dopants used in the transport layers.

In any above-mentioned compounds used in each layer of the OLED device, the hydrogen atoms can be partially or fully deuterated. Thus, any specifically listed substituent, such as, without limitation, methyl, phenyl, pyridyl, etc. may be undeuterated, partially deuterated, and fully deuterated versions thereof. Similarly, classes of substituents such as, without limitation, alkyl, aryl, cycloalkyl, heteroaryl, etc. also may be undeuterated, partially deuterated, and fully deuterated versions thereof.

Synthesis

Materials Synthesis—

All reactions were carried out under nitrogen atmosphere unless specified otherwise. All solvents for reactions are anhydrous and used as received from commercial sources.

Synthesis of Compound 3393 [Ir(L$_{A17}$)$_2$(L$_{B5}$)]

Synthesis of 6-(tert-butyl)-4-chloro-2H-pyran-2-one

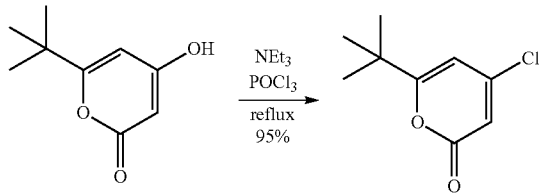

A solution of 6-(tert-butyl)-4-hydroxy-2H-pyran-2-one (9.50 g, 56.50 mmol), POCl$_3$ (31.9 mL, 198 mmol) and NEt$_3$ (7.8 mL, 56.50 mmol) was heated to reflux overnight. The reaction flask was cooled to rt and the reaction mixture was quenched with ice and extracted with EtOAc. The crude product was adsorbed onto Celite and purified via flash chromatography (CH$_2$Cl$_2$/EtOAc/Heptanes, 1:4:45) to provide 6-(tert-butyl)-4-chloro-2H-pyran-2-one as a golden oil (10.0 g, 95%).

Synthesis of 1-(tert-butyl)-3-chloronaphthalene

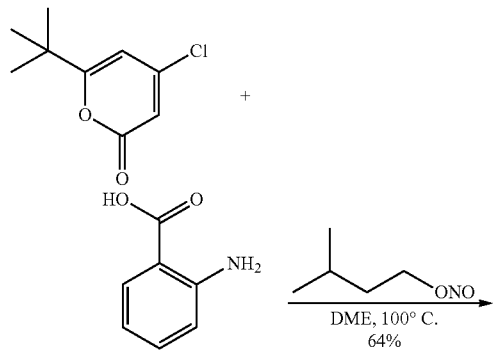

A solution of 6-(tert-butyl)-4-chloro-2H-pyran-2-one (8.90 g, 47.70 mmol) in 1,2-Dimethoxyethane (100 mL) was heated to 100° C. Subsequently, isoamyl nitrite (9.63 mL, 71.50 mmol), previously dissolved in 1,2-Dimethoxyethane (60 mL), and 2-aminobenzoic acid (9.81 g, 71.50 mmol), previously dissolved in 1,2-Dimethoxyethane (60 mL), were added to the reaction mixture simultaneously with the aid of addition funnels in a dropwise fashion. The reaction mixture was left to stir at 100° C. overnight. The reaction flask was cooled to rt and the reaction mixture was concentrated in vacuo. The crude product was adsorbed onto Celite and purified via flash chromatography (CH$_2$Cl$_2$/EtOAc/Heptanes, 1:2:47) to provide 1-(tert-butyl)-3-chloronaphthalene as a light yellow oil (6.7 g, 64%).

Synthesis of 2-(4-(tert-butyl)naphthalen-2-yl)-4,4,5,5-tetramethyl-1,3,2-dioxaborolane

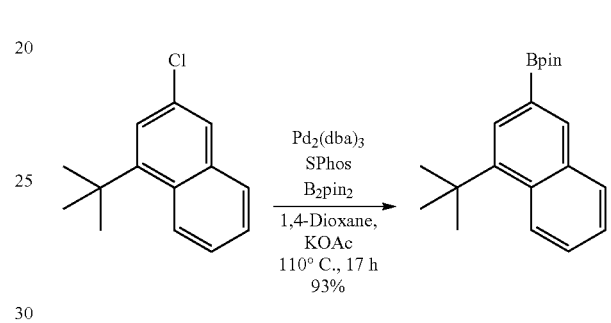

A solution of 1-(tert-butyl)-3-chloronaphthalene (6.20 g, 28.30 mmol), 4,4,4',4',5,5,5',5'-octamethyl-2,2'-bi(1,3,2-dioxaborolane) (9.36 g, 36.90 mmol), Pd$_2$(dba)$_3$ (0.52 g, 0.57 mmol), SPhos (0.93 g, 2.27 mmol), and KOAc (8.35 g, 85.00 mmol) in 1,4-Dioxane (90 mL) was heated to 110° C. for 17 h. After this time, the reaction flask was cooled to rt and the reaction mixture was filtered through a plug of Celite, eluting with EtOAc, and concentrated in vacuo. The crude product was adsorbed onto Celite and purified via flash chromatography (EtOAc/Heptanes, 1:49 to 1:9) to provide 2-(4-(tert-butyl)naphthalen-2-yl)-4,4,5,5-tetramethyl-1,3,2-dioxaborolane as an off-white solid (8.80 g, 93%).

Synthesis of 2-(4-(tert-butyl)naphthalen-2-yl)-4,5-dichloroquinoline

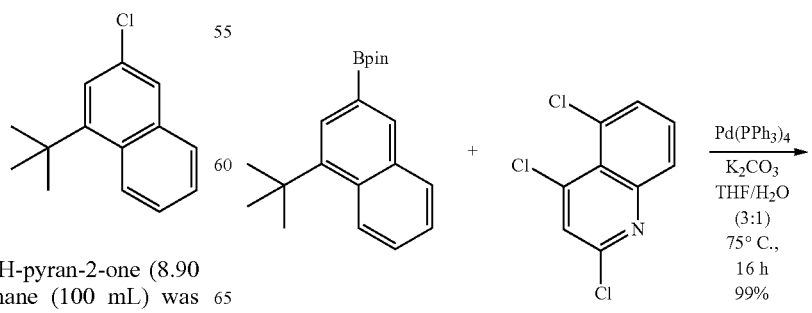

-continued

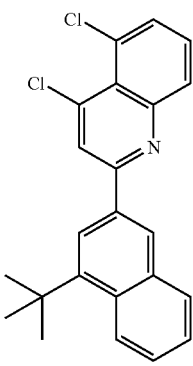

2-(4-(tert-butyl)naphthalen-2-yl)-4,4,5,5-tetramethyl-1,3,2-dioxaborolane (4.31 g, 13.90 mmol), 2,4,5-trichloroquinoline (3.20 g, 13.76 mmol), K$_2$CO$_3$ (5.71 g, 41.30 mmol) THF (51 mL) and H$_2$O (17 mL) were combined in a flask. The reaction mixture was purged with N$_2$ for 15 min followed by the addition of Pd(PPh$_3$)$_4$ (0.80 g, 0.69 mmol). The reaction mixture was then heated to 75° C. for 16 h. After this time, the reaction flask was cooled to rt and the reaction mixture was extracted with EtOAc. The crude product was adsorbed onto Celite and purified via flash chromatography (EtOAc/Heptanes, 1:49) to provide 2-(4-(tert-butyl)naphthalen-2-yl)-4,5-dichloroquinoline as a yellow solid (5.50 g, 99%).

Synthesis of 2-(4-(tert-butyl)naphthalen-2-yl)-4,5-dimethylquinoline

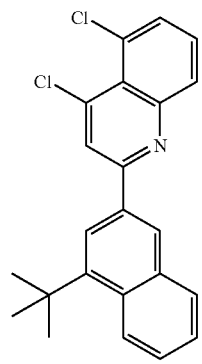

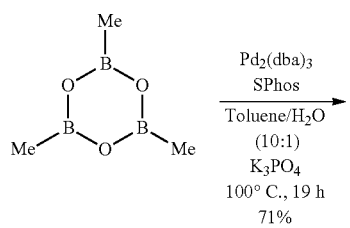

A solution of 2-(4-(tert-butypnaphthalen-2-yl)-4,5-dichloroquinoline (5.50 g, 14.46 mmol), Pd$_2$(dba)$_3$ (0.53 g, 0.58 mmol), SPhos (0.95 g, 2.31 mmol), trimethylboroxine (4.85 mL, 34.70 mmol) and K$_3$PO$_4$ (12.28 g, 57.80 mmol) in Toluene (65.0 mL) and H$_2$O (6.50 mL), purged with N$_2$ for 15 min, and was heated to 100° C. for 19 h. After this time, the reaction flask was then cooled to rt and the reaction mixture was extracted with EtOAc. The crude product was adsorbed onto Celite and purified via flash chromatography (EtOAc/Heptanes, 1:99 to 1:49) and then via reverse phase chromatography (MeCN/H$_2$O, 90:10 to 92/8 to 95/5) to provide 2-(4-(tert-butyl)naphthalen-2-yl)-4,5-dimethylquinoline as a white solid (3.50 g, 71%).

Synthesis of Iridium(III) Dimer

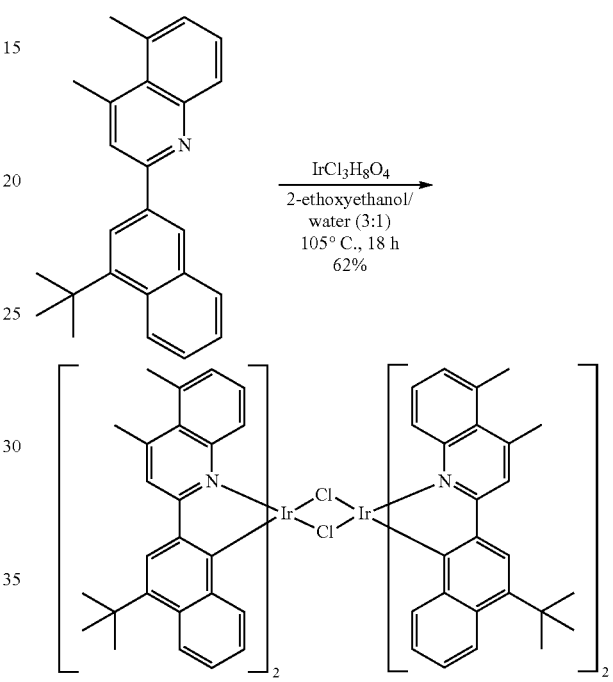

2-(4-(tert-butyl)naphthalen-2-yl)-4,5-dimethylquinoline (3.52 g, 10.36 mmol) was dissolved in 2-ethoxyethanol (42.0 mL) and water (14.0 mL) and the mixture was degassed with N$_2$ for 15 mins. Iridium(III) chloride tetrahydrate (1.28 g, 3.45 mmol) was then added and the reaction mixture was heated to 105° C., under N$_2$, for 16 h. After this time, the reaction flask was cooled to rt. The reaction mixture was diluted with MeOH and filtered to obtain dark brown precipitate, which was dried using a vacuum oven (1.94 g, 62%).

Synthesis of Compound 3393 [Ir(L$_{A17}$)$_2$(L$_{B5}$)]

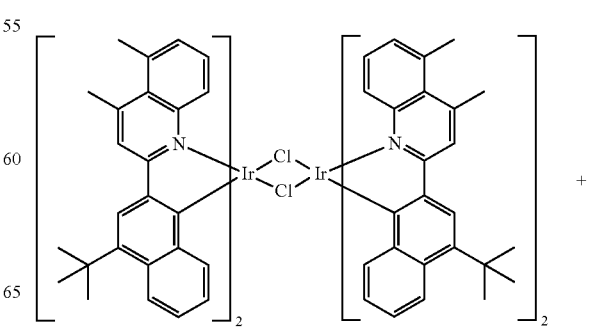

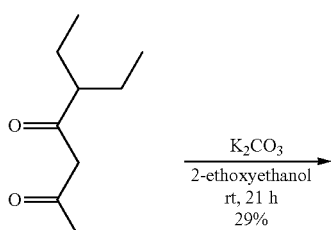

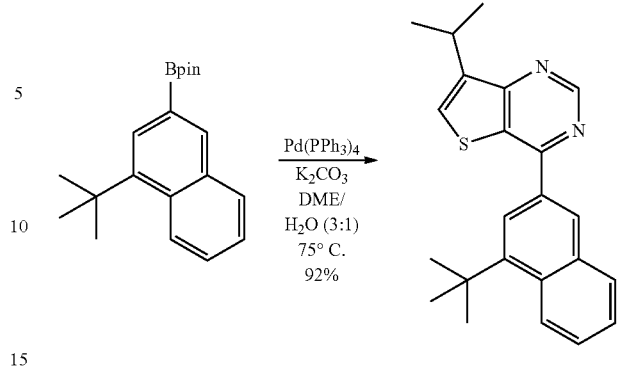

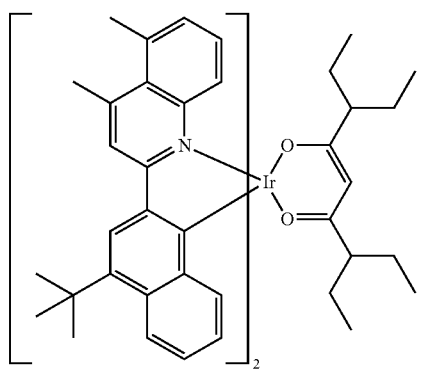

A solution of Iridium(III) dimer (1.00 g, 0.55 mmol) and 3,7-diethylnonane-4,6-dione (1.30 mL, 5.53 mmol) in 2-ethoxyethanol (18 mL) was degassed with N$_2$ for 15 min. K$_2$CO$_3$ (0.76 g, 5.53 mmol) was next added and the reaction mixture was left to stir at rt, under N$_2$, for 21 h. After this time, the reaction mixture was filtered through a plug of Celite, eluting first with MeOH followed by CH$_2$Cl$_2$ using a separate filter flask. The filtrate collected was then concentrated in vacuo. The crude product was adsorbed onto Celite and purified via flash chromatography (pretreated with Heptanes/triethylamine, 9:1) using CH$_2$Cl$_2$/Heptanes (1:99 to 1:49 to 1:9) to provide Compound 3393 [Ir(L$_{A17}$)$_2$(L$_{B5}$)] as a red solid (0.35 g, 29%).

Synthesis of Compound 3899 [Ir(L$_{A523}$)$_2$(L$_{B5}$)]

Synthesis of 4-(4-(tert-butypnaphthalen-2-yl)-7-isopropylthieno[3,2-d]pyrimidine 4-chloro-7-isopropylthieno[3,2-d]pyrimidine (2.10 g, 9.87 mmol), 2-(4-(tert-butyl)naphthalen-2-yl)-4,4,5,5-tetramethyl-1,3,2-dioxaborolane (3.22 g, 10.4 mmol), K$_2$CO$_3$ (3.41 g, 24.7 mmol), DME (53 mL) and H$_2$O (18 mL) were combined in a flask. The reaction mixture was purged with N$_2$ for 15 min followed by the addition Pd(PPh$_3$)$_4$ (0.57 g, 0.49 mmol). The reaction mixture was then heated to 75° C., under N$_2$, overnight. Upon completion of the reaction, the reaction flask was cooled to rt and the reaction mixture was extracted with EtOAc. The crude product was purified via flash chromatography Heptanes/EtOAc (9:1 to 4:1) to provide 4-(4-(tert-butyl)naphthalen-2-yl)-7-isopropylthieno[3,2-d]pyrimidine (3.26 g, 92% yield).

Synthesis of the Iridium(III) Dimer

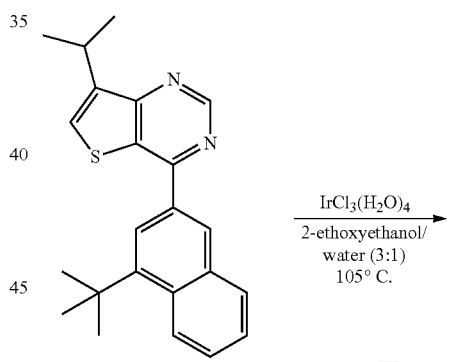

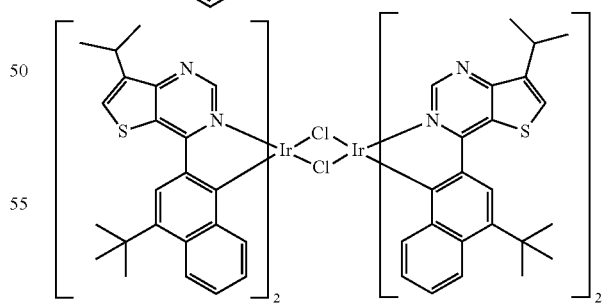

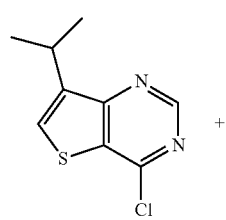

4-(4-(tert-butypnaphthalen-2-yl)-7-isopropylthieno[3,2-d]pyrimidine (3.16 g, 8.77 mmol) was dissolved in 2-ethoxyethanol (37 mL) and water (12 mL) and the mixture was degassed with N$_2$ for 15 mins. Iridium(III) chloride tetrahydrate (1.00 g, 2.70 mmol) was then added and the reaction mixture was heated to 105° C., under N$_2$, overnight. After this time, the reaction flask was cooled to rt. The reaction mixture was diluted with MeOH and filtered to obtain green precipitate, which was dried using a vacuum oven (quantitative).

Synthesis of Compound 3899 [Ir(L$_{A523}$)$_2$(L$_{B5}$)]

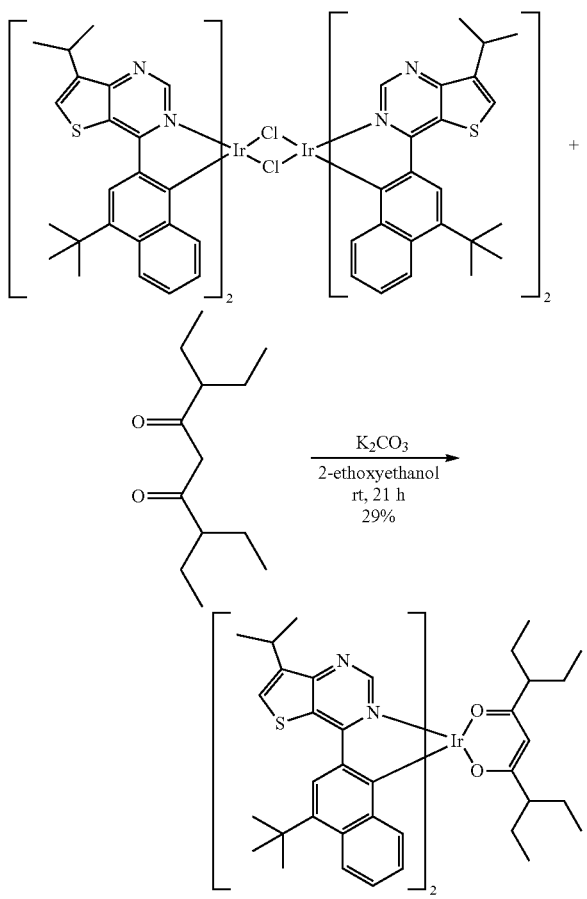

A solution of Iridium(III) dimer (1.50 g, 0.79 mmol) and 3,7-diethylnonane-4,6-dione (1.26 g, 5.94 mmol) in 2-ethoxyethanol (26 mL) was degassed with N$_2$ for 15 min. K$_2$CO$_3$ (0.82 g, 5.94 mmol) was next added and the reaction mixture was left to stir at rt, under N$_2$, overnight. After this time, the reaction mixture was filtered through a plug of Celite, eluting first with MeOH followed by CH$_2$Cl$_2$ using a separate filter flask. The filtrate collected was then concentrated in vacuo. The crude product was purified via flash chromatography (pretreated with Heptanes/triethylamine, 9:1) using CH$_2$Cl$_2$/Heptanes (1:4) to provide Compound 3899 [Ir(L$_{A523}$)$_2$(L$_{B5}$)] as a red solid (0.70 g, 79%).

Synthesis of Compound 5975 [Ir(L$_{A783}$)$_2$(L$_{B5}$)]

Synthesis of 3-Fluoronaphthalen-2-ol

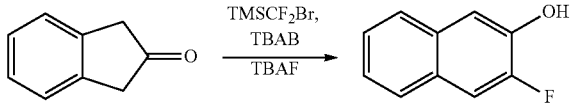

(Bromodifluoromethyl)trimethylsilane (35.3 ml, 227 mmol) was added to a solution of 1,3-dihydro-2H-inden-2-one (20 g, 151 mmol) and tetrabutylammonium bromide (4.88 g, 15.13 mmol) in toluene (500 ml). The reaction was heated to 100° C. and stirred for 2.5 hrs. (Bromodifluoromethyl)trimethylsilane (35.3 ml, 227 mmol) was added and the reaction stirred for a further 3 hrs at 100° C. The reaction was allowed to cool to r.t. and tetra-n-butylammonium fluoride (1M in THF) (30.3 ml, 30.3 mmol) was added. The reaction was allowed to stir at r.t. for ~18 h. The reaction was poured onto 1N HCl (aq) and was extracted with EtOAc. 1N NaOH (aq) was added to the organic phase and the layers separated. The aqueous phase was acidified by the addition of 1N HCl and reextracted with EtOAc. The organic phase was washed with brine, dried (MgSO$_4$) and concentrated under reduced pressure. The crude product was purified via flash chromatography (isohexane to 20% EtOAc in isohexane) to give 3-fluoronaphthalen-2-ol (8.9 g, 54.9 mmol, 36% yield).

Synthesis of 3-Fluoronaphthalen-2-yl trifluoromethanesulfonate

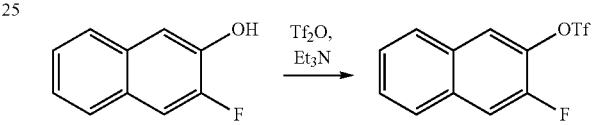

Tf$_2$O (11.1 ml, 65.9 mmol) was added to a solution of 3-fluoronaphthalen-2-ol (8.90 g, 54.9 mmol) and Et$_3$N (9.2 ml, 65.9 mmol) in DCM (200 ml) at 0° C. The reaction was stirred at this temperature for 1.5 h. The reaction was quenched via the addition of sat aq. NaHCO$_3$ and the mixture extracted with DCM (×2). The combined organic extracts were dried (MgSO$_4$) and concentrated under reduced pressure. The crude product was purified via flash chromatography (isohexane to 10% EtOAc in isohexane) to give 3-fluoronaphthalen-2-yl trifluoromethanesulfonate (13.3 g, 82% yield) as a colourless oil.

Synthesis of 2-(3-Fluoro-naphthalen-2-yl)-4,4,5,5-tetramethyl-[1,3,2]dioxaborolane

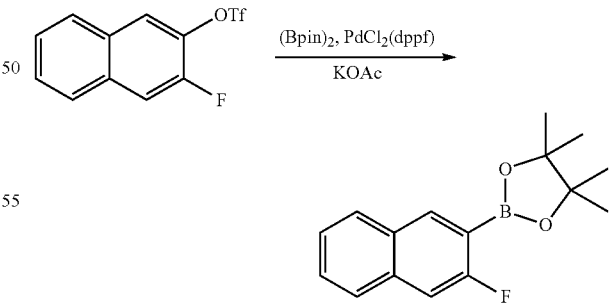

PdCl$_2$(dppf)-CH$_2$Cl$_2$ adduct (2.50 g, 3.06 mmol) was added to a degassed solution of 3-fluoronaphthalen-2-yl trifluoromethanesulfonate (18 g, 61.2 mmol), bis(pinacolato)diboron (46.6 g, 184 mmol) and potassium acetate (18 g, 184 mmol) in dioxane (200 ml). The reaction was heated to reflux for 2 h and was then allowed to cool to r.t. The reaction was partitioned between EtOAc and water and the layers separated. The organic phase was dried (MgSO₄) and concentrated under reduced pressure to give the crude material. The crude material was filtered through a pad of silica, washing with DCM. The filtrate was concentrated under reduced pressure to give a mixture of 2-(3-fluoro-naphthalen-2-yl)-4,4,5,5-tetramethyl-[1,3,2]dioxaborolane and bis(pinacolato)diboron NMR evidence).

Synthesis of (3-Fluoronaphthalen-2-yl)boronic acid

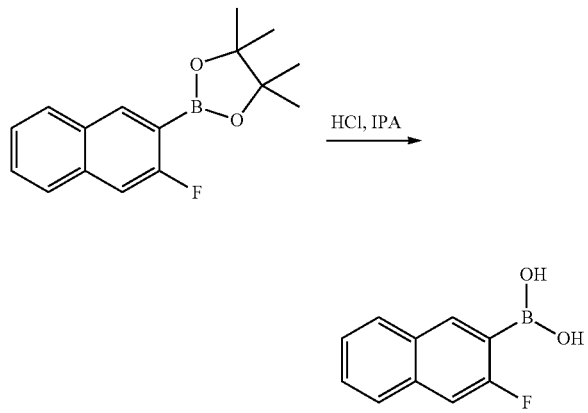

Concentrated HCl (153 ml, 1837 mmol) was added to a solution of crude 2-(3-fluoro-naphthalen-2-yl)-4,4,5,5-tetramethyl-[1,3,2]dioxaborolane and bis(pinacolato)diboron mixture (50 g) in IPA (400 ml). The reaction flask was heated to reflux for ~18 h. The reaction flask was allowed to cool to r.t. and the majority of the IPA was removed under reduced pressure. The resultant precipitate was filtered. The precipitate was purified by flash chromatography (4/1 to 1/1 isohexane/EtOAc) and recrystallisation from IPA/water. The recrystallisation gave 3 batches in total. The filtrate from the first recrystallisation yielded further material on prolonged standing/slow evaporation. Similarly a third batch was obtained from this second recrystallisation. All batches were taken up in MeOH, combined and concentrated under a flow of nitrogen. Drying in the vacuum oven for 3 days gave 7.1 g of (3-fluoronaphthalen-2-yl)boronic acid/2-(1-fluoronaphthalen-2-yl)-4,6-bis(3-fluoronaphthalen-2-yl)-1,3,5,2,4,6-trioxatriborinane for a 50% yield over 2 steps.

Synthesis of 4-(3-fluoronaphthalen-2-yl)-7-isopropylthieno[3,2-d]pyrimidine

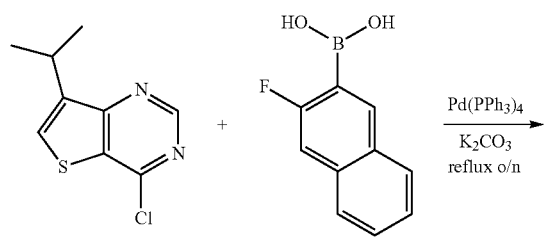

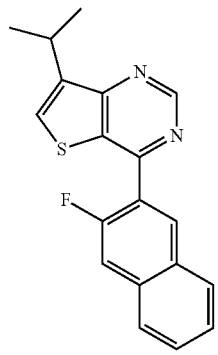

A 250 mL RBF was charged with 4-chloro-7-isopropylthieno[3,2-d]pyrimidine (3.0 g, 14.1 mmol), (3-fluoronaphthalen-2-yl)boronic acid (2.95 g, 15.5 mmol), potassium carbonate (4.87 g, 35.3 mmol), Pd(PPh₃)₄ (0.49 g, 0.42 mmol), THF (53 mL), and Water (18 mL), degassed with nitrogen and heated to reflux at 70° C. overnight. The reaction mixture was cooled to room temperature and washed with brine. The organic layer was dried over sodium sulfate, filtered and concentrated. The crude product was purified by flash chromatography (EtOAc/heptanes, 1:19) providing 4-(3-fluoronaphthalen-2-yl)-7-isopropylthieno[3,2-d]pyrimidine (4.20 g, 92% yield) as a viscous oil that crystallizes slowly upon sitting. Further purification was achieved by recrystallization from MeOH.

Synthesis of the Ir(III) Dimer

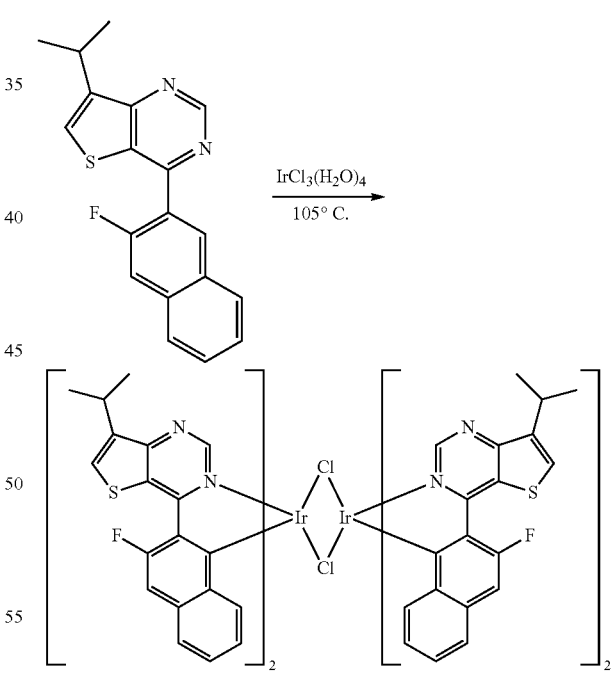

4-(3-fluoronaphthalen-2-yl)-7-isopropylthieno[3,2-d]pyrimidine (2.35 g, 8.77 mmol) was dissolved in 2-ethoxyethanol (30 mL) and water (10 mL) in a flask. The reaction was purged with nitrogen for 15 min, then iridium(III) chloride tetrahydrate (0.90 g, 2.43 mmol) was added. The reaction was heated in an oil bath set at 105° C. overnight under nitrogen. The reaction was allowed to cool, diluted with MeOH, filtered off a precipitate using MeOH, then dried in the vacuum oven for two hours to get 2.1 g of a dark red solid (98% yield). Used as is for next step.

Synthesis of Compound 5975 [Ir(L$_{A783}$)$_2$(L$_{B5}$)]

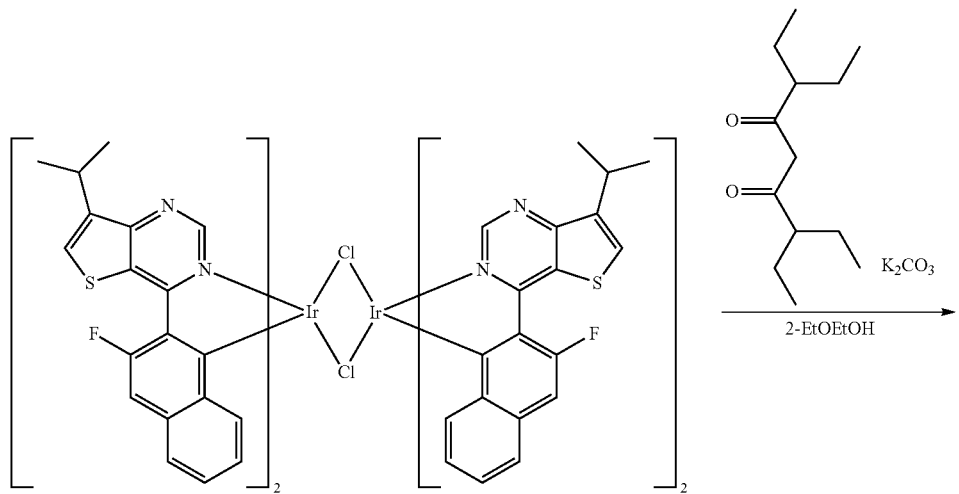

The dimer (1.00 g, 0.57 mmol), 3,7-diethylnonane-4,6-dione (0.92 g, 4.31 mmol), and 2-ethoxyethanol (19 mL) were combined in a flask. The reaction was purged with nitrogen for 15 minutes then potassium carbonate (0.60 g, 4.31 mmol) was added. The reaction was stirred at room temperature overnight under nitrogen. The reaction was diluted with MeOH then filtered off the solid using celite. The precipitate was recovered using DCM. The solid was purified via flash chromatography (heptanes/DCM, 4:1 to 3:1) to afford Compound 5975 [Ir(L$_{A783}$)$_2$(L$_{B5}$)] (0.70 g, 58% yield) as a red solid.

149

Synthesis of Compound 6040 [Ir(L$_{A848}$)$_2$(L$_{B5}$)]

Synthesis of 7-isopropyl-4-(3-methylnaphthalen-2-yl)thieno[3,2-d]pyrimidine

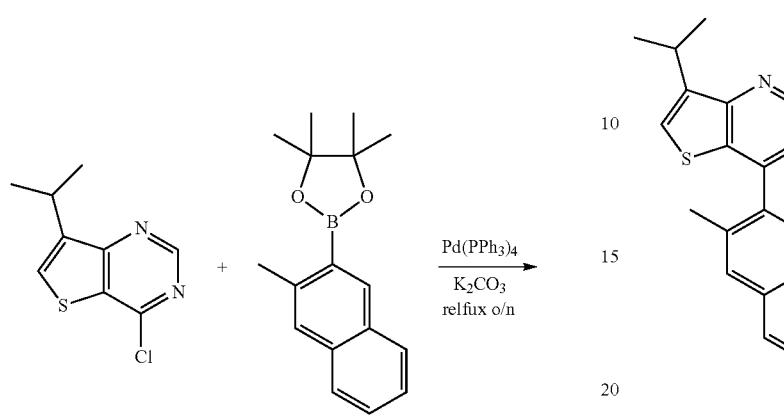

4-chloro-7-isopropylthieno[3,2-d]pyrimidine (3.0 g, 14.1 mmol), (4,4,5,5-tetramethyl-2-(3-methylnaphthalen-2-yl)-1,3,2-dioxaborolane (3.86 g, 14.4 mmol), potassium carbonate (4.87 g, 35.3 mmol), DME (75 mL), and water (25 mL) were combined in a flask. The reaction was purged with nitrogen for 15 minutes then palladium tetrakis (0.489 g, 0.423 mmol) was added. The reaction was heated to reflux in an oil bath overnight under nitrogen. The reaction mixture was extracted with EtOAc. The organic phase was washed with brine twice, dried with sodium sulfate, filtered and concentrated down to a brown solid. The brown solid was purified using flash chromatography (heptanes/EtOAc/DCM, 18:1:1 to 16:3:1) to afford 7-isopropyl-4-(3-methylnaphthalen-2-yl)thieno[3,2-d]pyrimidine (3.50 g, 78% yield) as a white solid.

150

Synthesis of the Ir(III) Dimer

(2.93 g, 9.21 mmol), 2-ethoxyethanol (54 mL) and water (18 mL) were combined in a flask. The reaction was purged with nitrogen for 15 minutes, then iridium(III) chloride tetrahydrate (1.05 g, 2.83 mmol) was added. The reaction was heated in an oil bath set at 105° C. overnight under nitrogen. The reaction was allowed to cool, diluted with MeOH, filtered off a precipitate using MeOH, then dried in the vacuum oven for two hours to get 2.2 g of a dark red solid (90% yield). Used as is for next step.

Synthesis of Compound 6040 [Ir(L$_{A848}$)$_2$(L$_{B5}$)]

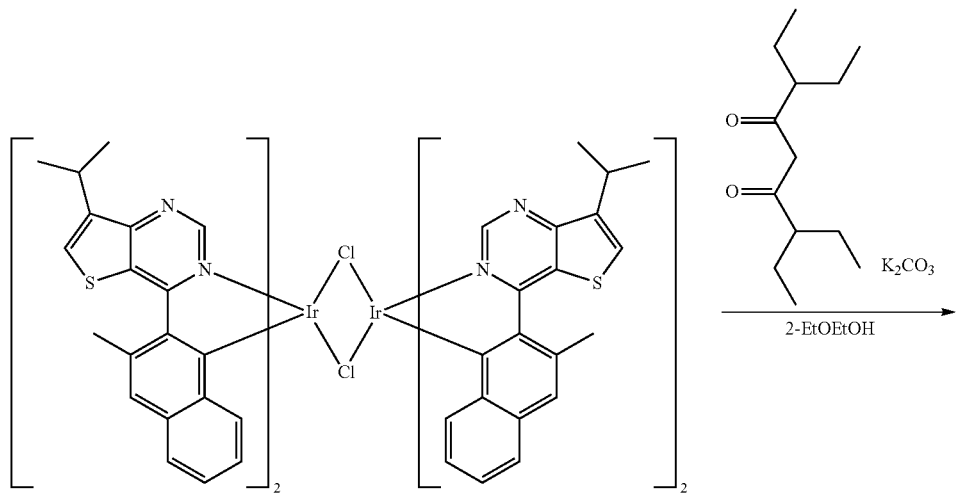

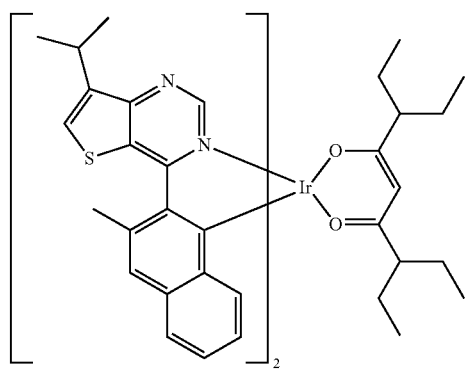

The dimer (2.20 g, 1.28 mmol), 3,7-diethylnonane-4,6-dione (2.71 ml, 12.8 mmol), and 2-ethoxyethanol (30 ml) were combined in a flask. The reaction was purged with nitrogen for 15 min then potassium carbonate (1.76 g, 12.8 mmol) was added. The reaction was stirred at room temperature over the weekend under nitrogen. The reaction was diluted with MeOH then filtered off a dark reddish brown solid using celite. The precipitate was recovered using DCM to get a red-brown solid. The solid was purified via flash chromatography, preconditioned with 75/15/10 heptanes/DCM/Et$_3$N then heptanes/DCM (19:1 to 17:3) to get 1.10 g of a red solid. The solid was dissolved in DCM and MeOH was added, the mixture was partially concentrated down on the rotovap at 30° C. bath temperature. The precipitate was filtered off and dried in the vacuum oven overnight to afford Compound 6040 [Ir(L$_{A848}$)$_2$(L$_{B5}$)] (0.94 g, 36%) as a red solid.

Synthesis of Comparative Compound 1

Synthesis of 4,5-dichloro-2-(3-methylnaphthalen-1-yl)quinoline

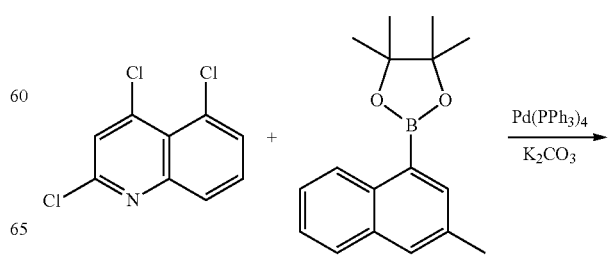

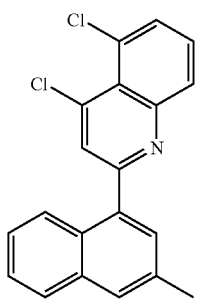

2,4,5-trichloroquinoline (3.05 g, 13.1 mmol), 4,4,5,5-tetramethyl-2-(3-methylnaphthalen-1-yl)-1,3,2-dioxaborolane (3.87 g, 14.4 mmol), and potassium carbonate (5.44 g, 39.4 mmol) were inserted in a flask. THF (98 mL) and Water (33 mL) were then added and the reaction mixture was degassed with nitrogen gas for 15 minutes. Palladium tetrakis (0.60 g, 0.53 mmol) was added and the reaction was heated to reflux overnight. Upon completion, water was added and the mixture was extracted with Ethyl Acetate. The crude material was purified via column chromatography using a mixture of Heptanes/Ethyl Acetate/DCM (90/5/5) as the solvent system. The product was then triturated from Methanol and then from Heptanes to afford 3.30 g (74% yield) of the title compound.

Synthesis of
4,5-dimethyl-2-(3-methylnaphthalen-1-yl)quinoline

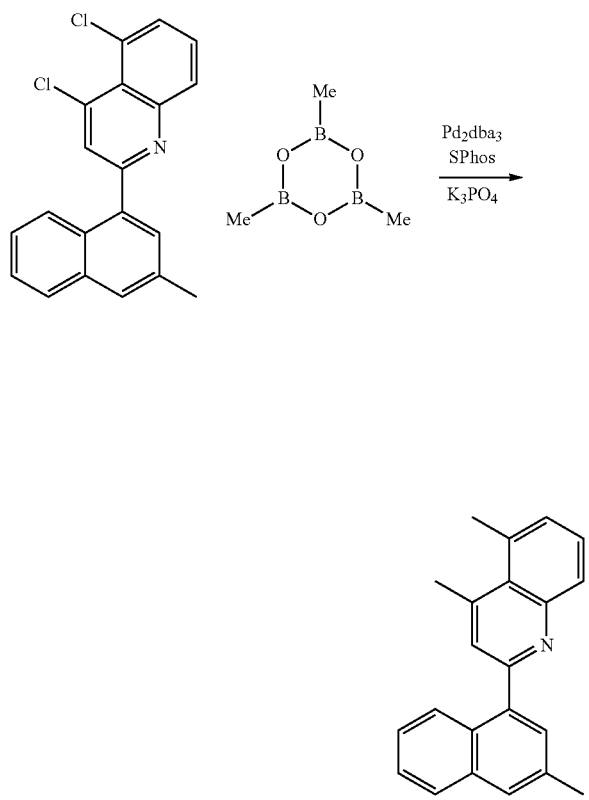

4,5-dichloro-2-(3-methylnaphthalen-1-yl)quinoline (3.10 g, 9.17 mmol), Pd$_2$(dba)$_3$ (0.17 g, 0.18 mmol), SPhos (0.30 g, 0.73 mmol), and potassium phosphate (5.84 g, 27.5 mmol) were inserted in a flask. Toluene (56 mL) and Water (6 mL) were added, followed by the addition of 2,4,6-trimethyl-1,3,5,2,4,6-trioxatriborinane (3.1 ml, 22.0 mmol) via syringe. The reaction mixture was degassed with nitrogen for 15 minutes and then was heated to reflux overnight. Upon completion, water was added to the mixture and it was extracted with Ethyl Acetate. The crude material was purified via column chromatography using Heptanes/Ethyl Acetate (90/10) as solvent system. The product still contained 0.45% impurity, so it was purified via column chromatography again using Heptanes/Ethyl Acetate (95/5) as solvent system. The title compound was afforded as a white solid (2.35 g, 86% yield).

Synthesis of the Ir(III) Dimer

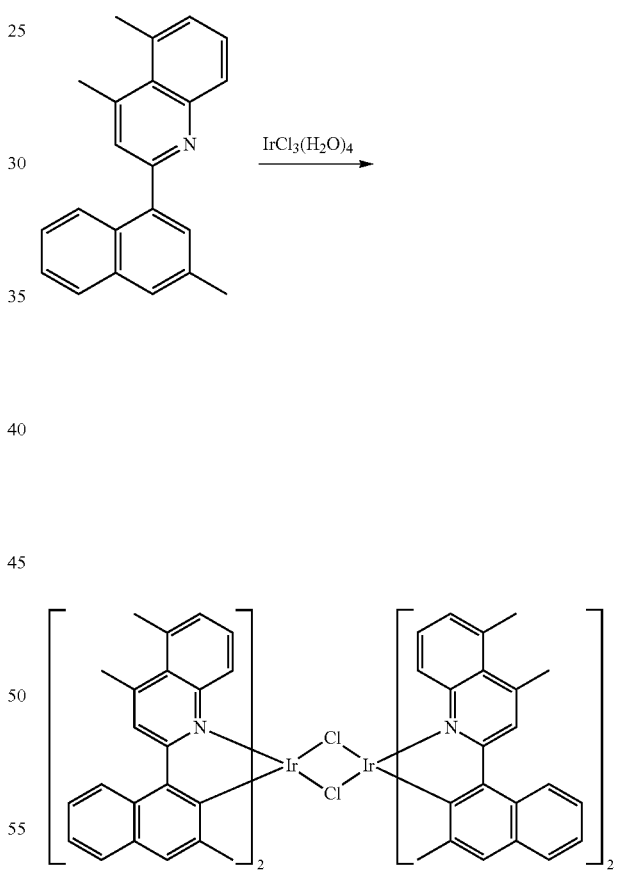

4,5-dimethyl-2-(3-methylnaphthalen-1-yl)quinoline (2.387 g, 8.03 mmol), 2-ethoxyethanol (39 mL) and Water (13 mL) were combined in a flask. The mixture was purged with nitrogen for 15 min, then iridium(III) chloride tetrahydrate (0.85 g, 2.29 mmol) was added and the reaction was heated at 105° C. overnight under nitrogen. The mixture was cooled down to room temperature, diluted with MeOH and filtered off the precipitate to afford 1.00 g (53% yield) of the Dimer.

Synthesis of Comparative Compound 1

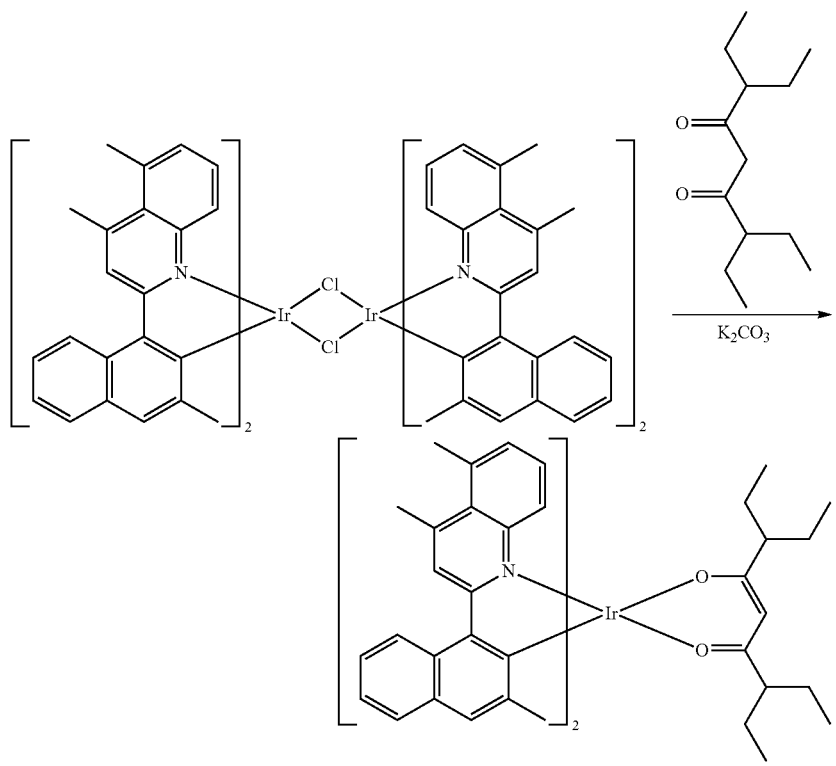

Ir(III) Dimer (1.00 g, 0.61 mmol), 3,7-diethylnonane-4,6-dione (1.44 mL, 6.09 mmol) and 2-ethoxyethanol (20 mL) were combined in a flask. The reaction was purged with nitrogen for 15 min, then potassium carbonate (0.84 g, 6.09 mmol) was added. The reaction was stirred at room temperature overnight. Methanol was added to the mixture and the precipitate was filtered off on a pad of celite. The solids on the Celite were then washed with DCM and the product was collected in a filtering flask. The collected product was solubilized in DCM and filtered on a pad of Silica. The product was then triturated in MeOH and recrystallized from DCM/EtOH to afford 0.85 g (70% yield) of the target.

EXPERIMENTAL

Device Examples

All example devices were fabricated by high vacuum (<10-7 Torr) thermal evaporation. The anode electrode was 1150 Å of indium tin oxide (ITO). The cathode consisted of 10 Å of Liq (8-hydroxyquinoline lithium) followed by 1,000 Å of Al. All devices were encapsulated with a glass lid sealed with an epoxy resin in a nitrogen glove box (<1 ppm of H2O and O2) immediately after fabrication, and a moisture getter was incorporated inside the package. The organic stack of the device examples consisted of sequentially, from the ITO surface, 100A of HATCN as the hole injection layer (HIL); 450 Å of HTM as a hole transporting layer (HTL); 400 Å of an emissive layer (EML) containing Compound H as a host, a stability dopant (SD) (18%), and Comparative Compound 1 or Compounds 3393, 3899, 5975, and 6040 as the emitter (3%); and 350 Å of Liq (8-hydroxyquinoline lithium) doped with 40% of ETM as the ETL. The emitter was selected to provide the desired color, efficiency and lifetime. The SD was added to the electron-transporting host to help transport positive charge in the emissive layer. The Comparative Example device was fabricated similarly to the device examples except that Comparative Compound 1 was used as the emitter in the EML. FIG. 1 shows the schematic device structure. Table 1 shows the device layer thickness and materials. The chemical structures of the device materials are shown below.

COMPOUND H

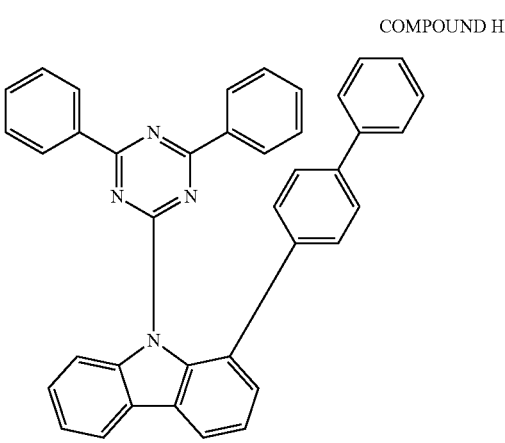

-continued
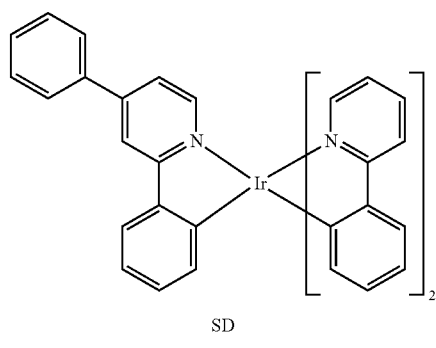
SD
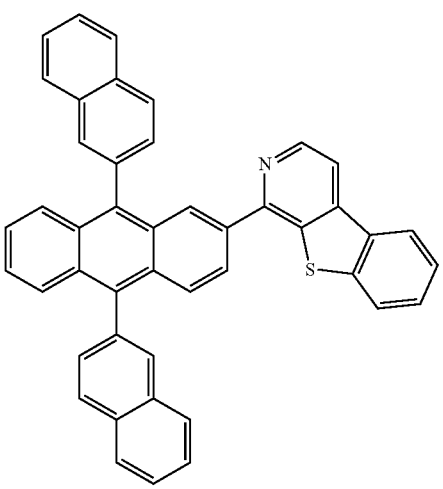
ETM
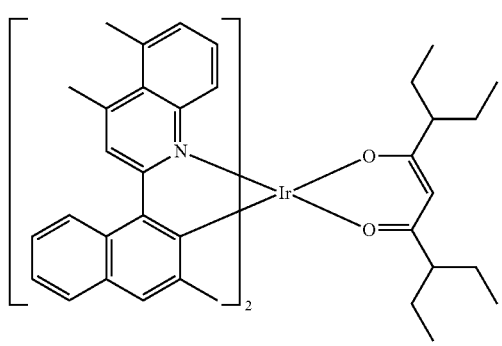
Comparative Compound 1
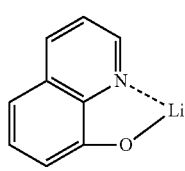
Liq
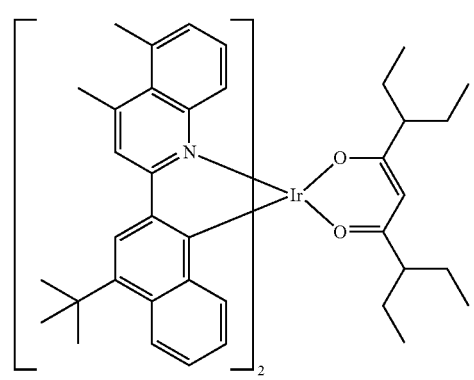
Compound 3,393
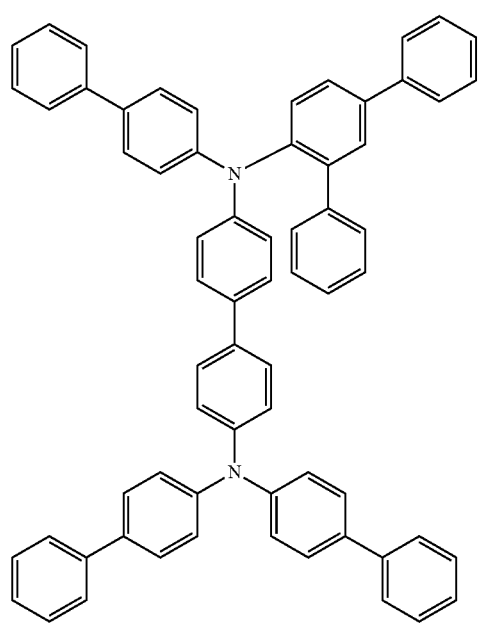
HTM
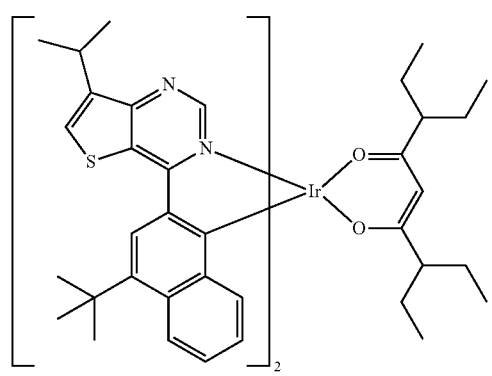
Compound 3,899

-continued

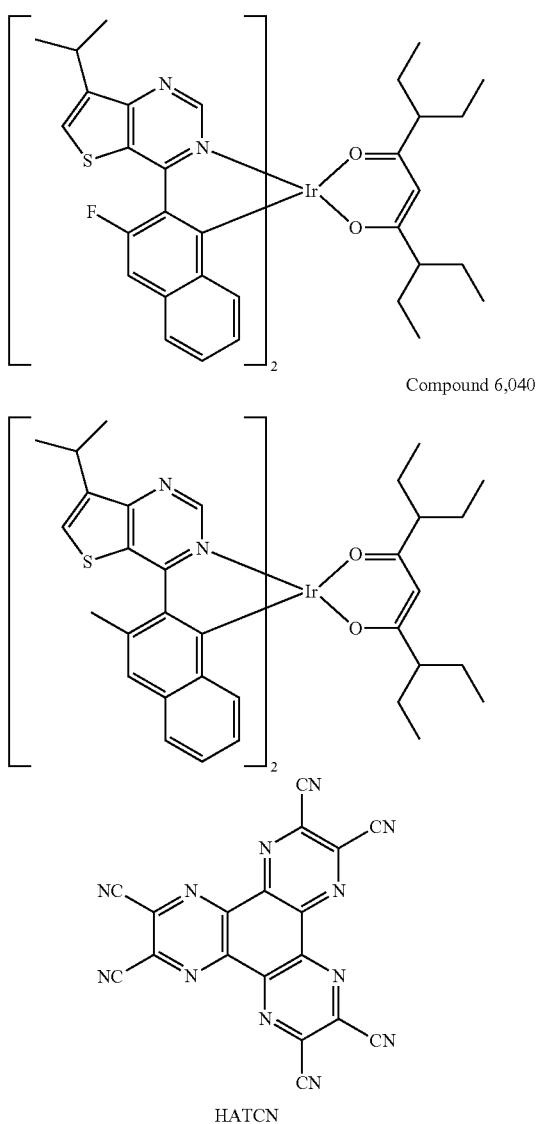

Compound 5,975

Compound 6,040

HATCN

The device performance data are summarized in Table 2. Comparative Compound 1 exhibited a Maximum Wavelength of emission (λ max) of 640 nm. The inventive compounds, namely Compounds 3,393; 3,899; and 5,975; were designed to be blue shifted compared to Comparative Compound 1 and to provide better external quantum efficiency (EQE). Compound 6,040 was designed to be red shifted. In order to afford better device performance, a different naphthalene regioisomer was used. We obtained a peak wavelength between 604 and 628 nm for the Inventive Compounds. On the other hand, Compound 6,040 was red shifted compared to Comparative Compound 1 with a peak wavelength at 653 nm. The Full Width at Half Maximum (FWHM) was also improved a lot with the inventive configuration wherein the Inventive Compounds showed a FWHM of 0.76 and 0.74 compared to 1.00 for the Comparative Compound 1. Compound 6,040 was slightly more broad at 1.10. Furthermore, a bulky side chain (t-butyl, cycloalkyl, etc.) needs to be included at the 4-position or any substitution at the 3-position of the naphthyl moiety in order to lock in the desired naphthalene orientation toward the iridium of the final material. The combination of the naphthyl regioismer combined with side chain allowed good performances for the inventive compounds. The EQE was much higher for the Inventive Compounds with relative value between 1.20 and 1.51.

TABLE 1

Device layer materials and thicknesses

| Layer | Material | Thickness [Å] |
|---|---|---|
| Anode | ITO | 1150 |
| HIL | HATCN | 100 |
| HTL | HTM | 450 |
| EML | Compound H: SD 18%:Emitter 3% | 400 |
| ETL | Liq: ETM 40% | 350 |
| EIL | Liq | 10 |
| Cathode | Al | 1000 |

TABLE 2

Performance of the devices with examples of red emitters.

| Device Example | Emitter | 1931 CIE x | 1931 CIE y | λ max [nm] | FWHM [nm] | At 10 mA/cm² Voltage [V] | At 10 mA/cm² EQE [%] |
|---|---|---|---|---|---|---|---|
| Example 1 | Compound 3,393 | 0.68 | 0.32 | 626 | 0.74 | 1.03 | 1.36 |
| Example 2 | Compound 3,899 | 0.68 | 0.32 | 628 | 0.74 | 1.03 | 1.51 |
| Example 3 | Compound 5,975 | 0.63 | 0.37 | 604 | 0.76 | 1.08 | 1.39 |
| Example 4 | Compound 6,040 | 0.69 | 0.31 | 653 | 1.10 | 1.03 | 1.20 |
| CE1 | Comparative Compound 1 | 0.68 | 0.32 | 640 | 1.00 | 1.00 | 1.00 |

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

We claim:

1. A neutral compound that has a structure of formula $(L_A)_n Ir(L_B)_{3-n}$;

wherein $L_B$ is a bidentate ligand;

wherein n is 1, 2, or 3; and wherein ligand $L_A$ has a structure of Formula I:

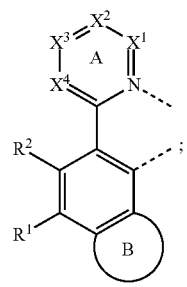

wherein Ring B represents a five- or six-membered aromatic ring;
wherein $R^3$ represents from none to the maximum number of substitutions;
wherein $X^1$, $X^2$, $X^3$, and $X^4$ are each independently a CR or N;
wherein at least one of $X^1$, $X^2$, or $X^3$ is nitrogen;
wherein (a) $R^1$ is $CR^{11}R^{12}R^{13}$ or joins with $R^2$ to form into a ring; or
(b) $R^2$ is not hydrogen, or
(c) both (a) and (b) are true;
wherein R, $R^1$, $R^2$, $R^{11}$, $R^{12}$, $R^{13}$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, acyl, carbonyl, carboxylic acid, ester, nitrile, isonitrile, sulfanyl, sulfinyl, sulfonyl, phosphino, and combinations thereof;
wherein, with the exception of a ring between R and $R^2$, any two substituents among R, $R^1$, $R^2$, $R^{11}$, $R^{12}$, $R^{13}$ are optionally joined to form into an aromatic ring;
wherein $L_A$ is coordinated to a metal M;
wherein $L_A$ is optionally linked with other ligands to comprise a tridentate, tetradentate, pentadentate, or hexadentate ligand;
wherein M is optionally coordinated to other ligands; and
wherein $L_B$ is $C_1$ to $C_7$ alkyl substituted or unsubstituted acetylacetonate.

2. The neutral compound of claim 1, wherein M is selected from the group consisting of Ir, Rh, Re, Ru, Os, Pt, Au, and Cu.

3. The neutral compound of claim 1, wherein M is Ir or Pt.

4. The neutral compound of claim 1, wherein $X^2$ is nitrogen.

5. The neutral compound of claim 1, wherein $R^1$ is tert-butyl or substituted tert-butyl.

6. The neutral compound of claim 1, wherein $R^1$ and $R^2$ form into an aromatic ring, which can be further substituted.

7. The neutral compound of claim 1, wherein $R^2$ is selected from the group consisting of deuterium, fluorine, alkyl, cycloalkyl, and combination thereof.

8. The neutral compound of claim 1, wherein Ring B is phenyl.

9. The neutral compound of claim 1, wherein the ligand $L_A$ is selected from the group consisting of:

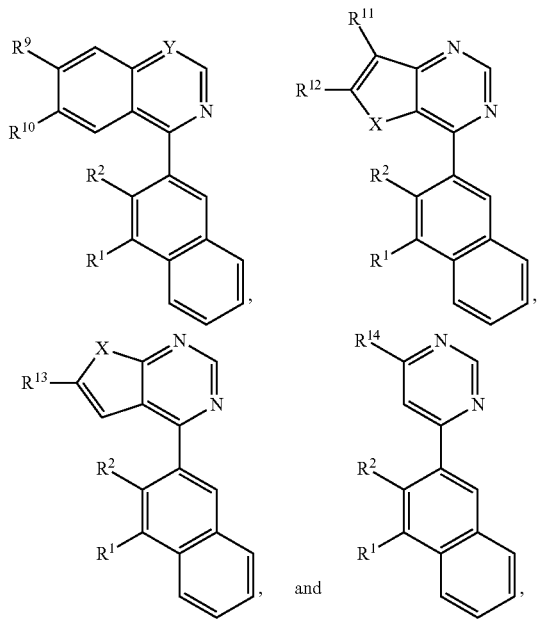

wherein X is S or O;
wherein Y is N;
wherein $R_1$, $R_2$, $R_9$, $R_{10}$, $R_{11}$, $R_{12}$, $R_{13}$, and $R_{14}$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof;
wherein any two substituents are optionally joined to form into a ring.

10. The neutral compound of claim 1, wherein $L_B$ is selected from the group consisting of:

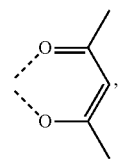

$L_{B1}$

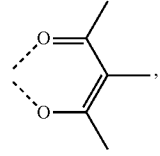

$L_{B2}$

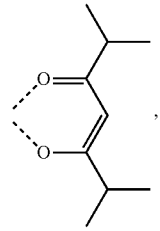

$L_{B3}$

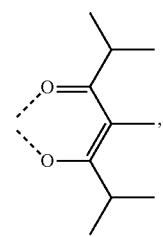 $L_{B4}$
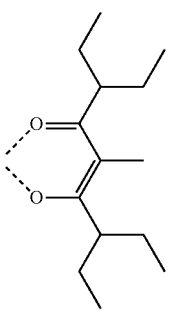 $L_{B5}$
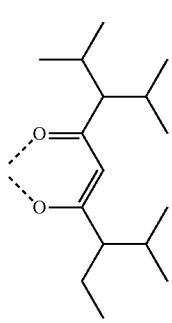 $L_{B6}$
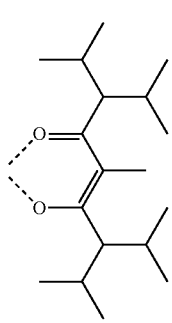 $L_{B7}$
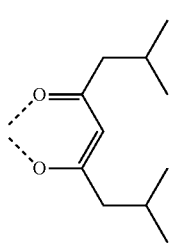 $L_{B8}$
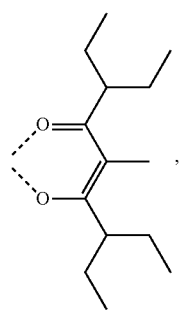 $L_{B9}$
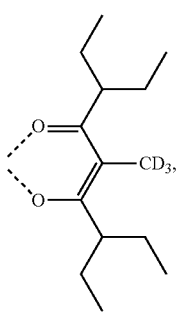 $L_{B10}$
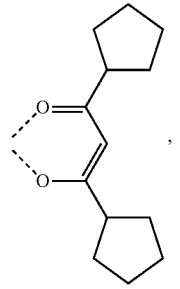 $L_{B11}$
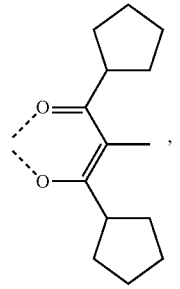 $L_{B12}$
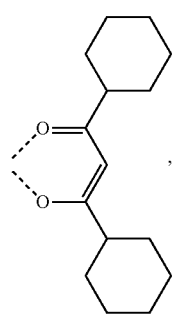 $L_{B13}$ $L_{B14}$ 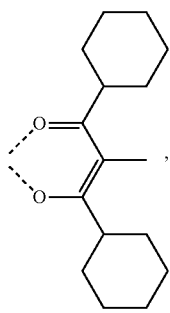

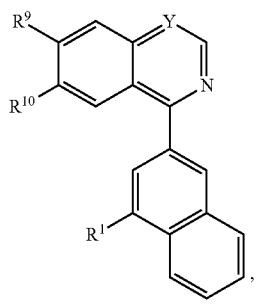

in which $R^1$, $R^9$, $R^{10}$, and Y are defined as provided below:

$L_{B15}$ 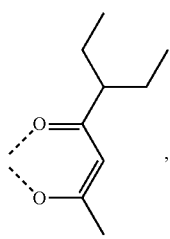

$L_{B16}$ 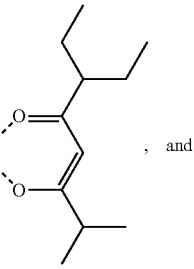

$L_{B17}$ 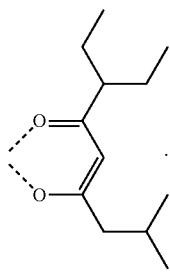

11. The neutral compound of claim 1, wherein at least two adjacent ones of $X^1$, $X^2$, $X^3$, and $X^4$ are CR and are fused into a five-membered aromatic ring.

12. The neutral compound of claim 1, wherein at least two adjacent ones of $X^1$, $X^2$, $X^3$, and $X^4$ are CR and are fused into a six-membered aromatic ring.

13. The neutral compound of claim 1, wherein the ligand $L_A$ is selected from the group consisting of:

$L_{A391}$ through $L_{A520}$ that are based on a structure of Formula III,

| Ligand | $R^1$ | $R^9$ | $R^{10}$ | Y |
|---|---|---|---|---|
| $L_{A391}$ | $R_{B6}$ | H | H | N |
| $L_{A392}$ | $R_{B6}$ | $R_{B1}$ | H | N |
| $L_{A393}$ | $R_{B6}$ | $R_{B3}$ | H | N |
| $L_{A394}$ | $R_{B6}$ | $R_{B4}$ | H | N |
| $L_{A395}$ | $R_{B6}$ | $R_{B7}$ | H | N |
| $L_{A396}$ | $R_{B6}$ | $R_{B10}$ | H | N |
| $L_{A397}$ | $R_{B6}$ | $R_{A3}$ | H | N |
| $L_{A398}$ | $R_{B6}$ | $R_{A34}$ | H | N |
| $L_{A399}$ | $R_{B6}$ | H | $R_{B1}$ | N |
| $L_{A400}$ | $R_{B6}$ | H | $R_{B2}$ | N |
| $L_{A401}$ | $R_{B6}$ | H | $R_{B3}$ | N |
| $L_{A402}$ | $R_{B6}$ | H | $R_{B4}$ | N |
| $L_{A403}$ | $R_{B6}$ | H | $R_{B7}$ | N |
| $L_{A404}$ | $R_{B6}$ | H | $R_{B10}$ | N |
| $L_{A405}$ | $R_{B6}$ | H | $R_{A3}$ | N |
| $L_{A406}$ | $R_{B6}$ | H | $R_{A34}$ | N |
| $L_{A407}$ | $R_{B6}$ | $R_{B1}$ | $R_{B1}$ | N |
| $L_{A408}$ | $R_{B6}$ | $R_{B3}$ | $R_{B3}$ | N |
| $L_{A409}$ | $R_{B6}$ | $R_{B4}$ | $R_{B4}$ | N |
| $L_{A410}$ | $R_{B6}$ | $R_{B7}$ | $R_{B7}$ | N |
| $L_{A411}$ | $R_{B6}$ | $R_{B10}$ | $R_{B10}$ | N |
| $L_{A412}$ | $R_{B6}$ | $R_{A3}$ | $R_{A3}$ | N |
| $L_{A413}$ | $R_{B6}$ | $R_{A34}$ | $R_{A34}$ | N |
| $L_{A414}$ | $R_{B6}$ | $R_{B1}$ | $R_{B3}$ | N |
| $L_{A415}$ | $R_{B6}$ | $R_{B1}$ | $R_{B4}$ | N |
| $L_{A416}$ | $R_{B6}$ | $R_{B1}$ | $R_{B7}$ | N |
| $L_{A417}$ | $R_{B6}$ | $R_{B1}$ | $R_{B10}$ | N |
| $L_{A418}$ | $R_{B6}$ | $R_{B1}$ | $R_{A3}$ | N |
| $L_{A419}$ | $R_{B6}$ | $R_{B1}$ | $R_{A34}$ | N |
| $L_{A420}$ | $R_{B6}$ | $R_{B3}$ | $R_{B1}$ | N |
| $L_{A421}$ | $R_{B6}$ | $R_{B3}$ | $R_{B4}$ | N |
| $L_{A422}$ | $R_{B6}$ | $R_{B3}$ | $R_{B7}$ | N |
| $L_{A423}$ | $R_{B6}$ | $R_{B3}$ | $R_{B10}$ | N |
| $L_{A424}$ | $R_{B6}$ | $R_{B3}$ | $R_{A3}$ | N |
| $L_{A425}$ | $R_{B6}$ | $R_{B3}$ | $R_{A34}$ | N |
| $L_{A426}$ | $R_{B6}$ | $R_{B4}$ | $R_{B1}$ | N |
| $L_{A427}$ | $R_{B6}$ | $R_{B4}$ | $R_{B3}$ | N |
| $L_{A428}$ | $R_{B6}$ | $R_{B4}$ | $R_{B7}$ | N |
| $L_{A429}$ | $R_{B6}$ | $R_{B4}$ | $R_{B10}$ | N |
| $L_{A430}$ | $R_{B6}$ | $R_{B4}$ | $R_{A3}$ | N |
| $L_{A431}$ | $R_{B6}$ | $R_{B4}$ | $R_{A34}$ | N |
| $L_{A432}$ | $R_{B6}$ | $R_{B7}$ | $R_{B1}$ | N |
| $L_{A433}$ | $R_{B6}$ | $R_{B7}$ | $R_{B3}$ | N |
| $L_{A434}$ | $R_{B6}$ | $R_{B7}$ | $R_{B4}$ | N |
| $L_{A435}$ | $R_{B6}$ | $R_{B7}$ | $R_{B10}$ | N |
| $L_{A436}$ | $R_{B6}$ | $R_{B7}$ | $R_{A3}$ | N |
| $L_{A437}$ | $R_{B6}$ | $R_{B7}$ | $R_{A34}$ | N |
| $L_{A438}$ | $R_{B6}$ | $R_{B10}$ | $R_{B1}$ | N |
| $L_{A439}$ | $R_{B6}$ | $R_{B10}$ | $R_{B3}$ | N |
| $L_{A440}$ | $R_{B6}$ | $R_{B10}$ | $R_{B4}$ | N |
| $L_{A441}$ | $R_{B6}$ | $R_{B10}$ | $R_{B7}$ | N |
| $L_{A442}$ | $R_{B6}$ | $R_{B10}$ | $R_{A3}$ | N |
| $L_{A443}$ | $R_{B6}$ | $R_{B10}$ | $R_{A34}$ | N |
| $L_{A444}$ | $R_{B6}$ | $R_{A3}$ | $R_{B1}$ | N |
| $L_{A445}$ | $R_{B6}$ | $R_{A3}$ | $R_{B3}$ | N |
| $L_{A446}$ | $R_{B6}$ | $R_{A3}$ | $R_{B4}$ | N |
| $L_{A447}$ | $R_{B6}$ | $R_{A3}$ | $R_{B7}$ | N |
| $L_{A448}$ | $R_{B6}$ | $R_{A3}$ | $R_{B10}$ | N |
| $L_{A449}$ | $R_{B6}$ | $R_{A3}$ | $R_{A34}$ | N |

-continued

| Ligand | $R^1$ | $R^9$ | $R^{10}$ | Y |
|---|---|---|---|---|
| $L_{A450}$ | $R_{B6}$ | $R_{A34}$ | $R_{B1}$ | N |
| $L_{A451}$ | $R_{B6}$ | $R_{A34}$ | $R_{B3}$ | N |
| $L_{A452}$ | $R_{B6}$ | $R_{A34}$ | $R_{B4}$ | N |
| $L_{A453}$ | $R_{B6}$ | $R_{A34}$ | $R_{B7}$ | N |
| $L_{A454}$ | $R_{B6}$ | $R_{A34}$ | $R_{B10}$ | N |
| $L_{A455}$ | $R_{B6}$ | $R_{A34}$ | $R_{A3}$ | N |
| $L_{A456}$ | $R_{B8}$ | H | H | N |
| $L_{A457}$ | $R_{B8}$ | $R_{B1}$ | H | N |
| $L_{A458}$ | $R_{B8}$ | $R_{B3}$ | H | N |
| $L_{A459}$ | $R_{B8}$ | $R_{B4}$ | H | N |
| $L_{A460}$ | $R_{B8}$ | $R_{B7}$ | H | N |
| $L_{A461}$ | $R_{B8}$ | $R_{B10}$ | H | N |
| $L_{A462}$ | $R_{B8}$ | $R_{A3}$ | H | N |
| $L_{A463}$ | $R_{B8}$ | $R_{A34}$ | H | N |
| $L_{A464}$ | $R_{B8}$ | H | $R_{B1}$ | N |
| $L_{A465}$ | $R_{B8}$ | H | $R_{B2}$ | N |
| $L_{A466}$ | $R_{B8}$ | H | $R_{B3}$ | N |
| $L_{A467}$ | $R_{B8}$ | H | $R_{B4}$ | N |
| $L_{A468}$ | $R_{B8}$ | H | $R_{B7}$ | N |
| $L_{A469}$ | $R_{B8}$ | H | $R_{B10}$ | N |
| $L_{A470}$ | $R_{B8}$ | H | $R_{A3}$ | N |
| $L_{A471}$ | $R_{B8}$ | H | $R_{A34}$ | N |
| $L_{A472}$ | $R_{B8}$ | $R_{B1}$ | $R_{B1}$ | N |
| $L_{A473}$ | $R_{B8}$ | $R_{B3}$ | $R_{B3}$ | N |
| $L_{A474}$ | $R_{B8}$ | $R_{B4}$ | $R_{B4}$ | N |
| $L_{A475}$ | $R_{B8}$ | $R_{B7}$ | $R_{B7}$ | N |
| $L_{A476}$ | $R_{B8}$ | $R_{B10}$ | $R_{B10}$ | N |
| $L_{A477}$ | $R_{B8}$ | $R_{A3}$ | $R_{A3}$ | N |
| $L_{A478}$ | $R_{B8}$ | $R_{A34}$ | $R_{A34}$ | N |
| $L_{A479}$ | $R_{B8}$ | $R_{B1}$ | $R_{B3}$ | N |
| $L_{A480}$ | $R_{B8}$ | $R_{B1}$ | $R_{B4}$ | N |
| $L_{A481}$ | $R_{B8}$ | $R_{B1}$ | $R_{B7}$ | N |
| $L_{A482}$ | $R_{B8}$ | $R_{B1}$ | $R_{B10}$ | N |
| $L_{A483}$ | $R_{B8}$ | $R_{B1}$ | $R_{A3}$ | N |
| $L_{A484}$ | $R_{B8}$ | $R_{B1}$ | $R_{A34}$ | N |
| $L_{A485}$ | $R_{B8}$ | $R_{B3}$ | $R_{B1}$ | N |
| $L_{A486}$ | $R_{B8}$ | $R_{B3}$ | $R_{B4}$ | N |
| $L_{A487}$ | $R_{B8}$ | $R_{B3}$ | $R_{B7}$ | N |
| $L_{A488}$ | $R_{B8}$ | $R_{B3}$ | $R_{B10}$ | N |
| $L_{A489}$ | $R_{B8}$ | $R_{B3}$ | $R_{A3}$ | N |
| $L_{A490}$ | $R_{B8}$ | $R_{B3}$ | $R_{A34}$ | N |
| $L_{A491}$ | $R_{B8}$ | $R_{B4}$ | $R_{B1}$ | N |
| $L_{A492}$ | $R_{B8}$ | $R_{B4}$ | $R_{B3}$ | N |
| $L_{A493}$ | $R_{B8}$ | $R_{B4}$ | $R_{B7}$ | N |
| $L_{A494}$ | $R_{B8}$ | $R_{B4}$ | $R_{B10}$ | N |
| $L_{A495}$ | $R_{B8}$ | $R_{B4}$ | $R_{A3}$ | N |
| $L_{A496}$ | $R_{B8}$ | $R_{B4}$ | $R_{A34}$ | N |
| $L_{A497}$ | $R_{B8}$ | $R_{B7}$ | $R_{B1}$ | N |
| $L_{A498}$ | $R_{B8}$ | $R_{B7}$ | $R_{B3}$ | N |
| $L_{A499}$ | $R_{B8}$ | $R_{B7}$ | $R_{B4}$ | N |
| $L_{A500}$ | $R_{B8}$ | $R_{B7}$ | $R_{B10}$ | N |
| $L_{A501}$ | $R_{B8}$ | $R_{B7}$ | $R_{A3}$ | N |
| $L_{A502}$ | $R_{B8}$ | $R_{B7}$ | $R_{A34}$ | N |
| $L_{A503}$ | $R_{B8}$ | $R_{B10}$ | $R_{B1}$ | N |
| $L_{A504}$ | $R_{B8}$ | $R_{B10}$ | $R_{B3}$ | N |
| $L_{A505}$ | $R_{B8}$ | $R_{B10}$ | $R_{B4}$ | N |
| $L_{A506}$ | $R_{B8}$ | $R_{B10}$ | $R_{B7}$ | N |
| $L_{A507}$ | $R_{B8}$ | $R_{B10}$ | $R_{A3}$ | N |
| $L_{A508}$ | $R_{B8}$ | $R_{B10}$ | $R_{A34}$ | N |
| $L_{A509}$ | $R_{B8}$ | $R_{A3}$ | $R_{B1}$ | N |
| $L_{A510}$ | $R_{B8}$ | $R_{A3}$ | $R_{B3}$ | N |
| $L_{A511}$ | $R_{B8}$ | $R_{A3}$ | $R_{B4}$ | N |
| $L_{A512}$ | $R_{B8}$ | $R_{A3}$ | $R_{B7}$ | N |
| $L_{A513}$ | $R_{B8}$ | $R_{A3}$ | $R_{B10}$ | N |
| $L_{A514}$ | $R_{B8}$ | $R_{A3}$ | $R_{A34}$ | N |
| $L_{A515}$ | $R_{B8}$ | $R_{A34}$ | $R_{B1}$ | N |
| $L_{A516}$ | $R_{B8}$ | $R_{A34}$ | $R_{B3}$ | N |
| $L_{A517}$ | $R_{B8}$ | $R_{A34}$ | $R_{B4}$ | N |
| $L_{A518}$ | $R_{B8}$ | $R_{A34}$ | $R_{B7}$ | N |
| $L_{A519}$ | $R_{B8}$ | $R_{A34}$ | $R_{B10}$ | N |
| $L_{A520}$ | $R_{B8}$ | $R_{A34}$ | $R_{A3}$ | N, |

$L_{A521}$ through $L_{A780}$ that are based on a structure of Formula IV,

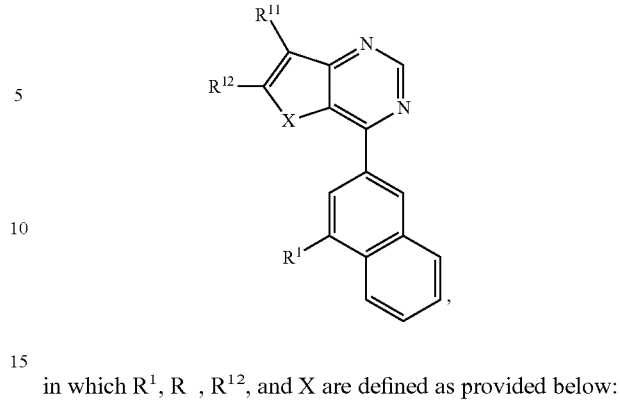

in which $R^1$, $R^{11}$, $R^{12}$, and X are defined as provided below:

| Ligand | $R^1$ | $R^{11}$ | $R^{12}$ | X |
|---|---|---|---|---|
| $L_{A521}$ | $R_{B6}$ | H | H | S |
| $L_{A522}$ | $R_{B6}$ | $R_{B1}$ | H | S |
| $L_{A523}$ | $R_{B6}$ | $R_{B3}$ | H | S |
| $L_{A524}$ | $R_{B6}$ | $R_{B4}$ | H | S |
| $L_{A525}$ | $R_{B6}$ | $R_{B7}$ | H | S |
| $L_{A526}$ | $R_{B6}$ | $R_{B10}$ | H | S |
| $L_{A527}$ | $R_{B6}$ | $R_{A3}$ | H | S |
| $L_{A528}$ | $R_{B6}$ | $R_{A34}$ | H | S |
| $L_{A529}$ | $R_{B6}$ | H | $R_{B1}$ | S |
| $L_{A530}$ | $R_{B6}$ | H | $R_{B2}$ | S |
| $L_{A531}$ | $R_{B6}$ | H | $R_{B3}$ | S |
| $L_{A532}$ | $R_{B6}$ | H | $R_{B4}$ | S |
| $L_{A533}$ | $R_{B6}$ | H | $R_{B7}$ | S |
| $L_{A534}$ | $R_{B6}$ | H | $R_{B10}$ | S |
| $L_{A535}$ | $R_{B6}$ | H | $R_{A3}$ | S |
| $L_{A536}$ | $R_{B6}$ | H | $R_{A34}$ | S |
| $L_{A537}$ | $R_{B6}$ | $R_{B1}$ | $R_{B1}$ | S |
| $L_{A538}$ | $R_{B6}$ | $R_{B3}$ | $R_{B3}$ | S |
| $L_{A539}$ | $R_{B6}$ | $R_{B4}$ | $R_{B4}$ | S |
| $L_{A540}$ | $R_{B6}$ | $R_{B7}$ | $R_{B7}$ | S |
| $L_{A541}$ | $R_{B6}$ | $R_{B10}$ | $R_{B10}$ | S |
| $L_{A542}$ | $R_{B6}$ | $R_{A3}$ | $R_{A3}$ | S |
| $L_{A543}$ | $R_{B6}$ | $R_{A34}$ | $R_{A34}$ | S |
| $L_{A544}$ | $R_{B6}$ | $R_{B1}$ | $R_{B3}$ | S |
| $L_{A545}$ | $R_{B6}$ | $R_{B1}$ | $R_{B4}$ | S |
| $L_{A546}$ | $R_{B6}$ | $R_{B1}$ | $R_{B7}$ | S |
| $L_{A547}$ | $R_{B6}$ | $R_{B1}$ | $R_{B10}$ | S |
| $L_{A548}$ | $R_{B6}$ | $R_{B1}$ | $R_{A3}$ | S |
| $L_{A549}$ | $R_{B6}$ | $R_{B1}$ | $R_{A34}$ | S |
| $L_{A550}$ | $R_{B6}$ | $R_{B3}$ | $R_{B1}$ | S |
| $L_{A551}$ | $R_{B6}$ | $R_{B3}$ | $R_{B4}$ | S |
| $L_{A552}$ | $R_{B6}$ | $R_{B3}$ | $R_{B7}$ | S |
| $L_{A553}$ | $R_{B6}$ | $R_{B3}$ | $R_{B10}$ | S |
| $L_{A554}$ | $R_{B6}$ | $R_{B3}$ | $R_{A3}$ | S |
| $L_{A555}$ | $R_{B6}$ | $R_{B3}$ | $R_{A34}$ | S |
| $L_{A556}$ | $R_{B6}$ | $R_{B4}$ | $R_{B1}$ | S |
| $L_{A557}$ | $R_{B6}$ | $R_{B4}$ | $R_{B3}$ | S |
| $L_{A558}$ | $R_{B6}$ | $R_{B4}$ | $R_{B7}$ | S |
| $L_{A559}$ | $R_{B6}$ | $R_{B4}$ | $R_{B10}$ | S |
| $L_{A560}$ | $R_{B6}$ | $R_{B4}$ | $R_{A3}$ | S |
| $L_{A561}$ | $R_{B6}$ | $R_{B4}$ | $R_{A34}$ | S |
| $L_{A562}$ | $R_{B6}$ | $R_{B7}$ | $R_{B1}$ | S |
| $L_{A563}$ | $R_{B6}$ | $R_{B7}$ | $R_{B3}$ | S |
| $L_{A564}$ | $R_{B6}$ | $R_{B7}$ | $R_{B4}$ | S |
| $L_{A565}$ | $R_{B6}$ | $R_{B7}$ | $R_{B10}$ | S |
| $L_{A566}$ | $R_{B6}$ | $R_{B7}$ | $R_{A3}$ | S |
| $L_{A567}$ | $R_{B6}$ | $R_{B7}$ | $R_{A34}$ | S |
| $L_{A568}$ | $R_{B6}$ | $R_{B10}$ | $R_{B1}$ | S |
| $L_{A569}$ | $R_{B6}$ | $R_{B10}$ | $R_{B3}$ | S |
| $L_{A570}$ | $R_{B6}$ | $R_{B10}$ | $R_{B4}$ | S |
| $L_{A571}$ | $R_{B6}$ | $R_{B10}$ | $R_{B7}$ | S |
| $L_{A572}$ | $R_{B6}$ | $R_{B10}$ | $R_{A3}$ | S |
| $L_{A573}$ | $R_{B6}$ | $R_{B10}$ | $R_{A34}$ | S |
| $L_{A574}$ | $R_{B6}$ | $R_{A3}$ | $R_{B1}$ | S |
| $L_{A575}$ | $R_{B6}$ | $R_{A3}$ | $R_{B3}$ | S |
| $L_{A576}$ | $R_{B6}$ | $R_{A3}$ | $R_{B4}$ | S |
| $L_{A577}$ | $R_{B6}$ | $R_{A3}$ | $R_{B7}$ | S |
| $L_{A578}$ | $R_{B6}$ | $R_{A3}$ | $R_{B10}$ | S |

-continued

| Ligand | R¹ | R¹¹ | R¹² | X |
|---|---|---|---|---|
| $L_{A579}$ | $R_{B6}$ | $R_{A3}$ | $R_{A434}$ | S |
| $L_{A580}$ | $R_{B6}$ | $R_{A434}$ | $R_{B1}$ | S |
| $L_{A581}$ | $R_{B6}$ | $R_{A434}$ | $R_{B3}$ | S |
| $L_{A582}$ | $R_{B6}$ | $R_{A434}$ | $R_{B4}$ | S |
| $L_{A583}$ | $R_{B6}$ | $R_{A434}$ | $R_{B7}$ | S |
| $L_{A584}$ | $R_{B6}$ | $R_{A434}$ | $R_{B10}$ | S |
| $L_{A585}$ | $R_{B6}$ | $R_{A434}$ | $R_{A3}$ | S |
| $L_{A586}$ | $R_{B8}$ | H | H | S |
| $L_{A587}$ | $R_{B8}$ | $R_{B1}$ | H | S |
| $L_{A588}$ | $R_{B8}$ | $R_{B3}$ | H | S |
| $L_{A589}$ | $R_{B8}$ | $R_{B4}$ | H | S |
| $L_{A590}$ | $R_{B8}$ | $R_{B7}$ | H | S |
| $L_{A591}$ | $R_{B8}$ | $R_{B10}$ | H | S |
| $L_{A592}$ | $R_{B8}$ | $R_{A3}$ | H | S |
| $L_{A593}$ | $R_{B8}$ | $R_{A434}$ | H | S |
| $L_{A594}$ | $R_{B8}$ | H | $R_{B1}$ | S |
| $L_{A595}$ | $R_{B8}$ | H | $R_{B2}$ | S |
| $L_{A596}$ | $R_{B8}$ | H | $R_{B3}$ | S |
| $L_{A597}$ | $R_{B8}$ | H | $R_{B4}$ | S |
| $L_{A598}$ | $R_{B8}$ | H | $R_{B7}$ | S |
| $L_{A599}$ | $R_{B8}$ | H | $R_{B10}$ | S |
| $L_{A600}$ | $R_{B8}$ | H | $R_{A3}$ | S |
| $L_{A601}$ | $R_{B8}$ | H | $R_{A434}$ | S |
| $L_{A602}$ | $R_{B8}$ | $R_{B1}$ | $R_{B1}$ | S |
| $L_{A603}$ | $R_{B8}$ | $R_{B3}$ | $R_{B3}$ | S |
| $L_{A604}$ | $R_{B8}$ | $R_{B4}$ | $R_{B4}$ | S |
| $L_{A605}$ | $R_{B8}$ | $R_{B7}$ | $R_{B7}$ | S |
| $L_{A606}$ | $R_{B8}$ | $R_{B10}$ | $R_{B10}$ | S |
| $L_{A607}$ | $R_{B8}$ | $R_{A3}$ | $R_{A3}$ | S |
| $L_{A608}$ | $R_{B8}$ | $R_{A434}$ | $R_{A434}$ | S |
| $L_{A609}$ | $R_{B8}$ | $R_{B1}$ | $R_{B3}$ | S |
| $L_{A610}$ | $R_{B8}$ | $R_{B1}$ | $R_{B4}$ | S |
| $L_{A611}$ | $R_{B8}$ | $R_{B1}$ | $R_{B7}$ | S |
| $L_{A612}$ | $R_{B8}$ | $R_{B1}$ | $R_{B10}$ | S |
| $L_{A613}$ | $R_{B8}$ | $R_{B1}$ | $R_{A3}$ | S |
| $L_{A614}$ | $R_{B8}$ | $R_{B1}$ | $R_{A434}$ | S |
| $L_{A615}$ | $R_{B8}$ | $R_{B3}$ | $R_{B1}$ | S |
| $L_{A616}$ | $R_{B8}$ | $R_{B3}$ | $R_{B4}$ | S |
| $L_{A617}$ | $R_{B8}$ | $R_{B3}$ | $R_{B7}$ | S |
| $L_{A618}$ | $R_{B8}$ | $R_{B3}$ | $R_{B10}$ | S |
| $L_{A619}$ | $R_{B8}$ | $R_{B3}$ | $R_{A3}$ | S |
| $L_{A620}$ | $R_{B8}$ | $R_{B3}$ | $R_{A434}$ | S |
| $L_{A621}$ | $R_{B8}$ | $R_{B4}$ | $R_{B1}$ | S |
| $L_{A622}$ | $R_{B8}$ | $R_{B4}$ | $R_{B3}$ | S |
| $L_{A623}$ | $R_{B8}$ | $R_{B4}$ | $R_{B7}$ | S |
| $L_{A624}$ | $R_{B8}$ | $R_{B4}$ | $R_{B10}$ | S |
| $L_{A625}$ | $R_{B8}$ | $R_{B4}$ | $R_{A3}$ | S |
| $L_{A626}$ | $R_{B8}$ | $R_{B4}$ | $R_{A434}$ | S |
| $L_{A627}$ | $R_{B8}$ | $R_{B7}$ | $R_{B1}$ | S |
| $L_{A628}$ | $R_{B8}$ | $R_{B7}$ | $R_{B3}$ | S |
| $L_{A629}$ | $R_{B8}$ | $R_{B7}$ | $R_{B4}$ | S |
| $L_{A630}$ | $R_{B8}$ | $R_{B7}$ | $R_{B10}$ | S |
| $L_{A631}$ | $R_{B8}$ | $R_{B7}$ | $R_{A3}$ | S |
| $L_{A632}$ | $R_{B8}$ | $R_{B7}$ | $R_{A434}$ | S |
| $L_{A633}$ | $R_{B8}$ | $R_{B10}$ | $R_{B1}$ | S |
| $L_{A634}$ | $R_{B8}$ | $R_{B10}$ | $R_{B3}$ | S |
| $L_{A635}$ | $R_{B8}$ | $R_{B10}$ | $R_{B4}$ | S |
| $L_{A636}$ | $R_{B8}$ | $R_{B10}$ | $R_{B7}$ | S |
| $L_{A637}$ | $R_{B8}$ | $R_{B10}$ | $R_{A3}$ | S |
| $L_{A638}$ | $R_{B8}$ | $R_{B10}$ | $R_{A434}$ | S |
| $L_{A639}$ | $R_{B8}$ | $R_{A3}$ | $R_{B1}$ | S |
| $L_{A640}$ | $R_{B8}$ | $R_{A3}$ | $R_{B3}$ | S |
| $L_{A641}$ | $R_{B8}$ | $R_{A3}$ | $R_{B4}$ | S |
| $L_{A642}$ | $R_{B8}$ | $R_{A3}$ | $R_{B7}$ | S |
| $L_{A643}$ | $R_{B8}$ | $R_{A3}$ | $R_{B10}$ | S |
| $L_{A644}$ | $R_{B8}$ | $R_{A3}$ | $R_{A434}$ | S |
| $L_{A645}$ | $R_{B8}$ | $R_{A434}$ | $R_{B1}$ | S |
| $L_{A646}$ | $R_{B8}$ | $R_{A434}$ | $R_{B3}$ | S |
| $L_{A647}$ | $R_{B8}$ | $R_{A434}$ | $R_{B4}$ | S |
| $L_{A648}$ | $R_{B8}$ | $R_{A434}$ | $R_{B7}$ | S |
| $L_{A649}$ | $R_{B8}$ | $R_{A434}$ | $R_{B10}$ | S |
| $L_{A650}$ | $R_{B8}$ | $R_{A434}$ | $R_{A3}$ | S |
| $L_{A651}$ | $R_{B6}$ | H | H | O |
| $L_{A652}$ | $R_{B6}$ | $R_{B1}$ | H | O |
| $L_{A653}$ | $R_{B6}$ | $R_{B3}$ | H | O |
| $L_{A654}$ | $R_{B6}$ | $R_{B4}$ | H | O |
| $L_{A655}$ | $R_{B6}$ | $R_{B7}$ | H | O |
| $L_{A656}$ | $R_{B6}$ | $R_{B10}$ | H | O |
| $L_{A657}$ | $R_{B6}$ | $R_{A3}$ | H | O |
| $L_{A658}$ | $R_{B6}$ | $R_{A434}$ | H | O |
| $L_{A659}$ | $R_{B6}$ | H | $R_{B1}$ | O |
| $L_{A660}$ | $R_{B6}$ | H | $R_{B2}$ | O |
| $L_{A661}$ | $R_{B6}$ | H | $R_{B3}$ | O |
| $L_{A662}$ | $R_{B6}$ | H | $R_{B4}$ | O |
| $L_{A663}$ | $R_{B6}$ | H | $R_{B7}$ | O |
| $L_{A664}$ | $R_{B6}$ | H | $R_{B10}$ | O |
| $L_{A665}$ | $R_{B6}$ | H | $R_{A3}$ | O |
| $L_{A666}$ | $R_{B6}$ | H | $R_{A434}$ | O |
| $L_{A667}$ | $R_{B6}$ | $R_{B1}$ | $R_{B1}$ | O |
| $L_{A668}$ | $R_{B6}$ | $R_{B3}$ | $R_{B3}$ | O |
| $L_{A669}$ | $R_{B6}$ | $R_{B4}$ | $R_{B4}$ | O |
| $L_{A670}$ | $R_{B6}$ | $R_{B7}$ | $R_{B7}$ | O |
| $L_{A671}$ | $R_{B6}$ | $R_{B10}$ | $R_{B10}$ | O |
| $L_{A672}$ | $R_{B6}$ | $R_{A3}$ | $R_{A3}$ | O |
| $L_{A673}$ | $R_{B6}$ | $R_{A434}$ | $R_{A434}$ | O |
| $L_{A674}$ | $R_{B6}$ | $R_{B1}$ | $R_{B3}$ | O |
| $L_{A675}$ | $R_{B6}$ | $R_{B1}$ | $R_{B4}$ | O |
| $L_{A676}$ | $R_{B6}$ | $R_{B1}$ | $R_{B7}$ | O |
| $L_{A677}$ | $R_{B6}$ | $R_{B1}$ | $R_{B10}$ | O |
| $L_{A678}$ | $R_{B6}$ | $R_{B1}$ | $R_{A3}$ | O |
| $L_{A679}$ | $R_{B6}$ | $R_{B1}$ | $R_{A434}$ | O |
| $L_{A680}$ | $R_{B6}$ | $R_{B3}$ | $R_{B1}$ | O |
| $L_{A681}$ | $R_{B6}$ | $R_{B3}$ | $R_{B4}$ | O |
| $L_{A682}$ | $R_{B6}$ | $R_{B3}$ | $R_{B7}$ | O |
| $L_{A683}$ | $R_{B6}$ | $R_{B3}$ | $R_{B10}$ | O |
| $L_{A684}$ | $R_{B6}$ | $R_{B3}$ | $R_{A3}$ | O |
| $L_{A685}$ | $R_{B6}$ | $R_{B3}$ | $R_{A434}$ | O |
| $L_{A686}$ | $R_{B6}$ | $R_{B4}$ | $R_{B1}$ | O |
| $L_{A687}$ | $R_{B6}$ | $R_{B4}$ | $R_{B3}$ | O |
| $L_{A688}$ | $R_{B6}$ | $R_{B4}$ | $R_{B7}$ | O |
| $L_{A689}$ | $R_{B6}$ | $R_{B4}$ | $R_{B10}$ | O |
| $L_{A690}$ | $R_{B6}$ | $R_{B4}$ | $R_{A3}$ | O |
| $L_{A691}$ | $R_{B6}$ | $R_{B4}$ | $R_{A434}$ | O |
| $L_{A692}$ | $R_{B6}$ | $R_{B7}$ | $R_{B1}$ | O |
| $L_{A693}$ | $R_{B6}$ | $R_{B7}$ | $R_{B3}$ | O |
| $L_{A694}$ | $R_{B6}$ | $R_{B7}$ | $R_{B4}$ | O |
| $L_{A695}$ | $R_{B6}$ | $R_{B7}$ | $R_{B10}$ | O |
| $L_{A696}$ | $R_{B6}$ | $R_{B7}$ | $R_{A3}$ | O |
| $L_{A697}$ | $R_{B6}$ | $R_{B7}$ | $R_{A434}$ | O |
| $L_{A698}$ | $R_{B6}$ | $R_{B10}$ | $R_{B1}$ | O |
| $L_{A699}$ | $R_{B6}$ | $R_{B10}$ | $R_{B3}$ | O |
| $L_{A700}$ | $R_{B6}$ | $R_{B10}$ | $R_{B4}$ | O |
| $L_{A701}$ | $R_{B6}$ | $R_{B10}$ | $R_{B7}$ | O |
| $L_{A702}$ | $R_{B6}$ | $R_{B10}$ | $R_{A3}$ | O |
| $L_{A703}$ | $R_{B6}$ | $R_{B10}$ | $R_{A434}$ | O |
| $L_{A704}$ | $R_{B6}$ | $R_{A3}$ | $R_{B1}$ | O |
| $L_{A705}$ | $R_{B6}$ | $R_{A3}$ | $R_{B3}$ | O |
| $L_{A706}$ | $R_{B6}$ | $R_{A3}$ | $R_{B4}$ | O |
| $L_{A707}$ | $R_{B6}$ | $R_{A3}$ | $R_{B7}$ | O |
| $L_{A708}$ | $R_{B6}$ | $R_{A3}$ | $R_{B10}$ | O |
| $L_{A709}$ | $R_{B6}$ | $R_{A3}$ | $R_{A434}$ | O |
| $L_{A710}$ | $R_{B6}$ | $R_{A434}$ | $R_{B1}$ | O |
| $L_{A711}$ | $R_{B6}$ | $R_{A434}$ | $R_{B3}$ | O |
| $L_{A712}$ | $R_{B6}$ | $R_{A434}$ | $R_{B4}$ | O |
| $L_{A713}$ | $R_{B6}$ | $R_{A434}$ | $R_{B7}$ | O |
| $L_{A714}$ | $R_{B6}$ | $R_{A434}$ | $R_{B10}$ | O |
| $L_{A715}$ | $R_{B6}$ | $R_{A434}$ | $R_{A3}$ | O |
| $L_{A716}$ | $R_{B8}$ | H | H | O |
| $L_{A717}$ | $R_{B8}$ | $R_{B1}$ | H | O |
| $L_{A718}$ | $R_{B8}$ | $R_{B3}$ | H | O |
| $L_{A719}$ | $R_{B8}$ | $R_{B4}$ | H | O |
| $L_{A720}$ | $R_{B8}$ | $R_{B7}$ | H | O |
| $L_{A721}$ | $R_{B8}$ | $R_{B10}$ | H | O |
| $L_{A722}$ | $R_{B8}$ | $R_{A3}$ | H | O |
| $L_{A723}$ | $R_{B8}$ | $R_{A434}$ | H | O |
| $L_{A724}$ | $R_{B8}$ | H | $R_{B1}$ | O |
| $L_{A725}$ | $R_{B8}$ | H | $R_{B2}$ | O |
| $L_{A726}$ | $R_{B8}$ | H | $R_{B3}$ | O |
| $L_{A727}$ | $R_{B8}$ | H | $R_{B4}$ | O |
| $L_{A728}$ | $R_{B8}$ | H | $R_{B7}$ | O |
| $L_{A729}$ | $R_{B8}$ | H | $R_{B10}$ | O |
| $L_{A730}$ | $R_{B8}$ | H | $R_{A3}$ | O |
| $L_{A731}$ | $R_{B8}$ | H | $R_{A434}$ | O |
| $L_{A732}$ | $R_{B8}$ | $R_{B1}$ | $R_{B1}$ | O |

-continued

| Ligand | R¹ | R¹¹ | R¹² | X |
|---|---|---|---|---|
| $L_{A733}$ | $R_{B8}$ | $R_{B3}$ | $R_{B3}$ | O |
| $L_{A734}$ | $R_{B8}$ | $R_{B4}$ | $R_{B4}$ | O |
| $L_{A735}$ | $R_{B8}$ | $R_{B7}$ | $R_{B7}$ | O |
| $L_{A736}$ | $R_{B8}$ | $R_{B10}$ | $R_{B10}$ | O |
| $L_{A737}$ | $R_{B8}$ | $R_{A3}$ | $R_{A3}$ | O |
| $L_{A738}$ | $R_{B8}$ | $R_{A34}$ | $R_{A34}$ | O |
| $L_{A739}$ | $R_{B8}$ | $R_{B1}$ | $R_{B3}$ | O |
| $L_{A740}$ | $R_{B8}$ | $R_{B1}$ | $R_{B4}$ | O |
| $L_{A741}$ | $R_{B8}$ | $R_{B1}$ | $R_{B7}$ | O |
| $L_{A742}$ | $R_{B8}$ | $R_{B1}$ | $R_{B10}$ | O |
| $L_{A743}$ | $R_{B8}$ | $R_{B1}$ | $R_{A3}$ | O |
| $L_{A744}$ | $R_{B8}$ | $R_{B1}$ | $R_{A34}$ | O |
| $L_{A745}$ | $R_{B8}$ | $R_{B3}$ | $R_{B1}$ | O |
| $L_{A746}$ | $R_{B8}$ | $R_{B3}$ | $R_{B4}$ | O |
| $L_{A747}$ | $R_{B8}$ | $R_{B3}$ | $R_{B7}$ | O |
| $L_{A748}$ | $R_{B8}$ | $R_{B3}$ | $R_{B10}$ | O |
| $L_{A749}$ | $R_{B8}$ | $R_{B3}$ | $R_{A3}$ | O |
| $L_{A750}$ | $R_{B8}$ | $R_{B3}$ | $R_{A34}$ | O |
| $L_{A751}$ | $R_{B8}$ | $R_{B4}$ | $R_{B1}$ | O |
| $L_{A752}$ | $R_{B8}$ | $R_{B4}$ | $R_{B3}$ | O |
| $L_{A753}$ | $R_{B8}$ | $R_{B4}$ | $R_{B7}$ | O |
| $L_{A754}$ | $R_{B8}$ | $R_{B4}$ | $R_{B10}$ | O |
| $L_{A755}$ | $R_{B8}$ | $R_{B4}$ | $R_{A3}$ | O |
| $L_{A756}$ | $R_{B8}$ | $R_{B4}$ | $R_{A34}$ | O |
| $L_{A757}$ | $R_{B8}$ | $R_{B7}$ | $R_{B1}$ | O |
| $L_{A758}$ | $R_{B8}$ | $R_{B7}$ | $R_{B3}$ | O |
| $L_{A759}$ | $R_{B8}$ | $R_{B7}$ | $R_{B4}$ | O |
| $L_{A760}$ | $R_{B8}$ | $R_{B7}$ | $R_{B10}$ | O |
| $L_{A761}$ | $R_{B8}$ | $R_{B7}$ | $R_{A3}$ | O |
| $L_{A762}$ | $R_{B8}$ | $R_{B7}$ | $R_{A34}$ | O |
| $L_{A763}$ | $R_{B8}$ | $R_{B10}$ | $R_{B1}$ | O |
| $L_{A764}$ | $R_{B8}$ | $R_{B10}$ | $R_{B3}$ | O |
| $L_{A765}$ | $R_{B8}$ | $R_{B10}$ | $R_{B4}$ | O |
| $L_{A766}$ | $R_{B8}$ | $R_{B10}$ | $R_{B7}$ | O |
| $L_{A767}$ | $R_{B8}$ | $R_{B10}$ | $R_{A3}$ | O |
| $L_{A768}$ | $R_{B8}$ | $R_{B10}$ | $R_{A34}$ | O |
| $L_{A769}$ | $R_{B8}$ | $R_{A3}$ | $R_{B1}$ | O |
| $L_{A770}$ | $R_{B8}$ | $R_{A3}$ | $R_{B3}$ | O |
| $L_{A771}$ | $R_{B8}$ | $R_{A3}$ | $R_{B4}$ | O |
| $L_{A772}$ | $R_{B8}$ | $R_{A3}$ | $R_{B7}$ | O |
| $L_{A773}$ | $R_{B8}$ | $R_{A3}$ | $R_{B10}$ | O |
| $L_{A774}$ | $R_{B8}$ | $R_{A3}$ | $R_{A34}$ | O |
| $L_{A775}$ | $R_{B8}$ | $R_{A34}$ | $R_{B1}$ | O |
| $L_{A776}$ | $R_{B8}$ | $R_{A34}$ | $R_{B3}$ | O |
| $L_{A777}$ | $R_{B8}$ | $R_{A34}$ | $R_{B4}$ | O |
| $L_{A778}$ | $R_{B8}$ | $R_{A34}$ | $R_{B7}$ | O |
| $L_{A779}$ | $R_{B8}$ | $R_{A34}$ | $R_{B10}$ | O |
| $L_{A780}$ | $R_{B8}$ | $R_{A34}$ | $R_{A3}$ | O, |

$L_{A781}$ through $L_{A1170}$ that are based on a structure of Formula IV,

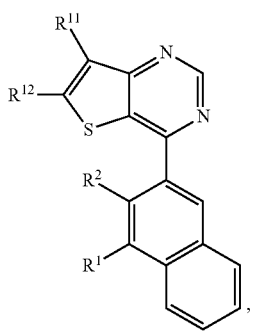

in which $R^1$, $R^2$, $R^{11}$, and $R^{12}$ are defined as provided below:

| Ligand | R¹ | R² | R¹¹ | R¹² |
|---|---|---|---|---|
| $L_{A781}$ | H | F | H | H |
| $L_{A782}$ | H | F | $R_{B1}$ | H |
| $L_{A783}$ | H | F | $R_{B3}$ | H |
| $L_{A784}$ | H | F | $R_{B4}$ | H |
| $L_{A785}$ | H | F | $R_{B7}$ | H |
| $L_{A786}$ | H | F | $R_{B10}$ | H |
| $L_{A787}$ | H | F | $R_{A3}$ | H |
| $L_{A788}$ | H | F | $R_{A34}$ | H |
| $L_{A789}$ | H | F | H | $R_{B1}$ |
| $L_{A790}$ | H | F | H | $R_{B2}$ |
| $L_{A791}$ | H | F | H | $R_{B3}$ |
| $L_{A792}$ | H | F | H | $R_{B4}$ |
| $L_{A793}$ | H | F | H | $R_{B7}$ |
| $L_{A794}$ | H | F | H | $R_{B10}$ |
| $L_{A795}$ | H | F | H | $R_{A3}$ |
| $L_{A796}$ | H | F | H | $R_{A34}$ |
| $L_{A797}$ | H | F | $R_{B1}$ | $R_{B1}$ |
| $L_{A798}$ | H | F | $R_{B3}$ | $R_{B3}$ |
| $L_{A799}$ | H | F | $R_{B4}$ | $R_{B4}$ |
| $L_{A800}$ | H | F | $R_{B7}$ | $R_{B7}$ |
| $L_{A801}$ | H | F | $R_{B10}$ | $R_{B10}$ |
| $L_{A802}$ | H | F | $R_{A3}$ | $R_{A3}$ |
| $L_{A803}$ | H | F | $R_{A34}$ | $R_{A34}$ |
| $L_{A804}$ | H | F | $R_{B1}$ | $R_{B3}$ |
| $L_{A805}$ | H | F | $R_{B1}$ | $R_{B4}$ |
| $L_{A806}$ | H | F | $R_{B1}$ | $R_{B7}$ |
| $L_{A807}$ | H | F | $R_{B1}$ | $R_{B10}$ |
| $L_{A808}$ | H | F | $R_{B1}$ | $R_{A3}$ |
| $L_{A809}$ | H | F | $R_{B1}$ | $R_{A34}$ |
| $L_{A810}$ | H | F | $R_{B3}$ | $R_{B1}$ |
| $L_{A811}$ | H | F | $R_{B3}$ | $R_{B4}$ |
| $L_{A812}$ | H | F | $R_{B3}$ | $R_{B7}$ |
| $L_{A813}$ | H | F | $R_{B3}$ | $R_{B10}$ |
| $L_{A814}$ | H | F | $R_{B3}$ | $R_{A3}$ |
| $L_{A815}$ | H | F | $R_{B3}$ | $R_{A34}$ |
| $L_{A816}$ | H | F | $R_{B4}$ | $R_{B1}$ |
| $L_{A817}$ | H | F | $R_{B4}$ | $R_{B3}$ |
| $L_{A818}$ | H | F | $R_{B4}$ | $R_{B7}$ |
| $L_{A819}$ | H | F | $R_{B4}$ | $R_{B10}$ |
| $L_{A820}$ | H | F | $R_{B4}$ | $R_{A3}$ |
| $L_{A821}$ | H | F | $R_{B4}$ | $R_{A34}$ |
| $L_{A822}$ | H | F | $R_{B7}$ | $R_{B1}$ |
| $L_{A823}$ | H | F | $R_{B7}$ | $R_{B3}$ |
| $L_{A824}$ | H | F | $R_{B7}$ | $R_{B4}$ |
| $L_{A825}$ | H | F | $R_{B7}$ | $R_{B10}$ |
| $L_{A826}$ | H | F | $R_{B7}$ | $R_{A3}$ |
| $L_{A827}$ | H | F | $R_{B7}$ | $R_{A34}$ |
| $L_{A828}$ | H | F | $R_{B10}$ | $R_{B1}$ |
| $L_{A829}$ | H | F | $R_{B10}$ | $R_{B3}$ |
| $L_{A830}$ | H | F | $R_{B10}$ | $R_{B4}$ |
| $L_{A831}$ | H | F | $R_{B10}$ | $R_{B7}$ |
| $L_{A832}$ | H | F | $R_{B10}$ | $R_{A3}$ |
| $L_{A833}$ | H | F | $R_{B10}$ | $R_{A34}$ |
| $L_{A834}$ | H | F | $R_{A3}$ | $R_{B1}$ |
| $L_{A835}$ | H | F | $R_{A3}$ | $R_{B3}$ |
| $L_{A836}$ | H | F | $R_{A3}$ | $R_{B4}$ |
| $L_{A837}$ | H | F | $R_{A3}$ | $R_{B7}$ |
| $L_{A838}$ | H | F | $R_{A3}$ | $R_{B10}$ |
| $L_{A839}$ | H | F | $R_{A3}$ | $R_{A34}$ |
| $L_{A840}$ | H | F | $R_{A34}$ | $R_{B1}$ |
| $L_{A841}$ | H | F | $R_{A34}$ | $R_{B3}$ |
| $L_{A842}$ | H | F | $R_{A34}$ | $R_{B4}$ |
| $L_{A843}$ | H | F | $R_{A34}$ | $R_{B7}$ |
| $L_{A844}$ | H | F | $R_{A34}$ | $R_{B10}$ |
| $L_{A845}$ | H | F | $R_{A34}$ | $R_{A3}$ |
| $L_{A846}$ | H | $R_{B1}$ | H | H |
| $L_{A847}$ | H | $R_{B1}$ | $R_{B1}$ | H |
| $L_{A848}$ | H | $R_{B1}$ | $R_{B3}$ | H |
| $L_{A849}$ | H | $R_{B1}$ | $R_{B4}$ | H |
| $L_{A850}$ | H | $R_{B1}$ | $R_{B7}$ | H |
| $L_{A851}$ | H | $R_{B1}$ | $R_{B10}$ | H |
| $L_{A852}$ | H | $R_{B1}$ | $R_{A3}$ | H |
| $L_{A853}$ | H | $R_{B1}$ | $R_{A34}$ | H |
| $L_{A854}$ | H | $R_{B1}$ | H | $R_{B1}$ |
| $L_{A855}$ | H | $R_{B1}$ | H | $R_{B2}$ |
| $L_{A856}$ | H | $R_{B1}$ | H | $R_{B3}$ |

| Ligand | R¹ | R² | R¹¹ | R¹² |
|---|---|---|---|---|
| $L_{A857}$ | H | $R_{B1}$ | H | $R_{B4}$ |
| $L_{A858}$ | H | $R_{B1}$ | H | $R_{B7}$ |
| $L_{A859}$ | H | $R_{B1}$ | H | $R_{B10}$ |
| $L_{A860}$ | H | $R_{B1}$ | H | $R_{A3}$ |
| $L_{A861}$ | H | $R_{B1}$ | H | $R_{A34}$ |
| $L_{A862}$ | H | $R_{B1}$ | $R_{B1}$ | $R_{B1}$ |
| $L_{A863}$ | H | $R_{B1}$ | $R_{B3}$ | $R_{B3}$ |
| $L_{A864}$ | H | $R_{B1}$ | $R_{B4}$ | $R_{B4}$ |
| $L_{A865}$ | H | $R_{B1}$ | $R_{B7}$ | $R_{B7}$ |
| $L_{A866}$ | H | $R_{B1}$ | $R_{B10}$ | $R_{B10}$ |
| $L_{A867}$ | H | $R_{B1}$ | $R_{A3}$ | $R_{A3}$ |
| $L_{A868}$ | H | $R_{B1}$ | $R_{A34}$ | $R_{A34}$ |
| $L_{A869}$ | H | $R_{B1}$ | $R_{B1}$ | $R_{B3}$ |
| $L_{A870}$ | H | $R_{B1}$ | $R_{B1}$ | $R_{B4}$ |
| $L_{A871}$ | H | $R_{B1}$ | $R_{B1}$ | $R_{B7}$ |
| $L_{A872}$ | H | $R_{B1}$ | $R_{B1}$ | $R_{B10}$ |
| $L_{A873}$ | H | $R_{B1}$ | $R_{B1}$ | $R_{A3}$ |
| $L_{A874}$ | H | $R_{B1}$ | $R_{B1}$ | $R_{A34}$ |
| $L_{A875}$ | H | $R_{B1}$ | $R_{B3}$ | $R_{B1}$ |
| $L_{A876}$ | H | $R_{B1}$ | $R_{B3}$ | $R_{B4}$ |
| $L_{A877}$ | H | $R_{B1}$ | $R_{B3}$ | $R_{B7}$ |
| $L_{A878}$ | H | $R_{B1}$ | $R_{B3}$ | $R_{B10}$ |
| $L_{A879}$ | H | $R_{B1}$ | $R_{B3}$ | $R_{A3}$ |
| $L_{A880}$ | H | $R_{B1}$ | $R_{B3}$ | $R_{A34}$ |
| $L_{A881}$ | H | $R_{B1}$ | $R_{B4}$ | $R_{B1}$ |
| $L_{A882}$ | H | $R_{B1}$ | $R_{B4}$ | $R_{B3}$ |
| $L_{A883}$ | H | $R_{B1}$ | $R_{B4}$ | $R_{B7}$ |
| $L_{A884}$ | H | $R_{B1}$ | $R_{B4}$ | $R_{B10}$ |
| $L_{A885}$ | H | $R_{B1}$ | $R_{B4}$ | $R_{A3}$ |
| $L_{A886}$ | H | $R_{B1}$ | $R_{B4}$ | $R_{A34}$ |
| $L_{A887}$ | H | $R_{B1}$ | $R_{B7}$ | $R_{B1}$ |
| $L_{A888}$ | H | $R_{B1}$ | $R_{B7}$ | $R_{B3}$ |
| $L_{A889}$ | H | $R_{B1}$ | $R_{B7}$ | $R_{B4}$ |
| $L_{A890}$ | H | $R_{B1}$ | $R_{B7}$ | $R_{B10}$ |
| $L_{A891}$ | H | $R_{B1}$ | $R_{B7}$ | $R_{A3}$ |
| $L_{A892}$ | H | $R_{B1}$ | $R_{B7}$ | $R_{A34}$ |
| $L_{A893}$ | H | $R_{B1}$ | $R_{B10}$ | $R_{B1}$ |
| $L_{A894}$ | H | $R_{B1}$ | $R_{B10}$ | $R_{B3}$ |
| $L_{A895}$ | H | $R_{B1}$ | $R_{B10}$ | $R_{B4}$ |
| $L_{A896}$ | H | $R_{B1}$ | $R_{B10}$ | $R_{B7}$ |
| $L_{A897}$ | H | $R_{B1}$ | $R_{B10}$ | $R_{A3}$ |
| $L_{A898}$ | H | $R_{B1}$ | $R_{B10}$ | $R_{A34}$ |
| $L_{A899}$ | H | $R_{B1}$ | $R_{A3}$ | $R_{B1}$ |
| $L_{A900}$ | H | $R_{B1}$ | $R_{A3}$ | $R_{B3}$ |
| $L_{A901}$ | H | $R_{B1}$ | $R_{A3}$ | $R_{B4}$ |
| $L_{A902}$ | H | $R_{B1}$ | $R_{A3}$ | $R_{B7}$ |
| $L_{A903}$ | H | $R_{B1}$ | $R_{A3}$ | $R_{B10}$ |
| $L_{A904}$ | H | $R_{B1}$ | $R_{A3}$ | $R_{A34}$ |
| $L_{A905}$ | H | $R_{B1}$ | $R_{A34}$ | $R_{B1}$ |
| $L_{A906}$ | H | $R_{B1}$ | $R_{A34}$ | $R_{B3}$ |
| $L_{A907}$ | H | $R_{B1}$ | $R_{A34}$ | $R_{B4}$ |
| $L_{A908}$ | H | $R_{B1}$ | $R_{A34}$ | $R_{B7}$ |
| $L_{A909}$ | H | $R_{B1}$ | $R_{A34}$ | $R_{B10}$ |
| $L_{A910}$ | H | $R_{B1}$ | $R_{A34}$ | $R_{A3}$ |
| $L_{A911}$ | $R_{B1}$ | F | H | H |
| $L_{A912}$ | $R_{B1}$ | F | $R_{B1}$ | H |
| $L_{A913}$ | $R_{B1}$ | F | $R_{B3}$ | H |
| $L_{A914}$ | $R_{B1}$ | F | $R_{B4}$ | H |
| $L_{A915}$ | $R_{B1}$ | F | $R_{B7}$ | H |
| $L_{A916}$ | $R_{B1}$ | F | $R_{B10}$ | H |
| $L_{A917}$ | $R_{B1}$ | F | $R_{A3}$ | H |
| $L_{A918}$ | $R_{B1}$ | F | $R_{A34}$ | H |
| $L_{A919}$ | $R_{B1}$ | F | H | $R_{B1}$ |
| $L_{A920}$ | $R_{B1}$ | F | H | $R_{B2}$ |
| $L_{A921}$ | $R_{B1}$ | F | H | $R_{B3}$ |
| $L_{A922}$ | $R_{B1}$ | F | H | $R_{B4}$ |
| $L_{A923}$ | $R_{B1}$ | F | H | $R_{B7}$ |
| $L_{A924}$ | $R_{B1}$ | F | H | $R_{B10}$ |
| $L_{A925}$ | $R_{B1}$ | F | H | $R_{A3}$ |
| $L_{A926}$ | $R_{B1}$ | F | H | $R_{A34}$ |
| $L_{A927}$ | $R_{B1}$ | F | $R_{B1}$ | $R_{B1}$ |
| $L_{A928}$ | $R_{B1}$ | F | $R_{B3}$ | $R_{B3}$ |
| $L_{A929}$ | $R_{B1}$ | F | $R_{B4}$ | $R_{B4}$ |
| $L_{A930}$ | $R_{B1}$ | F | $R_{B7}$ | $R_{B7}$ |
| $L_{A931}$ | $R_{B1}$ | F | $R_{B10}$ | $R_{B10}$ |
| $L_{A932}$ | $R_{B1}$ | F | $R_{A3}$ | $R_{A3}$ |
| $L_{A933}$ | $R_{B1}$ | F | $R_{A34}$ | $R_{A34}$ |
| $L_{A934}$ | $R_{B1}$ | F | $R_{B1}$ | $R_{B3}$ |
| $L_{A935}$ | $R_{B1}$ | F | $R_{B1}$ | $R_{B4}$ |
| $L_{A936}$ | $R_{B1}$ | F | $R_{B1}$ | $R_{B7}$ |
| $L_{A937}$ | $R_{B1}$ | F | $R_{B1}$ | $R_{B10}$ |
| $L_{A938}$ | $R_{B1}$ | F | $R_{B1}$ | $R_{A3}$ |
| $L_{A939}$ | $R_{B1}$ | F | $R_{B1}$ | $R_{A34}$ |
| $L_{A940}$ | $R_{B1}$ | F | $R_{B3}$ | $R_{B1}$ |
| $L_{A941}$ | $R_{B1}$ | F | $R_{B3}$ | $R_{B4}$ |
| $L_{A942}$ | $R_{B1}$ | F | $R_{B3}$ | $R_{B7}$ |
| $L_{A943}$ | $R_{B1}$ | F | $R_{B3}$ | $R_{B10}$ |
| $L_{A944}$ | $R_{B1}$ | F | $R_{B3}$ | $R_{A3}$ |
| $L_{A945}$ | $R_{B1}$ | F | $R_{B3}$ | $R_{A34}$ |
| $L_{A946}$ | $R_{B1}$ | F | $R_{B4}$ | $R_{B1}$ |
| $L_{A947}$ | $R_{B1}$ | F | $R_{B4}$ | $R_{B3}$ |
| $L_{A948}$ | $R_{B1}$ | F | $R_{B4}$ | $R_{B7}$ |
| $L_{A949}$ | $R_{B1}$ | F | $R_{B4}$ | $R_{B10}$ |
| $L_{A950}$ | $R_{B1}$ | F | $R_{B4}$ | $R_{A3}$ |
| $L_{A951}$ | $R_{B1}$ | F | $R_{B4}$ | $R_{A34}$ |
| $L_{A952}$ | $R_{B1}$ | F | $R_{B7}$ | $R_{B1}$ |
| $L_{A953}$ | $R_{B1}$ | F | $R_{B7}$ | $R_{B3}$ |
| $L_{A954}$ | $R_{B1}$ | F | $R_{B7}$ | $R_{B4}$ |
| $L_{A955}$ | $R_{B1}$ | F | $R_{B7}$ | $R_{B10}$ |
| $L_{A956}$ | $R_{B1}$ | F | $R_{B7}$ | $R_{A3}$ |
| $L_{A957}$ | $R_{B1}$ | F | $R_{B7}$ | $R_{A34}$ |
| $L_{A958}$ | $R_{B1}$ | F | $R_{B10}$ | $R_{B1}$ |
| $L_{A959}$ | $R_{B1}$ | F | $R_{B10}$ | $R_{B3}$ |
| $L_{A960}$ | $R_{B1}$ | F | $R_{B10}$ | $R_{B4}$ |
| $L_{A961}$ | $R_{B1}$ | F | $R_{B10}$ | $R_{B7}$ |
| $L_{A962}$ | $R_{B1}$ | F | $R_{B10}$ | $R_{A3}$ |
| $L_{A963}$ | $R_{B1}$ | F | $R_{B10}$ | $R_{A34}$ |
| $L_{A964}$ | $R_{B1}$ | F | $R_{A3}$ | $R_{B1}$ |
| $L_{A965}$ | $R_{B1}$ | F | $R_{A3}$ | $R_{B3}$ |
| $L_{A966}$ | $R_{B1}$ | F | $R_{A3}$ | $R_{B4}$ |
| $L_{A967}$ | $R_{B1}$ | F | $R_{A3}$ | $R_{B7}$ |
| $L_{A968}$ | $R_{B1}$ | F | $R_{A3}$ | $R_{B10}$ |
| $L_{A969}$ | $R_{B1}$ | F | $R_{A3}$ | $R_{A34}$ |
| $L_{A970}$ | $R_{B1}$ | F | $R_{A34}$ | $R_{B1}$ |
| $L_{A971}$ | $R_{B1}$ | F | $R_{A34}$ | $R_{B3}$ |
| $L_{A972}$ | $R_{B1}$ | F | $R_{A34}$ | $R_{B4}$ |
| $L_{A973}$ | $R_{B1}$ | F | $R_{A34}$ | $R_{B7}$ |
| $L_{A974}$ | $R_{B1}$ | F | $R_{A34}$ | $R_{B10}$ |
| $L_{A975}$ | $R_{B1}$ | F | $R_{A34}$ | $R_{A3}$ |
| $L_{A976}$ | $R_{B6}$ | F | H | H |
| $L_{A977}$ | $R_{B6}$ | F | $R_{B1}$ | H |
| $L_{A978}$ | $R_{B6}$ | F | $R_{B3}$ | H |
| $L_{A979}$ | $R_{B6}$ | F | $R_{B4}$ | H |
| $L_{A980}$ | $R_{B6}$ | F | $R_{B7}$ | H |
| $L_{A981}$ | $R_{B6}$ | F | $R_{B10}$ | H |
| $L_{A982}$ | $R_{B6}$ | F | $R_{A3}$ | H |
| $L_{A983}$ | $R_{B6}$ | F | $R_{A34}$ | H |
| $L_{A984}$ | $R_{B6}$ | F | H | $R_{B1}$ |
| $L_{A985}$ | $R_{B6}$ | F | H | $R_{B2}$ |
| $L_{A986}$ | $R_{B6}$ | F | H | $R_{B3}$ |
| $L_{A987}$ | $R_{B6}$ | F | H | $R_{B4}$ |
| $L_{A988}$ | $R_{B6}$ | F | H | $R_{B7}$ |
| $L_{A989}$ | $R_{B6}$ | F | H | $R_{B10}$ |
| $L_{A990}$ | $R_{B6}$ | F | H | $R_{A3}$ |
| $L_{A991}$ | $R_{B6}$ | F | H | $R_{A34}$ |
| $L_{A992}$ | $R_{B6}$ | F | $R_{B1}$ | $R_{B1}$ |
| $L_{A993}$ | $R_{B6}$ | F | $R_{B3}$ | $R_{B3}$ |
| $L_{A994}$ | $R_{B6}$ | F | $R_{B4}$ | $R_{B4}$ |
| $L_{A995}$ | $R_{B6}$ | F | $R_{B7}$ | $R_{B7}$ |
| $L_{A996}$ | $R_{B6}$ | F | $R_{B10}$ | $R_{B10}$ |
| $L_{A997}$ | $R_{B6}$ | F | $R_{A3}$ | $R_{A3}$ |
| $L_{A998}$ | $R_{B6}$ | F | $R_{A34}$ | $R_{A34}$ |
| $L_{A999}$ | $R_{B6}$ | F | $R_{B1}$ | $R_{B3}$ |
| $L_{A1000}$ | $R_{B6}$ | F | $R_{B1}$ | $R_{B4}$ |
| $L_{A1001}$ | $R_{B6}$ | F | $R_{B1}$ | $R_{B7}$ |
| $L_{A1002}$ | $R_{B6}$ | F | $R_{B1}$ | $R_{B10}$ |
| $L_{A1003}$ | $R_{B6}$ | F | $R_{B1}$ | $R_{A3}$ |
| $L_{A1004}$ | $R_{B6}$ | F | $R_{B1}$ | $R_{A34}$ |
| $L_{A1005}$ | $R_{B6}$ | F | $R_{B3}$ | $R_{B1}$ |
| $L_{A1006}$ | $R_{B6}$ | F | $R_{B3}$ | $R_{B4}$ |
| $L_{A1007}$ | $R_{B6}$ | F | $R_{B3}$ | $R_{B7}$ |
| $L_{A1008}$ | $R_{B6}$ | F | $R_{B3}$ | $R_{B10}$ |
| $L_{A1009}$ | $R_{B6}$ | F | $R_{B3}$ | $R_{A3}$ |
| $L_{A1010}$ | $R_{B6}$ | F | $R_{B3}$ | $R_{A34}$ |

-continued

| Ligand | R$^1$ | R$^2$ | R$^{11}$ | R$^{12}$ |
|---|---|---|---|---|
| L$_{41011}$ | R$_{B6}$ | F | R$_{B4}$ | R$_{B1}$ |
| L$_{41012}$ | R$_{B6}$ | F | R$_{B4}$ | R$_{B3}$ |
| L$_{41013}$ | R$_{B6}$ | F | R$_{B4}$ | R$_{B7}$ |
| L$_{41014}$ | R$_{B6}$ | F | R$_{B4}$ | R$_{B10}$ |
| L$_{41015}$ | R$_{B6}$ | F | R$_{B4}$ | R$_{A3}$ |
| L$_{41016}$ | R$_{B6}$ | F | R$_{B4}$ | R$_{A34}$ |
| L$_{41017}$ | R$_{B6}$ | F | R$_{B7}$ | R$_{B1}$ |
| L$_{41018}$ | R$_{B6}$ | F | R$_{B7}$ | R$_{B3}$ |
| L$_{41019}$ | R$_{B6}$ | F | R$_{B7}$ | R$_{B4}$ |
| L$_{41020}$ | R$_{B6}$ | F | R$_{B7}$ | R$_{B10}$ |
| L$_{41021}$ | R$_{B6}$ | F | R$_{B7}$ | R$_{A3}$ |
| L$_{41022}$ | R$_{B6}$ | F | R$_{B7}$ | R$_{A34}$ |
| L$_{41023}$ | R$_{B6}$ | F | R$_{B10}$ | R$_{B1}$ |
| L$_{41024}$ | R$_{B6}$ | F | R$_{B10}$ | R$_{B3}$ |
| L$_{41025}$ | R$_{B6}$ | F | R$_{B10}$ | R$_{B4}$ |
| L$_{41026}$ | R$_{B6}$ | F | R$_{B10}$ | R$_{B7}$ |
| L$_{41027}$ | R$_{B6}$ | F | R$_{B10}$ | R$_{A3}$ |
| L$_{41028}$ | R$_{B6}$ | F | R$_{B10}$ | R$_{A34}$ |
| L$_{41029}$ | R$_{B6}$ | F | R$_{A3}$ | R$_{B1}$ |
| L$_{41030}$ | R$_{B6}$ | F | R$_{A3}$ | R$_{B3}$ |
| L$_{41031}$ | R$_{B6}$ | F | R$_{A3}$ | R$_{B4}$ |
| L$_{41032}$ | R$_{B6}$ | F | R$_{A3}$ | R$_{B7}$ |
| L$_{41033}$ | R$_{B6}$ | F | R$_{A3}$ | R$_{B10}$ |
| L$_{41034}$ | R$_{B6}$ | F | R$_{A3}$ | R$_{A34}$ |
| L$_{41035}$ | R$_{B6}$ | F | R$_{A34}$ | R$_{B1}$ |
| L$_{41036}$ | R$_{B6}$ | F | R$_{A34}$ | R$_{B3}$ |
| L$_{41037}$ | R$_{B6}$ | F | R$_{A34}$ | R$_{B4}$ |
| L$_{41038}$ | R$_{B6}$ | F | R$_{A34}$ | R$_{B7}$ |
| L$_{41039}$ | R$_{B6}$ | F | R$_{A34}$ | R$_{B10}$ |
| L$_{41040}$ | R$_{B6}$ | F | R$_{A34}$ | R$_{A3}$ |
| L$_{41041}$ | R$_{B1}$ | R$_{B1}$ | H | H |
| L$_{41042}$ | R$_{B1}$ | R$_{B1}$ | R$_{B1}$ | H |
| L$_{41043}$ | R$_{B1}$ | R$_{B1}$ | R$_{B3}$ | H |
| L$_{41044}$ | R$_{B1}$ | R$_{B1}$ | R$_{B4}$ | H |
| L$_{41045}$ | R$_{B1}$ | R$_{B1}$ | R$_{B7}$ | H |
| L$_{41046}$ | R$_{B1}$ | R$_{B1}$ | R$_{B10}$ | H |
| L$_{41047}$ | R$_{B1}$ | R$_{B1}$ | R$_{A3}$ | H |
| L$_{41048}$ | R$_{B1}$ | R$_{B1}$ | R$_{A34}$ | H |
| L$_{41049}$ | R$_{B1}$ | R$_{B1}$ | H | R$_{B1}$ |
| L$_{41050}$ | R$_{B1}$ | R$_{B1}$ | H | R$_{B2}$ |
| L$_{41051}$ | R$_{B1}$ | R$_{B1}$ | H | R$_{B3}$ |
| L$_{41052}$ | R$_{B1}$ | R$_{B1}$ | H | R$_{B4}$ |
| L$_{41053}$ | R$_{B1}$ | R$_{B1}$ | H | R$_{B7}$ |
| L$_{41054}$ | R$_{B1}$ | R$_{B1}$ | H | R$_{B10}$ |
| L$_{41055}$ | R$_{B1}$ | R$_{B1}$ | H | R$_{A3}$ |
| L$_{41056}$ | R$_{B1}$ | R$_{B1}$ | H | R$_{A34}$ |
| L$_{41057}$ | R$_{B1}$ | R$_{B1}$ | R$_{B1}$ | R$_{B1}$ |
| L$_{41058}$ | R$_{B1}$ | R$_{B1}$ | R$_{B3}$ | R$_{B3}$ |
| L$_{41059}$ | R$_{B1}$ | R$_{B1}$ | R$_{B4}$ | R$_{B4}$ |
| L$_{41060}$ | R$_{B1}$ | R$_{B1}$ | R$_{B7}$ | R$_{B7}$ |
| L$_{41061}$ | R$_{B1}$ | R$_{B1}$ | R$_{B10}$ | R$_{B10}$ |
| L$_{41062}$ | R$_{B1}$ | R$_{B1}$ | R$_{A3}$ | R$_{A3}$ |
| L$_{41063}$ | R$_{B1}$ | R$_{B1}$ | R$_{A34}$ | R$_{A34}$ |
| L$_{41064}$ | R$_{B1}$ | R$_{B1}$ | R$_{B1}$ | R$_{B3}$ |
| L$_{41065}$ | R$_{B1}$ | R$_{B1}$ | R$_{B1}$ | R$_{B4}$ |
| L$_{41066}$ | R$_{B1}$ | R$_{B1}$ | R$_{B1}$ | R$_{B7}$ |
| L$_{41067}$ | R$_{B1}$ | R$_{B1}$ | R$_{B1}$ | R$_{B10}$ |
| L$_{41068}$ | R$_{B1}$ | R$_{B1}$ | R$_{B1}$ | R$_{A3}$ |
| L$_{41069}$ | R$_{B1}$ | R$_{B1}$ | R$_{B1}$ | R$_{A34}$ |
| L$_{41070}$ | R$_{B1}$ | R$_{B1}$ | R$_{B3}$ | R$_{B1}$ |
| L$_{41071}$ | R$_{B1}$ | R$_{B1}$ | R$_{B3}$ | R$_{B4}$ |
| L$_{41072}$ | R$_{B1}$ | R$_{B1}$ | R$_{B3}$ | R$_{B7}$ |
| L$_{41073}$ | R$_{B1}$ | R$_{B1}$ | R$_{B3}$ | R$_{B10}$ |
| L$_{41074}$ | R$_{B1}$ | R$_{B1}$ | R$_{B3}$ | R$_{A3}$ |
| L$_{41075}$ | R$_{B1}$ | R$_{B1}$ | R$_{B3}$ | R$_{A34}$ |
| L$_{41076}$ | R$_{B1}$ | R$_{B1}$ | R$_{B4}$ | R$_{B1}$ |
| L$_{41077}$ | R$_{B1}$ | R$_{B1}$ | R$_{B4}$ | R$_{B3}$ |
| L$_{41078}$ | R$_{B1}$ | R$_{B1}$ | R$_{B4}$ | R$_{B7}$ |
| L$_{41079}$ | R$_{B1}$ | R$_{B1}$ | R$_{B4}$ | R$_{B10}$ |
| L$_{41080}$ | R$_{B1}$ | R$_{B1}$ | R$_{B4}$ | R$_{A3}$ |
| L$_{41081}$ | R$_{B1}$ | R$_{B1}$ | R$_{B4}$ | R$_{A34}$ |
| L$_{41082}$ | R$_{B1}$ | R$_{B1}$ | R$_{B7}$ | R$_{B1}$ |
| L$_{41083}$ | R$_{B1}$ | R$_{B1}$ | R$_{B7}$ | R$_{B3}$ |
| L$_{41084}$ | R$_{B1}$ | R$_{B1}$ | R$_{B7}$ | R$_{B4}$ |
| L$_{41085}$ | R$_{B1}$ | R$_{B1}$ | R$_{B7}$ | R$_{B10}$ |
| L$_{41086}$ | R$_{B1}$ | R$_{B1}$ | R$_{B7}$ | R$_{A3}$ |
| L$_{41087}$ | R$_{B1}$ | R$_{B1}$ | R$_{B7}$ | R$_{A34}$ |
| L$_{41088}$ | R$_{B1}$ | R$_{B1}$ | R$_{B10}$ | R$_{B1}$ |
| L$_{41089}$ | R$_{B1}$ | R$_{B1}$ | R$_{B10}$ | R$_{B3}$ |
| L$_{41090}$ | R$_{B1}$ | R$_{B1}$ | R$_{B10}$ | R$_{B4}$ |
| L$_{41091}$ | R$_{B1}$ | R$_{B1}$ | R$_{B10}$ | R$_{B7}$ |
| L$_{41092}$ | R$_{B1}$ | R$_{B1}$ | R$_{B10}$ | R$_{A3}$ |
| L$_{41093}$ | R$_{B1}$ | R$_{B1}$ | R$_{B10}$ | R$_{A34}$ |
| L$_{41094}$ | R$_{B1}$ | R$_{B1}$ | R$_{A3}$ | R$_{B1}$ |
| L$_{41095}$ | R$_{B1}$ | R$_{B1}$ | R$_{A3}$ | R$_{B3}$ |
| L$_{41096}$ | R$_{B1}$ | R$_{B1}$ | R$_{A3}$ | R$_{B4}$ |
| L$_{41097}$ | R$_{B1}$ | R$_{B1}$ | R$_{A3}$ | R$_{B7}$ |
| L$_{41098}$ | R$_{B1}$ | R$_{B1}$ | R$_{A3}$ | R$_{B10}$ |
| L$_{41099}$ | R$_{B1}$ | R$_{B1}$ | R$_{A3}$ | R$_{A34}$ |
| L$_{41100}$ | R$_{B1}$ | R$_{B1}$ | R$_{A34}$ | R$_{B1}$ |
| L$_{41101}$ | R$_{B1}$ | R$_{B1}$ | R$_{A34}$ | R$_{B3}$ |
| L$_{41102}$ | R$_{B1}$ | R$_{B1}$ | R$_{A34}$ | R$_{B4}$ |
| L$_{41103}$ | R$_{B1}$ | R$_{B1}$ | R$_{A34}$ | R$_{B7}$ |
| L$_{41104}$ | R$_{B1}$ | R$_{B1}$ | R$_{A34}$ | R$_{B10}$ |
| L$_{41105}$ | R$_{B1}$ | R$_{B1}$ | R$_{A34}$ | R$_{A3}$ |
| L$_{41106}$ | R$_{B6}$ | R$_{B1}$ | H | H |
| L$_{41107}$ | R$_{B6}$ | R$_{B1}$ | R$_{B1}$ | H |
| L$_{41108}$ | R$_{B6}$ | R$_{B1}$ | R$_{B3}$ | H |
| L$_{41109}$ | R$_{B6}$ | R$_{B1}$ | R$_{B4}$ | H |
| L$_{41110}$ | R$_{B6}$ | R$_{B1}$ | R$_{B7}$ | H |
| L$_{41111}$ | R$_{B6}$ | R$_{B1}$ | R$_{B10}$ | H |
| L$_{41112}$ | R$_{B6}$ | R$_{B1}$ | R$_{A3}$ | H |
| L$_{41113}$ | R$_{B6}$ | R$_{B1}$ | R$_{A34}$ | H |
| L$_{41114}$ | R$_{B6}$ | R$_{B1}$ | H | R$_{B1}$ |
| L$_{41115}$ | R$_{B6}$ | R$_{B1}$ | H | R$_{B2}$ |
| L$_{41116}$ | R$_{B6}$ | R$_{B1}$ | H | R$_{B3}$ |
| L$_{41117}$ | R$_{B6}$ | R$_{B1}$ | H | R$_{B4}$ |
| L$_{41118}$ | R$_{B6}$ | R$_{B1}$ | H | R$_{B7}$ |
| L$_{41119}$ | R$_{B6}$ | R$_{B1}$ | H | R$_{B10}$ |
| L$_{41120}$ | R$_{B6}$ | R$_{B1}$ | H | R$_{A3}$ |
| L$_{41121}$ | R$_{B6}$ | R$_{B1}$ | H | R$_{A34}$ |
| L$_{41122}$ | R$_{B6}$ | R$_{B1}$ | R$_{B1}$ | R$_{B1}$ |
| L$_{41123}$ | R$_{B6}$ | R$_{B1}$ | R$_{B3}$ | R$_{B3}$ |
| L$_{41124}$ | R$_{B6}$ | R$_{B1}$ | R$_{B4}$ | R$_{B4}$ |
| L$_{41125}$ | R$_{B6}$ | R$_{B1}$ | R$_{B7}$ | R$_{B7}$ |
| L$_{41126}$ | R$_{B6}$ | R$_{B1}$ | R$_{B10}$ | R$_{B10}$ |
| L$_{41127}$ | R$_{B6}$ | R$_{B1}$ | R$_{A3}$ | R$_{A3}$ |
| L$_{41128}$ | R$_{B6}$ | R$_{B1}$ | R$_{A34}$ | R$_{A34}$ |
| L$_{41129}$ | R$_{B6}$ | R$_{B1}$ | R$_{B1}$ | R$_{B3}$ |
| L$_{41130}$ | R$_{B6}$ | R$_{B1}$ | R$_{B1}$ | R$_{B4}$ |
| L$_{41131}$ | R$_{B6}$ | R$_{B1}$ | R$_{B1}$ | R$_{B7}$ |
| L$_{41132}$ | R$_{B6}$ | R$_{B1}$ | R$_{B1}$ | R$_{B10}$ |
| L$_{41133}$ | R$_{B6}$ | R$_{B1}$ | R$_{B1}$ | R$_{A3}$ |
| L$_{41134}$ | R$_{B6}$ | R$_{B1}$ | R$_{B1}$ | R$_{A34}$ |
| L$_{41135}$ | R$_{B6}$ | R$_{B1}$ | R$_{B3}$ | R$_{B1}$ |
| L$_{41136}$ | R$_{B6}$ | R$_{B1}$ | R$_{B3}$ | R$_{B4}$ |
| L$_{41137}$ | R$_{B6}$ | R$_{B1}$ | R$_{B3}$ | R$_{B7}$ |
| L$_{41138}$ | R$_{B6}$ | R$_{B1}$ | R$_{B3}$ | R$_{B10}$ |
| L$_{41139}$ | R$_{B6}$ | R$_{B1}$ | R$_{B3}$ | R$_{A3}$ |
| L$_{41140}$ | R$_{B6}$ | R$_{B1}$ | R$_{B3}$ | R$_{A34}$ |
| L$_{41141}$ | R$_{B6}$ | R$_{B1}$ | R$_{B4}$ | R$_{B1}$ |
| L$_{41142}$ | R$_{B6}$ | R$_{B1}$ | R$_{B4}$ | R$_{B3}$ |
| L$_{41143}$ | R$_{B6}$ | R$_{B1}$ | R$_{B4}$ | R$_{B7}$ |
| L$_{41144}$ | R$_{B6}$ | R$_{B1}$ | R$_{B4}$ | R$_{B10}$ |
| L$_{41145}$ | R$_{B6}$ | R$_{B1}$ | R$_{B4}$ | R$_{A3}$ |
| L$_{41146}$ | R$_{B6}$ | R$_{B1}$ | R$_{B4}$ | R$_{A34}$ |
| L$_{41147}$ | R$_{B6}$ | R$_{B1}$ | R$_{B7}$ | R$_{B1}$ |
| L$_{41148}$ | R$_{B6}$ | R$_{B1}$ | R$_{B7}$ | R$_{B3}$ |
| L$_{41149}$ | R$_{B6}$ | R$_{B1}$ | R$_{B7}$ | R$_{B4}$ |
| L$_{41150}$ | R$_{B6}$ | R$_{B1}$ | R$_{B7}$ | R$_{B10}$ |
| L$_{41151}$ | R$_{B6}$ | R$_{B1}$ | R$_{B7}$ | R$_{A3}$ |
| L$_{41152}$ | R$_{B6}$ | R$_{B1}$ | R$_{B7}$ | R$_{A34}$ |
| L$_{41153}$ | R$_{B6}$ | R$_{B1}$ | R$_{B10}$ | R$_{B1}$ |
| L$_{41154}$ | R$_{B6}$ | R$_{B1}$ | R$_{B10}$ | R$_{B3}$ |
| L$_{41155}$ | R$_{B6}$ | R$_{B1}$ | R$_{B10}$ | R$_{B4}$ |
| L$_{41156}$ | R$_{B6}$ | R$_{B1}$ | R$_{B10}$ | R$_{B7}$ |
| L$_{41157}$ | R$_{B6}$ | R$_{B1}$ | R$_{B10}$ | R$_{A3}$ |
| L$_{41158}$ | R$_{B6}$ | R$_{B1}$ | R$_{B10}$ | R$_{A34}$ |
| L$_{41159}$ | R$_{B6}$ | R$_{B1}$ | R$_{A3}$ | R$_{B1}$ |
| L$_{41160}$ | R$_{B6}$ | R$_{B1}$ | R$_{A3}$ | R$_{B3}$ |
| L$_{41161}$ | R$_{B6}$ | R$_{B1}$ | R$_{A3}$ | R$_{B4}$ |
| L$_{41162}$ | R$_{B6}$ | R$_{B1}$ | R$_{A3}$ | R$_{B7}$ |
| L$_{41163}$ | R$_{B6}$ | R$_{B1}$ | R$_{A3}$ | R$_{B10}$ |
| L$_{41164}$ | R$_{B6}$ | R$_{B1}$ | R$_{A3}$ | R$_{A34}$ |

| Ligand | R¹ | R² | R¹¹ | R¹² |
|---|---|---|---|---|
| $L_{A1165}$ | $R_{B6}$ | $R_{B1}$ | $R_{A34}$ | $R_{B1}$ |
| $L_{A1166}$ | $R_{B6}$ | $R_{B1}$ | $R_{A34}$ | $R_{B3}$ |
| $L_{A1167}$ | $R_{B6}$ | $R_{B1}$ | $R_{A34}$ | $R_{B4}$ |
| $L_{A1168}$ | $R_{B6}$ | $R_{B1}$ | $R_{A34}$ | $R_{B7}$ |
| $L_{A1169}$ | $R_{B6}$ | $R_{B1}$ | $R_{A34}$ | $R_{B10}$ |
| $L_{A1170}$ | $R_{B6}$ | $R_{B1}$ | $R_{A34}$ | $R_{A3}$, |

$L_{A1171}$ through $L_{A1266}$ that are based on a structure of Formula V,

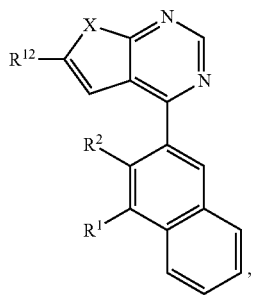

in which R¹, R², R¹³, and X are defined as provided below:

| Ligand | R¹ | R² | R¹³ | X |
|---|---|---|---|---|
| $L_{A1171}$ | $R_{B6}$ | H | H | S |
| $L_{A1172}$ | $R_{B6}$ | H | $R_{B1}$ | S |
| $L_{A1173}$ | $R_{B6}$ | H | $R_{B3}$ | S |
| $L_{A1174}$ | $R_{B6}$ | H | $R_{B4}$ | S |
| $L_{A1175}$ | $R_{B6}$ | H | $R_{B7}$ | S |
| $L_{A1176}$ | $R_{B6}$ | H | $R_{B10}$ | S |
| $L_{A1177}$ | $R_{B6}$ | H | $R_{A3}$ | S |
| $L_{A1178}$ | $R_{B6}$ | H | $R_{A34}$ | S |
| $L_{A1179}$ | $R_{B8}$ | H | $R_{B1}$ | S |
| $L_{A1180}$ | $R_{B8}$ | H | $R_{B2}$ | S |
| $L_{A1181}$ | $R_{B8}$ | H | $R_{B3}$ | S |
| $L_{A1182}$ | $R_{B8}$ | H | $R_{B4}$ | S |
| $L_{A1183}$ | $R_{B8}$ | H | $R_{B7}$ | S |
| $L_{A1184}$ | $R_{B8}$ | H | $R_{B10}$ | S |
| $L_{A1185}$ | $R_{B8}$ | H | $R_{A3}$ | S |
| $L_{A1186}$ | $R_{B8}$ | H | $R_{A34}$ | S |
| $L_{A1187}$ | $R_{B6}$ | F | H | S |
| $L_{A1188}$ | $R_{B6}$ | F | $R_{B1}$ | S |
| $L_{A1189}$ | $R_{B6}$ | F | $R_{B3}$ | S |
| $L_{A1190}$ | $R_{B6}$ | F | $R_{B4}$ | S |
| $L_{A1191}$ | $R_{B6}$ | F | $R_{B7}$ | S |
| $L_{A1192}$ | $R_{B6}$ | F | $R_{B10}$ | S |
| $L_{A1193}$ | $R_{B6}$ | F | $R_{A3}$ | S |
| $L_{A1194}$ | $R_{B6}$ | F | $R_{A34}$ | S |
| $L_{A1195}$ | $R_{B8}$ | F | $R_{B1}$ | S |
| $L_{A1196}$ | $R_{B8}$ | F | $R_{B2}$ | S |
| $L_{A1197}$ | $R_{B8}$ | F | $R_{B3}$ | S |
| $L_{A1198}$ | $R_{B8}$ | F | $R_{B4}$ | S |
| $L_{A1199}$ | $R_{B8}$ | F | $R_{B7}$ | S |
| $L_{A1200}$ | $R_{B8}$ | F | $R_{B10}$ | S |
| $L_{A1201}$ | $R_{B8}$ | F | $R_{A3}$ | S |
| $L_{A1202}$ | $R_{B8}$ | F | $R_{A34}$ | S |
| $L_{A1203}$ | $R_{B6}$ | $R_{B1}$ | H | S |
| $L_{A1204}$ | $R_{B6}$ | $R_{B1}$ | $R_{B1}$ | S |
| $L_{A1205}$ | $R_{B6}$ | $R_{B1}$ | $R_{B3}$ | S |
| $L_{A1206}$ | $R_{B6}$ | $R_{B1}$ | $R_{B4}$ | S |
| $L_{A1207}$ | $R_{B6}$ | $R_{B1}$ | $R_{B7}$ | S |
| $L_{A1208}$ | $R_{B6}$ | $R_{B1}$ | $R_{B10}$ | S |
| $L_{A1209}$ | $R_{B6}$ | $R_{B1}$ | $R_{A3}$ | S |
| $L_{A1210}$ | $R_{B6}$ | $R_{B1}$ | $R_{A34}$ | S |
| $L_{A1211}$ | $R_{B8}$ | $R_{B1}$ | $R_{B1}$ | S |
| $L_{A1212}$ | $R_{B8}$ | $R_{B1}$ | $R_{B2}$ | S |
| $L_{A1213}$ | $R_{B8}$ | $R_{B1}$ | $R_{B3}$ | S |
| $L_{A1214}$ | $R_{B8}$ | $R_{B1}$ | $R_{B4}$ | S |

| Ligand | R¹ | R² | R¹³ | X |
|---|---|---|---|---|
| $L_{A1215}$ | $R_{B8}$ | $R_{B1}$ | $R_{B7}$ | S |
| $L_{A1216}$ | $R_{B8}$ | $R_{B1}$ | $R_{B10}$ | S |
| $L_{A1217}$ | $R_{B8}$ | $R_{B1}$ | $R_{A3}$ | S |
| $L_{A1218}$ | $R_{B8}$ | $R_{B1}$ | $R_{A34}$ | S |
| $L_{A1219}$ | $R_{B6}$ | H | H | O |
| $L_{A1220}$ | $R_{B6}$ | H | $R_{B1}$ | O |
| $L_{A1221}$ | $R_{B6}$ | H | $R_{B3}$ | O |
| $L_{A1222}$ | $R_{B6}$ | H | $R_{B4}$ | O |
| $L_{A1223}$ | $R_{B6}$ | H | $R_{B7}$ | O |
| $L_{A1224}$ | $R_{B6}$ | H | $R_{B10}$ | O |
| $L_{A1225}$ | $R_{B6}$ | H | $R_{A3}$ | O |
| $L_{A1226}$ | $R_{B6}$ | H | $R_{A34}$ | O |
| $L_{A1227}$ | $R_{B8}$ | H | $R_{B1}$ | O |
| $L_{A1228}$ | $R_{B8}$ | H | $R_{B2}$ | O |
| $L_{A1229}$ | $R_{B8}$ | H | $R_{B3}$ | O |
| $L_{A1230}$ | $R_{B8}$ | H | $R_{B4}$ | O |
| $L_{A1231}$ | $R_{B8}$ | H | $R_{B7}$ | O |
| $L_{A1232}$ | $R_{B8}$ | H | $R_{B10}$ | O |
| $L_{A1233}$ | $R_{B8}$ | H | $R_{A3}$ | O |
| $L_{A1234}$ | $R_{B8}$ | H | $R_{A34}$ | O |
| $L_{A1235}$ | $R_{B6}$ | F | H | O |
| $L_{A1236}$ | $R_{B6}$ | F | $R_{B1}$ | O |
| $L_{A1237}$ | $R_{B6}$ | F | $R_{B3}$ | O |
| $L_{A1238}$ | $R_{B6}$ | F | $R_{B4}$ | O |
| $L_{A1239}$ | $R_{B6}$ | F | $R_{B7}$ | O |
| $L_{A1240}$ | $R_{B6}$ | F | $R_{B10}$ | O |
| $L_{A1241}$ | $R_{B6}$ | F | $R_{A3}$ | O |
| $L_{A1242}$ | $R_{B6}$ | F | $R_{A34}$ | O |
| $L_{A1243}$ | $R_{B8}$ | F | $R_{B1}$ | O |
| $L_{A1244}$ | $R_{B8}$ | F | $R_{B2}$ | O |
| $L_{A1245}$ | $R_{B8}$ | F | $R_{B3}$ | O |
| $L_{A1246}$ | $R_{B8}$ | F | $R_{B4}$ | O |
| $L_{A1247}$ | $R_{B8}$ | F | $R_{B7}$ | O |
| $L_{A1248}$ | $R_{B8}$ | F | $R_{B10}$ | O |
| $L_{A1249}$ | $R_{B8}$ | F | $R_{A3}$ | O |
| $L_{A1250}$ | $R_{B8}$ | F | $R_{A34}$ | O |
| $L_{A1251}$ | $R_{B6}$ | $R_{B1}$ | H | O |
| $L_{A1252}$ | $R_{B6}$ | $R_{B1}$ | $R_{B1}$ | O |
| $L_{A1253}$ | $R_{B6}$ | $R_{B1}$ | $R_{B3}$ | O |
| $L_{A1254}$ | $R_{B6}$ | $R_{B1}$ | $R_{B4}$ | O |
| $L_{A1255}$ | $R_{B6}$ | $R_{B1}$ | $R_{B7}$ | O |
| $L_{A1256}$ | $R_{B6}$ | $R_{B1}$ | $R_{B10}$ | O |
| $L_{A1257}$ | $R_{B6}$ | $R_{B1}$ | $R_{A3}$ | O |
| $L_{A1258}$ | $R_{B6}$ | $R_{B1}$ | $R_{A34}$ | O |
| $L_{A1259}$ | $R_{B8}$ | $R_{B1}$ | $R_{B1}$ | O |
| $L_{A1260}$ | $R_{B8}$ | $R_{B1}$ | $R_{B2}$ | O |
| $L_{A1261}$ | $R_{B8}$ | $R_{B1}$ | $R_{B3}$ | O |
| $L_{A1262}$ | $R_{B8}$ | $R_{B1}$ | $R_{B4}$ | O |
| $L_{A1263}$ | $R_{B8}$ | $R_{B1}$ | $R_{B7}$ | O |
| $L_{A1264}$ | $R_{B8}$ | $R_{B1}$ | $R_{B10}$ | O |
| $L_{A1265}$ | $R_{B8}$ | $R_{B1}$ | $R_{A3}$ | O |
| $L_{A1266}$ | $R_{B8}$ | $R_{B1}$ | $R_{A34}$ | O, |

$L_{A1267}$ through $L_{A1298}$ that are based on a structure of Formula VI, in which $R^1$, $R^2$, and $R^{14}$ are defined as provided below:

| Ligand | $R^1$ | $R^2$ | $R^{14}$ |
|---|---|---|---|
| $L_{41267}$ | $R_{B6}$ | H | H |
| $L_{41268}$ | $R_{B6}$ | H | $R_{B1}$ |
| $L_{41269}$ | $R_{B6}$ | H | $R_{B3}$ |
| $L_{41270}$ | $R_{B6}$ | H | $R_{B4}$ |
| $L_{41271}$ | $R_{B6}$ | H | $R_{B7}$ |
| $L_{41272}$ | $R_{B6}$ | H | $R_{B10}$ |
| $L_{41273}$ | $R_{B6}$ | H | $R_{A3}$ |
| $L_{41274}$ | $R_{B6}$ | H | $R_{A34}$ |
| $L_{41275}$ | $R_{B8}$ | H | H |
| $L_{41276}$ | $R_{B8}$ | H | $R_{B1}$ |
| $L_{41277}$ | $R_{B8}$ | H | $R_{B3}$ |
| $L_{41278}$ | $R_{B8}$ | H | $R_{B4}$ |
| $L_{41279}$ | $R_{B8}$ | H | $R_{B7}$ |
| $L_{41280}$ | $R_{B8}$ | H | $R_{B10}$ |
| $L_{41281}$ | $R_{B8}$ | H | $R_{A3}$ |
| $L_{41282}$ | $R_{B8}$ | H | $R_{A34}$ |
| $L_{41283}$ | H | $R_{B6}$ | H |
| $L_{41284}$ | H | $R_{B6}$ | $R_{B1}$ |
| $L_{41285}$ | H | $R_{B6}$ | $R_{B3}$ |
| $L_{41286}$ | H | $R_{B6}$ | $R_{B4}$ |
| $L_{41287}$ | H | $R_{B6}$ | $R_{B7}$ |
| $L_{41288}$ | H | $R_{B6}$ | $R_{B10}$ |
| $L_{41289}$ | H | $R_{B6}$ | $R_{A3}$ |
| $L_{41290}$ | H | $R_{B6}$ | $R_{A34}$ |
| $L_{41291}$ | H | $R_{B8}$ | H |
| $L_{41292}$ | H | $R_{B8}$ | $R_{B1}$ |
| $L_{41293}$ | H | $R_{B8}$ | $R_{B3}$ |
| $L_{41294}$ | H | $R_{B8}$ | $R_{B4}$ |
| $L_{41295}$ | H | $R_{B8}$ | $R_{B7}$ |
| $L_{41296}$ | H | $R_{B8}$ | $R_{B10}$ |
| $L_{41297}$ | H | $R_{B8}$ | $R_{A3}$ |
| $L_{41298}$ | H | $R_{B8}$ | $R_{A34}$; | wherein $R_{B1}$ to $R_{B4}$, $R_{B6}$ to $R_{B7}$, and $R_{B10}$ have the following structures:

$R_{B1}$

$R_{B2}$

$R_{B3}$

$R_{B4}$

$R_{B6}$

$R_{B7}$

$R_{B8}$

, and

$R_{B10}$ and wherein $R_{A3}$ and $R_{A34}$ have the following structures:

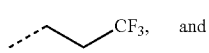
$R_{A3}$

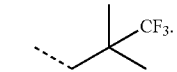
$R_{A34}$

14. The neutral compound of claim 13, wherein $L_{Bj}$ is selected from the following:

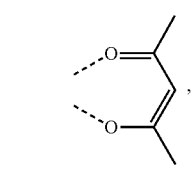
$L_{B1}$

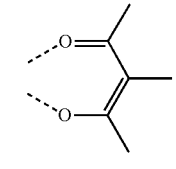
$L_{B2}$

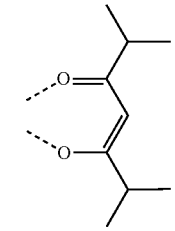
$L_{B3}$

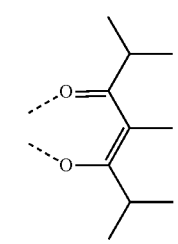
$L_{B4}$

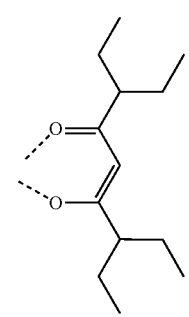
$L_{B5}$

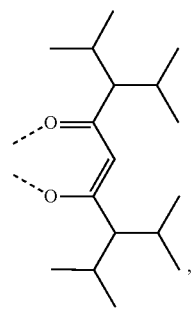 L<sub>B6</sub>
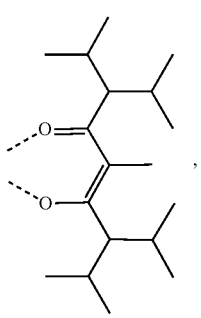 L$_{B7}$
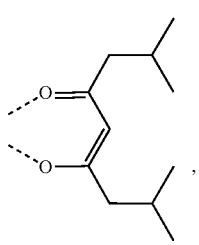 L$_{B8}$
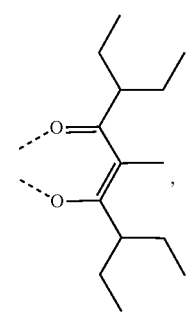 L$_{B9}$
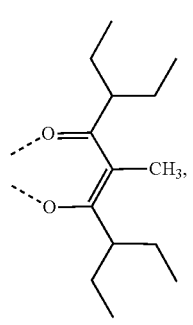 L$_{B10}$
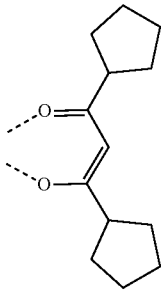 L$_{B11}$
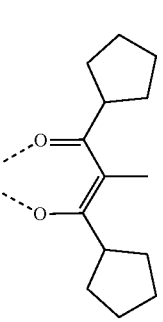 L$_{B12}$
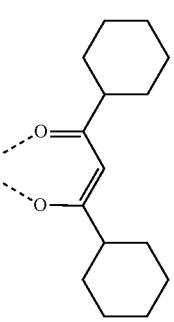 L$_{B13}$
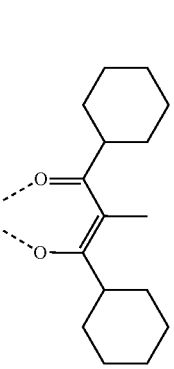 L$_{B14}$
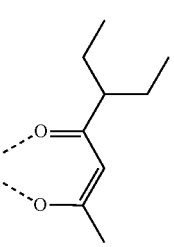 L$_{B15}$ -continued

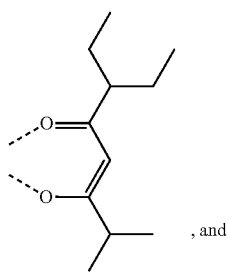

$L_{B16}$

, and

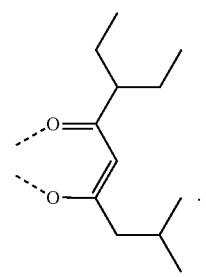

$L_{B17}$

15. A device comprising a first organic light emitting device, the first organic light emitting device comprising:
an anode;
a cathode; and
an organic layer, disposed between the anode and the cathode, comprising a neutral compound comprising a ligand $L_A$ of Formula I:

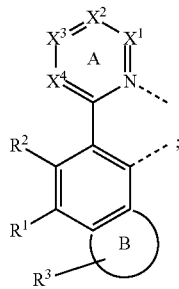

Formula I wherein Ring B represents a five- or six-membered aromatic ring;
wherein $R^3$ represents from none to the maximum number of substitutions;
wherein $X^1$, $X^2$, $X^3$, and $X^4$ are each independently a CR or N;
wherein at least one of $X^1$, $X^2$, or $X^3$ is nitrogen;
wherein (a) $R^1$ is $CR^{11}R^{12}R^{13}$ or joins with $R^2$ to form into a ring; or
(b) $R^2$ is not hydrogen, or
(c) both (a) and (b) are true;
wherein R, $R^1$, $R^2$, $R^3$, $R^{11}$, $R^{12}$, and $R^{13}$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, acyl, carbonyl, carboxylic acid, ester, nitrile, isonitrile, sulfanyl, sulfinyl, sulfonyl, phosphino, and combinations thereof;

wherein, with the exception of a ring between R and $R^2$, any two substituents among R, $R^1$, $R^2$, $R^3$, $R^{11}$, $R^{12}$, and $R^{13}$ are optionally joined to form into an aromatic ring;
wherein $L_A$ is coordinated to a metal M;
wherein $L_A$ is optionally linked with other ligands to comprise a tridentate, tetradentate, pentadentate, or hexadentate ligand; and
wherein M is optionally coordinated to other ligands.

16. The first device of claim 15, wherein the first device is selected from the group consisting of a consumer product, an electronic component module, an organic light-emitting device, and a lighting panel.

17. The first device of claim 15, wherein the organic layer is an emissive layer and the neutral compound is an emissive dopant or a non-emissive dopant.

18. The first device of claim 15, wherein the organic layer further comprises a host, wherein the host comprises at least one chemical group selected from the group consisting of carbazole, dibenzothiophene, dibenzofuran, dibenzoselenophene, azacarbazole, aza-dibenzothiophene, aza-dibenzofuran, and aza-dibenzoselenophene.

19. The first device of claim 15, wherein the organic layer further comprises a host, wherein the host is selected from the group consisting of:

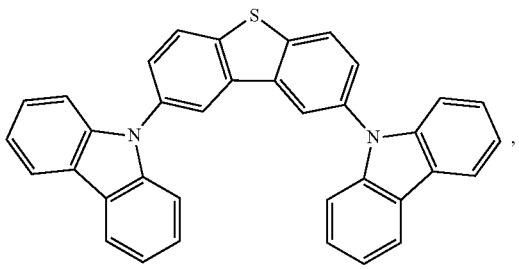

,

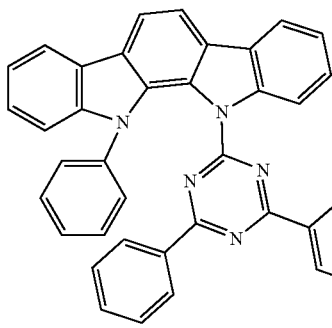

,

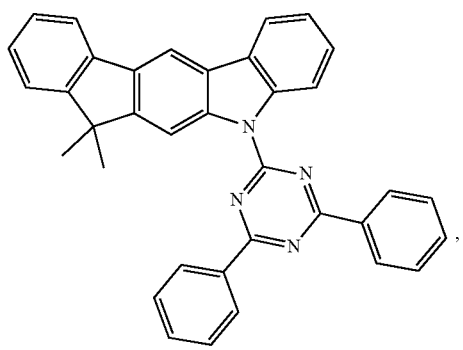

,

185
-continued
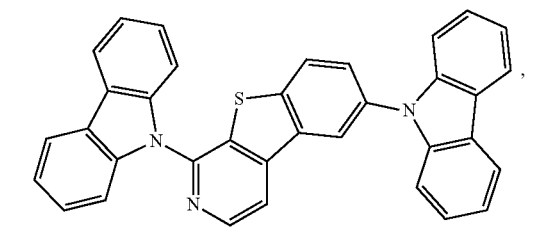
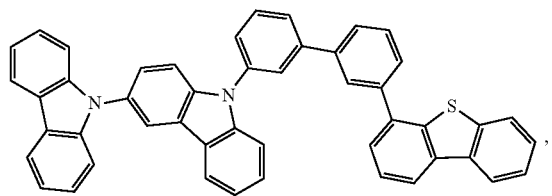
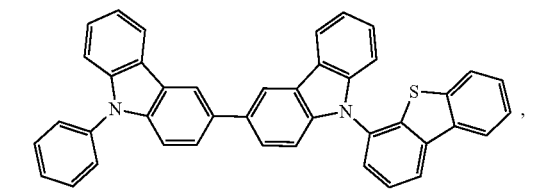
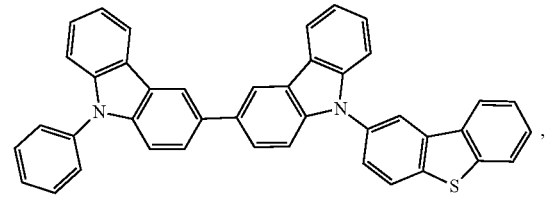
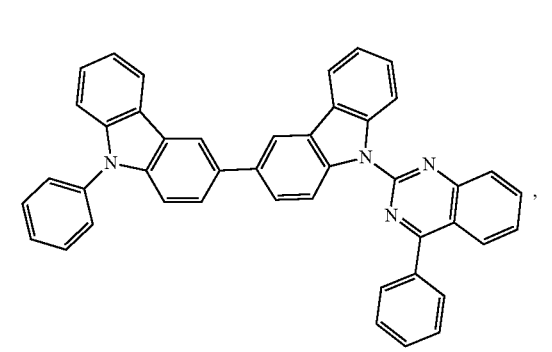
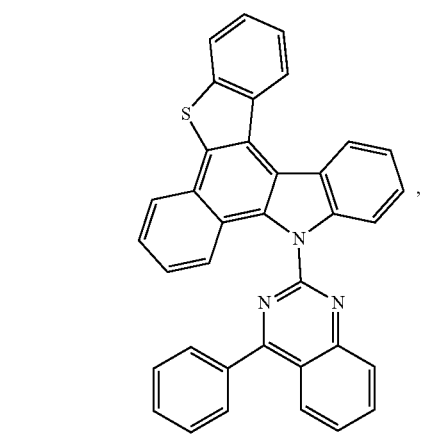
186
-continued
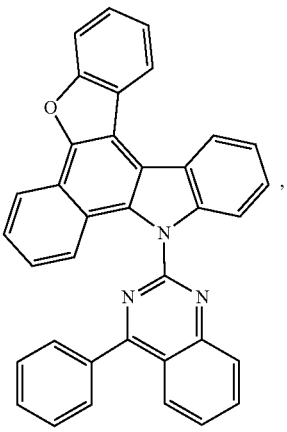
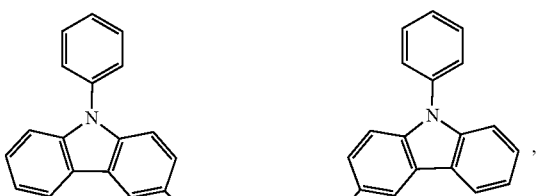
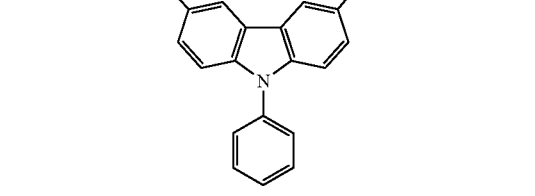
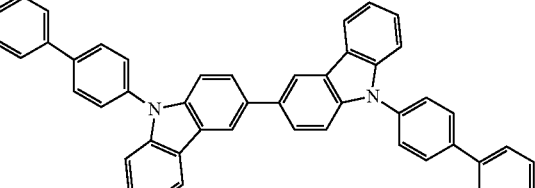
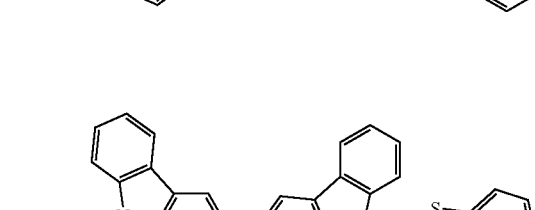
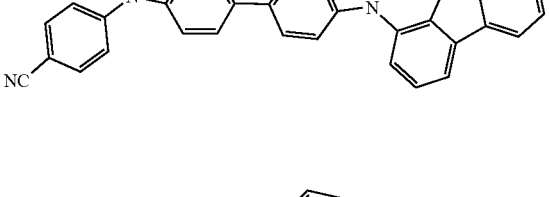
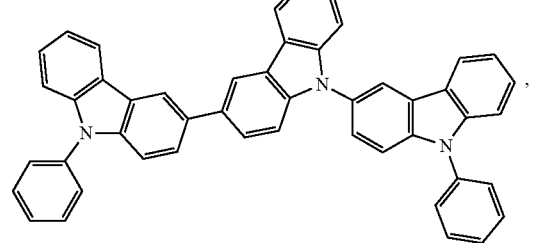

-continued

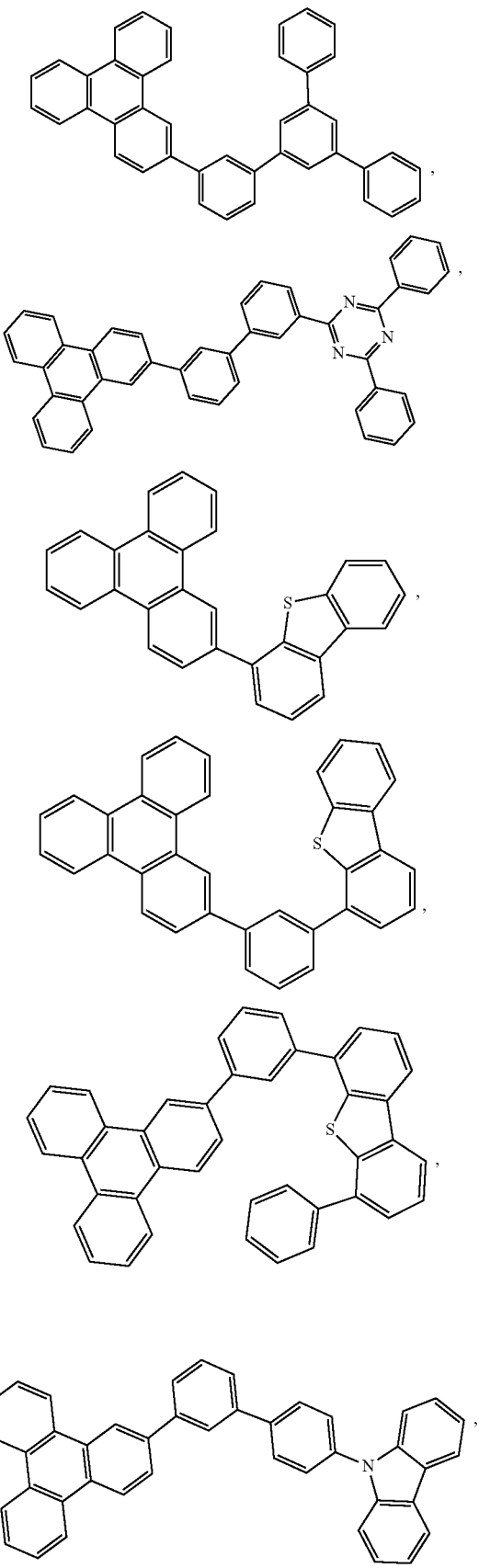

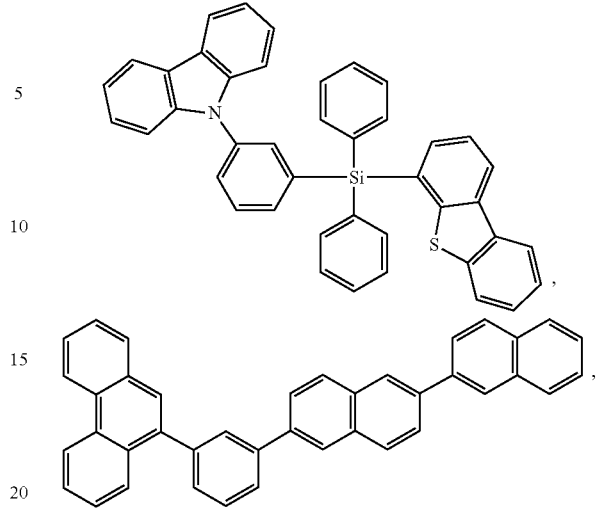

and combinations thereof.

20. A consumer product comprising a first device comprising a first organic light emitting device, wherein the first organic light emitting device comprising:
  an anode;
  a cathode; and
  an organic layer, disposed between the anode and the cathode, comprising a neutral compound comprising a ligand $L_A$ of Formula I:

Formula I

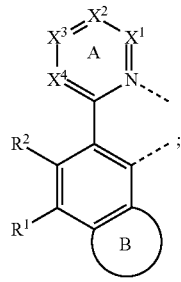

wherein Ring B represents a five- or six-membered aromatic ring;
wherein $R^3$ represents from none to the maximum number of substitutions;
wherein $X^1$, $X^2$, $X^3$, and $X^4$ are each independently a CR or N;
wherein at least one of $X^1$, $X^2$, or $X^3$ is nitrogen;
wherein (a) $R^1$ is $CR^{11}R^{12}R^{13}$ or joins with $R^2$ to form into a ring; or
  (b) $R^2$ is not hydrogen, or
  (c) both (a) and (b) are true;
wherein R, $R^1$, $R^2$, $R^3$, $R^{11}$, $R^{12}$, and $R^{13}$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, acyl, carbonyl, carboxylic acid, ester, nitrile, isonitrile, sulfanyl, sulfinyl, sulfonyl, phosphino, and combinations thereof;
wherein, with the exception of a ring between R and $R^2$, any two substituents among R, $R^1$, $R^2$, $R^3$, $R^{11}$, $R^{12}$, and $R^{13}$ are optionally joined to form into an aromatic ring;

wherein $L_A$ is coordinated to a metal M;

wherein $L_A$ is optionally linked with other ligands to comprise a tridentate, tetradentate, pentadentate, or hexadentate ligand; and wherein M is optionally coordinated to other ligands.

21. The consumer product of claim 20, wherein the consumer product is selected from the group consisting of flat panel displays, computer monitors, medical monitors, televisions, billboards, lights for interior or exterior illumination and/or signaling, heads-up displays, fully or partially transparent displays, flexible displays, laser printers, telephones, mobile phones, tablets, phablets, personal digital assistants (PDAs), wearable devices, laptop computers, digital cameras, camcorders, viewfinders, micro-displays, 3-D displays, virtual reality or augmented reality displays, vehicles, video walls comprising multiple displays tiled together, theater or stadium screen, and a sign.

\* \* \* \* \*